US012364749B2

(12) United States Patent
Che et al.

(10) Patent No.: US 12,364,749 B2
(45) **Date of Patent: *Jul. 22, 2025**

(54) RSV F PROTEIN MUTANTS

(71) Applicant: Pfizer Inc., New York, NY (US)

(72) Inventors: Ye Che, Niantic, CT (US); Philip Ralph Dormitzer, Sherborn, MA (US); Alexey Vyacheslavovich Gribenko, New City, NY (US); Luke David Handke, Nyack, NY (US); Avvari Krishna Prasad, Chapel Hill, NC (US); Xiayang Qiu, Mystic, CT (US); Mark Edward Ruppen, Cresco, PA (US); Xi Song, Waterford, CT (US); Kena Anne Swanson, Pearl River, NY (US); Srinivas Kodali, Hillsborough, NJ (US); Xin Xu, Mahwah, NJ (US); Kariann Sweeney Efferen, Stamford, CT (US); Ping Cai, New City, NY (US); Kristin Rachael Tompkins, Garrison, NY (US); Lorna Del Pilar Nunez, Briarcliff Manor, NY (US)

(73) Assignee: Pfizer Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/192,352

(22) Filed: Mar. 29, 2023

(65) Prior Publication Data

US 2023/0218738 A1 Jul. 13, 2023

Related U.S. Application Data

(62) Division of application No. 17/060,944, filed on Oct. 1, 2020, now abandoned, which is a division of application No. 16/242,799, filed on Jan. 8, 2019, now Pat. No. 10,821,171, which is a division of application No. 15/896,871, filed on Feb. 14, 2018, now Pat. No. 10,238,732, which is a division of application No. 15/385,611, filed on Dec. 20, 2016, now Pat. No. 9,950,058.

(60) Provisional application No. 62/421,184, filed on Nov. 11, 2016, provisional application No. 62/387,270, filed on Dec. 23, 2015.

(51) Int. Cl.

| | |
|---|---|
| ***A61K 39/155*** | (2006.01) |
| ***A61K 39/12*** | (2006.01) |
| ***C07K 14/005*** | (2006.01) |
| ***C07K 14/135*** | (2006.01) |
| ***C12N 7/00*** | (2006.01) |
| ***C12N 15/01*** | (2006.01) |
| *A61K 39/00* | (2006.01) |

(52) U.S. Cl.

CPC ............ *A61K 39/155* (2013.01); *A61K 39/12* (2013.01); *C07K 14/005* (2013.01); *C12N 7/00* (2013.01); *A61K 2039/575* (2013.01); *C07K 2319/02* (2013.01); *C07K 2319/21* (2013.01); *C07K 2319/22* (2013.01); *C07K 2319/40* (2013.01); *C07K 2319/70* (2013.01); *C07K 2319/735* (2013.01); *C12N 2760/18522* (2013.01); *C12N 2760/18534* (2013.01); *C12N 2760/18571* (2013.01)

(58) Field of Classification Search

None

See application file for complete search history.

(56) References Cited

PUBLICATIONS

Anderson et al. Strategic priorities for respiratory syncytial virus (RSV) vaccine development. Vaccine, Apr. 18, 2013; 31 Suppl 2: B209-B215.*

* cited by examiner

*Primary Examiner* — Nianxiang Zou

(74) *Attorney, Agent, or Firm* — Maria V. Marucci

(57) ABSTRACT

The present disclosure relates to RSV F protein mutants, nucleic acids or vectors encoding a RSV F protein mutant, compositions comprising a RSV F protein mutant or nucleic acid, and uses of the RSV F protein mutants, nucleic acids or vectors, and compositions.

18 Claims, 14 Drawing Sheets

Specification includes a Sequence Listing.

FIG. 1

MELLILKANAITTILTAVTFCFASGQNITEEFYQSTCSAVSKGYLSALRTGWYTSVITIE
LSNIKENKCNGTDAKVKLIKQELDKYKNAVTELQLLMQSTPATNNRARRELPRFMN
YTLNNAKKTNVTLSKKRKRRFLGFLLGVGSAIASGVAVSKVLHLEGEVNKIKSALLS
TNKAVVSLSNGVSVLTSKVLDLKNYIDKQLLPIVNKQSCSISNIETVIEFQQKNNRLLE
ITREFSVNAGVTTPVSTYMLTNSELLSLINDMPITNDQKKLMSNNVQIVRQQSYSIMS
IIKEEVLAYVVQLPLYGVIDTPCWKLHTSPLCTTNTKEGSNICLTRTDRGWYCDNAG
SVSFFPQAETCKVQSNRVFCDTMNSLTLPSEVNLCNVDIFNPKYDCKIMTSKTDVS
SSVITSLGAIVSCYGKTKCTASNKNRGIIKTFSNGCDYVSNKGVDTVSVGNTLYYVN
KQEGKSLYVKGEPIINFYDPLVFPSDEFDASISQVNEKINQSLAFIRKSDELLSAIGGY
IPEAPRDGQAYVRKDGEWVLLSTFLGGLVPRGSHHHHHHGSWSHPQFEK

SEQUENCE LISTING

```
Sequence total quantity: 326
SEQ ID NO: 1            moltype = AA  length = 574
FEATURE                 Location/Qualifiers
source                  1..574
                        mol_type = protein
                        organism = Human respiratory syncytial virus
SEQUENCE: 1
MELLILKANA ITTILTAVTF CFASGQNITE EFYQSTCSAV SKGYLSALRT GWYTSVITIE  60
LSNIKENKCN GTDAKVKLIK QELDKYKNAV TELQLLMQST PPTNNRARRE LPRFMNYTLN  120
NAKKTNVTLS KKRKRRFLGF LLGVGSAIAS GVAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEIN LCNVDIFNPK YDCKIMTSKT DVSSSVITSL GAIVSCYGKT  420
KCTASNKNRG IIKTFSNGCD YVSNKGMDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFSN                             574

SEQ ID NO: 2            moltype = AA  length = 574
FEATURE                 Location/Qualifiers
source                  1..574
                        mol_type = protein
                        organism = Human respiratory syncytial virus
SEQUENCE: 2
MELLIHRSSA IFLTLAVNAL YLTSSQNITE EFYQSTCSAV SRGYFSALRT GWYTSVITIE  60
LSNIKETKCN GTDTKVKLIK QELDKYKNAV TELQLLMQNT PAANNRARRE APQYMNYTIN  120
TTKNLNVSIS KKRKRRFLGF LLGVGSAIAS GIAVSKVLHL EGEVNKIKNA LLSTNKAVVS  180
LSNGVSVLTS KVLDLKNYIN NRLLPIVNQQ SCRISNIETV IEFQQMNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKNRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITTI IIVIIVVLLS  540
LIAIGLLLYC KAKNTPVTLS KDQLSGINNI AFSK                             574

SEQ ID NO: 3            moltype = AA  length = 568
FEATURE                 Location/Qualifiers
REGION                  1..568
                        note = synthetic polypeptide
source                  1..568
                        mol_type = protein
                        organism = synthetic construct
SEQUENCE: 3
MELLILKANA ITTILTAVTF CFASGQNITE EFYQSTCSAV SKGYLSALRT GWYTSVITIE  60
LSNIKENKCN GTDAKVKLIK QELDKYKNAV TELQLLMQST PATNNRARRE LPRFMNYTLN  120
NAKKTNVTLS KKRKRRFLGF LLGVGSAIAS GVAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLSAIGGYI PEAPRDGQAY VRKDGEWVLL  540
STFLGGLVPR GSHHHHHHGS WSHPQFEK                                    568

SEQ ID NO: 4            moltype = AA  length = 574
FEATURE                 Location/Qualifiers
source                  1..574
                        mol_type = protein
                        organism = Human respiratory syncytial virus
SEQUENCE: 4
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANSRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSSNVQI VRQQSYSIMS IIKEEVLAYV  300
VQLPLYGVID TPCWKLHTSP LCTTNTKEGS NICLTRTDRG WYCDNAGSVS FFPQAETCKV  360
```

```
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLA  540
LIAVGLLLYC KARSTPVTLS KDQLSGINNI AFSN                             574

SEQ ID NO: 5           moltype = AA  length = 568
FEATURE                Location/Qualifiers
REGION                 1..568
                       note = synthetic polypeptide
source                 1..568
                       mol_type = protein
                       organism = synthetic construct
SEQUENCE: 5
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANSRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSSNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLSAIGGYI PEAPRDGQAY VRKDGEWVLL  540
STFLGGLVPR GSHHHHHHGS WSHPQFEK                                   568

SEQ ID NO: 6           moltype = AA  length = 574
FEATURE                Location/Qualifiers
source                 1..574
                       mol_type = protein
                       organism = Human respiratory syncytial virus
SEQUENCE: 6
MELLIHRSSA IFLTLAINAL YLTSSQNITE EFYQSTCSAV SRGYFSALRT GWYTSVITIE  60
LSNIKETKCN GTDTKVKLIK QELDKYKNAV TELQLLMQNT PAANNRARRE APQYMNYTIN  120
TTKNLNVSIS KKRKRRFLGF LLGVGSAIAS GIAVSKVLHL EGEVNKIKNA LLSTNKAVVS  180
LSNGVSVLTS KVLDLKNYIN NQLLPIVNQQ SCRISNIETV IEFQQKNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKNRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITAI IIVIIVVLLS  540
LIAIGLLLYC KAKNTPVTLS KDQLSGINNI AFSK                             574

SEQ ID NO: 7           moltype = AA  length = 568
FEATURE                Location/Qualifiers
REGION                 1..568
                       note = synthetic peptide
source                 1..568
                       mol_type = protein
                       organism = synthetic construct
SEQUENCE: 7
MELLIHRSSA IFLTLAINAL YLTSSQNITE EFYQSTCSAV SRGYFSALRT GWYTSVITIE  60
LSNIKETKCN GTDTKVKLIK QELDKYKNAV TELQLLMQNT PAANNRARRE APQYMNYTIN  120
TTKNLNVSIS KKRKRRFLGF LLGVGSAIAS GIAVSKVLHL EGEVNKIKNA LLSTNKAVVS  180
LSNGVSVLTS KVLDLKNYIN NQLLPIVNQQ SCRISNIETV IEFQQKNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKNRG IIKTFSNGCD YVSNKGVDTV SVGNTLYYVN KLEGKNLYVK GEPIINYYDP  480
LVFPSDEFDA SISQVNEKIN QSLAFIRRSD ELLSAIGGYI PEAPRDGQAY VRKDGEWVLL  540
STFLGGLVPR GSHHHHHHGS WSHPQFEK                                   568

SEQ ID NO: 8           moltype = DNA  length = 1707
FEATURE                Location/Qualifiers
misc_feature           1..1707
                       note = Synthetic
source                 1..1707
                       mol_type = other DNA
                       organism = synthetic construct
SEQUENCE: 8
atggaacttc tgatcctgaa agccaacgcg attaccacta tcctgactgc cgtcaccttc  60
tgcttcgcat cgggacagaa cattaccgag gagttctacc agtccacctg ttcggcggtg  120
tccaagggtt acctctcggc cctgagaact ggctggtacc actgtgtgat tactatcgag  180
ctgagcaaca tcaaggagaa caagtgcaat ggaacggacg cgaaggtcaa gctgattaag  240
caggaactcg ataagtacaa gaacgccgtg accgagctcc agctgctgat gcaatcgacc  300
cctgccacta acaacagagc tcgccgggaa ctgccgcgct tcatgaatta caccctcaac  360
aacgcgaaga aaaccaacgt gaccctgtcc aagaagcgca agcggaggtt cctgggattc  420
ctgtgtggcg tgggctccgc aatcgcatcc ggagtggccg tgtccaaagt gctgcatctg  480
gagggggaag tgaacaagat caagtccgcc ctcctgtcaa ctaataaggc ggtggtgtcc  540
ctgagcaacg gagtcagcgt gtgtacatcc aaggtcctgg acctcaagaa ctacatcgac  600
aagcagctgt tgcccatcgt caacaagcag tcatgctcga ttagcaatat cgaaaccgtg  660
```

```
attgagttcc agcagaagaa caacagactg ctcgaaatta cccgggagtt ttccgtgaac  720
gccggagtga ccactcctgt gtccacctac atgcttacga actccgaact gctcagcctc  780
atcaacgata tgccgatcac taacgaccag aagaagttga tgagcaacaa tgtgcagatc  840
gtgcgccaac agtcctactc aatcatgtca attatcaagg aggaaatcct cgcctatgtg  900
gtgcaattgc ctctgtacgg agtcatcgac acaccctgct ggaagctgca cactagccca  960
ctctgtacga ccaacaccaa ggaaggttcc aacatctgcc tgactaggac cgatcggggc  1020
tggtattgcg ataatgctgg gtccgtgagc ttcttcccgc aagccgagac ttgcaaagtg  1080
cagtcaaacc gcgtgttctg tgacaccatg tgtagcctga ccctgccatc cgaagtcaac  1140
ctctgcaacg tggacatctt taacccgaaa tacgactgca agattatgac ctccaagacc  1200
gacgtcagca gctctgtcat cactagcctg ggagctattg tgtcctgcta cggaaagacc  1260
aaatgcactg cctcgaacaa gaacagaggc atcatcaaga ccttcagcaa cggctgtgac  1320
tacgtgtcca acaagggagt ggacaccgtg tccgtcggga acaccctgta ctacgtgaac  1380
aagcaggagg ggaagtcgct ctacgtcaag gggaaccga ttatcaattt ctacgacccc  1440
ctggtgttcc cttccgacga gttcgatgcc tccatatccc aagtcaacga gaagatcaac  1500
cagtctcttg ccttcatccg gaagtcggac gaactgctgt ccgccatcgg tggctatatt  1560
ccggaagccc ccagggatgg acaggcctac gtgcggaagg atggagaatg ggtgcttttg  1620
tccaccttcc tgggcggtct ggtgccccgc ggctcacacc atcatcacca ccacggttcg  1680
tggtcccacc ctcaatttga gaagtga                                    1707

SEQ ID NO: 9           moltype = DNA  length = 1707
FEATURE                Location/Qualifiers
misc_feature           1..1707
                       note = synthetic
source                 1..1707
                       mol_type = other DNA
                       organism = synthetic construct
SEQUENCE: 9
atggaacttc tgatcctgaa agccaacgcg attaccacta tcctgactgc cgtcaccttc  60
tgcttcgcat cgggacagaa cattaccgag gagttctacc agtccacctg ttcggcggtg  120
tccaagggtt acctctcggc cctgagaact ggctggtaca cctgtgtgat tactatcgag  180
ctgagcaaca tcaaggagaa caagtgcaat ggaacggacg cgaaggtcaa gctgattaag  240
caggaactcg ataagtacaa gaacgccgtg accgagctcc agctgctgat gcaatcgacc  300
cctgccacta acaacagagc tcgccgggaa ctgccgcgct tcatgaatta caccctcaac  360
aacgcgaaga aaaccaacgt gaccctgtcc aagaagcgca agcggaggtt cctgggattc  420
ctgttgggcg tgggctccgc aatcgcatcc ggagtggccg tgtccaaagt gctgcatctg  480
gagggggaag tgaacaagat caagtccgcc ctcctgtcaa ctaataaggc ggtggtgtcc  540
ctgagcaacg gagtcagcgt gtgtacatcc aaggtcctgg acctcaagaa ctacatcgac  600
aagcagctgt tgcccatcgt caacaagcag tcatgctcga ttagcaatat cgaaaccgtg  660
attgagttcc agcagaagaa caacagactg ctcgaaatta cccgggagtt ttccgtgaac  720
gccggagtga ccactcctgt gtccacctac atgcttacga actccgaact gctcagcctc  780
atcaacgata tgccgatcac taacgaccag aagaagttga tgagcaacaa tgtgcagatc  840
gtgcgccaac agtcctactc aatcatgtca attatcaagg aggaagtgct cgcctatgtg  900
gtgcaattgc ctctgtacgg agtcatcgac acaccctgct ggaagctgca cactagccca  960
ctctgtacga ccaacaccaa ggaaggttcc aacatctgcc tgactaggac cgatcggggc  1020
tggtattgcg ataatgctgg gtccgtgagc ttcttcccgc aagccgagac ttgcaaagtg  1080
cagtcaaacc gcgtgttctg tgacaccatg aacagcctga ccctgccatc cgaagtcaac  1140
ctctgcaacg tggacatctt taacccgaaa tacgactgca agattatgac ctccaagacc  1200
gacgtcagca gctctgtcat cactagcctg ggagctattg tgtcctgcta cggaaagacc  1260
aaatgcactg cctcgaacaa gaacagaggc atcatcaaga ccttcagcaa cggctgtgac  1320
tacgtgtcca acaagggagt ggacaccgtg tccgtcggga acaccctgta ctacgtgaac  1380
aagcaggagg ggaagtcgct ctacgtcaag gggaaccga ttatcaattt ctacgacccc  1440
ctggtgttcc cttcctccga gttcgatgcc tccatatccc aagtcaacga gaagatcaac  1500
cagtctcttg ccttcatccg gaagtcggac gaactgctgt ccgccatcgg tggctatatt  1560
ccggaagccc ccagggatgg acaggcctac gtgcggaagg atggagaatg ggtgcttttg  1620
tccaccttcc tgggcggtct ggtgccccgc ggctcacacc atcatcacca ccacggttcg  1680
tggtcccacc ctcaatttga gaagtga                                    1707

SEQ ID NO: 10          moltype = DNA  length = 1707
FEATURE                Location/Qualifiers
misc_feature           1..1707
                       note = synthetic
source                 1..1707
                       mol_type = other DNA
                       organism = synthetic construct
SEQUENCE: 10
atggaacttc tgatcctgaa agccaacgcg attaccacta tcctgactgc cgtcaccttc  60
tgcttcgcat cgggacagaa cattaccgag gagttctacc agtccacctg ttcggcggtg  120
tccaagggtt acctctcggc cctgagaact ggctggtacc actgtgtgat tactatcgag  180
ctgagcaaca tcaaggagaa caagtgcaat ggaacggacg cgaaggtcaa gctgattaag  240
caggaactcg ataagtacaa gaacgccgtg accgagctcc agctgctgat gcaatcgacc  300
cctgccacta acaacagagc tcgccgggaa ctgccgcgct tcatgaatta caccctcaac  360
aacgcgaaga aaaccaacgt gaccctgtcc aagaagcgca agcggaggtt cctgggattc  420
ctgttgggcg tgggctccgc aatcgcatcc ggagtggccg tgtccaaagt gctgcatctg  480
gagggggaag tgaacaagat caagtccgcc ctcctgtcaa ctaataaggc ggtggtgtcc  540
ctgagcaacg gagtcagcgt gtgtacaatc aaggtcctgg acctcaagaa ctacatcgac  600
aagcagctgt tgcccatcgt caacaagcag tcatgctcga ttagcaatat cgaaaccgtg  660
attgagttcc agcagaagaa caacagactg ctcgaaatta cccgggagtt ttccgtgaac  720
gccggagtga ccactcctgt gtccacctac atgcttacga actccgaact gctcagcctc  780
atcaacgata tgccgatcac taacgaccag aagaagttga tgagcaacaa tgtgcagatc  840
```

```
gtgcgccaac agtcctactc aatcatgtca attatcaagg aggaagtgct cgcctatgtg  900
gtgcaattgc ctctgtacgg agtcatcgac acaccctgct ggaagctgca cactagccca  960
ctctgtacga ccaacaccaa ggaaggttcc aacatctgcc tgactaggac cgatcggggc  1020
tggtattgcg ataatgctgg gtccgtgagc ttcttcccgc aagccgagac ttgcaaagtg  1080
cagtcaaacc gcgtgttctg tgacaccatg aacagcctga ccctgccatc cgaagtcaac  1140
ctctgcaacg tggacatctt taacccgaaa tacgactgca agattatgac ctccaagacc  1200
gacgtcagca gctctgtcat cactagcctg ggagctattg tgtcctgcta cggaaagacc  1260
aaatgcactg cctcgaacaa gaacagaggc atcatcaaga ccttcagcaa cggctgtgac  1320
tacgtgtcca acaagggagt ggacaccgtg tccgtcggga acaccctgta ctacgtgaac  1380
aagcaggagg ggaagtcgct ctacgtcaag gggaaccgaa ttatcaattt ctacgacccc  1440
ctggtgttcc cttccgacga gttcgatgcc tccatatccc aagtcaacga gaagatcaac  1500
cagtctcttg ccttcatccg gaagtcggac gaactgctgt ccgccatcgg tggctatatt  1560
ccggaagccc ccagggatgg acaggcctac gtgcggaagg atggagaatg ggtgcttttg  1620
tccaccttcc tgggcggtct ggtgccccgc ggctcacacc atcatcacca ccacggttcg  1680
tggtcccacc ctcaatttga gaagtga                                     1707
```

```
SEQ ID NO: 11          moltype = DNA  length = 1707
FEATURE                Location/Qualifiers
misc_feature           1..1707
                       note = synthetic
source                 1..1707
                       mol_type = other DNA
                       organism = synthetic construct
SEQUENCE: 11
atggaacttc tgatcctgaa agccaacgcg attaccacta tcctgactgc cgtcaccttc  60
tgcttcgcat cgggacagaa cattaccgag gagttctacc agtccacctg ttcggcggtg  120
tccaagggtt acctctcggc cctgagaact ggctggtaca ccagcgtgat tactatcgag  180
ctgagcaaca tcaaggagaa caagtgcaat ggaacggacg cgaaggtcaa gctgattaag  240
caggaactcg ataagtacaa gaacgccgtg accgagctcc agctgctgat gcaatcgacc  300
cctgcctgta acaacagagc tcgccgggaa ctgccgcgct tcatgaatta caccctcaac  360
aacgcgaaga aaaccaacgt gaccctgtcc aagaagcgca agcggaggtt cctgggattc  420
ctgttgggcg tgggctccgc atgtgcatcc ggagtggccg tgtccaaagt gctgcatctg  480
gagggggaag tgaacaagat caagtccgcc ctcctgtcaa ctaataaggc ggtggtgtcc  540
ctgagcaacg gagtcagcgt gctgacaatc aaggtcctgg acctcaagaa ctacatcgac  600
aagcagctgt tgcccatcgt caacaagcag tcatgctcga ttagcaatat cgaaaccgtg  660
attgagttcc agcagaagaa caacagactg ctcgaaatta cccgggagtt ttccgtgaac  720
gccggagtga ccactcctgt gtccacctac atgcttacga actccgaact gctcagcctc  780
atcaacgata tgccgatcac taacgaccag aagaagttga tgagcaacaa tgtgcagatc  840
gtgcgccaac agtcctactc aatcatgtca attatcaagg aggaagtgct cgcctatgtg  900
gtgcaattgc ctctgtacgg agtcatcgac acaccctgct ggaagctgca cactagccca  960
ctctgtacga ccaacaccaa ggaaggttcc aacatctgcc tgactaggac cgatcggggc  1020
tggtattgcg ataatgctgg gtccgtgagc ttcttcccgc aagccgagac ttgcaaagtg  1080
cagtcaaacc gcgtgttctg tgacaccatg aacagcctga ccctgccatc cgaagtcaac  1140
ctctgcaacg tggacatctt taacccgaaa tacgactgca agattatgac ctccaagacc  1200
gacgtcagca gctctgtcat cactagcctg ggagctattg tgtcctgcta cggaaagacc  1260
aaatgcactg cctcgaacaa gaacagaggc atcatcaaga ccttcagcaa cggctgtgac  1320
tacgtgtcca acaagggagt ggacaccgtg tccgtcggga acaccctgta ctacgtgaac  1380
aagcaggagg ggaagtcgct ctacgtcaag gggaaccgaa ttatcaattt ctacgacccc  1440
ctggtgttcc cttcctccga gttcgatgcc tccatatccc aagtcaacga gaagatcaac  1500
cagtctcttg ccttcatccg gaagtcggac gaactgctgt ccgccatcgg tggctatatt  1560
ccggaagccc ccagggatgg acaggcctac gtgcggaagg atggagaatg ggtgcttttg  1620
tccaccttcc tgggcggtct ggtgccccgc ggctcacacc atcatcacca ccacggttcg  1680
tggtcccacc ctcaatttga gaagtga                                     1707
```

```
SEQ ID NO: 12          moltype = DNA  length = 1707
FEATURE                Location/Qualifiers
misc_feature           1..1707
                       note = synthetic
source                 1..1707
                       mol_type = other DNA
                       organism = synthetic construct
SEQUENCE: 12
atggaacttc tgatcctgaa agccaacgcg attaccacta tcctgactgc cgtcaccttc  60
tgcttcgcat cgggacagaa cattaccgag gagttctacc agtccacctg ttcggcggtg  120
tccaagggtt acctctcggc cctgagaact ggctggtacc acagcgtgat tactatcgag  180
ctgagcaaca tcaaggagaa caagtgcaat ggaacggacg cgaaggtcaa gctgattaag  240
caggaactcg ataagtacaa gaacgccgtg accgagctcc agctgctgat gcaatcgacc  300
cctgcctgta acaacagagc tcgccgggaa ctgccgcgct tcatgaatta caccctcaac  360
aacgcgaaga aaaccaacgt gaccctgtcc aagaagcgca agcggaggtt cctgggattc  420
ctgttgggcg tgggctccgc atgtgcatcc ggagtggccg tgtccaaagt gctgcatctg  480
gagggggaag tgaacaagat caagtccgcc ctcctgtcaa ctaataaggc ggtggtgtcc  540
ctgagcaacg gagtcagcgt gctgacaatc aaggtcctgg acctcaagaa ctacatcgac  600
aagcagctgt tgcccatcgt caacaagcag tcatgctcga ttagcaatat cgaaaccgtg  660
attgagttcc agcagaagaa caacagactg ctcgaaatta cccgggagtt ttccgtgaac  720
gccggagtga ccactcctgt gtccacctac atgcttacga actccgaact gctcagcctc  780
atcaacgata tgccgatcac taacgaccag aagaagttga tgagcaacaa tgtgcagatc  840
gtgcgccaac agtcctactc aatcatgtca attatcaagg aggaaatcct cgcctatgtg  900
gtgcaattgc ctctgtacgg agtcatcgac acaccctgct ggaagctgca cactagccca  960
ctctgtacga ccaacaccaa ggaaggttcc aacatctgcc tgactaggac cgatcggggc  1020
```

-continued

```
tggtattgcg ataatgctgg gtccgtgagc ttcttcccgc aagccgagac ttgcaaagtg  1080
cagtcaaacc gcgtgttctg tgacaccatg aacagcctga ccctgccatc cgaagtcaac  1140
ctctgcaacg tggacatctt taacccgaaa tacgactgca agattatgac ctccaagacc  1200
gacgtcagca gctctgtcat cactagcctg ggagctattg tgtcctgcta cggaaagacc  1260
aaatgcactg cctcgaacaa gaacagaggc atcatcaaga ccttcagcaa cggctgtgac  1320
tacgtgtcca acaagggagt ggacaccgtg tccgtcggga acaccctgta ctacgtgaac  1380
aagcaggagg ggaagtcgct ctacgtcaag gggaaccga ttatcaattt ctacgacccc  1440
ctggtgttcc cttcctccga gttcgatgcc tccatatccc aagtcaacga gaagatcaac  1500
cagtctcttg ccttcatccg gaagtcggac gaactgctgt ccgccatcgg tggctatatt  1560
ccggaagccc ccagggatgg acaggcctac gtgcggaagg atggagaatg ggtgcttttg  1620
tccaccttcc tgggcggtct ggtgccccgc ggctcacacc atcatcacca ccacggttcg  1680
tggtcccacc ctcaatttga gaagtga                                        1707
```

```
SEQ ID NO: 13          moltype = DNA  length = 1707
FEATURE                Location/Qualifiers
misc_feature           1..1707
                       note = synthetic
source                 1..1707
                       mol_type = other DNA
                       organism = synthetic construct
SEQUENCE: 13
atggaacttc tgatcctgaa agccaacgcg attaccacta tcctgactgc cgtcaccttc  60
tgcttcgcat cgggacagaa cattaccgag gagttctacc agtccacctg ttcggcggtg  120
tccaagggtt acctctcggc cctgagaact ggctggtacc actgtgtgat tactatcgag  180
ctgagcaaca tcaaggagaa caagtgcaat ggaacggacg cgaaggtcaa gctgattaag  240
caggaactcg ataagtacaa gaacgccgtg accgagctcc agctgctgat gcaatcgacc  300
cctgccacta acaacagagc tcgccgggaa ctgccgcgct tcatgaatta caccctcaac  360
aacgcgaaga aaaccaacgt gaccctgtcc aagaagcgca agcggaggtt cctgggattc  420
ctgttgggcg tgggctccgc aatcgcatcc ggagtggccg tgtccaaagt gctgcatctg  480
gagggggaag tgaacaagat caagtccgcc ctcctgtcaa ctaataaggc ggtggtgtcc  540
ctgagcaacg gagtcagcgt gtgtacatcc aaggtcctgg acctcaagaa ctacatcgac  600
aagcagctgt tgcccatcgt caacaagcag tcatgctcga ttagcaatat cgaaaccgtg  660
attgagttcc agcagaagaa caacagactg ctcgaaatta cccgggagtt ttccgtgaac  720
gccggagtga ccactcctgt gtccacctac atgcttacga actccgaact gctcagcctc  780
atcaacgata tgccgatcac taacgaccag aagaagttga tgagcaacaa tgtgcagatc  840
gtgcgccaac agtcctactc aatcatgtca attatcaagg aggaagtgct cgcctatgtg  900
gtgcaattgc ctctgtacgg agtcatcgac acaccctgct ggaagctgca cactagccca  960
ctctgtacga ccaacaccaa ggaaggttcc aacatctgcc tgactaggac cgatcggggc  1020
tggtattgcg ataatgctgg gtccgtgagc ttcttcccgc aagccgagac ttgcaaagtg  1080
cagtcaaacc gcgtgttctg tgacaccatg aacagcctga ccctgccatc cgaagtcaac  1140
ctctgcaacg tggacatctt taacccgaaa tacgactgca agattatgac ctccaagacc  1200
gacgtcagca gctctgtcat cactagcctg ggagctattg tgtcctgcta cggaaagacc  1260
aaatgcactg cctcgaacaa gaacagaggc atcatcaaga ccttcagcaa cggctgtgac  1320
tacgtgtcca acaagggagt ggacaccgtg tccgtcggga acaccctgta ctacgtgaac  1380
aagcaggagg ggaagtcgct ctacgtcaag gggaaccga ttatcaattt ctacgacccc  1440
ctggtgttcc cttcctccga gttcgatgcc tccatatccc aagtcaacga gaagatcaac  1500
cagtctcttg ccttcatccg gaagtcggac gaactgctgt ccgccatcgg tggctatatt  1560
ccggaagccc ccagggatgg acaggcctac gtgcggaagg atggagaatg ggtgcttttg  1620
tccaccttcc tgggcggtct ggtgccccgc ggctcacacc atcatcacca ccacggttcg  1680
tggtcccacc ctcaatttga gaagtga                                        1707
```

```
SEQ ID NO: 14          moltype = DNA  length = 1707
FEATURE                Location/Qualifiers
misc_feature           1..1707
                       note = synthetic
source                 1..1707
                       mol_type = other DNA
                       organism = synthetic construct
SEQUENCE: 14
atggaacttc tgatcctgaa agccaacgcg attaccacta tcctgactgc cgtcaccttc  60
tgcttcgcat cgggacagaa cattaccgag gagttctacc agtccacctg ttcggcggtg  120
tccaagggtt acctctcggc cctgagaact ggctggtaca cctgtgtgat tactatcgag  180
ctgagcaaca tcaaggagaa caagtgcaat ggaacggacg cgaaggtcaa gctgattaag  240
caggaactcg ataagtacaa gaacgccgtg accgagctcc agctgctgat gcaatcgacc  300
cctgccacta acaacagagc tcgccgggaa ctgccgcgct tcatgaatta caccctcaac  360
aacgcgaaga aaaccaacgt gaccctgtcc aagaagcgca agcggaggtt cctgggattc  420
ctgttgggcg tgggctccgc aatcgcatcc ggagtggccg tgtccaaagt gctgcatctg  480
gagggggaag tgaacaagat caagtccgcc ctcctgtcaa ctaataaggc ggtggtgtcc  540
ctgagcaacg gagtcagcgt gtgtacaatc aaggtcctgg acctcaagaa ctacatcgac  600
aagcagctgt tgcccatcgt caacaagcag tcatgctcga ttagcaatat cgaaaccgtg  660
attgagttcc agcagaagaa caacagactg ctcgaaatta cccgggagtt ttccgtgaac  720
gccggagtga ccactcctgt gtccacctac atgcttacga actccgaact gctcagcctc  780
atcaacgata tgccgatcac taacgaccag aagaagttga tgagcaacaa tgtgcagatc  840
gtgcgccaac agtcctactc aatcatgtca attatcaagg aggaagtgct cgcctatgtg  900
gtgcaattgc ctctgtacgg agtcatcgac acaccctgct ggaagctgca cactagccca  960
ctctgtacga ccaacaccaa ggaaggttcc aacatctgcc tgactaggac cgatcggggc  1020
tggtattgcg ataatgctgg gtccgtgagc ttcttcccgc aagccgagac ttgcaaagtg  1080
cagtcaaacc gcgtgttctg tgacaccatg aacagcctga ccctgccatc cgaagtcaac  1140
ctctgcaacg tggacatctt taacccgaaa tacgactgca agattatgac ctccaagacc  1200
```

-continued

```
gacgtcagca gctctgtcat cactagcctg ggagctattg tgtcctgcta cggaaagacc  1260
aaatgcactg cctcgaacaa gaacagaggc atcatcaaga ccttcagcaa cggctgtgac  1320
tacgtgtcca acaagggagt ggacaccgtg tccgtcggga acaccctgta ctacgtgaac  1380
aagcaggagg ggaagtcgct ctacgtcaag gggga accga ttatcaattt ctacgacccc  1440
ctggtgttcc cttcctccga gttcgatgcc tccatatccc aagtcaacga gaagatcaac  1500
cagtctcttg ccttcatccg gaagtcggac gaactgctgt ccgccatcgg tggctatatt  1560
ccggaagccc ccagggatgg acaggcctac gtgcggaagg atggagaatg ggtgcttttg  1620
tccaccttcc tgggcggtct ggtgccccgc ggctcacacc atcatcacca ccacggttcg  1680
tggtcccacc ctcaatttga gaagtga                                      1707

SEQ ID NO: 15           moltype = DNA  length = 1707
FEATURE                 Location/Qualifiers
misc_feature            1..1707
                        note = synthetic
source                  1..1707
                        mol_type = other DNA
                        organism = synthetic construct
SEQUENCE: 15
atggaacttc tgatcctgaa agccaacgcg attaccacta tcctgactgc cgtcaccttc  60
tgcttcgcat cgggacagaa cattaccgag gagttctacc agtccacctg ttcggcggtg  120
tccaagggtt acctctcggc cctgagaact ggctggtacc actgtgtgat tactatcgag  180
ctgagcaaca tcaaggagaa caagtgcaat ggaacggacg cgaaggtcaa gctgattaag  240
caggaactcg ataagtacaa gaacgccgtg accgagctcc agctgctgat gcaatcgacc  300
cctgccacta acaacagagc tcgccgggaa ctgccgcgct tcatgaatta caccctcaac  360
aacgcgaaga aaaccaacgt gaccctgtcc aagaagcgca agcggaggtt cctgggattc  420
ctgttgggcg tgggctccgc aatcgcatcc ggagtggccg tgtccaaagt gctgcatctg  480
gagggggaag tgaacaagat caagtccgcc ctcctgtcaa ctaataaggc ggtggtgtcc  540
ctgagcaacg gagtcagcgt gtgtacaatc aaggtcctgg acctcaagaa ctacatcgac  600
aagcagctgt tgcccatcgt caacaagcag tcatgctcga ttagcaatat cgaaaccgtg  660
attgagttcc agcagaagaa caacagactg ctcgaaatta cccgggagtt ttccgtgaac  720
gccggagtga ccactcctgt gtccacctac atgcttacga actccgaact gctcagcctc  780
atcaacgata tgccgatcac taacgaccag aagaagttga tgagcaacaa tgtgcagatc  840
gtgcgccaac agtcctactc aatcatgtca attatcaagg aggaagtgct cgcctatgtg  900
gtgcaattgc ctctgtacgg agtcatcgac acaccctgct ggaagctgca cactagccca  960
ctctgtacga ccaacaccaa ggaaggttcc aacatctgcc tgactaggac cgatcggggc  1020
tggtattgcg ataatgctgg gtccgtgagc ttcttcccgc aagccgagac ttgcaaagtg  1080
cagtcaaacc gcgtgttctg tgacaccatg aacagcctga ccctgccatc cgaagtcaac  1140
ctctgcaacg tggacatctt taacccgaaa tacgactgca agattatgac ctccaagacc  1200
gacgtcagca gctctgtcat cactagcctg ggagctattg tgtcctgcta cggaaagacc  1260
aaatgcactg cctcgaacaa gaacagaggc atcatcaaga ccttcagcaa cggctgtgac  1320
tacgtgtcca acaagggagt ggacaccgtg tccgtcggga acaccctgta ctacgtgaac  1380
aagcaggagg ggaagtcgct ctacgtcaag gggaaccga ttatcaattt ctacgacccc  1440
ctggtgttcc cttcctccga gttcgatgcc tccatatccc aagtcaacga gaagatcaac  1500
cagtctcttg ccttcatccg gaagtcggac gaactgctgt ccgccatcgg tggctatatt  1560
ccggaagccc ccagggatgg acaggcctac gtgcggaagg atggagaatg ggtgcttttg  1620
tccaccttcc tgggcggtct ggtgccccgc ggctcacacc atcatcacca ccacggttcg  1680
tggtcccacc ctcaatttga gaagtga                                      1707

SEQ ID NO: 16           moltype = DNA  length = 1707
FEATURE                 Location/Qualifiers
misc_feature            1..1707
                        note = synthetic
source                  1..1707
                        mol_type = other DNA
                        organism = synthetic construct
SEQUENCE: 16
atggaacttc tgatcctgaa agccaacgcg attaccacta tcctgactgc cgtcaccttc  60
tgcttcgcat cgggacagaa cattaccgag gagttctacc agtccacctg ttcggcggtg  120
tccaagggtt acctctcggc cctgagaact ggctggtaca ccagcgtgat tactatcgag  180
ctgagcaaca tcaaggagaa caagtgcaat ggaacggacg cgaaggtcaa gctgattaag  240
caggaactcg ataagtacaa gaacgccgtg accgagctcc agctgctgat gcaatcgacc  300
cctgccacta acaacagagc tcgccgggaa ctgccgcgct tcatgaatta caccctcaac  360
aacgcgaaga aaaccaacgt gaccctgtcc aagaagcgca agcggaggtt cctgggattc  420
ctgttgggcg tgggctccgc aatcgcatcc ggagtggccg tgtgtaaagt gctgcatctg  480
gagggggaag tgaacaagat caagtccgcc ctcctgtcaa ctaataaggc ggtggtgtcc  540
ctgagcaacg gagtcagcgt gctgacaatc aaggtcctgg acctcaagaa ctacatcgac  600
aagcagctgt tgcccatcgt caacaagcag tcatgctcga ttagcaatat cgaaaccgtg  660
attgagttcc agcagaagaa caacagactg ctcgaaatta cccgggagtt ttccgtgaac  720
gccggagtga ccactcctgt gtccacctac atgcttacga actccgaact gctcagcctc  780
atcaacgata tgccgatcac taacgaccag aagaagttga tgagcaacaa tgtgcagatc  840
gtgcgccaac agtcctactc aatcatgtgc attatcaagg aggaagtgct cgcctatgtg  900
gtgcaattgc ctctgtacgg agtcatcgac acaccctgct ggaagctgca cactagccca  960
ctctgtacga ccaacaccaa ggaaggttcc aacatctgcc tgactaggac cgatcggggc  1020
tggtattgcg ataatgctgg gtccgtgagc ttcttcccgc aagccgagac ttgcaaagtg  1080
cagtcaaacc gcgtgttctg tgacaccatg aacagcctga ccctgccatc cgaagtcaac  1140
ctctgcaacg tggacatctt taacccgaaa tacgactgca agattatgac ctccaagacc  1200
gacgtcagca gctctgtcat cactagcctg ggagctattg tgtcctgcta cggaaagacc  1260
aaatgcactg cctcgaacaa gaacagaggc atcatcaaga ccttcagcaa cggctgtgac  1320
tacgtgtcca acaagggagt ggacaccgtg tccgtcggga acaccctgta ctacgtgaac  1380
```

```
aagcaggagg ggaagtcgct ctacgtcaag ggggaaccga ttatcaattt ctacgacccc  1440
ctggtgttcc cttcctccga gttcgatgcc tccatatccc aagtcaacga gaagatcaac  1500
cagtctcttg ccttcatccg gaagtcggac gaactgctgt ccgccatcgg tggctatatt  1560
ccggaagccc ccagggatgg acaggcctac gtgcggaagg atggagaatg ggtgcttttg  1620
tccaccttcc tgggcggtct ggtgccccgc ggctcacacc atcatcacca ccacggttcg  1680
tggtcccacc ctcaatttga gaagtga                                       1707

SEQ ID NO: 17          moltype = DNA  length = 1707
FEATURE                Location/Qualifiers
misc_feature           1..1707
                       note = synthetic
source                 1..1707
                       mol_type = other DNA
                       organism = synthetic construct
SEQUENCE: 17
atggaacttc tgatcctgaa agccaacgcg attaccacta tcctgactgc cgtcaccttc  60
tgcttcgcat cgggacagaa cattaccgag gagttctacc agtccacctg ttcggcggtg  120
tccaagggtt acctctcggc cctgagaact ggctggtacc actgtgtgat tactatcgag  180
ctgagcaaca tcaaggagaa caagtgcaat ggaacggacg cgaaggtcaa gctgattaag  240
caggaactcg ataagtacaa gaacgccgtg accgagctcc agctgctgat gcaatcgacc  300
cctgccacta acaacagagc tcgccgggaa ctgccgcgct tcatgaatta caccctcaac  360
aacgcgaaga aaaccaacgt gaccctgtcc aagaagcgca agcggaggtt cctgggattc  420
ctgtgtggcg tgggctccgc aatcgcatcc ggagtggccg tgtccaaagt gctgcatctg  480
gagggggaag tgaacaagat caagtccgcc ctcctgtcaa ctaataaggc ggtggtgtcc  540
ctgagcaacg gagtcagcgt gtgtacatcc aaggtcctgg acctcaagaa ctacatcgac  600
aagcagctgt tgcccatcgt caacaagcag tcatgctcga ttagcaatat cgaaaccgtg  660
attgagttcc agcagaagaa caacagactg ctcgaaatta cccgggagtt ttccgtgaac  720
gccggagtga ccactcctgt gtccacctac atgcttacga actccgaact gctcagcctc  780
atcaacgata tgccgatcac taacgaccag aagaagttga tgagcaacaa tgtgcagatc  840
gtgcgccaac agtcctactc aatcatgtca attatcaagg aggaaatcct cgcctatgtg  900
gtgcaattgc ctctgtacgg agtcatcgac acaccctgct ggaagctgca cactagccca  960
ctctgtacga ccaacaccaa ggaaggttcc aacatctgcc tgactaggac cgatcggggc  1020
tggtattgcg ataatgctgg gtccgtgagc ttcttcccgc aagccgagac ttgcaaagtg  1080
cagtcaaacc gcgtgttctg tgacaccatg tgtagcctga ccctgccatc cgaagtcaac  1140
ctctgcaacg tggacatctt taacccgaaa tacgactgca agattatgac ctccaagacc  1200
gacgtcagca gctctgtcat cactagcctg ggagctattg tgtcctgcta cggaaagacc  1260
aaatgcactg cctcgaacaa gaacagaggc atcatcaaga ccttcagcaa cggctgtgac  1320
tacgtgtcca acaagggagt ggacaccgtg tccgtcggga acaccctgta ctacgtgaac  1380
aagcaggagg ggaagtcgct ctacgtcaag ggggaaccga ttatcaattt ctacgacccc  1440
ctggtgttcc cttccagcca gttcagtgcc tccatatccc aagtcaacga gaagatcaac  1500
cagtctcttg ccttcatccg gaagtcggac gaactgctgt ccgccatcgg tggctatatt  1560
ccggaagccc ccagggatgg acaggcctac gtgcggaagg atggagaatg ggtgcttttg  1620
tccaccttcc tgggcggtct ggtgccccgc ggctcacacc atcatcacca ccacggttcg  1680
tggtcccacc ctcaatttga gaagtga                                       1707

SEQ ID NO: 18          moltype = AA  length = 1707
FEATURE                Location/Qualifiers
REGION                 1..1707
                       note = synthetic
source                 1..1707
                       mol_type = protein
                       organism = synthetic construct
SEQUENCE: 18
ATGGAACTTC TGATCCTGAA AGCCAACGCG ATTACCACTA TCCTGACTGC CGTCACCTTC  60
TGCTTCGCAT CGGGACAGAA CATTACCGAG GAGTTCTACC AGTCCACCTG TTCGGCGGTG  120
TCCAAGGGTT ACCTCTCGGC CCTGAGAACT GGCTGGTACC ACAGCGTGAT TACTATCGAG  180
CTGAGCAACA TCAAGGAGAA CAAGTGCAAT GGAACGGACG CGAAGGTCAA GCTGATTAAG  240
CAGGAACTCG ATAAGTACAA GAACGCCGTG ACCGAGCTCC AGCTGCTGAT GCAATCGACC  300
CCTGCCACTA ACAACAGAGC TCGCCGGGAA CTGCCGCGCT TCATGAATTA CACCCTCAAC  360
AACGCGAAGA AAACCAACGT GACCCTGTCC AAGAAGCGCA AGCGGAGGTT CCTGGGATTC  420
CTGTTGGGCG TGGGCTCCGC AATCGCATCC GGAGTGGCCG TGTGTAAAGT GCTGCATCTG  480
GAGGGGGAAG TGAACAAGAT CAAGTCCGCC CTCCTGTCAA CTAATAAGGC GGTGGTGTCC  540
CTGAGCAACG GAGTCAGCGT GCTGACAATC AAGGTCCTGG ACCTCAAGAA CTACATCGAC  600
AAGCAGCTGT TGCCCATCGT CAACAAGCAG TCATGCTCGA TTAGCAATAT CGAAACCGTG  660
ATTGAGTTCC AGCAGAAGAA CAACAGACTG CTCGAAATTA CCCGGGAGTT TTCCGTGAAC  720
GCCGGAGTGA CCACTCCTGT GTCCACCTAC ATGCTTACGA ACTCCGAACT GCTCAGCCTC  780
ATCAACGATA TGCCGATCAC TAACGACCAG AAGAAGTTGA TGAGCAACAA TGTGCAGATC  840
GTGCGCCAAC AGTCCTACTC AATCATGTGC ATTATCAAGG AGGAAATCCT CGCCTATGTG  900
GTGCAATTGC CTCTGTACGG AGTCATCGAC ACACCCTGCT GGAAGCTGCA CACTAGCCCA  960
CTCTGTACGA CCAACACCAA GGAAGGTTCC AACATCTGCC TGACTAGGAC CGATCGGGGC  1020
TGGTATTGCG ATAATGCTGG GTCCGTGAGC TTCTTCCCGC AAGCCGAGAC TTGCAAAGTG  1080
CAGTCAAACC GCGTGTTCTG TGACACCATG AACAGCCTGA CCCTGCCATC CGAAGTCAAC  1140
CTCTGCAACG TGGACATCTT TAACCCGAAA TACGACTGCA AGATTATGAC CTCCAAGACC  1200
GACGTCAGCA GCTCTGTCAT CACTAGCCTG GGAGCTATTG TGTCCTGCTA CGGAAAGACC  1260
AAATGCACTG CCTCGAACAA GAACAGAGGC ATCATCAAGA CCTTCAGCAA CGGCTGTGAC  1320
TACGTGTCCA ACAAGGGAGT GGACACCGTG TCCGTCGGGA ACACCCTGTA CTACGTGAAC  1380
AAGCAGGAGG GGAAGTCGCT CTACGTCAAG GGGGAACCGA TTATCAATTT CTACGACCCC  1440
CTGGTGTTCC CTTCCGACGA GTTCGATGCC TCCATATCCC AAGTCAACGA GAAGATCAAC  1500
CAGTCTCTTG CCTTCATCCG GAAGTCGGAC GAACTGCTGT CCGCCATCGG TGGCTATATT  1560
```

-continued

```
CCGGAAGCCC CCAGGGATGG ACAGGCCTAC GTGCGGAAGG ATGGAGAATG GGTGCTTTTG  1620
TCCACCTTCC TGGGCGGTCT GGTGCCCCGC GGCTCACACC ATCATCACCA CCACGGTTCG  1680
TGGTCCCACC CTCAATTTGA GAAGTGA                                      1707

SEQ ID NO: 19          moltype = AA  length = 568
FEATURE                Location/Qualifiers
REGION                 1..568
                       note = synthetic
source                 1..568
                       mol_type = protein
                       organism = synthetic construct
SEQUENCE: 19
MELLILKANA ITTILTAVTF CFASGQNITE EFYQSTCSAV SKGYLSALRT GWYTSVITIE  60
LSNIKENKCN GTDAKVKLIK QELDKYKNAV TELQLLMQST PACNNRARRE LPRFMNYTLN  120
NAKKTNVTLS KKRKRRFLGF LLGVGSACAS GVAVSKVLHL EGEVNKIKSA LLSTNKAVVS  180
LSNGVSVLTI KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSSEFDA SISQVNEKIN QSLAFIRKSD ELLSAIGGYI PEAPRDGQAY VRKDGEWVLL  540
STFLGGLVPR GSHHHHHHGS WSHPQFEK                                     568

SEQ ID NO: 20          moltype = AA  length = 568
FEATURE                Location/Qualifiers
REGION                 1..568
                       note = synthetic
source                 1..568
                       mol_type = protein
                       organism = synthetic construct
SEQUENCE: 20
MELLILKANA ITTILTAVTF CFASGQNITE EFYQSTCSAV SKGYLSALRT GWYHSVITIE  60
LSNIKENKCN GTDAKVKLIK QELDKYKNAV TELQLLMQST PACNNRARRE LPRFMNYTLN  120
NAKKTNVTLS KKRKRRFLGF LLGVGSACAS GVAVSKVLHL EGEVNKIKSA LLSTNKAVVS  180
LSNGVSVLTI KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEILAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSSEFDA SISQVNEKIN QSLAFIRKSD ELLSAIGGYI PEAPRDGQAY VRKDGEWVLL  540
STFLGGLVPR GSHHHHHHGS WSHPQFEK                                     568

SEQ ID NO: 21          moltype = AA  length = 568
FEATURE                Location/Qualifiers
REGION                 1..568
                       note = synthetic
source                 1..568
                       mol_type = protein
                       organism = synthetic construct
SEQUENCE: 21
MELLILKANA ITTILTAVTF CFASGQNITE EFYQSTCSAV SKGYLSALRT GWYHCVITIE  60
LSNIKENKCN GTDAKVKLIK QELDKYKNAV TELQLLMQST PATNNRARRE LPRFMNYTLN  120
NAKKTNVTLS KKRKRRFLGF LLGVGSAIAS GVAVSKVLHL EGEVNKIKSA LLSTNKAVVS  180
LSNGVSVCTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSSEFDA SISQVNEKIN QSLAFIRKSD ELLSAIGGYI PEAPRDGQAY VRKDGEWVLL  540
STFLGGLVPR GSHHHHHHGS WSHPQFEK                                     568

SEQ ID NO: 22          moltype = AA  length = 126
FEATURE                Location/Qualifiers
REGION                 1..126
                       note = synthetic
source                 1..126
                       mol_type = protein
                       organism = synthetic construct
SEQUENCE: 22
QVQLVQSGAE VKKPGSSVMV SCQASGGPLR NYIINWLRQA PGQGPEWMGG IIPVLGTVHY  60
APKFQGRVTI TADESTDTAY IHLISLRSED TAMYYCATET ALVVSTTYLP HYFDNWGQGT  120
LVTVSS                                                             126

SEQ ID NO: 23          moltype = AA  length = 108
FEATURE                Location/Qualifiers
REGION                 1..108
                       note = synthetic
source                 1..108
                       mol_type = protein
```

```
                          organism = synthetic construct
SEQUENCE: 23
DIQMTQSPSS LSAAVGDRVT ITCQASQDIV NYLNWYQQKP GKAPKLLIYV ASNLETGVPS  60
RFSGSGSGTD FSLTISSLQP EDVATYYCQQ YDNLPLTFGG GTKVEIKR               108

SEQ ID NO: 24             moltype = AA  length = 123
FEATURE                   Location/Qualifiers
REGION                    1..123
                          note = synthetic
source                    1..123
                          mol_type = protein
                          organism = synthetic construct
SEQUENCE: 24
EVQLVESGGG VVQPGRSLRL SCAASGFSFS HYAMHWVRQA PGKGLEWVAV ISYDGENTYY  60
ADSVKGRFSI SRDNSKNTVS LQMNSLRPED TALYYCARDR IVDDYYYYGM DVWGQGATVT  120
VSS                                                                123

SEQ ID NO: 25             moltype = AA  length = 111
FEATURE                   Location/Qualifiers
REGION                    1..111
                          note = synthetic
source                    1..111
                          mol_type = protein
                          organism = synthetic construct
SEQUENCE: 25
DIQMTQSPSS LSASVGDRVT ITCQASQDIK KYLNWYHQKP GKVPELLMHD ASNLETGVPS  60
RFSGRGSGTD FTLTISSLQP EDIGTYYCQQ YDNLPPLTFG GGTKVEIKRT V           111

SEQ ID NO: 26             moltype = AA  length = 124
FEATURE                   Location/Qualifiers
REGION                    1..124
                          note = synthetic
source                    1..124
                          mol_type = protein
                          organism = synthetic construct
SEQUENCE: 26
QVQLVQSGAE VKKPGATVKV SCKISGHTLI KLSIHWVRQA PGKGLEWMGG YEGEVDEIFY  60
AQKFQHRLTV IADTATDTVY MELGRLTSDD TAVYFCGTLG VTVTEAGLGI DDYWGQGTLV  120
TVSS                                                               124

SEQ ID NO: 27             moltype = AA  length = 108
FEATURE                   Location/Qualifiers
REGION                    1..108
                          note = synthetic
source                    1..108
                          mol_type = protein
                          organism = synthetic construct
SEQUENCE: 27
EIVLTQSPGT LSLSPGERAT LSCRASQIVS RNHLAWYQQK PGQAPRLLIF GASSRATGIP  60
VRFSGSGSGT DFTLTINGLA PEDFAVYYCL SSDSSIFTFG PGTKVDFK               108

SEQ ID NO: 28             moltype = AA  length = 124
FEATURE                   Location/Qualifiers
REGION                    1..124
                          note = synthetic
source                    1..124
                          mol_type = protein
                          organism = synthetic construct
SEQUENCE: 28
EVQLVESGGG LVKPGGSLRL SCAASGFTFS SYSMNWVRQA PGKGLEWVSS ISASSSYSDY  60
ADSAKGRFTI SRDNAKTSLF LQMNSLRAED TAIYFCARAR ATGYSSITPY FDIWGQGTLV  120
TVSS                                                               124

SEQ ID NO: 29             moltype = AA  length = 110
FEATURE                   Location/Qualifiers
REGION                    1..110
                          note = synthetic
source                    1..110
                          mol_type = protein
                          organism = synthetic construct
SEQUENCE: 29
QSVVTQTPSV SGAPGQRVTI SCTGSSSNIG AGYDVHWYQQ LPGTAPKLLI YDNNNRPSGV  60
PDRFSASKSG TSASLAITGL QAEDEADYYC QSYDRNLSGV FGTGTKVTVL             110

SEQ ID NO: 30             moltype = AA  length = 120
FEATURE                   Location/Qualifiers
REGION                    1..120
                          note = synthetic
source                    1..120
```

-continued

```
                          mol_type = protein
                          organism = synthetic construct
SEQUENCE: 30
QVTLKESGPG ILQPSQTLSL TCSFSGFSLS TSGMGVSWIR QPSGKGLEWL AHIYWDDDKR  60
YNPSLKSRLT ISKDTSRNQV FLKITSVDTA DTATYYCARL YGFTYGFAYW GQGTLVTVSA  120

SEQ ID NO: 31             moltype = AA  length = 111
FEATURE                   Location/Qualifiers
REGION                    1..111
                          note = Synthetic
source                    1..111
                          mol_type = protein
                          organism = synthetic construct
SEQUENCE: 31
DIVLTQSPAS LAVSLGQRAT IFCRASQSVD YNGISYMHWF QQKPGQPPKL LIYAASNPES  60
GIPARFTGSG SGTDFTLNIH PVEEEDAATY YCQQIIEDPW TFGGGTKLEI K          111

SEQ ID NO: 32             moltype = AA  length = 568
FEATURE                   Location/Qualifiers
REGION                    1..568
                          note = Synthetic
source                    1..568
                          mol_type = protein
                          organism = synthetic construct
SEQUENCE: 32
MELLILKANA ITTILTAVTF CFASGQNITE EFYQSTCSAV SKGYLSALRT GWYHCVITIE  60
LSNIKENKCN GTDAKVKLIK QELDKYKNAV TELQLLMQST PATNNRARRE LPRFMNYTLN  120
NAKKTNVTLS KKRKRRFLGF LCGVGSAIAS GVAVSKVLHL EGEVNKIKSA LLSTNKAVVS  180
LSNGVSVCTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEILAYV  300
VQLPLYGVID TPCWKLHTSP LCTTNTKEGS NICLTRTDRG WYCDNAGSVS FFPQAETCKV  360
QSNRVFCDTM CSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLSAIGGYI PEAPRDGQAY VRKDGEWVLL  540
STFLGGLVPR GSHHHHHHGS WSHPQFEK                                    568

SEQ ID NO: 33             moltype = AA  length = 568
FEATURE                   Location/Qualifiers
REGION                    1..568
                          note = Synthetic
source                    1..568
                          mol_type = protein
                          organism = synthetic construct
SEQUENCE: 33
MELLILKANA ITTILTAVTF CFASGQNITE EFYQSTCSAV SKGYLSALRT GWYTCVITIE  60
LSNIKENKCN GTDAKVKLIK QELDKYKNAV TELQLLMQST PATNNRARRE LPRFMNYTLN  120
NAKKTNVTLS KKRKRRFLGF LLGVGSAIAS GVAVSKVLHL EGEVNKIKSA LLSTNKAVVS  180
LSNGVSVCTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSSEFDA SISQVNEKIN QSLAFIRKSD ELLSAIGGYI PEAPRDGQAY VRKDGEWVLL  540
STFLGGLVPR GSHHHHHHGS WSHPQFEK                                    568

SEQ ID NO: 34             moltype = AA  length = 568
FEATURE                   Location/Qualifiers
REGION                    1..568
                          note = Synthetic
source                    1..568
                          mol_type = protein
                          organism = synthetic construct
SEQUENCE: 34
MELLILKANA ITTILTAVTF CFASGQNITE EFYQSTCSAV SKGYLSALRT GWYHCVITIE  60
LSNIKENKCN GTDAKVKLIK QELDKYKNAV TELQLLMQST PATNNRARRE LPRFMNYTLN  120
NAKKTNVTLS KKRKRRFLGF LLGVGSAIAS GVAVSKVLHL EGEVNKIKSA LLSTNKAVVS  180
LSNGVSVCTI KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLSAIGGYI PEAPRDGQAY VRKDGEWVLL  540
STFLGGLVPR GSHHHHHHGS WSHPQFEK                                    568

SEQ ID NO: 35             moltype = AA  length = 568
FEATURE                   Location/Qualifiers
REGION                    1..568
                          note = Synthetic
source                    1..568
```

```
                       mol_type = protein
                       organism = synthetic construct
SEQUENCE: 35
MELLILKANA ITTILTAVTF CFASGQNITE EFYQSTCSAV SKGYLSALRT GWYTCVITIE  60
LSNIKENKCN GTDAKVKLIK QELDKYKNAV TELQLLMQST PATNNRARRE LPRFMNYTLN  120
NAKKTNVTLS KKRKRRFLGF LLGVGSAIAS GVAVSKVLHL EGEVNKIKSA LLSTNKAVVS  180
LSNGVSVCTI KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSSEFDA SISQVNEKIN QSLAFIRKSD ELLSAIGGYI PEAPRDGQAY VRKDGEWVLL  540
STFLGGLVPR GSHHHHHHGS WSHPQFEK                                    568

SEQ ID NO: 36          moltype = AA  length = 568
FEATURE                Location/Qualifiers
REGION                 1..568
                       note = Synthetic
source                 1..568
                       mol_type = protein
                       organism = synthetic construct
SEQUENCE: 36
MELLILKANA ITTILTAVTF CFASGQNITE EFYQSTCSAV SKGYLSALRT GWYHCVITIE  60
LSNIKENKCN GTDAKVKLIK QELDKYKNAV TELQLLMQST PATNNRARRE LPRFMNYTLN  120
NAKKTNVTLS KKRKRRFLGF LLGVGSAIAS GVAVSKVLHL EGEVNKIKSA LLSTNKAVVS  180
LSNGVSVCTI KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSSEFDA SISQVNEKIN QSLAFIRKSD ELLSAIGGYI PEAPRDGQAY VRKDGEWVLL  540
STFLGGLVPR GSHHHHHHGS WSHPQFEK                                    568

SEQ ID NO: 37          moltype = AA  length = 568
FEATURE                Location/Qualifiers
REGION                 1..568
                       note = Synthetic
source                 1..568
                       mol_type = protein
                       organism = synthetic construct
SEQUENCE: 37
MELLILKANA ITTILTAVTF CFASGQNITE EFYQSTCSAV SKGYLSALRT GWYTSVITIE  60
LSNIKENKCN GTDAKVKLIK QELDKYKNAV TELQLLMQST PATNNRARRE LPRFMNYTLN  120
NAKKTNVTLS KKRKRRFLGF LLGVGSAIAS GVAVCKVLHL EGEVNKIKSA LLSTNKAVVS  180
LSNGVSVLTI KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMC IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSSEFDA SISQVNEKIN QSLAFIRKSD ELLSAIGGYI PEAPRDGQAY VRKDGEWVLL  540
STFLGGLVPR GSHHHHHHGS WSHPQFEK                                    568

SEQ ID NO: 38          moltype = AA  length = 568
FEATURE                Location/Qualifiers
REGION                 1..568
                       note = Synthetic
source                 1..568
                       mol_type = protein
                       organism = synthetic construct
SEQUENCE: 38
MELLILKANA ITTILTAVTF CFASGQNITE EFYQSTCSAV SKGYLSALRT GWYHCVITIE  60
LSNIKENKCN GTDAKVKLIK QELDKYKNAV TELQLLMQST PATNNRARRE LPRFMNYTLN  120
NAKKTNVTLS KKRKRRFLGF LCGVGSAIAS GVAVSKVLHL EGEVNKIKSA LLSTNKAVVS  180
LSNGVSVCTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEILAYV  300
VQLPLYGVID TPCWKLHTSP LCTTNTKEGS NICLTRTDRG WYCDNAGSVS FFPQAETCKV  360
QSNRVFCDTM CSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSSQFSA SISQVNEKIN QSLAFIRKSD ELLSAIGGYI PEAPRDGQAY VRKDGEWVLL  540
STFLGGLVPR GSHHHHHHGS WSHPQFEK                                    568

SEQ ID NO: 39          moltype = AA  length = 568
FEATURE                Location/Qualifiers
REGION                 1..568
                       note = synthetic
source                 1..568
                       mol_type = protein
                       organism = synthetic construct
SEQUENCE: 39
```

```
MELLILKANA ITTILTAVTF CFASGQNITE EFYQSTCSAV SKGYLSALRT GWYHSVITIE  60
LSNIKENKCN GTDAKVKLIK QELDKYKNAV TELQLLMQST PATNNRARRE LPRFMNYTLN  120
NAKKTNVTLS KKRKRRFLGF LLGVGSAIAS GVAVCKVLHL EGEVNKIKSA LLSTNKAVVS  180
LSNGVSVLTI KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMC IIKEEILAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLSAIGGYI PEAPRDGQAY VRKDGEWVLL  540
STFLGGLVPR GSHHHHHHGS WSHPQFEK                                    568

SEQ ID NO: 40           moltype = AA  length = 26
FEATURE                 Location/Qualifiers
REGION                  1..26
                        note = Synthetic
source                  1..26
                        mol_type = protein
                        organism = synthetic construct
SEQUENCE: 40
YIPEAPRDGQ AYVRKDGEWV LLSTFL                                        26

SEQ ID NO: 41           moltype = AA  length = 84
FEATURE                 Location/Qualifiers
REGION                  1..84
                        note = synthetic polypeptide
source                  1..84
                        mol_type = protein
                        organism = synthetic construct
SEQUENCE: 41
QNITEEFYQS TCSAVSKGYL SALRTGWYTS VITIELSNIK ENKCNGTDAK VKLIKQELDK  60
YKNAVTELQL LMQSTPACNN RARR                                          84

SEQ ID NO: 42           moltype = AA  length = 377
FEATURE                 Location/Qualifiers
REGION                  1..377
                        note = synthetic polypeptide
source                  1..377
                        mol_type = protein
                        organism = synthetic construct
SEQUENCE: 42
FLGFLLGVGS ACASGVAVSK VLHLEGEVNK IKSALLSTNK AVVSLSNGVS VLTIKVLDLK  60
NYIDKQLLPI VNKQSCSISN IETVIEFQQK NNRLLEITRE FSVNAGVTTP VSTYMLTNSE  120
LLSLINDMPI TNDQKKLMSN NVQIVRQQSY SIMSIIKEEV LAYVVQLPLY GVIDTPCWKL  180
HTSPLCTTNT KEGSNICLTR TDRGWYCDNA GSVSFFPQAE TCKVQSNRVF CDTMNSLTLP  240
SEVNLCNVDI FNPKYDCKIM TSKTDVSSSV ITSLGAIVSC YGKTKCTASN KNRGIIKTFS  300
NGCDYVSNKG VDTVSVGNTL YYVNKQEGKS LYVKGEPIIN FYDPLVFPSS EFDASISQVN  360
EKINQSLAFI RKSDELL                                                  377

SEQ ID NO: 43           moltype = AA  length = 84
FEATURE                 Location/Qualifiers
REGION                  1..84
                        note = synthetic polypeptide
source                  1..84
                        mol_type = protein
                        organism = synthetic construct
SEQUENCE: 43
QNITEEFYQS TCSAVSKGYL SALRTGWYTS VITIELSNIK ENKCNGTDAK VKLIKQELDK  60
YKNAVTELQL LMQSTPPCNN RARR                                          84

SEQ ID NO: 44           moltype = AA  length = 377
FEATURE                 Location/Qualifiers
REGION                  1..377
                        note = synthetic polypeptide
source                  1..377
                        mol_type = protein
                        organism = synthetic construct
SEQUENCE: 44
FLGFLLGVGS ACASGVAVSK VLHLEGEVNK IKSALLSTNK AVVSLSNGVS VLTIKVLDLK  60
NYIDKQLLPI VNKQSCSISN IETVIEFQQK NNRLLEITRE FSVNAGVTTP VSTYMLTNSE  120
LLSLINDMPI TNDQKKLMSN NVQIVRQQSY SIMSIIKEEV LAYVVQLPLY GVIDTPCWKL  180
HTSPLCTTNT KEGSNICLTR TDRGWYCDNA GSVSFFPQAE TCKVQSNRVF CDTMNSLTLP  240
SEINLCNVDI FNPKYDCKIM TSKTDVSSSV ITSLGAIVSC YGKTKCTASN KNRGIIKTFS  300
NGCDYVSNKG MDTVSVGNTL YYVNKQEGKS LYVKGEPIIN FYDPLVFPSS EFDASISQVN  360
EKINQSLAFI RKSDELL                                                  377

SEQ ID NO: 45           moltype = AA  length = 84
FEATURE                 Location/Qualifiers
REGION                  1..84
                        note = synthetic polypeptide
```

```
source                  1..84
                        mol_type = protein
                        organism = synthetic construct
SEQUENCE: 45
QNITEEFYQS TCSAVSKGYL SALRTGWYTS VITIELSNIK ENKCNGTDAK VKLIKQELDK  60
YKNAVTELQL LMQSTPACNS RARR                                         84

SEQ ID NO: 46           moltype = AA  length = 377
FEATURE                 Location/Qualifiers
REGION                  1..377
                        note = synthetic polypeptide
source                  1..377
                        mol_type = protein
                        organism = synthetic construct
SEQUENCE: 46
FLGFLLGVGS ACASGIAVSK VLHLEGEVNK IKSALLSTNK AVVSLSNGVS VLTIKVLDLK  60
NYIDKQLLPI VNKQSCSISN IETVIEFQQK NNRLLEITRE FSVNAGVTTP VSTYMLTNSE  120
LLSLINDMPI TNDQKKLMSS NVQIVRQQSY SIMSIIKEEV LAYVVQLPLY GVIDTPCWKL  180
HTSPLCTTNT KEGSNICLTR TDRGWYCDNA GSVSFFPQAE TCKVQSNRVF CDTMNSLTLP  240
SEVNLCNIDI FNPKYDCKIM TSKTDVSSSV ITSLGAIVSC YGKTKCTASN KNRGIIKTFS  300
NGCDYVSNKG VDTVSVGNTL YYVNKQEGKS LYVKGEPIIN FYDPLVFPSS EFDASISQVN  360
EKINQSLAFI RKSDELL                                                 377

SEQ ID NO: 47           moltype = AA  length = 84
FEATURE                 Location/Qualifiers
REGION                  1..84
                        note = synthetic polypeptide
source                  1..84
                        mol_type = protein
                        organism = synthetic construct
SEQUENCE: 47
QNITEEFYQS TCSAVSRGYF SALRTGWYTS VITIELSNIK ETKCNGTDTK VKLIKQELDK  60
YKNAVTELQL LMQNTPACNN RARR                                         84

SEQ ID NO: 48           moltype = AA  length = 377
FEATURE                 Location/Qualifiers
REGION                  1..377
                        note = synthetic polypeptide
source                  1..377
                        mol_type = protein
                        organism = synthetic construct
SEQUENCE: 48
FLGFLLGVGS ACASGIAVSK VLHLEGEVNK IKNALLSTNK AVVSLSNGVS VLTIKVLDLK  60
NYINNRLLPI VNQQSCRISN IETVIEFQQM NSRLLEITRE FSVNAGVTTP LSTYMLTNSE  120
LLSLINDMPI TNDQKKLMSS NVQIVRQQSY SIMSIIKEEV LAYVVQLPIY GVIDTPCWKL  180
HTSPLCTTNI KEGSNICLTR TDRGWYCDNA GSVSFFPQAD TCKVQSNRVF CDTMNSLTLP  240
SEVSLCNTDI FNSKYDCKIM TSKTDISSSV ITSLGAIVSC YGKTKCTASN KNRGIIKTFS  300
NGCDYVSNKG VDTVSVGNTL YYVNKLEGKN LYVKGEPIIN YYDPLVFPSS EFDASISQVN  360
EKINQSLAFI RRSDELL                                                 377

SEQ ID NO: 49           moltype = AA  length = 84
FEATURE                 Location/Qualifiers
REGION                  1..84
                        note = synthetic polypeptide
source                  1..84
                        mol_type = protein
                        organism = synthetic construct
SEQUENCE: 49
QNITEEFYQS TCSAVSRGYF SALRTGWYTS VITIELSNIK ETKCNGTDTK VKLIKQELDK  60
YKNAVTELQL LMQNTPACNN RARR                                         84

SEQ ID NO: 50           moltype = AA  length = 377
FEATURE                 Location/Qualifiers
REGION                  1..377
                        note = synthetic polypeptide
source                  1..377
                        mol_type = protein
                        organism = synthetic construct
SEQUENCE: 50
FLGFLLGVGS ACASGIAVSK VLHLEGEVNK IKNALLSTNK AVVSLSNGVS VLTIKVLDLK  60
NYINNQLLPI VNQQSCRISN IETVIEFQQK NSRLLEITRE FSVNAGVTTP LSTYMLTNSE  120
LLSLINDMPI TNDQKKLMSS NVQIVRQQSY SIMSIIKEEV LAYVVQLPIY GVIDTPCWKL  180
HTSPLCTTNI KEGSNICLTR TDRGWYCDNA GSVSFFPQAD TCKVQSNRVF CDTMNSLTLP  240
SEVSLCNTDI FNSKYDCKIM TSKTDISSSV ITSLGAIVSC YGKTKCTASN KNRGIIKTFS  300
NGCDYVSNKG VDTVSVGNTL YYVNKLEGKN LYVKGEPIIN YYDPLVFPSS EFDASISQVN  360
EKINQSLAFI RRSDELL                                                 377

SEQ ID NO: 51           moltype = AA  length = 84
FEATURE                 Location/Qualifiers
```

-continued

```
REGION                1..84
                      note = synthetic polypeptide
source                1..84
                      mol_type = protein
                      organism = synthetic construct
SEQUENCE: 51
QNITEEFYQS TCSAVSKGYL SALRTGWYHS VITIELSNIK ENKCNGTDAK VKLIKQELDK  60
YKNAVTELQL LMQSTPACNN RARR                                         84

SEQ ID NO: 52         moltype = AA  length = 377
FEATURE               Location/Qualifiers
REGION                1..377
                      note = synthetic polypeptide
source                1..377
                      mol_type = protein
                      organism = synthetic construct
SEQUENCE: 52
FLGFLLGVGS ACASGVAVSK VLHLEGEVNK IKSALLSTNK AVVSLSNGVS VLTIKVLDLK  60
NYIDKQLLPI VNKQSCSISN IETVIEFQQK NNRLLEITRE FSVNAGVTTP VSTYMLTNSE  120
LLSLINDMPI TNDQKKLMSN NVQIVRQQSY SIMSIIKEEI LAYVVQLPLY GVIDTPCWKL  180
HTSPLCTTNT KEGSNICLTR TDRGWYCDNA GSVSFFPQAE TCKVQSNRVF CDTMNSLTLP  240
SEVNLCNVDI FNPKYDCKIM TSKTDVSSSV ITSLGAIVSC YGKTKCTASN KNRGIIKTFS  300
NGCDYVSNKG VDTVSVGNTL YYVNKQEGKS LYVKGEPIIN FYDPLVFPSS EFDASISQVN  360
EKINQSLAFI RKSDELL                                                 377

SEQ ID NO: 53         moltype = AA  length = 84
FEATURE               Location/Qualifiers
REGION                1..84
                      note = synthetic polypeptide
source                1..84
                      mol_type = protein
                      organism = synthetic construct
SEQUENCE: 53
QNITEEFYQS TCSAVSKGYL SALRTGWYHS VITIELSNIK ENKCNGTDAK VKLIKQELDK  60
YKNAVTELQL LMQSTPPCNN RARR                                         84

SEQ ID NO: 54         moltype = AA  length = 377
FEATURE               Location/Qualifiers
REGION                1..377
                      note = synthetic polypeptide
source                1..377
                      mol_type = protein
                      organism = synthetic construct
SEQUENCE: 54
FLGFLLGVGS ACASGVAVSK VLHLEGEVNK IKSALLSTNK AVVSLSNGVS VLTIKVLDLK  60
NYIDKQLLPI VNKQSCSISN IETVIEFQQK NNRLLEITRE FSVNAGVTTP VSTYMLTNSE  120
LLSLINDMPI TNDQKKLMSN NVQIVRQQSY SIMSIIKEEI LAYVVQLPLY GVIDTPCWKL  180
HTSPLCTTNT KEGSNICLTR TDRGWYCDNA GSVSFFPQAE TCKVQSNRVF CDTMNSLTLP  240
SEINLCNVDI FNPKYDCKIM TSKTDVSSSV ITSLGAIVSC YGKTKCTASN KNRGIIKTFS  300
NGCDYVSNKG MDTVSVGNTL YYVNKQEGKS LYVKGEPIIN FYDPLVFPSS EFDASISQVN  360
EKINQSLAFI RKSDELL                                                 377

SEQ ID NO: 55         moltype = AA  length = 84
FEATURE               Location/Qualifiers
REGION                1..84
                      note = synthetic polypeptide
source                1..84
                      mol_type = protein
                      organism = synthetic construct
SEQUENCE: 55
QNITEEFYQS TCSAVSKGYL SALRTGWYHS VITIELSNIK ENKCNGTDAK VKLIKQELDK  60
YKNAVTELQL LMQSTPACNS RARR                                         84

SEQ ID NO: 56         moltype = AA  length = 377
FEATURE               Location/Qualifiers
REGION                1..377
                      note = synthetic polypeptide
source                1..377
                      mol_type = protein
                      organism = synthetic construct
SEQUENCE: 56
FLGFLLGVGS ACASGIAVSK VLHLEGEVNK IKSALLSTNK AVVSLSNGVS VLTIKVLDLK  60
NYIDKQLLPI VNKQSCSISN IETVIEFQQK NNRLLEITRE FSVNAGVTTP VSTYMLTNSE  120
LLSLINDMPI TNDQKKLMSS NVQIVRQQSY SIMSIIKEEI LAYVVQLPLY GVIDTPCWKL  180
HTSPLCTTNT KEGSNICLTR TDRGWYCDNA GSVSFFPQAE TCKVQSNRVF CDTMNSLTLP  240
SEVNLCNIDI FNPKYDCKIM TSKTDVSSSV ITSLGAIVSC YGKTKCTASN KNRGIIKTFS  300
NGCDYVSNKG VDTVSVGNTL YYVNKQEGKS LYVKGEPIIN FYDPLVFPSS EFDASISQVN  360
EKINQSLAFI RKSDELL                                                 377
```

```
SEQ ID NO: 57          moltype = AA  length = 84
FEATURE                Location/Qualifiers
REGION                 1..84
                       note = synthetic polypeptide
source                 1..84
                       mol_type = protein
                       organism = synthetic construct
SEQUENCE: 57
QNITEEFYQS TCSAVSRGYF SALRTGWYHS VITIELSNIK ETKCNGTDTK VKLIKQELDK  60
YKNAVTELQL LMQNTPACNN RARR                                         84

SEQ ID NO: 58          moltype = AA  length = 377
FEATURE                Location/Qualifiers
REGION                 1..377
                       note = synthetic polypeptide
source                 1..377
                       mol_type = protein
                       organism = synthetic construct
SEQUENCE: 58
FLGFLLGVGS ACASGIAVSK VLHLEGEVNK IKNALLSTNK AVVSLSNGVS VLTIKVLDLK  60
NYINNRLLPI VNQQSCRISN IETVIEFQQM NSRLLEITRE FSVNAGVTTP LSTYMLTNSE  120
LLSLINDMPI TNDQKKLMSS NVQIVRQQSY SIMSIIKEEI LAYVVQLPIY GVIDTPCWKL  180
HTSPLCTTNI KEGSNICLTR TDRGWYCDNA GSVSFFPQAD TCKVQSNRVF CDTMNSLTLP  240
SEVSLCNTDI FNSKYDCKIM TSKTDISSSV ITSLGAIVSC YGKTKCTASN KNRGIIKTFS  300
NGCDYVSNKG VDTVSVGNTL YYVNKLEGKN LYVKGEPIIN YYDPLVFPSS EFDASISQVN  360
EKINQSLAFI RRSDELL                                                 377

SEQ ID NO: 59          moltype = AA  length = 84
FEATURE                Location/Qualifiers
REGION                 1..84
                       note = synthetic polypeptide
source                 1..84
                       mol_type = protein
                       organism = synthetic construct
SEQUENCE: 59
QNITEEFYQS TCSAVSRGYF SALRTGWYHS VITIELSNIK ETKCNGTDTK VKLIKQELDK  60
YKNAVTELQL LMQNTPACNN RARR                                         84

SEQ ID NO: 60          moltype = AA  length = 377
FEATURE                Location/Qualifiers
REGION                 1..377
                       note = synthetic polypeptide
source                 1..377
                       mol_type = protein
                       organism = synthetic construct
SEQUENCE: 60
FLGFLLGVGS ACASGIAVSK VLHLEGEVNK IKNALLSTNK AVVSLSNGVS VLTIKVLDLK  60
NYINNQLLPI VNQQSCRISN IETVIEFQQK NSRLLEITRE FSVNAGVTTP LSTYMLTNSE  120
LLSLINDMPI TNDQKKLMSS NVQIVRQQSY SIMSIIKEEI LAYVVQLPIY GVIDTPCWKL  180
HTSPLCTTNI KEGSNICLTR TDRGWYCDNA GSVSFFPQAD TCKVQSNRVF CDTMNSLTLP  240
SEVSLCNTDI FNSKYDCKIM TSKTDISSSV ITSLGAIVSC YGKTKCTASN KNRGIIKTFS  300
NGCDYVSNKG VDTVSVGNTL YYVNKLEGKN LYVKGEPIIN YYDPLVFPSS EFDASISQVN  360
EKINQSLAFI RRSDELL                                                 377

SEQ ID NO: 61          moltype = AA  length = 84
FEATURE                Location/Qualifiers
REGION                 1..84
                       note = synthetic polypeptide
source                 1..84
                       mol_type = protein
                       organism = synthetic construct
SEQUENCE: 61
QNITEEFYQS TCSAVSKGYL SALRTGWYHC VITIELSNIK ENKCNGTDAK VKLIKQELDK  60
YKNAVTELQL LMQSTPATNN RARR                                         84

SEQ ID NO: 62          moltype = AA  length = 377
FEATURE                Location/Qualifiers
REGION                 1..377
                       note = synthetic polypeptide
source                 1..377
                       mol_type = protein
                       organism = synthetic construct
SEQUENCE: 62
FLGFLLGVGS AIASGVAVSK VLHLEGEVNK IKSALLSTNK AVVSLSNGVS VCTSKVLDLK  60
NYIDKQLLPI VNKQSCSISN IETVIEFQQK NNRLLEITRE FSVNAGVTTP VSTYMLTNSE  120
LLSLINDMPI TNDQKKLMSN NVQIVRQQSY SIMSIIKEEV LAYVVQLPLY GVIDTPCWKL  180
HTSPLCTTNT KEGSNICLTR TDRGWYCDNA GSVSFFPQAE TCKVQSNRVF CDTMNSLTLP  240
SEVNLCNVDI FNPKYDCKIM TSKTDVSSSV ITSLGAIVSC YGKTKCTASN KNRGIIKTFS  300
NGCDYVSNKG VDTVSVGNTL YYVNKQEGKS LYVKGEPIIN FYDPLVFPSS EFDASISQVN  360
```

-continued

```
EKINQSLAFI RKSDELL                                              377

SEQ ID NO: 63          moltype = AA  length = 84
FEATURE                Location/Qualifiers
REGION                 1..84
                       note = synthetic polypeptide
source                 1..84
                       mol_type = protein
                       organism = synthetic construct
SEQUENCE: 63
QNITEEFYQS TCSAVSKGYL SALRTGWYHC VITIELSNIK ENKCNGTDAK VKLIKQELDK  60
YKNAVTELQL LMQSTPPTNN RARR                                      84

SEQ ID NO: 64          moltype = AA  length = 377
FEATURE                Location/Qualifiers
REGION                 1..377
                       note = synthetic polypeptide
source                 1..377
                       mol_type = protein
                       organism = synthetic construct
SEQUENCE: 64
FLGFLLGVGS AIASGVAVSK VLHLEGEVNK IKSALLSTNK AVVSLSNGVS VCTSKVLDLK  60
NYIDKQLLPI VNKQSCSISN IETVIEFQQK NNRLLEITRE FSVNAGVTTP VSTYMLTNSE  120
LLSLINDMPI TNDQKKLMSN NVQIVRQQSY SIMSIIKEEV LAYVVQLPLY GVIDTPCWKL  180
HTSPLCTTNT KEGSNICLTR TDRGWYCDNA GSVSFFPQAE TCKVQSNRVF CDTMNSLTLP  240
SEINLCNVDI FNPKYDCKIM TSKTDVSSSV ITSLGAIVSC YGKTKCTASN KNRGIIKTFS  300
NGCDYVSNKG MDTVSVGNTL YYVNKQEGKS LYVKGEPIIN FYDPLVFPSS EFDASISQVN  360
EKINQSLAFI RKSDELL                                              377

SEQ ID NO: 65          moltype = AA  length = 84
FEATURE                Location/Qualifiers
REGION                 1..84
                       note = synthetic polypeptide
source                 1..84
                       mol_type = protein
                       organism = synthetic construct
SEQUENCE: 65
QNITEEFYQS TCSAVSKGYL SALRTGWYHC VITIELSNIK ENKCNGTDAK VKLIKQELDK  60
YKNAVTELQL LMQSTPAANS RARR                                      84

SEQ ID NO: 66          moltype = AA  length = 377
FEATURE                Location/Qualifiers
REGION                 1..377
                       note = synthetic polypeptide
source                 1..377
                       mol_type = protein
                       organism = synthetic construct
SEQUENCE: 66
FLGFLLGVGS AIASGIAVSK VLHLEGEVNK IKSALLSTNK AVVSLSNGVS VCTSKVLDLK  60
NYIDKQLLPI VNKQSCSISN IETVIEFQQK NNRLLEITRE FSVNAGVTTP VSTYMLTNSE  120
LLSLINDMPI TNDQKKLMSS NVQIVRQQSY SIMSIIKEEV LAYVVQLPLY GVIDTPCWKL  180
HTSPLCTTNT KEGSNICLTR TDRGWYCDNA GSVSFFPQAE TCKVQSNRVF CDTMNSLTLP  240
SEVNLCNIDI FNPKYDCKIM TSKTDVSSSV ITSLGAIVSC YGKTKCTASN KNRGIIKTFS  300
NGCDYVSNKG VDTVSVGNTL YYVNKQEGKS LYVKGEPIIN FYDPLVFPSS EFDASISQVN  360
EKINQSLAFI RKSDELL                                              377

SEQ ID NO: 67          moltype = AA  length = 84
FEATURE                Location/Qualifiers
REGION                 1..84
                       note = synthetic polypeptide
source                 1..84
                       mol_type = protein
                       organism = synthetic construct
SEQUENCE: 67
QNITEEFYQS TCSAVSRGYF SALRTGWYHC VITIELSNIK ETKCNGTDTK VKLIKQELDK  60
YKNAVTELQL LMQNTPAANN RARR                                      84

SEQ ID NO: 68          moltype = AA  length = 377
FEATURE                Location/Qualifiers
REGION                 1..377
                       note = synthetic polypeptide
source                 1..377
                       mol_type = protein
                       organism = synthetic construct
SEQUENCE: 68
FLGFLLGVGS AIASGIAVSK VLHLEGEVNK IKNALLSTNK AVVSLSNGVS VCTSKVLDLK  60
NYINNRLLPI VNQQSCRISN IETVIEFQQM NSRLLEITRE FSVNAGVTTP LSTYMLTNSE  120
LLSLINDMPI TNDQKKLMSS NVQIVRQQSY SIMSIIKEEV LAYVVQLPIY GVIDTPCWKL  180
HTSPLCTTNI KEGSNICLTR TDRGWYCDNA GSVSFFPQAD TCKVQSNRVF CDTMNSLTLP  240
```

-continued

```
SEVSLCNTDI FNSKYDCKIM TSKTDISSSV ITSLGAIVSC YGKTKCTASN KNRGIIKTFS  300
NGCDYVSNKG VDTVSVGNTL YYVNKLEGKN LYVKGEPIIN YYDPLVFPSS EFDASISQVN  360
EKINQSLAFI RRSDELL                                                  377

SEQ ID NO: 69          moltype = AA  length = 84
FEATURE                Location/Qualifiers
REGION                 1..84
                       note = synthetic polypeptide
source                 1..84
                       mol_type = protein
                       organism = synthetic construct
SEQUENCE: 69
QNITEEFYQS TCSAVSRGYF SALRTGWYHC VITIELSNIK ETKCNGTDTK VKLIKQELDK  60
YKNAVTELQL LMQNTPAANN RARR                                         84

SEQ ID NO: 70          moltype = AA  length = 377
FEATURE                Location/Qualifiers
REGION                 1..377
                       note = synthetic polypeptide
source                 1..377
                       mol_type = protein
                       organism = synthetic construct
SEQUENCE: 70
FLGFLLGVGS AIASGIAVSK VLHLEGEVNK IKNALLSTNK AVVSLSNGVS VCTSKVLDLK  60
NYINNQLLPI VNQQSCRISN IETVIEFQQK NSRLLEITRE FSVNAGVTTP LSTYMLTNSE  120
LLSLINDMPI TNDQKKLMSS NVQIVRQQSY SIMSIIKEEV LAYVVQLPIY GVIDTPCWKL  180
HTSPLCTTNI KEGSNICLTR TDRGWYCDNA GSVSFFPQAD TCKVQSNRVF CDTMNSLTLP  240
SEVSLCNTDI FNSKYDCKIM TSKTDISSSV ITSLGAIVSC YGKTKCTASN KNRGIIKTFS  300
NGCDYVSNKG VDTVSVGNTL YYVNKLEGKN LYVKGEPIIN YYDPLVFPSS EFDASISQVN  360
EKINQSLAFI RRSDELL                                                  377

SEQ ID NO: 71          moltype = AA  length = 84
FEATURE                Location/Qualifiers
REGION                 1..84
                       note = synthetic polypeptide
source                 1..84
                       mol_type = protein
                       organism = synthetic construct
SEQUENCE: 71
QNITEEFYQS TCSAVSKGYL SALRTGWYHC VITIELSNIK ENKCNGTDAK VKLIKQELDK  60
YKNAVTELQL LMQSTPATNN RARR                                         84

SEQ ID NO: 72          moltype = AA  length = 377
FEATURE                Location/Qualifiers
REGION                 1..377
                       note = synthetic polypeptide
source                 1..377
                       mol_type = protein
                       organism = synthetic construct
SEQUENCE: 72
FLGFLLGVGS AIASGVAVSK VLHLEGEVNK IKSALLSTNK AVVSLSNGVS VCTIKVLDLK  60
NYIDKQLLPI VNKQSCSISN IETVIEFQQK NNRLLEITRE FSVNAGVTTP VSTYMLTNSE  120
LLSLINDMPI TNDQKKLMSN NVQIVRQQSY SIMSIIKEEV LAYVVQLPLY GVIDTPCWKL  180
HTSPLCTTNT KEGSNICLTR TDRGWYCDNA GSVSFFPQAE TCKVQSNRVF CDTMNSLTLP  240
SEVNLCNVDI FNPKYDCKIM TSKTDVSSSV ITSLGAIVSC YGKTKCTASN KNRGIIKTFS  300
NGCDYVSNKG VDTVSVGNTL YYVNKQEGKS LYVKGEPIIN FYDPLVFPSS EFDASISQVN  360
EKINQSLAFI RKSDELL                                                  377

SEQ ID NO: 73          moltype = AA  length = 84
FEATURE                Location/Qualifiers
REGION                 1..84
                       note = synthetic polypeptide
source                 1..84
                       mol_type = protein
                       organism = synthetic construct
SEQUENCE: 73
QNITEEFYQS TCSAVSKGYL SALRTGWYHC VITIELSNIK ENKCNGTDAK VKLIKQELDK  60
YKNAVTELQL LMQSTPPTNN RARR                                         84

SEQ ID NO: 74          moltype = AA  length = 377
FEATURE                Location/Qualifiers
REGION                 1..377
                       note = synthetic polypeptide
source                 1..377
                       mol_type = protein
                       organism = synthetic construct
SEQUENCE: 74
FLGFLLGVGS AIASGVAVSK VLHLEGEVNK IKSALLSTNK AVVSLSNGVS VCTIKVLDLK  60
NYIDKQLLPI VNKQSCSISN IETVIEFQQK NNRLLEITRE FSVNAGVTTP VSTYMLTNSE  120
```

-continued

```
LLSLINDMPI TNDQKKLMSN NVQIVRQQSY SIMSIIKEEV LAYVVQLPLY GVIDTPCWKL  180
HTSPLCTTNT KEGSNICLTR TDRGWYCDNA GSVSFFPQAE TCKVQSNRVF CDTMNSLTLP  240
SEINLCNVDI FNPKYDCKIM TSKTDVSSSV ITSLGAIVSC YGKTKCTASN KNRGIIKTFS  300
NGCDYVSNKG MDTVSVGNTL YYVNKQEGKS LYVKGEPIIN FYDPLVFPSS EFDASISQVN  360
EKINQSLAFI RKSDELL                                                377

SEQ ID NO: 75          moltype = AA  length = 84
FEATURE                Location/Qualifiers
REGION                 1..84
                       note = synthetic polypeptide
source                 1..84
                       mol_type = protein
                       organism = synthetic construct
SEQUENCE: 75
QNITEEFYQS TCSAVSKGYL SALRTGWYHC VITIELSNIK ENKCNGTDAK VKLIKQELDK  60
YKNAVTELQL LMQSTPAANS RARR                                        84

SEQ ID NO: 76          moltype = AA  length = 377
FEATURE                Location/Qualifiers
REGION                 1..377
                       note = synthetic polypeptide
source                 1..377
                       mol_type = protein
                       organism = synthetic construct
SEQUENCE: 76
FLGFLLGVGS AIASGIAVSK VLHLEGEVNK IKSALLSTNK AVVSLSNGVS VCTIKVLDLK  60
NYIDKQLLPI VNKQSCSISN IETVIEFQQK NNRLLEITRE FSVNAGVTTP VSTYMLTNSE  120
LLSLINDMPI TNDQKKLMSS NVQIVRQQSY SIMSIIKEEV LAYVVQLPLY GVIDTPCWKL  180
HTSPLCTTNT KEGSNICLTR TDRGWYCDNA GSVSFFPQAE TCKVQSNRVF CDTMNSLTLP  240
SEVNLCNIDI FNPKYDCKIM TSKTDVSSSV ITSLGAIVSC YGKTKCTASN KNRGIIKTFS  300
NGCDYVSNKG VDTVSVGNTL YYVNKQEGKS LYVKGEPIIN FYDPLVFPSS EFDASISQVN  360
EKINQSLAFI RKSDELL                                                377

SEQ ID NO: 77          moltype = AA  length = 84
FEATURE                Location/Qualifiers
REGION                 1..84
                       note = synthetic polypeptide
source                 1..84
                       mol_type = protein
                       organism = synthetic construct
SEQUENCE: 77
QNITEEFYQS TCSAVSRGYF SALRTGWYHC VITIELSNIK ETKCNGTDTK VKLIKQELDK  60
YKNAVTELQL LMQNTPAANN RARR                                        84

SEQ ID NO: 78          moltype = AA  length = 377
FEATURE                Location/Qualifiers
REGION                 1..377
                       note = synthetic polypeptide
source                 1..377
                       mol_type = protein
                       organism = synthetic construct
SEQUENCE: 78
FLGFLLGVGS AIASGIAVSK VLHLEGEVNK IKNALLSTNK AVVSLSNGVS VCTIKVLDLK  60
NYINNRLLPI VNQQSCRISN IETVIEFQQM NSRLLEITRE FSVNAGVTTP LSTYMLTNSE  120
LLSLINDMPI TNDQKKLMSS NVQIVRQQSY SIMSIIKEEV LAYVVQLPIY GVIDTPCWKL  180
HTSPLCTTNI KEGSNICLTR TDRGWYCDNA GSVSFFPQAD TCKVQSNRVF CDTMNSLTLP  240
SEVSLCNTDI FNSKYDCKIM TSKTDISSSV ITSLGAIVSC YGKTKCTASN KNRGIIKTFS  300
NGCDYVSNKG VDTVSVGNTL YYVNKLEGKN LYVKGEPIIN YYDPLVFPSS EFDASISQVN  360
EKINQSLAFI RRSDELL                                                377

SEQ ID NO: 79          moltype = AA  length = 84
FEATURE                Location/Qualifiers
REGION                 1..84
                       note = synthetic polypeptide
source                 1..84
                       mol_type = protein
                       organism = synthetic construct
SEQUENCE: 79
QNITEEFYQS TCSAVSRGYF SALRTGWYHC VITIELSNIK ETKCNGTDTK VKLIKQELDK  60
YKNAVTELQL LMQNTPAANN RARR                                        84

SEQ ID NO: 80          moltype = AA  length = 377
FEATURE                Location/Qualifiers
REGION                 1..377
                       note = synthetic polypeptide
source                 1..377
                       mol_type = protein
                       organism = synthetic construct
SEQUENCE: 80
```

-continued

```
FLGFLLGVGS AIASGIAVSK VLHLEGEVNK IKNALLSTNK AVVSLSNGVS VCTIKVLDLK  60
NYINNQLLPI VNQQSCRISN IETVIEFQQK NSRLLEITRE FSVNAGVTTP LSTYMLTNSE  120
LLSLINDMPI TNDQKKLMSS NVQIVRQQSY SIMSIIKEEV LAYVVQLPIY GVIDTPCWKL  180
HTSPLCTTNI KEGSNICLTR TDRGWYCDNA GSVSFFPQAD TCKVQSNRVF CDTMNSLTLP  240
SEVSLCNTDI FNSKYDCKIM TSKTDISSSV ITSLGAIVSC YGKTKCTASN KNRGIIKTFS  300
NGCDYVSNKG VDTVSVGNTL YYVNKLEGKN LYVKGEPIIN YYDPLVFPSS EFDASISQVN  360
EKINQSLAFI RRSDELL                                                377

SEQ ID NO: 81           moltype = AA  length = 574
FEATURE                 Location/Qualifiers
REGION                  1..574
                        note = F protein of human RSV subtype A/ABI35685
source                  1..574
                        mol_type = protein
                        organism = Human respiratory syncytial virus
SEQUENCE: 81
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKNNNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKA DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNVGK STTNIMITTI IIVIIVILLL  540
LIAVGLFLYC KARSTPVTLS KDQLSGINNI AFSN                              574

SEQ ID NO: 82           moltype = AA  length = 573
FEATURE                 Location/Qualifiers
REGION                  1..573
                        note = F protein of human RSV subtype A/AAS93651
source                  1..573
                        mol_type = protein
                        organism = Human respiratory syncytial virus
SEQUENCE: 82
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKNNNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNVGK STTNIMITTI IIVIIVILLL  540
LIAVGLFLYC KARSTPVTLS KDQLSGINNI AFS                               573

SEQ ID NO: 83           moltype = AA  length = 574
FEATURE                 Location/Qualifiers
REGION                  1..574
                        note = F protein of human RSV subtype A/AEO45830
source                  1..574
                        mol_type = protein
                        organism = Human respiratory syncytial virus
SEQUENCE: 83
MELPILKTNA ITTIFAAVTL CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKNNNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNVGK STTNIMITTI IIVIIVILLL  540
LIAVGLFLYC KARSTPVTLS KDQLSGINNI AFSN                              574

SEQ ID NO: 84           moltype = AA  length = 574
FEATURE                 Location/Qualifiers
REGION                  1..574
                        note = F protein of human RSV subtype A/AFM55244
source                  1..574
                        mol_type = protein
                        organism = Human respiratory syncytial virus
SEQUENCE: 84
MELPILKTNA ITTIFAAVTL CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKNNNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
```

```
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNVGK STTNIMITTI IIVIIVILLL  540
LIAVGLFLYC KARSTPVTLS KDQLSGINNI AFSN                             574

SEQ ID NO: 85          moltype = AA  length = 574
FEATURE                Location/Qualifiers
REGION                 1..574
                       note = F protein of human RSV subtype A/AFM55442
source                 1..574
                       mol_type = protein
                       organism = Human respiratory syncytial virus
SEQUENCE: 85
MELPILKTNA ITTIFAAVTL CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKNNNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNVGK STTNIMITTI IIVIIVILLL  540
LIAVGLFLYC KARSTPVTLS KEQLSGINNI AFSN                             574

SEQ ID NO: 86          moltype = AA  length = 574
FEATURE                Location/Qualifiers
REGION                 1..574
                       note = F protein of human RSV subtype A/AFM55255
source                 1..574
                       mol_type = protein
                       organism = Human respiratory syncytial virus
SEQUENCE: 86
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKNNNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTINTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNVGK STTNIMITTI IIVIIVILLL  540
LIAVGLFLYF KARSTPVTLS KDQLSGINNI AFSN                             574

SEQ ID NO: 87          moltype = AA  length = 574
FEATURE                Location/Qualifiers
REGION                 1..574
                       note = F protein of human RSV subtype A/AFM55288
source                 1..574
                       mol_type = protein
                       organism = Human respiratory syncytial virus
SEQUENCE: 87
MDLPILKTNA ITTIFAAVTL CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKNNNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTINTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNVGK STTNIMITTI IIVIIVILLL  540
LIAVGLFLYC KARSTPVTLS KDQLSGINNI AFSN                             574

SEQ ID NO: 88          moltype = AA  length = 574
FEATURE                Location/Qualifiers
REGION                 1..574
                       note = F protein of human RSV subtype A/AFM95385
SITE                   91
                       note = misc_feature - X can be any naturally occurring
                        amino acid
SITE                   363
                       note = misc_feature - X can be any naturally occurring
                        amino acid
source                 1..574
                       mol_type = protein
                       organism = Human respiratory syncytial virus
SEQUENCE: 88
MELPILKTNA ITTILAAVTL CFASSQNITE EFYQSTCSAV SKGYLSALRT GWYTSVITIE  60
LSNIKENKCN GTDAKVKLIK QELDKYKNAV XELQLLMQST PAANNRARRE LPRFMNYTLN  120
NTKNNNVTLS KKRKRRFLGF LLGVGSAIAS GIAVSKVLHL EGEVNKIKSA LLSTNKAVVS  180
```

-continued

```
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSXRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNVGK STTNIMITTI IIVIIVILLL  540
LIAVGLFLYC KARSTPVTLS KDQLSGINNI AFSN                             574

SEQ ID NO: 89          moltype = AA  length = 574
FEATURE                Location/Qualifiers
REGION                 1..574
                       note = F protein of human RSV subtype A/AFM95400
source                 1..574
                       mol_type = protein
                       organism = Human respiratory syncytial virus
SEQUENCE: 89
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST SAANNRARRE LPRFMNYTLN  120
NTKNNNVTLS NKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNVGK STTNIMITTI IIVIIVILLL  540
LIAVGLFLYC KARSTPVTLS KDQLSGINNI AFSN                             574

SEQ ID NO: 90          moltype = AA  length = 574
FEATURE                Location/Qualifiers
REGION                 1..574
                       note = F protein of human RSV subtype A/AAM68157
source                 1..574
                       mol_type = protein
                       organism = Human respiratory syncytial virus
SEQUENCE: 90
MDLPILKTNA ITTILAAVSL CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKNNNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNVGK STTNIMITTI IIVIIVILLL  540
LIAVGLFLYC KARSTPVTLS KDQLSGINNI AFSN                             574

SEQ ID NO: 91          moltype = AA  length = 574
FEATURE                Location/Qualifiers
REGION                 1..574
                       note = F protein of human RSV subtype A/AAM68160
source                 1..574
                       mol_type = protein
                       organism = Human respiratory syncytial virus
SEQUENCE: 91
MDLPILKTNA ITTILAAVLL CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKNNNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNVGK STTNIMITTI IIVIIVILLL  540
LIAVGLFLYC KARSTPVTLS KDQLSGINNI AFSN                             574

SEQ ID NO: 92          moltype = AA  length = 574
FEATURE                Location/Qualifiers
REGION                 1..574
                       note = F protein of human RSV subtype A/AEO45859
source                 1..574
                       mol_type = protein
                       organism = Human respiratory syncytial virus
SEQUENCE: 92
MDLPILKTNA ITAILAAVSL CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKNNNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
```

```
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNVGK STTNIMITTI IIVIIVILLL  540
LIAVGLFLYC KARSTPVTLS KDQLSGINNI AFSN                             574

SEQ ID NO: 93          moltype = AA  length = 574
FEATURE                Location/Qualifiers
REGION                 1..574
                       note = F protein of human RSV subtype A/AEQ63444
source                 1..574
                       mol_type = protein
                       organism = Human respiratory syncytial virus
SEQUENCE: 93
MDLPILKTNA ITAILAAVSL CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKNNNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNVGK STTNIMITTI IIVIIVILLL  540
LIAVGLFLYC KARSTPVTLS KDQLSGINNI AFSN                             574

SEQ ID NO: 94          moltype = AA  length = 569
FEATURE                Location/Qualifiers
REGION                 1..569
                       note = F protein of human RSV subtype A/AEQ98752
source                 1..569
                       mol_type = protein
                       organism = Human respiratory syncytial virus
SEQUENCE: 94
MDLPILKTNA ITAILAVVSL CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKNNNITLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNVGK STTNIMITTI IIVIIVILLL  540
LIAVGLFLYC KARSTPVTLS KDQLSGINN                                   569

SEQ ID NO: 95          moltype = AA  length = 574
FEATURE                Location/Qualifiers
REGION                 1..574
                       note = F protein of human RSV subtype A/AFM55299
source                 1..574
                       mol_type = protein
                       organism = Human respiratory syncytial virus
SEQUENCE: 95
MDLPILKTKA ITTILAAVSL CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NNKNNNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNVGK STTNIMITTI IIVIIVILLL  540
LIAVGLFLYC KARSTPVTLS KDQLSGINNI AFSN                             574

SEQ ID NO: 96          moltype = AA  length = 574
FEATURE                Location/Qualifiers
REGION                 1..574
                       note = F protein of human RSV subtype A/AEO45850
source                 1..574
                       mol_type = protein
                       organism = Human respiratory syncytial virus
SEQUENCE: 96
MELPILKTNA ITTILTAVTF CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKNNNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNVGK STTNIMITTI IIVIIVILLL  540
```

-continued

```
LIAVGLLLYC KARSTPVTLS KDQLSGINNI AFSN                              574

SEQ ID NO: 97           moltype = AA  length = 574
FEATURE                 Location/Qualifiers
REGION                  1..574
                        note = F protein of human RSV subtype A/AEO45869
source                  1..574
                        mol_type = protein
                        organism = Human respiratory syncytial virus
SEQUENCE: 97
MELPILKTNA ITAILAAVSL CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKNNNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNVGK STTNIMITTI IIVIIVILLL  540
LIAVGLLLYC KARSTPVTLS KDQLSGINNI AFSN                              574

SEQ ID NO: 98           moltype = AA  length = 574
FEATURE                 Location/Qualifiers
REGION                  1..574
                        note = F protein of human RSV subtype A/AEO45879
source                  1..574
                        mol_type = protein
                        organism = Human respiratory syncytial virus
SEQUENCE: 98
MELPILKTNA ITTIFAAVTL CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKNNNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFSN                              574

SEQ ID NO: 99           moltype = AA  length = 574
FEATURE                 Location/Qualifiers
REGION                  1..574
                        note = F protein of human RSV subtype A/AEO45909
source                  1..574
                        mol_type = protein
                        organism = Human respiratory syncytial virus
SEQUENCE: 99
MELPILKTNA ITTIFAAVTL CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKNNNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNVGK STTNIMITTI IIVIIVILLL  540
LIAVGLLLYC KARSTPVTVI NDQLSGINNI AFSN                              574

SEQ ID NO: 100          moltype = AA  length = 574
FEATURE                 Location/Qualifiers
REGION                  1..574
                        note = F protein of human RSV subtype A/AAM68154
source                  1..574
                        mol_type = protein
                        organism = Human respiratory syncytial virus
SEQUENCE: 100
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKTTNVTLS RKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSIS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLCVK GEPIINFYDP  480
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFSS                              574

SEQ ID NO: 101          moltype = AA  length = 574
```

-continued

```
FEATURE                Location/Qualifiers
REGION                 1..574
                       note = F protein of human RSV subtype A/ADZ95777
SITE                   272
                       note = misc_feature - X can be any naturally occurring
                        amino acid
source                 1..574
                       mol_type = protein
                       organism = Human respiratory syncytial virus
SEQUENCE: 101
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKTANVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KXLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFSS                              574

SEQ ID NO: 102         moltype = AA  length = 574
FEATURE                Location/Qualifiers
REGION                 1..574
                       note = F protein of human RSV subtype A/AEC32087
source                 1..574
                       mol_type = protein
                       organism = Human respiratory syncytial virus
SEQUENCE: 102
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST QAANNRARRE LPRFMNYTLN  120
NTKTTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFSS                              574

SEQ ID NO: 103         moltype = AA  length = 574
FEATURE                Location/Qualifiers
REGION                 1..574
                       note = F protein of human RSV subtype A/AEO45929
source                 1..574
                       mol_type = protein
                       organism = Human respiratory syncytial virus
SEQUENCE: 103
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKTTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFSS                              574

SEQ ID NO: 104         moltype = AA  length = 574
FEATURE                Location/Qualifiers
REGION                 1..574
                       note = F protein of human RSV subtype A/AFM55211
source                 1..574
                       mol_type = protein
                       organism = Human respiratory syncytial virus
SEQUENCE: 104
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKTTNVTLS RKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFSS                              574

SEQ ID NO: 105         moltype = AA  length = 574
```

-continued

```
FEATURE               Location/Qualifiers
REGION                1..574
                      note = F protein of human RSV subtype A/AFM55222
source                1..574
                      mol_type = protein
                      organism = Human respiratory syncytial virus
SEQUENCE: 105
MELPILKTNV ITTILAAVTL CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKTTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFSS                            574

SEQ ID NO: 106        moltype = AA  length = 574
FEATURE               Location/Qualifiers
REGION                1..574
                      note = F protein of human RSV subtype A/AFM55332
source                1..574
                      mol_type = protein
                      organism = Human respiratory syncytial virus
SEQUENCE: 106
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST PATNNRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFSS                            574

SEQ ID NO: 107        moltype = AA  length = 573
FEATURE               Location/Qualifiers
REGION                1..573
                      note = F protein of human RSV subtype A/AAS93649
source                1..573
                      mol_type = protein
                      organism = Human respiratory syncytial virus
SEQUENCE: 107
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFS                             573

SEQ ID NO: 108        moltype = AA  length = 574
FEATURE               Location/Qualifiers
REGION                1..574
                      note = F protein of human RSV subtype A/ADZ95778
source                1..574
                      mol_type = protein
                      organism = Human respiratory syncytial virus
SEQUENCE: 108
MELPILKTNA ITTILAAVTL CFASSQNITE EFYQSTCSAV SKGYLSALRT GWYTSVITIE  60
LSSIKENKCN GTDAKVKLIK QELDKYKNAV TELQLLMQST PAANNRARRE LPRFMNYTLN  120
NTKTTNVTLS RKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMFNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFSS                            574

SEQ ID NO: 109        moltype = AA  length = 574
FEATURE               Location/Qualifiers
REGION                1..574
                      note = F protein of human RSV subtype A/AFM55420
```

```
source                  1..574
                        mol_type = protein
                        organism = Human respiratory syncytial virus
SEQUENCE: 109
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKTTNVTLS RKRKRRFLGF LLGVGSAIAS GIAVSKVLHL EGEVNKIKSA LLSTNKAVVS  180
LSNGVSVLTS KVLDLKNYID KQLLPVVNKQ SCRISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFSS                            574

SEQ ID NO: 110          moltype = AA  length = 574
FEATURE                 Location/Qualifiers
REGION                  1..574
                        note = F protein of human RSV subtype A/AEO45840
source                  1..574
                        mol_type = protein
                        organism = Human respiratory syncytial virus
SEQUENCE: 110
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKTTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNVGK STTNIMITTI IIVIIVILLS  540
LIAVGLLLYC KARSTPVTVS KDQLSGINNI AFSN                            574

SEQ ID NO: 111          moltype = AA  length = 574
FEATURE                 Location/Qualifiers
REGION                  1..574
                        note = F protein of human RSV subtype A/AEO45949
source                  1..574
                        mol_type = protein
                        organism = Human respiratory syncytial virus
SEQUENCE: 111
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKTTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNVGK STTNIMITTI IIVIIVILLS  540
LIAVGLLLYC KARSTPVTLS KDQLSGINNI AFSS                            574

SEQ ID NO: 112          moltype = AA  length = 574
FEATURE                 Location/Qualifiers
REGION                  1..574
                        note = F protein of human RSV subtype A/1701388A
source                  1..574
                        mol_type = protein
                        organism = Human respiratory syncytial virus
SEQUENCE: 112
MELPILKTNT ITTILAAVTL CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAVK STTNIMITTI IIVIIVILLS  540
LIAVGLLLYC KARSTPVTLS KDQLSGINNI AFSN                            574

SEQ ID NO: 113          moltype = AA  length = 574
FEATURE                 Location/Qualifiers
REGION                  1..574
                        note = F protein of human RSV subtype A/AEQ63487
source                  1..574
                        mol_type = protein
                        organism = Human respiratory syncytial virus
```

```
SEQUENCE: 113
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKNTNVTVS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPNEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFSN                             574

SEQ ID NO: 114          moltype = AA  length = 574
FEATURE                 Location/Qualifiers
REGION                  1..574
                        note = F protein of human RSV subtype A/AEQ63520
source                  1..574
                        mol_type = protein
                        organism = Human respiratory syncytial virus
SEQUENCE: 114
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKNTNVTVS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFSN                             574

SEQ ID NO: 115          moltype = AA  length = 573
FEATURE                 Location/Qualifiers
REGION                  1..573
                        note = F protein of human RSV subtype A/AAS93653
source                  1..573
                        mol_type = protein
                        organism = Human respiratory syncytial virus
SEQUENCE: 115
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKNTNVTVS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFS                              573

SEQ ID NO: 116          moltype = AA  length = 574
FEATURE                 Location/Qualifiers
REGION                  1..574
                        note = F protein of human RSV subtype A/AFM95365
source                  1..574
                        mol_type = protein
                        organism = Human respiratory syncytial virus
SEQUENCE: 116
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKNTNVTVS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKYD ELLHNVNAGK STTNIMITTI IIVIIVILLS  540
LIAVGLLLYC KARSTPVTLS KDQLSGINNI AFSN                             574

SEQ ID NO: 117          moltype = AA  length = 574
FEATURE                 Location/Qualifiers
REGION                  1..574
                        note = F protein of human RSV subtype A/AFM95376
source                  1..574
                        mol_type = protein
                        organism = Human respiratory syncytial virus
SEQUENCE: 117
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
```

-continued

```
NTKNTNVTVS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSNEFDA SISQVNEKIN QSLAFIRKSD ELLHNVNAGK STTNIMITTI IIVIIVILLS  540
LIAVGLLLYC KARSTPVTLS KDQLSGINNI AFSN                              574

SEQ ID NO: 118         moltype = AA  length = 574
FEATURE                Location/Qualifiers
REGION                 1..574
                       note = F protein of human RSV subtype A/AEQ63312
source                 1..574
                       mol_type = protein
                       organism = Human respiratory syncytial virus
SEQUENCE: 118
MELPVLKTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQADTCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFSN                              574

SEQ ID NO: 119         moltype = AA  length = 574
FEATURE                Location/Qualifiers
REGION                 1..574
                       note = F protein of human RSV subtype A/AEO23051
source                 1..574
                       mol_type = protein
                       organism = Human respiratory syncytial virus
SEQUENCE: 119
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANSRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFSN                              574

SEQ ID NO: 120         moltype = AA  length = 574
FEATURE                Location/Qualifiers
REGION                 1..574
                       note = F protein of human RSV subtype A/AEQ63334
source                 1..574
                       mol_type = protein
                       organism = Human respiratory syncytial virus
SEQUENCE: 120
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANSRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQADTCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFSN                              574

SEQ ID NO: 121         moltype = AA  length = 574
FEATURE                Location/Qualifiers
REGION                 1..574
                       note = F protein of human RSV subtype A/AEQ63367
SITE                   32
                       note = misc_feature - X can be any naturally occurring
                        amino acid
source                 1..574
                       mol_type = protein
                       organism = Human respiratory syncytial virus
SEQUENCE: 121
MELPILKTNA ITTILAAVTL CFASSQNITE EXYQSTCSAV SKGYLSALRT GWYTSVITIE  60
LSNIKENKCN GTDAKVKLIK QELDKYKNAV TELQLLMQST PAANSRARRE LPRFMNYTLN  120
```

-continued

```
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFSN                              574

SEQ ID NO: 122         moltype = AA  length = 574
FEATURE                Location/Qualifiers
REGION                 1..574
                       note = F protein of human RSV subtype A/AFM55563
source                 1..574
                       mol_type = protein
                       organism = Human respiratory syncytial virus
SEQUENCE: 122
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST QAANSRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFSN                              574

SEQ ID NO: 123         moltype = AA  length = 574
FEATURE                Location/Qualifiers
REGION                 1..574
                       note = F protein of human RSV subtype A/AFM55552
source                 1..574
                       mol_type = protein
                       organism = Human respiratory syncytial virus
SEQUENCE: 123
MELPILNTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANSRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFSN                              574

SEQ ID NO: 124         moltype = AA  length = 574
FEATURE                Location/Qualifiers
REGION                 1..574
                       note = F protein of human RSV subtype A/AFX60137
source                 1..574
                       mol_type = protein
                       organism = Human respiratory syncytial virus
SEQUENCE: 124
MELPILNTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANSRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNKKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFSN                              574

SEQ ID NO: 125         moltype = AA  length = 574
FEATURE                Location/Qualifiers
REGION                 1..574
                       note = F protein of human RSV subtype A/AFX60173
source                 1..574
                       mol_type = protein
                       organism = Human respiratory syncytial virus
SEQUENCE: 125
MELPILNTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANSRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
```

-continued

```
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTSIMITTI IIVIIVILLS  540
LIAVGLLLYC KARSTPVTLS KDQLSGINNI AFSN                              574

SEQ ID NO: 126          moltype = AA  length = 574
FEATURE                 Location/Qualifiers
REGION                  1..574
                        note = F protein of human RSV subtype A/AFM55365
source                  1..574
                        mol_type = protein
                        organism = Human respiratory syncytial virus
SEQUENCE: 126
MELPILKTNA ITTILAAVTL CFTSSQNITE EFYQSTCSAV SKGYLSALRT GWYTSVITIE  60
LSNIKENKCN GTDAKVKLIK QELDKYKNAV TELQLLMQST PAANSRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKIHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFSN                              574

SEQ ID NO: 127          moltype = AA  length = 574
FEATURE                 Location/Qualifiers
REGION                  1..574
                        note = F protein of human RSV subtype A/AAO72323
source                  1..574
                        mol_type = protein
                        organism = Human respiratory syncytial virus
SEQUENCE: 127
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIATV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVMD TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STINIMITTI IIVIIVILLS  540
LIAVGLLLYC KARSTPVTLS KDQLSGINNI AFSN                              574

SEQ ID NO: 128          moltype = AA  length = 574
FEATURE                 Location/Qualifiers
REGION                  1..574
                        note = F protein of human RSV subtype A/AAO72324
source                  1..574
                        mol_type = protein
                        organism = Human respiratory syncytial virus
SEQUENCE: 128
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIATV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPFDEFDA SISQVNEKIN QSLAFIRKSD ELLHNVNAGK STINIMITTI IIVIIVILLS  540
LIAVGLLLYC KARSTPVTLS KDQLSGINNI AFSN                              574

SEQ ID NO: 129          moltype = AA  length = 574
FEATURE                 Location/Qualifiers
REGION                  1..574
                        note = F protein of human RSV subtype A/ACY68435
source                  1..574
                        mol_type = protein
                        organism = Human respiratory syncytial virus
SEQUENCE: 129
MELPILKTNA ITTILAAVTL CFASSQNITE EFYQSTCSAV SKGYLSALRT GWYTSVITIE  60
LSTIKENKCN GTDAKVKLIK QELDKYKNAV TELQLLMQST PAANNRARRE LPRFMNYTLN  120
NAKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
```

```
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFSS                              574

SEQ ID NO: 130         moltype = AA  length = 574
FEATURE                Location/Qualifiers
REGION                 1..574
                       note = F protein of human RSV subtype A/AEC32085
source                 1..574
                       mol_type = protein
                       organism = Human respiratory syncytial virus
SEQUENCE: 130
MELPILKTNA ITTILAAVTL CFASSQNITE EFYQSTCSAV SKGYLSALRT GWYTSVITIE  60
LSTIKENKCN GTDAKGKLIK QELDKYKNAV TELQLLMQST PAANNRARRE LPRFMNYTLN  120
NAKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTKIMITTI IIVIIVILLS  540
LIAVGLLLYC KARSTPVTLS KDQLSGINNI AFSS                              574

SEQ ID NO: 131         moltype = AA  length = 574
FEATURE                Location/Qualifiers
REGION                 1..574
                       note = F protein of human RSV subtype A/AFM55266
source                 1..574
                       mol_type = protein
                       organism = Human respiratory syncytial virus
SEQUENCE: 131
MELPILKTNA ITTILAAVTF CFASSQNITE EFYQSTCSAV SKGYLSALRT GWYTSVITIE  60
LSNIKENKCN GTDAKVKLIK QELDKYKNAV TELQLLMQST PASNNRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIVVILLS  540
LIAVGLLLYC KARSTPVTLS KDQLSGINNI AFSS                              574

SEQ ID NO: 132         moltype = AA  length = 574
FEATURE                Location/Qualifiers
REGION                 1..574
                       note = F protein of human RSV subtype A/AFM55277
source                 1..574
                       mol_type = protein
                       organism = Human respiratory syncytial virus
SEQUENCE: 132
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST PASNNRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNSK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIVVILLS  540
LIAVGLLLYC KARSTPVTLS KDQLSGINNI AFSS                              574

SEQ ID NO: 133         moltype = AA  length = 574
FEATURE                Location/Qualifiers
REGION                 1..574
                       note = F protein of human RSV subtype A/AFM55354
source                 1..574
                       mol_type = protein
                       organism = Human respiratory syncytial virus
SEQUENCE: 133
MELPILKTNA ITTILAAVTL CFVSSQNITE EFYQSTCSAV SKGYLSALRT GWYTSVITIE  60
LSNIKENKCN GTDAKVKLIK QELDKYKNAV TELQLLMQST PASNNRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIVVILLS  540
LIAVGLLLYC KARSTPVTLS KDQLSGINNI AFSS                              574
```

-continued

```
SEQ ID NO: 134         moltype = AA  length = 565
FEATURE                Location/Qualifiers
REGION                 1..565
                       note = F protein of human RSV subtype A/AEO12131
source                 1..565
                       mol_type = protein
                       organism = Human respiratory syncytial virus
SEQUENCE: 134
MELPILKTNA ITTILAAVTL CFTSSQNITE EFYQSTCSAV SKGYLSALRT GWYTSVITIE  60
LSNIKENKCN GTDAKVKLIK QELDKYKNAV TELQLLMQST PAANSRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSSNVQT VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKID QSLAFIRKSD ELLHNVNAGK STTNIMITTI IIVIIVILLA  540
LIAVGLLLYC KARSTPVTLS KDQLR                                      565

SEQ ID NO: 135         moltype = AA  length = 574
FEATURE                Location/Qualifiers
REGION                 1..574
                       note = F protein of human RSV subtype A/AEO23052
source                 1..574
                       mol_type = protein
                       organism = Human respiratory syncytial virus
SEQUENCE: 135
MELPILKANA ISTILAAVTL CFASSQNITE EFYQSTCSAV SKGYLSALRT GWYTSVITIE  60
LSNIKENKCN GTDAKVKLIK QELDKYKNAV TELQLLMQST PAANSRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSSNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLA  540
LIAVGLLLYC KARSTPVTLS KDQLSGINNI AFSN                            574

SEQ ID NO: 136         moltype = AA  length = 574
FEATURE                Location/Qualifiers
REGION                 1..574
                       note = F protein of human RSV subtype A/AEQ63389
source                 1..574
                       mol_type = protein
                       organism = Human respiratory syncytial virus
SEQUENCE: 136
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANSRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSSNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLA  540
LIAVGLLLYC KARSTPVTLS KDQLSGINNI AFSN                            574

SEQ ID NO: 137         moltype = AA  length = 569
FEATURE                Location/Qualifiers
REGION                 1..569
                       note = F protein of human RSV subtype A/AEQ98748
source                 1..569
                       mol_type = protein
                       organism = Human respiratory syncytial virus
SEQUENCE: 137
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANSRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSSNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLA  540
LIAVGLLLYC KARSTPVTLS KDQLSGINN                                  569

SEQ ID NO: 138         moltype = AA  length = 569
FEATURE                Location/Qualifiers
REGION                 1..569
```

```
                        note = F protein of human RSV subtype A/AEQ98747
source                  1..569
                        mol_type = protein
                        organism = Human respiratory syncytial virus
SEQUENCE: 138
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANSRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSSNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVITVILLA  540
LIAVGLLLYC KARSTPVTLS KDQLSGINN                                  569

SEQ ID NO: 139          moltype = AA  length = 569
FEATURE                 Location/Qualifiers
REGION                  1..569
                        note = F protein of human RSV subtype A/AEQ98749
source                  1..569
                        mol_type = protein
                        organism = Human respiratory syncytial virus
SEQUENCE: 139
MELPILKTNA ITTILAAVTF CFASSQNITE EFYQSTCSAV SKGYLSALRT GWYTSVITIE  60
LSNIKENKCN GTDAKVKLIK QELDKYKNAV TELQLLMQST PAANSRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSSNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLA  540
LIAVGLLLYC KARSTPVTLS KDQLSGINN                                  569

SEQ ID NO: 140          moltype = AA  length = 569
FEATURE                 Location/Qualifiers
REGION                  1..569
                        note = F protein of human RSV subtype A/AEQ98753
source                  1..569
                        mol_type = protein
                        organism = Human respiratory syncytial virus
SEQUENCE: 140
MELPILKTNA ITTILAAVIL CFASSQNITE EFYQSTCSAV SKGYLSALRT GWYTSVITIE  60
LSNIKENKCN GTDAKVKLIK QELDKYKNAV TELQLLMQST PAANSRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSSNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLA  540
LIAVGLLLYC KARSTPVTLS KDQLSGINN                                  569

SEQ ID NO: 141          moltype = AA  length = 569
FEATURE                 Location/Qualifiers
REGION                  1..569
                        note = F protein of human RSV subtype A/AEQ98755
source                  1..569
                        mol_type = protein
                        organism = Human respiratory syncytial virus
SEQUENCE: 141
MELPILKTNA ITTILAAVTL CFASSQNITE EFYQSTCSAV SKGYLSALRT GWYTSVIAIE  60
LSNIKENKCN GTDAKVKLIK QELDKYKNAV TELQLLMQST PAANSRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSSNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLA  540
LIAVGLLLYC KARSTPVTLS KDQLSGINN                                  569

SEQ ID NO: 142          moltype = AA  length = 569
FEATURE                 Location/Qualifiers
REGION                  1..569
                        note = F protein of human RSV subtype A/AEQ98757
source                  1..569
                        mol_type = protein
```

```
                         organism = Human respiratory syncytial virus
SEQUENCE: 142
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANSRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPISTY MLTNSELLSL INDMPITNDQ KKLMSSNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLA  540
LIAVGLLLYC KARSTPVTLS KDQLSGINN                                  569

SEQ ID NO: 143           moltype = AA  length = 574
FEATURE                  Location/Qualifiers
REGION                   1..574
                         note = F protein of human RSV subtype A/AFV46409
source                   1..574
                         mol_type = protein
                         organism = Human respiratory syncytial virus
SEQUENCE: 143
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANSRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSSNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDT SISQVNEKIN QSLAFIRKSD ELLHNVNAGK STTNIMITTI IIVIIVILLA  540
LIAVGLLLYC KARSTPVTLS KDQLSGINNI AFSN                             574

SEQ ID NO: 144           moltype = AA  length = 574
FEATURE                  Location/Qualifiers
REGION                   1..574
                         note = F protein of human RSV subtype A/AFV46417
source                   1..574
                         mol_type = protein
                         organism = Human respiratory syncytial virus
SEQUENCE: 144
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANSRTRRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSSNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLA  540
LIAVGLLLYC KARSTPVTLS KDQLSGINNI AFSN                             574

SEQ ID NO: 145           moltype = AA  length = 574
FEATURE                  Location/Qualifiers
REGION                   1..574
                         note = F protein of human RSV subtype A/AFX60128
source                   1..574
                         mol_type = protein
                         organism = Human respiratory syncytial virus
SEQUENCE: 145
MELPILKTNA ITTILAAVTL CFTSSQNITE EFYQSTCSAV SKGYLSALRT GWYTSVITIE  60
LSNIKENKCN GTDAKVKLIK QELDKYKNAV TELQLLMQST PAANSRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSSNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLA  540
LIAVGLLLYC KARSTPVTLS KDQLSGINNI AFSN                             574

SEQ ID NO: 146           moltype = AA  length = 574
FEATURE                  Location/Qualifiers
REGION                   1..574
                         note = F protein of human RSV subtype A/AFX60187
source                   1..574
                         mol_type = protein
                         organism = Human respiratory syncytial virus
SEQUENCE: 146
MELPILKTNA ITTILAAVTL CFSSSQNITE EFYQSTCSAV SKGYLSALRT GWYTSVITIE  60
```

-continued

```
LSNIKENKCN GTDAKVKLIK QELDKYKNAV TELQLLMQST PAANSRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSSNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLA  540
LIAVGLLLYC KARSTPVTLS KDQLSGINNI AFSN                              574

SEQ ID NO: 147         moltype = AA  length = 574
FEATURE                Location/Qualifiers
REGION                 1..574
                       note = F protein of human RSV subtype A/AFX60129
source                 1..574
                       mol_type = protein
                       organism = Human respiratory syncytial virus
SEQUENCE: 147
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANSRARRE LPRFMNYTLN  120
NTKNTNITLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSSNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLA  540
LIAVGLLLYC KARSTPVTLS KDQLSGINNI AFSN                              574

SEQ ID NO: 148         moltype = AA  length = 574
FEATURE                Location/Qualifiers
REGION                 1..574
                       note = F protein of human RSV subtype A/AFX60135
source                 1..574
                       mol_type = protein
                       organism = Human respiratory syncytial virus
SEQUENCE: 148
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANSRARRE LPRFMNYTLN  120
NTKNTNVTLS KKRKRRFLGF LLGVGSAIAS GTAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSSNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLA  540
LIAVGLLLYC KARSTPVTLS KDQLSGINNI AFSN                              574

SEQ ID NO: 149         moltype = AA  length = 574
FEATURE                Location/Qualifiers
REGION                 1..574
                       note = F protein of human RSV subtype A/AFX60141
SITE                   292
                       note = misc_feature - X can be any naturally occurring
                        amino acid
source                 1..574
                       mol_type = protein
                       organism = Human respiratory syncytial virus
SEQUENCE: 149
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANSRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSSNVQI VRQQSYSIMS IXKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLA  540
LIAVGLLLYC KARSTPVTLS KDQLSGINNI AFSN                              574

SEQ ID NO: 150         moltype = AA  length = 574
FEATURE                Location/Qualifiers
REGION                 1..574
                       note = F protein of human RSV subtype A/AFX60148
source                 1..574
                       mol_type = protein
                       organism = Human respiratory syncytial virus
SEQUENCE: 150
MELPILKTNA ITTILAAVTL CFASSQNITE EFYQSTCSAV SKGYLSALRT GWYTSVITIE  60
```

-continued

```
LSNIKENKCN GTDAKVKLIK QELDKYKNAV TELQLLMQST PAANSRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSSNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISLVNEKIN QSLAFIRKSD ELLHNVNAGK STTNIMITTI IIVIIVILLA  540
LIAVGLLLYC KARSTPVTLS KDQLSGINNI AFSN                             574

SEQ ID NO: 151          moltype = AA  length = 574
FEATURE                 Location/Qualifiers
REGION                  1..574
                        note = F protein of human RSV subtype A/AFX60151
source                  1..574
                        mol_type = protein
                        organism = Human respiratory syncytial virus
SEQUENCE: 151
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANSRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSILNIETV IEFQQKNNRL LEITREFSVN  240
AGVTTPVSTY MLTNSELLSL INDMPITNDQ KKLMSSNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLA  540
LIAVGLLLYC KARSTPVTLS KDQLSGINNI AFSN                             574

SEQ ID NO: 152          moltype = AA  length = 574
FEATURE                 Location/Qualifiers
REGION                  1..574
                        note = F protein of human RSV subtype A/AFX60169
source                  1..574
                        mol_type = protein
                        organism = Human respiratory syncytial virus
SEQUENCE: 152
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST PSANSRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSSNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLA  540
LIAVGLLLYC KARSTPVTLS KDQLSGINNI AFSN                             574

SEQ ID NO: 153          moltype = AA  length = 574
FEATURE                 Location/Qualifiers
REGION                  1..574
                        note = F protein of human RSV subtype A/AFX60200
source                  1..574
                        mol_type = protein
                        organism = Human respiratory syncytial virus
SEQUENCE: 153
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANSRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSSNVQI VRQQSYSIMS IIKEEVLAYV  300
VQLPLYGVID TPCWKLHTSP LCTTNTKVGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLA  540
LIAVGLLLYC KARSTPVTLS KDQLSGINNI AFSN                             574

SEQ ID NO: 154          moltype = AA  length = 574
FEATURE                 Location/Qualifiers
REGION                  1..574
                        note = F protein of human RSV subtype A/AFX60201
source                  1..574
                        mol_type = protein
                        organism = Human respiratory syncytial virus
SEQUENCE: 154
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANSRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
```

-continued

```
AGVTTPVSTY MLTNSELLSL INDMPITNDQ KKLMSSNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNVGK STTNIMITTI IIVIIVILLA  540
LIAVGLLLYC KARSTPVTLS KDQLSGINNI AFSN                             574

SEQ ID NO: 155         moltype = AA  length = 574
FEATURE                Location/Qualifiers
REGION                 1..574
                       note = F protein of human RSV subtype A/AFM55343
source                 1..574
                       mol_type = protein
                       organism = Human respiratory syncytial virus
SEQUENCE: 155
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANSRARRE LPRFMNYTLN  120
NTKNANVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSSNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLA  540
LIAVGLLLYC KARSTPVTLS KDQLSGINNI AFSN                             574

SEQ ID NO: 156         moltype = AA  length = 574
FEATURE                Location/Qualifiers
REGION                 1..574
                       note = F protein of human RSV subtype A/AFV46401
source                 1..574
                       mol_type = protein
                       organism = Human respiratory syncytial virus
SEQUENCE: 156
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANSRARRE LPRFMNYTLN  120
NTKNINVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSSNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLA  540
LIAVGLLLYC KARSTPVTLS KDQLSGINNI AFSN                             574

SEQ ID NO: 157         moltype = AA  length = 574
FEATURE                Location/Qualifiers
REGION                 1..574
                       note = F protein of human RSV subtype A/AFV46410
source                 1..574
                       mol_type = protein
                       organism = Human respiratory syncytial virus
SEQUENCE: 157
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST PTANSRARRE LPRFMNYTLN  120
NTKNINVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSSNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLA  540
LIAVGLLLYC KARSTPVTLS KDQLSGINNI AFSN                             574

SEQ ID NO: 158         moltype = AA  length = 569
FEATURE                Location/Qualifiers
REGION                 1..569
                       note = F protein of human RSV subtype A/AEQ98756
source                 1..569
                       mol_type = protein
                       organism = Human respiratory syncytial virus
SEQUENCE: 158
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANSRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSSNVQI VRQQSYSIMS IIKEEVLAYV  300
VQLPLYGVID TPCWKLHTSP LCTTNIKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
```

-continued

```
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLA  540
LIAVGLLLYC KARSTPVTLS KDQLSGINN                                    569

SEQ ID NO: 159         moltype = AA  length = 574
FEATURE                Location/Qualifiers
REGION                 1..574
                       note = F protein of human RSV subtype A/AFV46403
source                 1..574
                       mol_type = protein
                       organism = Human respiratory syncytial virus
SEQUENCE: 159
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST SAANSRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSSNVQI VRQQSYSIMS IIKEEVLAYV  300
VQLPLYGVID TPCWKLHTSP LCTTNIKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLA  540
LIAVGLLLYC KARSTPVTLS KDQLSGINNI AFSN                              574

SEQ ID NO: 160         moltype = AA  length = 574
FEATURE                Location/Qualifiers
REGION                 1..574
                       note = F protein of human RSV subtype A/AFX60202
source                 1..574
                       mol_type = protein
                       organism = Human respiratory syncytial virus
SEQUENCE: 160
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST SAANSRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSSNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLA  540
LIAVGLLLYC KARSTPVTLS KDQLSGINNI AFSN                              574

SEQ ID NO: 161         moltype = AA  length = 574
FEATURE                Location/Qualifiers
REGION                 1..574
                       note = F protein of human RSV subtype A/AFV46413
source                 1..574
                       mol_type = protein
                       organism = Human respiratory syncytial virus
SEQUENCE: 161
MELPILKTNA ITTILAAITL CFASSQNITE EFYQSTCSAV SKGYLSALRT GWYTSVITIE  60
LSNIKENKCN GTDAKVKLIK QELDKYKNAV TELQLLMQST PAANSRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSSNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLA  540
LIAVGLLLYC KARSTPVTLS KDQLSGINNI AFSN                              574

SEQ ID NO: 162         moltype = AA  length = 574
FEATURE                Location/Qualifiers
REGION                 1..574
                       note = F protein of human RSV subtype A/AFV46414
source                 1..574
                       mol_type = protein
                       organism = Human respiratory syncytial virus
SEQUENCE: 162
MELPILKTNA ITTILAAITL CFASSQNITE EFYQSTCSAV SKGYLSALRT GWYTSVITIE  60
LSNIKENKCN GTDAKVKLIK QELDKYKNAV IELQLLMQST PAANSRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSSNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLA  540
LIAVGLLLYC KARSTPVTLS KDQLSGINNI AFSN                              574
```

```
SEQ ID NO: 163          moltype = AA  length = 574
FEATURE                 Location/Qualifiers
REGION                  1..574
                        note = F protein of human RSV subtype A/AFX60208
source                  1..574
                        mol_type = protein
                        organism = Human respiratory syncytial virus
SEQUENCE: 163
MELPILKTNA ITTILAAVTL CFASSQNITE EFYQSTCSAV SKGYLSALRT GWYTSVITIE  60
LSNIKENKCN GTDAKVKLIK QELDKYKNAV IELQLLMQST PAANSRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSSNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLA  540
LIAVGLLLYC KARSTPVTLS KDQLSGINNI AFSN                            574

SEQ ID NO: 164          moltype = AA  length = 574
FEATURE                 Location/Qualifiers
REGION                  1..574
                        note = F protein of human RSV subtype A/AFV46419
source                  1..574
                        mol_type = protein
                        organism = Human respiratory syncytial virus
SEQUENCE: 164
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANSRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSSNVQI VRQQSYSIMS IIKEEVLAYV  300
VQLPLYGVID TPCWKLHTSP LCTTNTKEGS NICITRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLA  540
LIAVGLLLYC KARSTPVTLS KDQLSGINNI AFSN                            574

SEQ ID NO: 165          moltype = AA  length = 574
FEATURE                 Location/Qualifiers
REGION                  1..574
                        note = F protein of human RSV subtype A/AFV46420
source                  1..574
                        mol_type = protein
                        organism = Human respiratory syncytial virus
SEQUENCE: 165
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANSRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSSNVQI VRQQSYSIMS IIKEEVLAYV  300
VQLPLYGVID TPCWKLHTSP LCTTNTKEGS NICITRTDRG WYCDNAGSVS FFPQAETCKV  360
QSNRVFCDTM NSLTLPSEVN FCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLA  540
LIAVGLLLYC KARSTPVTLS KDQLSGINNI AFSN                            574

SEQ ID NO: 166          moltype = AA  length = 574
FEATURE                 Location/Qualifiers
REGION                  1..574
                        note = F protein of human RSV subtype A/AFX60138
source                  1..574
                        mol_type = protein
                        organism = Human respiratory syncytial virus
SEQUENCE: 166
MELPILKTNS ITTILAAVTL CFASSQNITE EFYQSTCSAV SKGYLSALRT GWYTSVITIE  60
LSNIKENKCN GTDTKVKLIK QELDKYKNAV TELQLLMQST PAANSRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSSNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLA  540
LIAVGLLLYC KARSTPVTLS KDQLSGINNI AFSN                            574

SEQ ID NO: 167          moltype = AA  length = 574
FEATURE                 Location/Qualifiers
```

-continued

```
REGION                 1..574
                       note = F protein of human RSV subtype A/AFX60150
source                 1..574
                       mol_type = protein
                       organism = Human respiratory syncytial virus
SEQUENCE: 167
MELPILKTNA ITTILAAVTL CFASSQNITE EFYQSTCSAV SKGYLSALRT GWYTSVITIE  60
LSNIKENKCN GTDTKVKLIK QELDKYKNAV TELQLLMQST PAANSRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSSNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLA  540
LIAVGLLLYC KARSTPVTLS KDQLSGINNI AFSN                             574

SEQ ID NO: 168         moltype = AA  length = 574
FEATURE                Location/Qualifiers
REGION                 1..574
                       note = F protein of human RSV subtype A/AFX60162
source                 1..574
                       mol_type = protein
                       organism = Human respiratory syncytial virus
SEQUENCE: 168
MELPILKTNA ITTILAAVTL CFASSQNITE EFYQSTCSAV SKGYLSALRT GWYTSVITIE  60
LSNIKENKCN GTDAKVKLIK QELDKYKNAV TELQLFMQST PAANSRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSSNVQI VRQQSYSIMS IIKEEVLAYV  300
VQLPLYGVID TPCWKLHTSP LCTINTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLA  540
LIAVGLLLYC KARSTPVTLS KDQLSGINNI AFSN                             574

SEQ ID NO: 169         moltype = AA  length = 574
FEATURE                Location/Qualifiers
REGION                 1..574
                       note = F protein of human RSV subtype A/AFX60190
source                 1..574
                       mol_type = protein
                       organism = Human respiratory syncytial virus
SEQUENCE: 169
MELPILKTNA ITTILAAVTL CFASSQNITE EFYQSTCSAV SKGYLSALRT GWYTSVITIE  60
LSNIKENKCN GTDAKVKLIK QELDKYKNAV TELQLFMQST PAANSRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSSNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLA  540
LIAVGLLLYC KARSTPVTLS KDQLSGINNI AFSN                             574

SEQ ID NO: 170         moltype = AA  length = 574
FEATURE                Location/Qualifiers
REGION                 1..574
                       note = F protein of human RSV subtype A/AFX95851
source                 1..574
                       mol_type = protein
                       organism = Human respiratory syncytial virus
SEQUENCE: 170
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANSRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSSNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLA  540
LIAVGLLLYC KARSTPVTLG KDQLSGINNI AFNN                             574

SEQ ID NO: 171         moltype = AA  length = 574
FEATURE                Location/Qualifiers
REGION                 1..574
                       note = F protein of human RSV subtype A/AFM55387
source                 1..574
```

```
                        mol_type = protein
                        organism = Human respiratory syncytial virus
SEQUENCE: 171
MELPILKTNA ITIILAAVTL CFASSQNITE EFYQSTCSAV SKGYLSALRT GWYTSVITIE  60
LSNIKENKCN GTDAKVKLIK QELDKYKNAV TELQLLMQST PAANSRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSSNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLA  540
LIAVGLLLYC KARSAPVTLS KDQLSGINNI AFSN                              574

SEQ ID NO: 172          moltype = AA  length = 574
FEATURE                 Location/Qualifiers
REGION                  1..574
                        note = F protein of human RSV subtype A/AFM55530
source                  1..574
                        mol_type = protein
                        organism = Human respiratory syncytial virus
SEQUENCE: 172
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANSRARRE LPRFMNYTLN  120
STKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSSNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQINEKIN QSLAFIRKSD ELLHNVNAGK STTNIMITTI IIVIIVILLA  540
LIAVGLLLYC KARSTPVTLS KDQLSGINNI AFSN                              574

SEQ ID NO: 173          moltype = AA  length = 574
FEATURE                 Location/Qualifiers
REGION                  1..574
                        note = F protein of human RSV subtype A/AEO45919
source                  1..574
                        mol_type = protein
                        organism = Human respiratory syncytial virus
SEQUENCE: 173
MELPILKINA ITTILAAITL CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKNTNVTVS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNVGK STTNIMITTI IIVIIVILLS  540
LIAVGLLLYC KARSTPVTLS KDQLSGINNI AFSN                              574

SEQ ID NO: 174          moltype = AA  length = 573
FEATURE                 Location/Qualifiers
REGION                  1..573
                        note = F protein of human RSV subtype A/AAS93655
source                  1..573
                        mol_type = protein
                        organism = Human respiratory syncytial virus
SEQUENCE: 174
MELPILKTNA ITTILAAATL CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCENAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNVGK STTNIMITTI IIVIIVILLS  540
LIAVGLLLYC KARSTPVTLS KDQLSGINNI AFS                               573

SEQ ID NO: 175          moltype = AA  length = 573
FEATURE                 Location/Qualifiers
REGION                  1..573
                        note = F protein of human RSV subtype A/AAS93656
source                  1..573
                        mol_type = protein
                        organism = Human respiratory syncytial virus
SEQUENCE: 175
```

-continued

```
MELPILKTNA ITTILAAAIL CFTSSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNVGK STTNIMITTI IIVIIVILLS  540
LIAVGLLLYC RARSTPVTLS KDQLSGINNI AFS                              573

SEQ ID NO: 176          moltype = AA  length = 574
FEATURE                 Location/Qualifiers
REGION                  1..574
                        note = F protein of human RSV subtype A/AEO45939
source                  1..574
                        mol_type = protein
                        organism = Human respiratory syncytial virus
SEQUENCE: 176
MDLPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST PASNNRARRE LPRFMNYTLN  120
NTKNTNVTLS KKRKRRFLGF LLGVGSAIAS GIAVSKVLHL EGEVNKIKSA LLSTNKAVVS  180
FIDGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNVGK STTNIMITTI IIVIIVILLS  540
LIAVGLLLYC KARSTPVTLS KDQLSGINNI AFSN                             574

SEQ ID NO: 177          moltype = AA  length = 574
FEATURE                 Location/Qualifiers
REGION                  1..574
                        note = F protein of human RSV subtype A/P11209
source                  1..574
                        mol_type = protein
                        organism = Human respiratory syncytial virus
SEQUENCE: 177
MELPILKTNA ITAILAAVTL CFASSQNITE EFYQSTCSAV SKGYLSALRT GWYTSVITIE  60
LSNIKENKCN GTDAKVKLIK QELDKYKSAV TELQLLMQST PATNNRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPLAETCKV  360
QSNRVFCDTM NSLTLPSEVN LCNIDIFNPK YDCKIMTSKT DVSSSVITSL GAIVSCYGKT  420
KCTASNKDRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFSN                             574

SEQ ID NO: 178          moltype = AA  length = 574
FEATURE                 Location/Qualifiers
REGION                  1..574
                        note = F protein of human RSV subtype A/AAC57027
source                  1..574
                        mol_type = protein
                        organism = Human respiratory syncytial virus
SEQUENCE: 178
MELPILKTNA ITAILAAVTL CFASSQNITE EFYQSTCSAV SKGYLSALRT GWYTSVITIE  60
LSNIKENKCN GTDAKVKLIK QELDKYKSAV TELQLLMQST PATNNRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPLAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFSN                             574

SEQ ID NO: 179          moltype = AA  length = 574
FEATURE                 Location/Qualifiers
REGION                  1..574
                        note = F protein of human RSV subtype A/NP_044596
source                  1..574
                        mol_type = protein
                        organism = Human respiratory syncytial virus
SEQUENCE: 179
MELPILKTNA ITAILAAVTL CFASSQNITE EFYQTTCSAV SKGYLSALRT GWYTSVITIE  60
LSNIKENKCN GTDAKVKLIK QELDKYKSAV TELQLLMQST PATNNRARRE LPRFMNYTLN  120
NTKNTNVTLS KKRKRRFLGF LLGVGSAIAS GIAVSKVLHL EGEVNKIKSA LLSTNKAVVS  180
```

-continued

```
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPLAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STINIMITTI IIVIIVILLS  540
LIAVGLLLYC KARSTPVTLS KDQLSGINNI AFSN                             574

SEQ ID NO: 180         moltype = AA  length = 574
FEATURE                Location/Qualifiers
REGION                 1..574
                       note = F protein of human RSV subtype A/AAM44851
source                 1..574
                       mol_type = protein
                       organism = Human respiratory syncytial virus
SEQUENCE: 180
MELPILKANA ITTILAAVTL CFVSSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKNLYVK GEPIINFYDP  480
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFSS                             574

SEQ ID NO: 181         moltype = AA  length = 574
FEATURE                Location/Qualifiers
REGION                 1..574
                       note = F protein of human RSV subtype A/AFX60127
source                 1..574
                       mol_type = protein
                       organism = Human respiratory syncytial virus
SEQUENCE: 181
MELPILKANA ITTILTAVTL CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKNTNVTLS KKRKRRFLGF LLGVGSAIAS GIAVSKVLHL EGEVNKIKNA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKNLYVK GEPIINFYDP  480
LVFPSDEFDA SISQVNEKIN QSLAFIRKSD ELLHNVNAGK STTNIMITTI IIVIVVILLS  540
LIVVGLLLYC KARSTPVTLS KDQLSGINNI AFSS                             574

SEQ ID NO: 182         moltype = AA  length = 574
FEATURE                Location/Qualifiers
REGION                 1..574
                       note = F protein of human RSV subtype A/AFX60156
source                 1..574
                       mol_type = protein
                       organism = Human respiratory syncytial virus
SEQUENCE: 182
MELPILKANA ITTILAAVIL CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKNTNVTLS KKRKRRFLGF LLGVGSAIAS GIAVSKVLHL EGEVNKIKNA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKNLYVK GEPIINFYDP  480
LVFPSDEFDA SISQVNEKIN QSLAFIRKSD ELLHNVNAGK STTNIMITTI IIVIVVILLS  540
LIVVGLLLYC KARSTPVTLS KDQLSGINNI AFSS                             574

SEQ ID NO: 183         moltype = AA  length = 574
FEATURE                Location/Qualifiers
REGION                 1..574
                       note = F protein of human RSV subtype A/AAO72325
source                 1..574
                       mol_type = protein
                       organism = Human respiratory syncytial virus
SEQUENCE: 183
MELPILKTNA ITTILAAVTL CFASSQNITE EFYQSTCSAV SKGYLSALRT GWYTSVITIE  60
LSNIKENKCN GTDAKAKLIK QELDKYKNAV TELQLLMQST PAANNRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLHLKNYID KQFLPIVNKQ SCSISNIATV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVMD TPCWKLHTSP LCTTNTKEGS NICLTRTDRG WYCDNAGSVS FFPQAETCKV  360
```

-continued

```
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STINIMITTI IIVIIVILLS  540
LIAVGLLLYC KARSTPVTLS KDQLSGINNI AFSS                              574

SEQ ID NO: 184          moltype = AA  length = 574
FEATURE                 Location/Qualifiers
REGION                  1..574
                        note = F protein of human RSV subtype A/P12568
source                  1..574
                        mol_type = protein
                        organism = Human respiratory syncytial virus
SEQUENCE: 184
MELPILKANA ITTILAAVTF CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKKTNVTLS KKRKRRFLGF LLGVGSAIAS GTAVSKVLHL EGEVNKIKSA LLSTNKAVVS  180
LSNGVSVLTS KVLDLKNYID KQLLPIVNKQ SCRISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YASNKGVDTV SVGNTLYYVN KQEGKSLYVK GEPIINFYDP  480
LVFPSDEFDA SISQVNEKIN QSLAFIRKSD ELLHHVNAGK STTNIMITTI IIVIIVILLS  540
LIAVGLLLYC KARSTPVTLS KDQLSGINNI AFSN                              574

SEQ ID NO: 185          moltype = AA  length = 574
FEATURE                 Location/Qualifiers
REGION                  1..574
                        note = F protein of human RSV subtype A/1512372A
source                  1..574
                        mol_type = protein
                        organism = Human respiratory syncytial virus
SEQUENCE: 185
MELPILKANA ITTILAAVTF CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKKTNVTLS KKRKRRFLGF LLGVGSAIAS GTAVSKVLHL EGEVNKIKSA LLSTNKAVVS  180
LSNGVSVLTS KVLDLKNYID KQLLPIVDKQ SCRISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YASNKGVDTV SVGNTLYYVN KQEGKSLYVK GEPIINFYDP  480
LVFPSDEFDA SISQVNEKIN QSLAFIRKSD ELLHHVNAGK STTNIMITTI IIVIIVILLS  540
LIAVGLLLYC KARSTPVTLS KDQLSGINNI AFSN                              574

SEQ ID NO: 186          moltype = AA  length = 574
FEATURE                 Location/Qualifiers
REGION                  1..574
                        note = F protein of human RSV subtype A/AAQ97026
source                  1..574
                        mol_type = protein
                        organism = Human respiratory syncytial virus
SEQUENCE: 186
MELPILKANA ITTILAAVTF CFASSQNITE EFYQSTCSAV SKGYLSALRT GWYTSVITIE  60
LSNIKENKCN GTDAKVKLIK QELDKYKNAV TELQLLMQST SAANNRARRE LPRFMNYTLN  120
NTKKTNVTLS KKRKRRFLGF LLGVGSAIAS GTAVSKVLHL EGEVNKIKSA LLSTNKAVVS  180
LSNGVSVLTS KVLDLKNYID KQLLPIVNKQ SCRISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YGCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHHVNAGK STTNIMITTI IIVIIVILLS  540
LIAVGLLLYC KARSTPVTLS KDQLSGINNI AFSN                              574

SEQ ID NO: 187          moltype = AA  length = 574
FEATURE                 Location/Qualifiers
REGION                  1..574
                        note = F protein of human RSV subtype A/AAQ97031
source                  1..574
                        mol_type = protein
                        organism = Human respiratory syncytial virus
SEQUENCE: 187
MELPILKANA ITTILAAVTF CFASSQNITE EFYQSTCSAV SKGYLSALRT GWYTSVITIE  60
LSNIKENKCN GTDAKVKLIK QELDKYKNAV TELQLLMQST SAANNRARRE LPRFMNYTLN  120
NTKKTNVTLS KKRKRRFLGF LLGVGSAIAS GTAVSKVLHL EGEVNKIKSA LLSTNKAVVS  180
LSNGVSVLTS KVLDLKNYID KQLLPIVNKQ SCRISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHHVNAGK STTNIMITTI IIVIIVILLS  540
```

-continued

```
LIAVGLLLYC KARSTPVTLS KDQLSGINNI AFSN                         574

SEQ ID NO: 188         moltype = AA  length = 574
FEATURE                Location/Qualifiers
REGION                 1..574
                       note = F protein of human RSV subtype A/AAQ97027
source                 1..574
                       mol_type = protein
                       organism = Human respiratory syncytial virus
SEQUENCE: 188
MELPILKANA ITTILAAVTF CFASSQNITE EFYQSTCSAV SKGYLSALRT GWYTSVITIE  60
LSNIKENKCN GTDAKVKLIK QELDKYKNAV TELQLLMQST SAANNRARRE LPRFMNYTLN  120
NTKKTNVTLS KKRKRRFLGF LLGVGSAIAS GTAVSKVLHL EGEVNKIKSA LLSTNKAVVS  180
LSNGVSVLTS KVLDLKNYID KQLLPIVNKQ SCRISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCRIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHHVNAGK STTNIMITTI IIVIIVILLS  540
LIAVGLLLYC KARSTPVTLS KDQLSGINNI AFSN                         574

SEQ ID NO: 189         moltype = AA  length = 574
FEATURE                Location/Qualifiers
REGION                 1..574
                       note = F protein of human RSV subtype A/AAQ97028
source                 1..574
                       mol_type = protein
                       organism = Human respiratory syncytial virus
SEQUENCE: 189
MELPILKANA ITTILAAVTF CFASSQNITE EFYQSTCSAV SKGYLSALRT GWYTSVITIE  60
LSNIKENKCN GTDAKVKLIK QELDKYKNAV TELQLLMQST SAANNRARRE LPRFMNYTLN  120
NTKKTNVTLS KKRKRRFLGF LLGVGSAIAS GTAVSKVLHL EGEVNKIKSA LLSTNKAVVS  180
LSNGVSVLTS KVLDLKNYID KQLLPIVNKQ SCRISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFEA SISQVNEKIN QSLAFIRKSD ELLHHVNAGK STTNIMITTI IIVIIVILLS  540
LIAVGLLLYC KARSTPVTLS KDQLSGINNI AFSN                         574

SEQ ID NO: 190         moltype = AA  length = 574
FEATURE                Location/Qualifiers
REGION                 1..574
                       note = F protein of human RSV subtype A/AAQ97029
source                 1..574
                       mol_type = protein
                       organism = Human respiratory syncytial virus
SEQUENCE: 190
MELPILKANA ITTILAAVTF CFASSQNITE EFYQSTCSAV SKGYLSALRT GWYTSVITIE  60
LSNIKENKCN GTDAKVKLIK QELDKYKNAV TELQLLMQST SAANNRARRE LPRFMNYTLN  120
NTKKTNVTLS KKRKRRFLGL LLGVGSAIAS GTAVSKVLHL EGEVNKIKSA LLSTNKAVVS  180
LSNGVSVLTS KVLDLKNYID KQLLPIVNKQ SCRISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHHVNAGK STTNIMITTI IIVIIVILLS  540
LIAVGLLLYC KARSTPVTLS KDQLSGINNI AFSN                         574

SEQ ID NO: 191         moltype = AA  length = 574
FEATURE                Location/Qualifiers
REGION                 1..574
                       note = F protein of human RSV subtype A/AAQ97030
source                 1..574
                       mol_type = protein
                       organism = Human respiratory syncytial virus
SEQUENCE: 191
MELPILKANA ITTILAAVTF CFASSQNITE EFYQSTCSAV SKGYLSALRT GWYTSVITIE  60
LSNIKENKCN GTDAKVKLIK QELDKYKNAV TELQLLMQST SAANNRARRE LPRFMNYTLN  120
NTKKTNVTLS KKRKRRFLGF LLGAGSAIAS GTAVSKVLHL EGEVNKIKSA LLSTNKAVVS  180
LSNGVSVLTS KVLDLKNYID KQLLPIVNKQ SCRISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHHVNAGK STTNIMITTI IIVIIVILLS  540
LIAVGLLLYC KARSTPVTLS KDQLSGINNI AFSN                         574

SEQ ID NO: 192         moltype = AA  length = 574
```

```
FEATURE                Location/Qualifiers
REGION                 1..574
                       note = F protein of human RSV subtype A/ABQ42594
source                 1..574
                       mol_type = protein
                       organism = Human respiratory syncytial virus
SEQUENCE: 192
MELPILKANA ITTILAAVTF CFASSQNITE EFYQSTCSAV SKGYLSALRT GWYTSVITIE  60
LSNIKENKCN GTDAKVKLMK QELDKYKNAV TELQLLMQST PAANNRARRE LPRFMNYTLN  120
NTKKTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCRISNIETV IEFQQKNNRL LEITREFSVN  240
VGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFSN                              574

SEQ ID NO: 193         moltype = AA  length = 574
FEATURE                Location/Qualifiers
REGION                 1..574
                       note = F protein of human RSV subtype A/CAA81295
source                 1..574
                       mol_type = protein
                       organism = Human respiratory syncytial virus
SEQUENCE: 193
MELPILKANA ITTILAAVTF CFASSQNITE EFYQSTCSAV SKGYLSALRT GWYTSVITIE  60
LSNIKENKCN GTDAKVKLMK QELDKYKNAV TELQLLMQST PAANNRARRE LPRFMNYTLN  120
NTKKTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCRISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFSN                              574

SEQ ID NO: 194         moltype = AA  length = 574
FEATURE                Location/Qualifiers
REGION                 1..574
                       note = F protein of human RSV subtype A/ACO83302
source                 1..574
                       mol_type = protein
                       organism = Human respiratory syncytial virus
SEQUENCE: 194
MELPILKANA ITTILAAVTF CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKKTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCRISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHHVNAGK STTNIMITTI IIVIIVILLS  540
LIAVGLLLYC KARSTPVTLS KDQLSGINNI AFSN                              574

SEQ ID NO: 195         moltype = AA  length = 574
FEATURE                Location/Qualifiers
REGION                 1..574
                       note = F protein of human RSV subtype A/ADZ95781
source                 1..574
                       mol_type = protein
                       organism = Human respiratory syncytial virus
SEQUENCE: 195
MELPILKANA ITTILAAVTF CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKKTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCRISNIETV IEFQQKNNRL LEITREFSVN  240
AGVTTPVSTY MLTNSELLSL INDMPITNDQ KNLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHHVNAGK STTNIMITTI IIVIIVILLS  540
LIAVGLLLYC KARSTPVTLS KDQLSGINNI AFSN                              574

SEQ ID NO: 196         moltype = AA  length = 574
FEATURE                Location/Qualifiers
REGION                 1..574
                       note = F protein of human RSV subtype A/ADZ95782
```

```
                         -continued
source               1..574
                     mol_type = protein
                     organism = Human respiratory syncytial virus
SEQUENCE: 196
MELPILKANA ITTILAAVTF CFASSQNITE EFYQSTCSAV SKGYLSALRT GWYTSVITIE    60
LSNIKENKCN GTDAKVKLIK QELDKYKNAV TELQLLMQST PAANNRARRE LPRFMNYTLN   120
NTKKTNVTLS KKRKRRFLGF LLGVGSAIAS GIAVSKVLHL EGEVNKIKSA LLSTNKAVVS   180
LSNGVSVLTS KVLDLKNYID KQLLPIVNKQ SCRISNIETV IEFQQKNNRL LEITREFSVN   240
AGVTTPVSTY MLTNSELLSL INDMPITNDQ KMLMSNNVQI VRQQSYSIMS IIKEEVLAYV   300
VQLPLYGVID TPCWKLHTSP LCTTNTKEGS NICLTRTDRG WYCDNAGSVS FFPQAETCKV   360
QSNRVFCDTM NSLTLPSEVN LCNVDIFNPK YDCKIMTSKT DVSSSVITSL GAIVSCYGKT   420
KCTASNKNRG IIKTFSNGCD YVSNKGVDTV SVGNTLYYVN KQEGKSLYVK GEPIINFYDP   480
LVFPSDEFDA SISQVNEKIN QSLAFIRKSD ELLHHVNAGK STTNIMITTI IIVIIVILLS   540
LIAVGLLLYC KARSTPVTLS KDQLSGINNI AFSN                              574

SEQ ID NO: 197       moltype = AA  length = 574
FEATURE              Location/Qualifiers
REGION               1..574
                     note = F protein of human RSV subtype A/ADZ95783
source               1..574
                     mol_type = protein
                     organism = Human respiratory syncytial virus
SEQUENCE: 197
MELPILKANA ITTILAAVTF CFASSQNITE EFYQSTCSAV SKGYLSALRT GWYTSVITIE    60
LSNIKENKCN GTDAKVKLIK QELDKYKNAV TELQLLMQST PAANNRARRE LPRFMNYTLN   120
NTKKTNVTLS KKRKRRFLGF LLGVGSAIAS GIAVSKVLHL EGEVNKIKSA LLSTNKAVVS   180
LSNGVSVLTS KVLDLKNYID KQLLPIVNKQ SCRISNIETV IEFQQKNNRL LEITREFSVN   240
AGVTTPVSTY MLTNSELLSL INDMPITNDQ KTLMSNNVQI VRQQSYSIMS IIKEEVLAYV   300
VQLPLYGVID TPCWKLHTSP LCTTNTKEGS NICLTRTDRG WYCDNAGSVS FFPQAETCKV   360
QSNRVFCDTM NSLTLPSEVN LCNVDIFNPK YDCKIMTSKT DVSSSVITSL GAIVSCYGKT   420
KCTASNKNRG IIKTFSNGCD YVSNKGVDTV SVGNTLYYVN KQEGKSLYVK GEPIINFYDP   480
LVFPSDEFDA SISQVNEKIN QSLAFIRKSD ELLHHVNAGK STTNIMITTI IIVIIVILLS   540
LIAVGLLLYC KARSTPVTLS KDQLSGINNI AFSN                              574

SEQ ID NO: 198       moltype = AA  length = 574
FEATURE              Location/Qualifiers
REGION               1..574
                     note = F protein of human RSV subtype A/ADZ95784
source               1..574
                     mol_type = protein
                     organism = Human respiratory syncytial virus
SEQUENCE: 198
MELPILKANA ITTILAAVTF CFASSQNITE EFYQSTCSAV SKGYLSALRT GWYTSVITIE    60
LSNIKENKCN GTDAKVKLIK QELDKYKNAV TELQLLMQST PAANNRARRE LPRFMNYTLN   120
NTKKTNVTLS KKRKRRFLGF LLGVGSAIAS GIAVSKVLHL EGEVNKIKSA LLSTNKAVVS   180
LSNGVSVLTS KVLDLKNYID KQLLPIVNKQ SCRISNIETV IEFQQKNNRL LEITREFSVN   240
AGVTTPVSTY MLTNSELLSL INDMPITNDQ KQLMSNNVQI VRQQSYSIMS IIKEEVLAYV   300
VQLPLYGVID TPCWKLHTSP LCTTNTKEGS NICLTRTDRG WYCDNAGSVS FFPQAETCKV   360
QSNRVFCDTM NSLTLPSEVN LCNVDIFNPK YDCKIMTSKT DVSSSVITSL GAIVSCYGKT   420
KCTASNKNRG IIKTFSNGCD YVSNKGVDTV SVGNTLYYVN KQEGKSLYVK GEPIINFYDP   480
LVFPSDEFDA SISQVNEKIN QSLAFIRKSD ELLHHVNAGK STTNIMITTI IIVIIVILLS   540
LIAVGLLLYC KARSTPVTLS KDQLSGINNI AFSN                              574

SEQ ID NO: 199       moltype = AA  length = 574
FEATURE              Location/Qualifiers
REGION               1..574
                     note = F protein of human RSV subtype A/ADZ95785
source               1..574
                     mol_type = protein
                     organism = Human respiratory syncytial virus
SEQUENCE: 199
MELPILKANA ITTILAAVTF CFASSQNITE EFYQSTCSAV SKGYLSALRT GWYTSVITIE    60
LSNIKENKCN GTDAKVKLIK QELDKYKNAV TELQLLMQST PAANNRARRE LPRFMNYTLN   120
NTKKTNVTLS KKRKRRFLGF LLGVGSAIAS GIAVSKVLHL EGEVNKIKSA LLSTNKAVVS   180
LSNGVSVLTS KVLDLKNYID KQLLPIVNKQ SCRISNIETV IEFQQKNNRL LEITREFSVN   240
AGVTTPVSTY MLTNSELLSL INDMPITNDQ KELMSNNVQI VRQQSYSIMS IIKEEVLAYV   300
VQLPLYGVID TPCWKLHTSP LCTTNTKEGS NICLTRTDRG WYCDNAGSVS FFPQAETCKV   360
QSNRVFCDTM NSLTLPSEVN LCNVDIFNPK YDCKIMTSKT DVSSSVITSL GAIVSCYGKT   420
KCTASNKNRG IIKTFSNGCD YVSNKGVDTV SVGNTLYYVN KQEGKSLYVK GEPIINFYDP   480
LVFPSDEFDA SISQVNEKIN QSLAFIRKSD ELLHHVNAGK STTNIMITTI IIVIIVILLS   540
LIAVGLLLYC KARSTPVTLS KDQLSGINNI AFSN                              574

SEQ ID NO: 200       moltype = AA  length = 574
FEATURE              Location/Qualifiers
REGION               1..574
                     note = F protein of human RSV subtype A/AAX23994
source               1..574
                     mol_type = protein
                     organism = Human respiratory syncytial virus
```

-continued

```
SEQUENCE: 200
MELPILKANA ITTILAAVTF CFASSQNITE EFYQSTCSAV SKGYLSALRT GWYTSVITIE  60
LSNIKENKCN GTDAKVKLIN QELDKYKNAV TELQLLMQST TAANNRARRE LPRFMNYTLN  120
NTKKTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCRISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHHVNAGK STTNIMITTI IIVIIVILLS  540
LIAVGLLLYC KARSTPVTLS KDQLSGINNI AFSN                             574

SEQ ID NO: 201         moltype = AA  length = 574
FEATURE                Location/Qualifiers
REGION                 1..574
                       note = F protein of human RSV subtype A/AC083297
source                 1..574
                       mol_type = protein
                       organism = Human respiratory syncytial virus
SEQUENCE: 201
MELPILKANA ITTILAAVTF CFASSQNITE EFYQSTCSAV SKGYLSALRT GWYTSVITIE  60
LSNIKKNKCN GTDAKVKLMK QELDKYKNAV TELQLLMQST PAANNRARRE LPRFMNYTLN  120
NTKKTNVTLS KKRKRRFLGF LLGVGSAIAS GIAVSKVLHL EGEVNKIKSA LLSTNKAVVS  180
LSNGVSVLTS RVLDLKNYID KQLLPIVNKQ SCRISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAEKCKV  360
QSNRVFCDTM YSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLS  540
LIAVGLLLYC KARSTPITLS KDQLSGINNI AFSN                             574

SEQ ID NO: 202         moltype = AA  length = 574
FEATURE                Location/Qualifiers
REGION                 1..574
                       note = F protein of human RSV subtype A/AEQ63378
REGION                 428..435
                       note = misc_feature - X can be any naturally occurring
                        amino acid
source                 1..574
                       mol_type = protein
                       organism = Human respiratory syncytial virus
SEQUENCE: 202
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQSA PAANSRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSSNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKXXX XXXXXSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLA  540
LIAVGLLLYC KARSTPVTLS KDQLSGINNI AFSN                             574

SEQ ID NO: 203         moltype = AA  length = 574
FEATURE                Location/Qualifiers
REGION                 1..574
                       note = F protein of human RSV subtype A/AEO45889
source                 1..574
                       mol_type = protein
                       organism = Human respiratory syncytial virus
SEQUENCE: 203
MELPILKTNA ITTIFAAVTL CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKNNNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNVGK STTNIMITTI IIVIIVILLL  540
LIAVGLFLYC KARSTPVTVI DDYLSGINNI SFIY                             574

SEQ ID NO: 204         moltype = AA  length = 574
FEATURE                Location/Qualifiers
REGION                 1..574
                       note = F protein of human RSV subtype A/AAC55970
source                 1..574
                       mol_type = protein
                       organism = Human respiratory syncytial virus
```

```
SEQUENCE: 204
MELLILKANA ITTILTAVTF CFASGQNITE EFYQSTCSAV SKGYLSALRT GWYTSVITIE  60
LSNIKENKCN GTDAKVKLIK QELDKYKNAV TELQLLMQST PATNNRARRE LPRFMNYTLN  120
NAKKTNVTLS KKRKRRFLGF LLGVGSAIAS GVAVSKVLHL EGEVNKIKSA LLSTNKAVVS  180
LSNGVSVLTS KVLDLKNYID KQLLPIVNKQ SCSISNIATV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STINIMITTI IIVIIVILLS  540
LIAVGLLLYC KARSTPVTLS KDQLSGINNI AFSN                            574

SEQ ID NO: 205         moltype = AA  length = 574
FEATURE                Location/Qualifiers
REGION                 1..574
                       note = F protein of human RSV subtype A/CAA26143
source                 1..574
                       mol_type = protein
                       organism = Human respiratory syncytial virus
SEQUENCE: 205
MELLILKANA ITTILTAVTF CFASGQNITE EFYQSTCSAV SKGYLSALRT GWYTSVITIE  60
LSNIKENKCN GTDAKVKLIK QELDKYKNAV TELQLLMQST PATNNRARRE LPRFMNYTLN  120
NAKKTNVTLS KKRKRRFLGF LLGVGSAIAS GVAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WFCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFSN                            574

SEQ ID NO: 206         moltype = AA  length = 574
FEATURE                Location/Qualifiers
REGION                 1..574
                       note = F protein of human RSV subtype A/ACO83301
source                 1..574
                       mol_type = protein
                       organism = Human respiratory syncytial virus
SEQUENCE: 206
MELLILKANA ITTILTAVTF CFASGQNITE EFYQSTCSAV SKGYLSALRT GWYTSVITIE  60
LSNIKKNKCN GTDAKIKLIK QELDKYKNAV TELQLLMQST PATNNRARRE LPRFMNYTLN  120
NAKKTNVTLS KKRKRRFLGF LLGVGSAIAS GVAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAVK STTNIMITTI IIVIIVILLS  540
LIAVGLLLYC KARSTPVTLS KDQLSGINNI AFSN                            574

SEQ ID NO: 207         moltype = AA  length = 574
FEATURE                Location/Qualifiers
REGION                 1..574
                       note = F protein of human RSV subtype A/AEQ63564
source                 1..574
                       mol_type = protein
                       organism = Human respiratory syncytial virus
SEQUENCE: 207
MELLILKANA ITTILTAVTF CFASGQNITE EFYQSTCSAV SKGYLSALRT GWYTSVITIE  60
LSNIKKNKCN GTDAKVKLIK QELDKYKNAV TELQLLMQST QATNNRARRE LPRFMNYTLN  120
NAKKTNVTLS KKRKRRFLGF LLGVGSAIAS GVAVSKVLHL EGEVNKIKSA LLSTNKAVVS  180
LSNGVSVLTS KVLDLKNYID KQVLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFSN                            574

SEQ ID NO: 208         moltype = AA  length = 574
FEATURE                Location/Qualifiers
REGION                 1..574
                       note = F protein of human RSV subtype A/AGG39418
source                 1..574
                       mol_type = protein
                       organism = Human respiratory syncytial virus
SEQUENCE: 208
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
```

```
NTKTTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNTDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFSS                             574

SEQ ID NO: 209         moltype = AA  length = 574
FEATURE                Location/Qualifiers
REGION                 1..574
                       note = F protein of human RSV subtype A/AGG39397
source                 1..574
                       mol_type = protein
                       organism = Human respiratory syncytial virus
SEQUENCE: 209
MELPIIKANA ITTILIAVTF CFASSQNITE EFYQSTCSAV SKGYLSALRT GWYTSVITIE  60
LSNIKENKCN GTDAKVKLIK QELDKYKNAV TELQLLMQST TAANNRARRE LPRFMNYTLN  120
NAKKTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQADTCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFSN                             574

SEQ ID NO: 210         moltype = AA  length = 574
FEATURE                Location/Qualifiers
REGION                 1..574
                       note = F protein of human RSV subtype A/AHY21463
source                 1..574
                       mol_type = protein
                       organism = Human respiratory syncytial virus
SEQUENCE: 210
MELPILKTNA ITTIFAAVTL CFASSQNITE EFYQSTCSAV SKGYLSALRT GWYTSVITVE  60
LSNIKENKCN GTDAKVKLIK QELDKYKNAV TELQLLMQST PAANNRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFSN                             574

SEQ ID NO: 211         moltype = AA  length = 574
FEATURE                Location/Qualifiers
REGION                 1..574
                       note = F protein of human RSV subtype B/BAE96918
source                 1..574
                       mol_type = protein
                       organism = Human respiratory syncytial virus
SEQUENCE: 211
MELLIHRSSA IFLTLAINAL YLTSSQNITE EFYQSTCSAV SRGYFSALRT GWYTSVITIE  60
LSNIKETKCN GTDTKVKLIK QELDKYKNAV TELQLLMQNT PAANNRARRE APQYMNYTIN  120
TTKNLNVSIS KKRKRRFLGF LLGVGSAIAS GIAVSKVLHL EGEVNKIKNA LLSTNKAVVS  180
LSNGVSVLTS KVLDLKNYIN NQLLPIVNQQ SCRISNIETV IEFQQKNSRL LEITREFSVN  240
AGVTTPLSTY MLTNSELLSL INDMPITNDQ KKLMSSNVQI VRQQSYSIMS IMKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKNRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITVI IIVIIVVLLS  540
LIAIGLLLYC KAKNTPVTLS KDQLSGINNI AFSK                             574

SEQ ID NO: 212         moltype = AA  length = 574
FEATURE                Location/Qualifiers
REGION                 1..574
                       note = F protein of human RSV subtype B/AFD34266
source                 1..574
                       mol_type = protein
                       organism = Human respiratory syncytial virus
SEQUENCE: 212
MELLIHRSSA IFLTLAINAL YLTSSQNITE EFYQSTCSAV SRGYFSALRT GWYTSVITIE  60
LSNIKETKCN GTDTKVKLIK QELDKYKNAV TELQLLMQNT PAANNRARRE APQYMNYTIN  120
TTKNLNVSIS KKRKRRFLGF LLGVGSAIAS GIAVSKVLHL EGEVNKIKNA LLSTNKAVVS  180
LSNGVSVLTS KVLDLKNYIN NQLLPIVNQQ SCRISNIETV IEFQQKNSRL LEITREFSVN  240
AGVTTPLSTY MLTNSELLSL INDMPITNDQ KKLMSSNVQI VRQQSYSIMS IIKEEVLAYV  300
```

-continued

```
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKNRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITVI IIVIIVVLLS  540
LIAIGLLLYC KAKNTPVTLS KDQLSGINNI AFSK                              574

SEQ ID NO: 213         moltype = AA  length = 574
FEATURE                Location/Qualifiers
REGION                 1..574
                       note = F protein of human RSV subtype B/AFP99059
source                 1..574
                       mol_type = protein
                       organism = Human respiratory syncytial virus
SEQUENCE: 213
MELLIHRSSA IFLTLAINAL YLTSSQNITE EFYQSTCSAV SRGYLSALRT GWYTSVITIE  60
LSNIKETKCN GTDTKVKLIK QELDKYKNAV TELQLLMQNT PAANNRARRE APQYMNYTIN  120
TTKNLNVSIS KKRKRRFLGF LLGVGSAIAS GIAVSKVLHL EGEVNKIKNA LLSTNKAVVS  180
LSNGVSVLTS KVLDLKNYIN NQLLPIVNQQ SCRISNIETV IEFQQKNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKNRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITVI IIVIIVVLLS  540
LIAIGLLLYC KAKNTPVTLS KDQLSGINNI AFSK                              574

SEQ ID NO: 214         moltype = AA  length = 574
FEATURE                Location/Qualifiers
REGION                 1..574
                       note = F protein of human RSV subtype B/AFP99064
source                 1..574
                       mol_type = protein
                       organism = Human respiratory syncytial virus
SEQUENCE: 214
MELLIHRSSA IFLTLAINAL YLTSSQNITE EFYQSTCSAV SRGYLSALRT GWYTSVITIE  60
LSNIKETKCN GTDTKVKLIK QELDKYKNAV TELQLLMQNT PAANNRARRE APQYMNYTIN  120
TTKNLNVSIS KKRKRRFLGF LLGVGSAIAS GVAVSKVLHL EGEVNKIKNA LLSTNKAVVS  180
LSNGVSVLTS KVLDLKNYIN NQLLPIVNQQ SCRISNIETV IEFQQKNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKNRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITVI IIVIIVVLLS  540
LIAIGLLLYC KAKNTPVTLS KDQLSGINNI AFSK                              574

SEQ ID NO: 215         moltype = AA  length = 574
FEATURE                Location/Qualifiers
REGION                 1..574
                       note = F protein of human RSV subtype B/AFD34259
source                 1..574
                       mol_type = protein
                       organism = Human respiratory syncytial virus
SEQUENCE: 215
MELLIYRSSA IFLTLAINAL YLTSSQNITE EFYQSTCSAV SRGYFSALRT GWYTSVITIE  60
LSNIKETKCN GTDTKVKLIK QELDKYKNAV TELQLLMQNT PAANNRARRE APQYMNYTIN  120
TTKNLNVSIS KKRKRRFLGF LLGVGSAIAS GMAVSKVLHL EGEVNKIKNA LLSTNKAVVS  180
LSNGVSVLTS KVLDLKNYIN NQLLPIVNQQ SCRISNIETV IEFQQKNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKNRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITVI IIVIIVVLLS  540
LIAIGLLLYC KAKNTPVTLS KDQLSGINNI AFSK                              574

SEQ ID NO: 216         moltype = AA  length = 574
FEATURE                Location/Qualifiers
REGION                 1..574
                       note = F protein of human RSV subtype B/ADZ95780
SITE                   275
                       note = misc_feature - X can be any naturally occurring
                        amino acid
source                 1..574
                       mol_type = protein
                       organism = Human respiratory syncytial virus
SEQUENCE: 216
MELLIHRSSA IFLTLAINAL YLTSSQNITE EFYQSTCSAV SRGYFSALRT GWYTSVITIE  60
LSNIKETKCN GTDTKVKLIK QELDKYKNAV TELQLLMQNT PAANNRARRE APQYMNYTIN  120
TTKNLNVSIS KKRKRRFLGF LLGVGSAIAS GIAVSKVLHL EGEVNKIKNA LLSTNKAVVS  180
LSNGVSVLTS KVLDLKNYIN NQLLPIVNQQ SCRISNIETV IEFQQKNSRL LEITREFSVN  240
AGVTTPLSTY MLTNSELLSL INDMPITNDQ KKLMXSNVQI VRQQSYSIMS IIKEEVLAYV  300
```

```
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKNRG IIKTFSNGCD YVSNKGVDTV SVGNTLYYVN KLEGKNLYVR GEPIINYYDP  480
LVFPSDEFDA SISQVNEKIN QSLAFIRRSD ELLHNVNTGK STTNIMITVI IIVIIVVLLS  540
LIAIGLLLYC KAKNTPVTLS KDQLSGINNI AFSK                              574

SEQ ID NO: 217         moltype = AA  length = 574
FEATURE                Location/Qualifiers
REGION                 1..574
                       note = F protein of human RSV subtype B/ADZ95776
SITE                   272
                       note = misc_feature - X can be any naturally occurring
                        amino acid
source                 1..574
                       mol_type = protein
                       organism = Human respiratory syncytial virus
SEQUENCE: 217
MELLIHRSSA IFLTLAINAL YLTSSQNITE EFYQSTCSAV SRGYFSALRT GWYTSVITIE  60
LSNIKETKCN GTDTKVKLIK QELDKYKNAV TELQLLMQNT PAANNRARRE APQYMNYTIN  120
TTKNLNVSIS KKRKRRFLGF LLGVGSAIAS GIAVSKVLHL EGEVNKIKNA LLSTNKAVVS  180
LSNGVSVLTS KVLDLKNYIN NQLLPIVNQQ SCRISNIETV IEFQQKNSRL LEITREFSVN  240
AGVTTPLSTY MLTNSELLSL INDMPITNDQ KXLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKNRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITAI IIVIIVVLLS  540
LIAIGLLLYC KAKNTPVTLS KDQLSGINNI AFSK                              574

SEQ ID NO: 218         moltype = AA  length = 574
FEATURE                Location/Qualifiers
REGION                 1..574
                       note = F protein of human RSV subtype B/ADZ95779
source                 1..574
                       mol_type = protein
                       organism = Human respiratory syncytial virus
SEQUENCE: 218
MELLIHRSSA IFLTLAINAL YLTSSQNITE EFYQSTCSAV SRGYFSALRT GWYTSVITIE  60
LSNIKETKCN GTDTKVKLIK QELDKYKNAV TELQLLMQNT PAANNRARRE APQYMNYTIN  120
TTKNLNVSIS KKRKRRFLGF LLGVGSAIAS GIAVSKVLHL EGEVNKIKNA LLSTNKAVVS  180
LSNGVSVLTS KVLDLKNYIN NQLLPIVNQQ SCRISNIETV IEFQQKNSRL LEITREFSVN  240
AGVTTPLSTY MLTNSELLSL INDMPITNDQ KKLMLSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKNRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITAI IIVIIVVLLS  540
LIAIGLLLYC KAKNTPVTLS KDQLSGINNI AFSK                              574

SEQ ID NO: 219         moltype = AA  length = 574
FEATURE                Location/Qualifiers
REGION                 1..574
                       note = F protein of human RSV subtype B/AFD34262
source                 1..574
                       mol_type = protein
                       organism = Human respiratory syncytial virus
SEQUENCE: 219
MELLIHRSSA IFLTLAINAL YLTSSQNITE EFYQSTCSAV SRGYFSALRT GWYTSVITIE  60
LSNIKETKCN GTDTKVKLIK QELDKYKNAV TELQLLMQNT PAANNRARRE APQYMNYTIN  120
TTKNLNVSIS KKRKRRFLGF LLGVGSAIAS GIAVSKVLHL EGEVNKIKNA LLSTNKAVVS  180
LSNGVSVLTS KVLDLKNYIN NQLLPIVNQQ SCRISNIETV IEFQQKNSRL LEITREFSVN  240
AGVTTPLSTH MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKNRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITAI IIVIIVVLLS  540
LIAIGLLLYC KAKNTPVTLS KDQLSGINNI AFSK                              574

SEQ ID NO: 220         moltype = AA  length = 573
FEATURE                Location/Qualifiers
REGION                 1..573
                       note = F protein of human RSV subtype B/AAS93660
source                 1..573
                       mol_type = protein
                       organism = Human respiratory syncytial virus
SEQUENCE: 220
MELLIHRSSA IFLTLAINAL YLTSSQNITE EFYQSTCSVV SRGYFSALRT GWYTSVITIE  60
LSNIKETKCN GTDTKVKLIK QELDKYKNAV TELQLLMQNT PAANNRARRE APQYMNYTIN  120
TTKNLNVSIS KKRKRRFLGF LLGVGSAIAS GIAVSKVLHL EGEVNKIKNA LLSTNKAVVS  180
LSNGVSVLTS KVLDLKNYIN NQLLPIVNQQ SCRISNIETV IEFQQKNSRL LEITREFSVN  240
AGVTTPLSTY MLTNSELLSL INDMPITNDQ KKLMSSNVQI VRQQSYSIMS IIKEEVLAYV  300
```

```
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKNRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITAI IIVIIVVLLS  540
LIAIGLLLYC KAKNTPVTLS KDQLSGINNI AFR                               573

SEQ ID NO: 221         moltype = AA  length = 573
FEATURE                Location/Qualifiers
REGION                 1..573
                       note = F protein of human RSV subtype B/AAS93661
source                 1..573
                       mol_type = protein
                       organism = Human respiratory syncytial virus
SEQUENCE: 221
MELLIHRSSA IFLTLAINAL YLTSSQNITE EFYQSTCSAV SRGYFSALRT GWYTSVITIE  60
LSNIKETKCN GTDTKVKLIK QELDKYKNAV TELQLLMQNT PAANNRARRE APQYMNYTIN  120
TTKNLNVSIS KKRKRRFLGF LLGVGSAIAS GIAVSKVLHL EGEVNKIKNA LLSTNKAVVS  180
LSNGVSVLTS KVLDLKNYIN NQLLPIVNQQ SCRISNIETV IEFQQKNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKNRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITAI IIVIIVVLLS  540
LIAIGLLLYC KAKNTPVTLS KDQLSGINNI AFR                               573

SEQ ID NO: 222         moltype = AA  length = 573
FEATURE                Location/Qualifiers
REGION                 1..573
                       note = F protein of human RSV subtype B/AAS93663
source                 1..573
                       mol_type = protein
                       organism = Human respiratory syncytial virus
SEQUENCE: 222
MELLIHRSSA IFLTFAINAL YLTSSQNITE EFYQSTCSAV SRGYFSALRT GWYTSVITIE  60
LSNIKETKCN GTDTKVKLIK QELDKYKNAV TELQLLMQNT PAANNRARRE APQYMNYTIN  120
TTKNLNVSIS KKRKRRFLGF LLGVGSAIAS GIAVSKVLHL EGEVNKIKNA LLSTNKAVVS  180
LSNGVSVLTS KVLDLKNYIN NQLLPIVNQQ SCRISNIETV IEFQQKNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKNRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITAI IIVIIVVLLS  540
LIAIGLLLYC KAKNTPVTLS KDQLSGINNI AFR                               573

SEQ ID NO: 223         moltype = AA  length = 573
FEATURE                Location/Qualifiers
REGION                 1..573
                       note = F protein of human RSV subtype B/AAS93664
source                 1..573
                       mol_type = protein
                       organism = Human respiratory syncytial virus
SEQUENCE: 223
MELLIHRSSA IFLTLAINAL YLTSSQNITE EFYQSTCSAV SRGYFSALRT GWYTSVITIE  60
LSNIKETKCN GTDTKVKLIK QELDKYKNAV TELQLLMQNT PAANNRARRE APHYMNYTIN  120
TTKNLNVSIS KKRKRRFLGF LLGVGSAIAS GIAVSKVLHL EGEVNKIKNA LLSTNKAVVS  180
LSNGVSVLTS KVLDLKNYIN NQLLPIVNQQ SCRISNIETV IEFQQKNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKNRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITAI IIVIIVVLLS  540
LIAIGLLLYC KAKNTPVTLS KDQLSGINNI AFR                               573

SEQ ID NO: 224         moltype = AA  length = 564
FEATURE                Location/Qualifiers
REGION                 1..564
                       note = F protein of human RSV subtype B/AEN74946
source                 1..564
                       mol_type = protein
                       organism = Human respiratory syncytial virus
SEQUENCE: 224
MELLIHRSSA IFLTLAINAL YLTSSQNITE EFYQSTCSAV SRGYFSALRT GWYTSVITIE  60
LSNIKETKCN GTDTKVKLIK QELDKYKNAV TELQLLMQNT PAANNRARRE APQYMNYTIN  120
TTKNLNVSIS KKRKRRFLGF LLGVGSAIAS GIAVSKVLHL EGEVNKIKNA LLSTNKAVVS  180
LSNGVSVLTS KVLDLKNYIN NQLLPIVNKQ SCRISNIETV IEFQQKNSRL LEITREFSVN  240
AGVTTPLSTY MLTNSELLSL INDMPITNDQ KKLMSSNAQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKNRG IIKTFSNGCD YVSNKGVDTV SVGNTLYYVN KLEGKNLYVK GEPIINYYDP  480
```

-continued

```
LVFPSDEFDA SISQVNEKIN QSLAFIRRSD ELLHNVNTGK STTNIMITAI IIVIIVVLLS  540
LIAIGLLLYC KAKNTPVTLS KDQL                                         564

SEQ ID NO: 225         moltype = AA  length = 574
FEATURE                Location/Qualifiers
REGION                 1..574
                       note = F protein of human RSV subtype B/AFX60215
source                 1..574
                       mol_type = protein
                       organism = Human respiratory syncytial virus
SEQUENCE: 225
MELLIHRSSA IFLTLAINAL YLTSSQNITE EFYQSTCSAV SRGYFSALRT GWYTSVITIE  60
LSNIKETKCN GTDTKVKLIK QELDKYKNAV TELQLLMQNT PAANNRARRE APQYMNYTIN  120
TTKNLNVSIS KKRKRRFLGF LLGVGSAIAS GIAVSKVLHL EGEVNKIKNA LLSTNKAVVS  180
LSNGVSVLTS KVLDLKNYIN NQLLPIVNKQ SCRISNIETV IEFQQKNSRL LEITREFSVN  240
AGVTTPLSTY MLTNSELLSL INDMPITNDQ KKLMSSNAQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKNRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITAI IIVIIVVLLS  540
LIAIGLLLYC KAKNTPVTLS KDQLSGINNI AFSK                              574

SEQ ID NO: 226         moltype = AA  length = 574
FEATURE                Location/Qualifiers
REGION                 1..574
                       note = F protein of human RSV subtype B/AFD34260
source                 1..574
                       mol_type = protein
                       organism = Human respiratory syncytial virus
SEQUENCE: 226
MELLIHRSSA IFLTLAINAL YLTSSQNITE EFYQSTCSAV SRGYFSALRT GWYTSVITIE  60
LSNIKETKCN GTDTKVKLIK QELDKYKNAV TELQLLMQNT PAANNRARRE APQYMNYTIN  120
TTKNLNVSIS KKRKRRFLGF LLGVGSAIAS GIAVSKVLHL EGEVNKIKNA LLSTNKAVVS  180
LSNGVSVLTS KVLDLKNYIN NQLLPIVNKQ SCRISNIETV IEFQQKNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DVSSSVITSL GAIVSCYGKT  420
KCTASNKNRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITAI IIVIIVVLLS  540
LIAIGLLLYC KAKNTPVTLS KDQLSGINNI AFSK                              574

SEQ ID NO: 227         moltype = AA  length = 574
FEATURE                Location/Qualifiers
REGION                 1..574
                       note = F protein of human RSV subtype B/AEO23054
source                 1..574
                       mol_type = protein
                       organism = Human respiratory syncytial virus
SEQUENCE: 227
MELLIHRSSA IFLTLAINAL YLTSSQNITE EFYQSTCSAV SRGYFSALRT GWYTSVITIE  60
LSNIKETKCN GTDTKVKLIK QELDKYKNAV TELQLLMQNT PAANNRARRE APQYMNYTIN  120
TTKNLNVSTS KKRKRRFLGF LLGVGSAIAS GIAVSKVLHL EGEVNKIKNA LLATNKAVVS  180
LSNGVSVLTS KVLDLKNYIN NQLLPIVNQQ SCRISNIETV IEFQQKNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKNRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITAI IIVIIVVLLS  540
LIAIGLLLYC KAKNTPVTLS KDQLSGINNI AFSK                              574

SEQ ID NO: 228         moltype = AA  length = 574
FEATURE                Location/Qualifiers
REGION                 1..574
                       note = F protein of human RSV subtype B/AFI25262
source                 1..574
                       mol_type = protein
                       organism = Human respiratory syncytial virus
SEQUENCE: 228
MELLIHRSSA IFLTLAINAL YLTSSQNITE EFYQSTCSAV SRGYFSALRT GWYTSVITIE  60
LSNIKEIKCN GTDTKVKLIK QELDKYKNAV TELQLLMQNT PAANNRARRE APQYMNYTIN  120
TTKNLNVSIS KKRKRRFLGF LLGVGSAIAS GIAVSKVLHL EGEVNKIKNA LLSTNKAVVS  180
LSNGVSVLTS KVLDLKNYIN NQLLPIVNQQ SCRISNIETV IEFQQKNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKNRG IIKTFSNGCD YVSNKGVDTV SVGNTLYYVN KLEGKNLYVK GEPIINYYDP  480
LVFPSDEFDS SISQVNEKIN QSLAFIRRSD ELLHNVNTGK STTNIMITAI IIVIIVVLLS  540
LIAIGLLLYC KAKNTPVTLS KDQLSGINNI AFSK                              574
```

-continued

```
SEQ ID NO: 229          moltype = AA  length = 574
FEATURE                 Location/Qualifiers
REGION                  1..574
                        note = F protein of human RSV subtype B/AFD34261
source                  1..574
                        mol_type = protein
                        organism = Human respiratory syncytial virus
SEQUENCE: 229
MELLIHRSSA IFLTLAINAL YLTSSQNITE EFYQSTCSAV SRGYFSALRT GWYTSVITIE  60
LSNIKETKCN GTDTKVKLIK QELDKYKNAV TELQLLMQNT PAANNRARRE APQYMNYTIN  120
TTKNLNVSIS KKRKRRFLGF LLGVGSAIAS GIAVSKVLHL EGEVNKIKNA LLSTNKAVVS  180
LSNGVSVLTS KVLDLKNYIN NQLLPIVNQQ SCRISNIETV IEFQQKNSRL LEITREFGVN  240
AGVTTPLSTY MLTNSELLSL INDMPITNDQ KKLMSSNVQI VRQQSYSIMS IIKEEVLAYV  300
VQLPIYGVID THCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKNRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITAI IIVIIVVLLS  540
LIAIGLLLYC KAKNTPVTLS KDQLSGINNI AFSK                             574

SEQ ID NO: 230          moltype = AA  length = 573
FEATURE                 Location/Qualifiers
REGION                  1..573
                        note = F protein of human RSV subtype B/AAS93657
source                  1..573
                        mol_type = protein
                        organism = Human respiratory syncytial virus
SEQUENCE: 230
MELLIHRSSA ILLTLAINAL YLTSSQNITE EFYQSTCSAV SRGYFSALRT GWYTSVITIE  60
LSNIKETKCN GTDTKVKLIK QELDKYKNAV TELQLLMQNT PAANNRARRE APQYMNYTIN  120
TTKNLNVSIS KKRKRRFLGF LLGVGSAIAS GIAVSKVLHL EGEVNKIKNA LLSTNKAVVS  180
LSNGVSVLTS KVLDLKNYIN NQLLPIVNQQ SCRISNIETV IEFQQKNSRL LEITREFSVN  240
AGVTTPLSTY MLTNSELLSL INDMPITNDQ KKLMSSNVQI VRQQSYSIMS IIKEEVLAYV  300
VQLPIYGVID THCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKNRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITAI IIVIIVVLLS  540
LIAIGLLLYC KAKNTPVTLS KDQLSGINNI AFR                              573

SEQ ID NO: 231          moltype = AA  length = 573
FEATURE                 Location/Qualifiers
REGION                  1..573
                        note = F protein of human RSV subtype B/AAS93659
source                  1..573
                        mol_type = protein
                        organism = Human respiratory syncytial virus
SEQUENCE: 231
MELVIHRSSA IFLTLAINAL YLTSSQNITE EFYQSTCSAV SRGYFSALRT GWYTSVITIE  60
LSNIKETKCN GTDTKVKLIK QELDKYKNAV TELQLLMQNT PAANNRARRE APQYMNYTIN  120
TTKNLNVSIS KKRKRRFLGF LLGVGSAIAS GIAVSKVLHL EGEVNKIKNA LLSTNKAVVS  180
LSNGVSVLTS KVLDLKNYIN NQLLPIVNQQ SCRISNIETV IEFQQKNSRL LEITREFSVN  240
AGVTTPLSTY MLTNSELLSL INDMPITNDQ KKLMSSNVQI VRQQSYSIMS VIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKNRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITAI IIVIIVVLLS  540
LIAIGLLLYC KAKNTPVTLS KDQLSGINNI AFR                              573

SEQ ID NO: 232          moltype = AA  length = 574
FEATURE                 Location/Qualifiers
REGION                  1..574
                        note = F protein of human RSV subtype B/AEQ63586
source                  1..574
                        mol_type = protein
                        organism = Human respiratory syncytial virus
SEQUENCE: 232
MELLIHRSSA IFLTLAINAL YLTSSQNITE EFYQSTCSAV SRGYLSALRT GWYTSVITIE  60
LSNIKETKCN GTDTKVKLIK QELDKYKNAV TELQLLMQNT PAANNRARRE APQYMNYTIN  120
TTKNLNVSIS KKRKRRFLGF LLGVGSAIAS GIAVSKVLHL EGEVNKIKNA LLSTNKAVVS  180
LSNGVSVLTS KVLDLKNYIN NQLLPIVNQQ SCRISNIETV IEFQQKNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKNRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITAI IIVIIVVLLS  540
LIAIGLLLYC KAKNTPVTLS KDQLSGINNI AFSK                             574

SEQ ID NO: 233          moltype = AA  length = 574
FEATURE                 Location/Qualifiers
REGION                  1..574
```

```
                        note = F protein of human RSV subtype B/AEQ63608
source                  1..574
                        mol_type = protein
                        organism = Human respiratory syncytial virus
SEQUENCE: 233
MELLIHRSSA IFLTLAINAL YLTSSQNITE EFYQSTCSAV SRGYLSALRT GWYTSVITIE  60
LSNIKETKCN GTDTKVKLIK QELDKYKNAV TELQLLMQNT PTANNRARRE APQYMNYTIN  120
TTKNLNVSIS KKRKRRFLGF LLGVGSAIAS GIAVSKVLHL EGEVNKIKNA LLSTNKAVVS  180
LSNGVSVLTS KVLDLKNYIN NQLLPIVNQQ SCRISNIETV IEFQQKNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKNRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITAI IIVIIVVLLS  540
LIAIGLLLYC KAKNTPVTLS KDQLSGINNI AFSK                             574

SEQ ID NO: 234          moltype = AA  length = 574
FEATURE                 Location/Qualifiers
REGION                  1..574
                        note = F protein of human RSV subtype B/AEQ63641
source                  1..574
                        mol_type = protein
                        organism = Human respiratory syncytial virus
SEQUENCE: 234
MELLIHRSSA IFLTLAINAF YLTSSQNITE EFYQSTCSAV SRGYLSALRT GWYTSVITIE  60
LSNIKETKCN GTDTKVKLIK QELDKYKNAV TELQLLMQNT PAANNRARRE APQYMNYTIN  120
TTKNLNVSIS KKRKRRFLGF LLGVGSAIAS GIAVSKVLHL EGEVNKIKNA LLSTNKAVVS  180
LSNGVSVLTS KVLDLKNYIN NQLLPIVNQQ SCRISNIETV IEFQQKNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKNRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITAI IIVIIVVLLS  540
LIAIGLLLYC KAKNTPVTLS KDQLSGINNI AFSK                             574

SEQ ID NO: 235          moltype = AA  length = 573
FEATURE                 Location/Qualifiers
REGION                  1..573
                        note = F protein of human RSV subtype B/AAS93666
source                  1..573
                        mol_type = protein
                        organism = Human respiratory syncytial virus
SEQUENCE: 235
MELLIHRSSA IFLTLAINAL YLTSSQNITE EFYQSTCSAV SRGYLSALRT GWYTSVITIE  60
LSNIKETKCN GTDTKVKLIK QELDKYKNAV TELQLLMQNT PAANNRARRE APQYMNYTIN  120
TTKNLNVSIS KKRKRRFLGF LLGVGSAIAS GIAVSKVLHL EGEVNKIKNA LLSTNKAVVS  180
LSNGVSVLTS KVLDLKNYIN NQLLPIVNQQ SCRISNIETV IEFQQKNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKNRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITAI IIVIIVVLLS  540
LIAIGLLLYC KAKNTPVTLS KDQLSGINNI AFR                              573

SEQ ID NO: 236          moltype = AA  length = 574
FEATURE                 Location/Qualifiers
REGION                  1..574
                        note = F protein of human RSV subtype B/AFX60212
source                  1..574
                        mol_type = protein
                        organism = Human respiratory syncytial virus
SEQUENCE: 236
MELLIHRSSA IFLTLAINAL YLTSSQNITE EFYQSTCSAV SRGYLSALRT GWYTSVITIE  60
LSNIKETKCN GTDTKVKLIK QELDKYKNAV TELQLLMQNT PAANNRARRE APQYMNYTIN  120
TTKNPNVSIS KKRKRRFLGF LLGVGSAIAS GIAVSKVLHL EGEVNKIKNA LLSTNKAVVS  180
LSNGVSVLTS KVLDLKNYIN NQLLPIVNQQ SCRISNIETV IEFQQKNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKNRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITAI IIVIIVVLLS  540
LIAIGLLLYC KAKNTPVTLS KDQLSGINNI AFSK                             574

SEQ ID NO: 237          moltype = AA  length = 573
FEATURE                 Location/Qualifiers
REGION                  1..573
                        note = F protein of human RSV subtype B/AFX60214
source                  1..573
                        mol_type = protein
```

```
                         organism = Human respiratory syncytial virus
SEQUENCE: 237
ELLIHRSSAI FLTLAINALY LTSSQNITEE FYQSTCSAVS RGYLSALRTG WYTSVITIEL  60
SNIKEIKCNG TDTKVKLIKQ ELDKYKNAVT ELQLLMQNTP AANNRARREA PQYMNYTINT  120
TKNPNVSISK KRKRRFLGFL LGVGSAIASG IAVSKVLHLE GEVNKIKNAL LSTNKAVVSL  180
SNGVSVLTSK VLDLKNYINN QLLPIVNQQS CRISNIETVI EFQQKNSRLL EITREFSVNA  240
GVTTPLSTYM LTNSELLSLI NDMPITNDQK KLMSSNVQIV RQQSYSIMSI IKEEVLAYVV  300
QLPIYGVIDT PCWKLHTSPL CTTNIKEGSN ICLTRTDRGW YCDNAGSVSF FPQADTCKVQ  360
SNRVFCDTMN SLTLPSEVSL CNTDIFNSKY DCKIMTSKTD ISSSVITSLG AIVSCYGKTK  420
CTASNKNRGI IKTFSNGCDY VSNKGVDTVS VGNTLYYVNK LEGKNLYVKG EPIINYYDPL  480
VFPSDEFDAS ISQVNEKINQ SLAFIRRSDE LLHNVNTGKS TTNIMITAII IVIIVVLLSL  540
IAIGLLLYCK AKNTPVTLSK DQLSGINNIA FSK                              573

SEQ ID NO: 238           moltype = AA  length = 574
FEATURE                  Location/Qualifiers
REGION                   1..574
                         note = F protein of human RSV subtype B/AFX60219
source                   1..574
                         mol_type = protein
                         organism = Human respiratory syncytial virus
SEQUENCE: 238
MELLIHRSSA IFLTLAINAL YLTSSQNITE EFYQSTCSAV SRGYLSALRT GWYTSVITIE  60
LSNIKETKCN GTDTKVKLIK QELDKYKNAV TELQLLMQNT PAANNRARRE APQYMNYTIN  120
TTKNPNVSIS KKRKRRFLGF LLGVGSAIAS GIAVSKVLHL EGEVNKIKNA LLSTNKAVVS  180
LSNGVSVLTS KVLDLKNYIN NQLLPIVNQQ SCRISNIETV IEFQQKNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKNRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIIITAI IIVIIVVLLS  540
LIAIGLLLYC KAKNTPVTLS KDQLSGINNI AFSK                             574

SEQ ID NO: 239           moltype = AA  length = 574
FEATURE                  Location/Qualifiers
REGION                   1..574
                         note = F protein of human RSV subtype B/AFD34265
source                   1..574
                         mol_type = protein
                         organism = Human respiratory syncytial virus
SEQUENCE: 239
MELLIHRSSA IFLTLAINAL YLTSSQNITE EFYQSTCSAV SRGYLSALRT GWYTSVITIE  60
LSNIKETKCN GTDTKVKLIK QELDKYKNAV TELQLLMQNT PAANNRARRE ASQYMNYTIN  120
TTKNLNVSIS KKRKRRFLGF LLGVGSAIAS GIAVSKVLHL EGEVNKIKNA LLSTNKAVVS  180
LSNGVSVLTS KVLDLKNYIN NQLLPIVNQQ SCRISNIETV IEFQQKNSRL LEIAREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKNRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITAI IIVIIVVLLS  540
LIAIGLLLYC KAKNTPVTLS KDQLSGINNI AFSK                             574

SEQ ID NO: 240           moltype = AA  length = 574
FEATURE                  Location/Qualifiers
REGION                   1..574
                         note = F protein of human RSV subtype B/AEQ63597
source                   1..574
                         mol_type = protein
                         organism = Human respiratory syncytial virus
SEQUENCE: 240
MELLIHRSSA IFLTLAINAL YLTSSQNITE EFYQSTCSAV SRGYLSALRT GWYTSVITIE  60
LSNIKETKCN GTDTKVKLIK QELDKYKNAV TELQLLMQNT PAVNNRARRE APQYMNYTIN  120
TTKNLNVSIS KKRKRRFLGF LLGVGSAIAS GIAVSKVLHL EGEVNKIKNA LLSTNKAVVS  180
LSNGVSVLTS KVLDLKNYIN NQLLPIVNQQ SCRISNIETV IEFQQKNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKI  360
QSNRVFCDTM NSLTLPSEVS LCNTDIFNSK YDCKIMTSKT DISSSVITSL GAIVSCYGKT  420
KCTASNKNRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITAI IIVIIVVLLS  540
LIAIGLLLYC KAKNTPVTLS KDQLSGINNI AFSK                             574

SEQ ID NO: 241           moltype = AA  length = 574
FEATURE                  Location/Qualifiers
REGION                   1..574
                         note = F protein of human RSV subtype B/AFP99060
source                   1..574
                         mol_type = protein
                         organism = Human respiratory syncytial virus
SEQUENCE: 241
MELLIHRSSA IFLTLAINAL YLTSSQNITE EFYQSTCSAV SRGYLSALRT GWYTSVITIE  60
```

```
LSNIKETKCN GTDTKVKLIK QELDKYKNAV TELQLLMQNT PAVNNRARRE APQYMNYTIN    120
TTKNLNVSIS KKRKRRFLGF LLGVGSAIAS GIAVSKVLHL EGEVNKIKNA LLSTNKAVVS    180
LSNGVSVLTS KVLDLKNYIN NQLLPIVNQQ SCRISNIETV IEFQQKNSRL LEITREFSVN    240
AGVTTPLSTY MLTNSELLSL INDMPITNDQ KKLMSSNVQI VRQQSYSIMS IIKEEVLAYV    300
VQLPIYGVID TPCWKLHTSP LCTTNIKEGS NICLTRTDRG WYCDNAGSVS FFPQADTCKV    360
QSNRVFCDTM NSLTLPSEVS LCNTDIFNSK YDCKIMTSKT DISSSVITSL GAIVSCYGKT    420
KCTASNKNRG IIKTFSNGCD YVSNKGVDTV SVGNTLYYVN KLEGKNLYVK GEPIINYYDP    480
LVFPSDEFDA SISQVNEKIN QSLAFIRRSD ELLHNVNTGK STTNIMITAI IIVIIVVLLS    540
LIAIGLLLYC KAKNTPVTLS KDQLSGINNI AFSK                                574

SEQ ID NO: 242          moltype = AA   length = 574
FEATURE                 Location/Qualifiers
REGION                  1..574
                        note = F protein of human RSV subtype B/AEQ63630
source                  1..574
                        mol_type = protein
                        organism = Human respiratory syncytial virus
SEQUENCE: 242
MELLIHRSSA IFLTLAINAL YLTSSQNITE EFYQSTCSAV SRGYLSALRT GWYTSVITIE     60
LSNIKETKCN GTDTKVKLIK QELDKYKNAV TELQLLMQNT PAVNNRARRE APQYMNYTIN    120
TTKNLNVSIS KKRKRRFLGF LLGVGSAIAS GIAVSKVLHL EGEVNKIKNA LLSTNKAVVS    180
LSNGVSVLTS KVLDLKNYIN NQLLPIVNQQ SCRISNIETV IEFQQKNSRL LEITREFSVN    240
ARVTTPLSTY MLTNSELLSL INDMPITNDQ KKLMSSNVQI VRQQSYSIMS IIKEEVLAYV    300
VQLPIYGVID TPCWKLHTSP LCTTNIKEGS NICLTRTDRG WYCDNAGSVS FFPQADTCKV    360
QSNRVFCDTM NSLTLPSEVS LCNTDIFNSK YDCKIMTSKT DISSSVITSL GAIVSCYGKT    420
KCTASNKNRG IIKTFSNGCD YVSNKGVDTV SVGNTLYYVN KLEGKNLYVK GEPIINYYDP    480
LVFPSDEFDA SISQVNEKIN QSLAFIRRSD ELLHNVNTGK STTNIMITAI IIVIIVVLLS    540
LIAIGLLLYC KAKNTPVTLS KDQLSGINNI AFSK                                574

SEQ ID NO: 243          moltype = AA   length = 574
FEATURE                 Location/Qualifiers
REGION                  1..574
                        note = F protein of human RSV subtype B/AFP99061
source                  1..574
                        mol_type = protein
                        organism = Human respiratory syncytial virus
SEQUENCE: 243
MELLIHRSSA IFLTLAINAL YLTSSQNITE EFYQSTCSAV SRGYLSALRT GWYTSVITIE     60
LSNIKEIKCN GTDTKVKLIK QELDKYKNAV TELQLLMQNT PAVNNRARRE APQYMNYTIN    120
TTKNLNVSIS KKRKRRFLGF LLGVGSAIAS GIAVSKVLHL EGEVNKIKNA LLSTNKAVVS    180
LSNGVSVLTS KVLDLKNYIN NQLLPIVNQQ SCRISNIETV IEFQQKNSRL LEITREFSVN    240
AGVTTPLSTY MLTNSELLSL INDMPITNDQ KKLMSSNVQI VRQQSYSIMS IIKEEVLAYV    300
VQLPIYGVID TPCWKLHTSP LCTTNIKEGS NICLTRTDRG WYCDNAGSVS FFPQADTCKV    360
QSNRVFCDTM NSLTLPSEVS LCNTDIFNSK YDCKIMTSKT DISSSVITSL GAIVSCYGKT    420
KCTASNKNRG IIKTFSNGCD YVSNKGVDTV SVGNTLYYVN KLEGKNLYVK GEPIINYYDP    480
LVFPSDEFDA SISQVNEKIN QSLAFIRRSD ELLHNVNTGK STTNIMITAI IIVIIVVLLS    540
LIAIGLLLYC KAKNTPVTLS KDQLSGINNI AFSK                                574

SEQ ID NO: 244          moltype = AA   length = 574
FEATURE                 Location/Qualifiers
REGION                  1..574
                        note = F protein of human RSV subtype B/AFX60213
source                  1..574
                        mol_type = protein
                        organism = Human respiratory syncytial virus
SEQUENCE: 244
MELLIHRSSA IFLTLAINAL YLTSSQNITE EFYQSTCSAV SRGYLSALRT GWYTSVITIE     60
LSNIKETKCN GTDTKVKLIK QELDKYKNAV TELQLLMQNT PAVNNRARRE APQYMNYTIN    120
TTKNLNVSIS KKRKRRFLGF LLGVGSAIAS GIAVSKVLHL EGEVNKIKNA LQSTNKAVVS    180
LSNGVSVLTS KVLDLKNYIN NQLLPIVNQQ SCRISNIETV IEFQQKNSRL LEITREFSVN    240
AGVTTPLSTY MLTNSELLSL INDMPITNDQ KKLMSSNVQI VRQQSYSIMS IIKEEVLAYV    300
VQLPIYGVID TPCWKLHTSP LCTTNIKEGS NICLTRTDRG WYCDNAGSVS FFPQADTCKV    360
QSNRVFCDTM NSLTLPSEVS LCNTDIFNSK YDCKIMTSKT DISSSVITSL GAIVSCYGKT    420
KCTASNKNRG IIKTFSNGCD YVSNKGVDTV SVGNTLYYVN KLEGKNLYVK GEPIINYYDP    480
LVFPSDEFDA SISQVNEKIN QSLAFIRRSD ELLHNVNTGK STTNIMITAI IIVIIVVLLS    540
LIAIGLLLYC KAKNTPVTLS KDQLSGINNI AFSK                                574

SEQ ID NO: 245          moltype = AA   length = 574
FEATURE                 Location/Qualifiers
REGION                  1..574
                        note = F protein of human RSV subtype B/AFX60220
source                  1..574
                        mol_type = protein
                        organism = Human respiratory syncytial virus
SEQUENCE: 245
MELLIHRSSA IFLTLAINAL YITSSQNITE EFYQSTCSAV SRGYLSALRT GWYTSVITIE     60
LSNIKETKCN GTDTKVKLIK QELDKYKNAV TELQLLMQNT PAVNNRARRE APQYMNYTIN    120
TTKNLNVSIS KKRKRRFLGF LLGVGSAIAS GIAVSKVLHL EGEVNKIKNA LQSTNKAVVS    180
LSNGVSVLTS KVLDLKNYIN NQLLPIVNQQ SCRISNIETV IEFQQKNSRL LEITREFSVN    240
```

```
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKNRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITAI IIVIIVVLLS  540
LIAIGLLLYC KAKNTPVTLS KDQLSGINNI AFSK                              574

SEQ ID NO: 246         moltype = AA  length = 574
FEATURE                Location/Qualifiers
REGION                 1..574
                       note = F protein of human RSV subtype B/AFX60222
source                 1..574
                       mol_type = protein
                       organism = Human respiratory syncytial virus
SEQUENCE: 246
MELLIHRSSA IFLTLAINAL YITSSQNITE EFYQSTCSAV SRGYLSALRT GWYTSVITIE  60
LSNIKETKCN GTDTKVKLIK QELDKYKNAV TELQLLMQNT PAVNNRARRE APQYMNYTIN  120
TTKNLNVSIS KKRKRRFLGF LLGVGSAIAS GIAVSKVLHL EGEVNKIKNA LQSTNKAVVS  180
LSNGVSVLTS KVLDLKNYIN NQLLPIVNQQ ICRISNIETV IEFQQKNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKNRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITAI IIVIIVVLLS  540
LIAIGLLLYC KAKNTPVTLS KDQLSGINNI AFSK                              574

SEQ ID NO: 247         moltype = AA  length = 574
FEATURE                Location/Qualifiers
REGION                 1..574
                       note = F protein of human RSV subtype B/AFX60231
source                 1..574
                       mol_type = protein
                       organism = Human respiratory syncytial virus
SEQUENCE: 247
MELLIHRSSA IFLTLAINAL YLTSSQNITE EFYQSTCSAV SRGYLSALRT GWYTSVITIE  60
LSNIKETKCN GTDTKVKLIK QELDKYKNAV TELQLLMQNT PAVNNRARRE APQYMNYTIN  120
TTRNLNVSIS KKRKRRFLGF LLGVGSAIAS GIAVSKVLHL EGEVNKIKNA LQSTNKAVVS  180
LSNGVSVLTS KVLDLKNYIN NQLLPIVNQQ SCRISNIETV IEFQQKNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKNRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITAI IIVIIVVLLS  540
LIAIGLLLYC KAKNTPVTLS KDQLSGINNI AFSK                              574

SEQ ID NO: 248         moltype = AA  length = 574
FEATURE                Location/Qualifiers
REGION                 1..574
                       note = F protein of human RSV subtype B/AFX60232
source                 1..574
                       mol_type = protein
                       organism = Human respiratory syncytial virus
SEQUENCE: 248
MELLIYRSSA IFLTLAINAL YLTSSQNITE EFYQSTCSAV SRGYLSALRT GWYTSVITIE  60
LSNIKETKCN GTDTKVKLIK QELDKYKNAV TELQLLMQNT PAVNNRARRE APQYMNYTIN  120
TTKNLNVSIS KKRKRRFLGF LLGVGSAIAS GIAVSKVLHL EGEVNKIKNA LQSTNKAVVS  180
LSNGVSVLTS KVLDLKNYIN NQLLPIVNQQ SCRISNIETV IEFQQKNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKNRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITAI IIVIIVVLLS  540
LIAIGLLLYC KAKNTPVTLS KDQLSGINNI AFSK                              574

SEQ ID NO: 249         moltype = AA  length = 574
FEATURE                Location/Qualifiers
REGION                 1..574
                       note = F protein of human RSV subtype B/AFX60234
source                 1..574
                       mol_type = protein
                       organism = Human respiratory syncytial virus
SEQUENCE: 249
MELLIHRSSA IFLTLAINAL YLTSSQNITE EFYQSTCSAV SRGYLSALRT GWYTSVITIE  60
LSNIKETKCN GTDTKVKLIK QELDKYKNAV TELQLLMQNT PAVNNRARRE APQYMNYTIN  120
TTKNLNVSIS KKRKRRFLGF LLGVGSAIAS GIAVSKVLHL EGEVNKIKNA LQSTNKAVVS  180
LSNGVSVLTS KVLDLKNYIN NQLLPIVNKQ SCRISNIETV IEFQQKNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
```

-continued

```
KCTASNKNRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITAI IIVIIVVLLS  540
LIAIGLLLYC KAKNTPVTLS KDQLSGINNI AFSK                             574

SEQ ID NO: 250         moltype = AA  length = 573
FEATURE                Location/Qualifiers
REGION                 1..573
                       note = F protein of human RSV subtype B/AAS93662
source                 1..573
                       mol_type = protein
                       organism = Human respiratory syncytial virus
SEQUENCE: 250
MELLIHRSSA IFLTLSINAL YLTSSQNITE EFYQSTCSAV SRGYFSALRT GWYTSVITIE  60
LSNIKETKCN GTDTKVKLIK QELDKYKNAV TELQLLMQNT PATNNRARRE APQYMNYTIN  120
TTKNLNVSIS KKRKRRFLGF LLGVGSAIAS GIAVSKVLHL EGEVNKIKNA LLSTNKAVVS  180
LSNGVSVLTS KVLDLKNYIN NQLLPIVNQQ SCRISNIETV IEFQQKNSRL LEITREFSVN  240
AGVTTPLSTY MLTNSELLSL INDMPITNDQ KKLMSSNVQI VRQQSYSIMS IIKEEVLAYV  300
VQLPIYGVID TQCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKNRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITAI IIVIIVVLLS  540
LIAIGLLLYC KAKNTPVTLS KDQLSGINNI AFR                              573

SEQ ID NO: 251         moltype = AA  length = 574
FEATURE                Location/Qualifiers
REGION                 1..574
                       note = F protein of human RSV subtype B/AAB82446
source                 1..574
                       mol_type = protein
                       organism = Human respiratory syncytial virus
SEQUENCE: 251
MELLIHRLSA IFLTLAINAL YLTSSQNITE EFYQSTCSAV SRGYFSALRT GWYTSVITIE  60
LSNIKETKCN GTDTKVKLIK QELDKYKNAV TELQLLMQNT PAANNRARRE APQYMNYTIN  120
TTKNLNVSIS KKRKRRFLGF LLGVGSAIAS GIAVSKVLHL EGEVNKIKNA LLSTNKAVVS  180
LSNGVSVLTS KVLDLKNYIN NQLLPIVNQQ SCRISNIGTV IEFQQKNSRL LEINREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKNRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITTI IIVIIVVLLS  540
LIAIGLLLYC KAKNTPVTLS KDQLSGINNI AFSK                             574

SEQ ID NO: 252         moltype = AA  length = 574
FEATURE                Location/Qualifiers
REGION                 1..574
                       note = F protein of human RSV subtype B/NP_056863
source                 1..574
                       mol_type = protein
                       organism = Human respiratory syncytial virus
SEQUENCE: 252
MELLIHRLSA IFLTLAINAL YLTSSQNITE EFYQSTCSAV SRGYFSALRT GWYTSVITIE  60
LSNIKETKCN GTDTKVKLIK QELDKYKNAV TELQLLMQNT PAANNRARRE APQYMNYTIN  120
TTKNLNVSIS KKRKRRFLGF LLGVGSAIAS GIAVSKVLHL EGEVNKIKNA LLSTNKAVVS  180
LSNGVSVLTS KVLDLKNYIN NQLLPIVNQQ SCRISNIETV IEFQQKNSRL LEINREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKNRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITTI IIVIIVVLLS  540
LIAIGLLLYC KAKNTPVTLS KDQLSGINNI AFSK                             574

SEQ ID NO: 253         moltype = AA  length = 574
FEATURE                Location/Qualifiers
REGION                 1..574
                       note = F protein of human RSV subtype B/AAR14266
source                 1..574
                       mol_type = protein
                       organism = Human respiratory syncytial virus
SEQUENCE: 253
MELLIHRSSA IFLTLAINAL YLTSSQNITE EFYQSTCSAV SRGYFSALRT GWYTSVITIE  60
LSNIKETKCN GTDTKVKLIK QELDKYKNAV TELQLLTQNT PAANNRARRE APQYMNYTIN  120
TTKNLNVSIS KKRKRRFLGF LLGVGSAIAS GIAVSKVLHL EGEVNKIKNA LLSTNKAVVS  180
LSNGVSVLTS KVLDLKSYIN NQLLPIVNQQ SCRISNIETV IEFQQKNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKNRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITTI IIVIIVVLLS  540
LIAIGLLLYC KAKNTPVTLS KDQLSGINNI AFSK                             574
```

```
SEQ ID NO: 254          moltype = AA  length = 574
FEATURE                 Location/Qualifiers
REGION                  1..574
                        note = F protein of human RSV subtype B/ADZ95775
source                  1..574
                        mol_type = protein
                        organism = Human respiratory syncytial virus
SEQUENCE: 254
MELLIHRSSA IFLTLAINAL YLTSSQNITE EFYQSTCSAV SRGYFSALRT GWYTSVITIE     60
LSNIQETKCN GTDTKVKLIK QELDKYKNAV TELQLLMQNT PAVNNRARRE APQYMNHTIN    120
TTKNLNVSIS KKRKRRFLGF LLGVGSAIAS GIAVSKVLHL EGEVNKIKNA LLSTNKAVVS    180
LSNGVSVLTS KVLDLKNYIN NQLLPIVNQQ SCRISNIETV IEFQQKNSRL LEITREFSVN    240
AGVTTPLSTY MLTNSELLSL INDMPITNDQ KELMSSNVQI VRQQSYSIMS IIKEEVLAYV    300
VQLPIYGVID TPCWKLHTSP LCTTNIKEGS NICLTRTDRG WYCDNAGSVS FFPQADTCKV    360
QSNRVFCDTM NSLTLPSEVS LCNTDIFNSK YDCKIMTSKT DISSSVITSL GAIVSCYGKT    420
KCTASNKNRG IIKTFSNGCD YVSNKGVDTV SVGNTLYYVN KLEGKNLYVK GEPIINYYDP    480
LVFPSDEFDA SISQVNEKIN QSLAFIRRSD ELLHNVNTGK STTNIMITAI IIVIIVVLLS    540
LIAIGLLLYC KAKNTPVTLS KDQLSGINNI AFSK                                574

SEQ ID NO: 255          moltype = AA  length = 564
FEATURE                 Location/Qualifiers
REGION                  1..564
                        note = F protein of human RSV subtype B/AEN74944
source                  1..564
                        mol_type = protein
                        organism = Human respiratory syncytial virus
SEQUENCE: 255
MELLIHRSSA IFLTLAINAL YLTSSQNITE EFYQSTCSAV SRGYFSALRT GWYTSVITIE     60
LSNIKETKCN GTDTKVKLIK QELDKYKNAV TELQLLMQNT PAANNRARRE APQYMNYTIN    120
TTKNLNVSIS KKRKRRFLGF LLGVGSAIAS GMAVSKVLHL EGEVNKIKNA LLSTNKAVVS    180
LSNGVSVLTS KVLDLKNYIN NQLLPIVNQQ SCRISNIETV IEFQQKNSRL LEITRGFSVN    240
AGVTTPLSTY MLTNSELLSL INDMPITNDQ KKLMSSNVQI VRQQSYSIMS IIKEEVLAYV    300
VQLPIYGVID TPCWKLHTSP LCTTNIKEGS NICLTRTDRG WYCDNAGSVS FFPQADTCKV    360
QSNRVFCDTM NSLTLPSEVS LCNTDIFNSK YDCKIMTSKT DISSSVITSL GAIVSCYGKT    420
KCTASNKNRG IIKTFSNGCD YVSNKGVDTV SVGNTLCYVN KLEGKNLYVK GEPIINYYDP    480
LVFPSDEFDA SISQVNEKIN QSLAFIRRSD ELLHNVNTGK STTNIMITAI IIVIIVVLLS    540
LIAIGLLLYC KAKTTPVTLS KDQL                                           564

SEQ ID NO: 256          moltype = AA  length = 564
FEATURE                 Location/Qualifiers
REGION                  1..564
                        note = F protein of human RSV subtype B/AEN74945
source                  1..564
                        mol_type = protein
                        organism = Human respiratory syncytial virus
SEQUENCE: 256
MELLIHRSSA IFLTLAINAL YLTSSQNITE EFYQSTCSAV SRGYFSALRT GWYTSVITIE     60
LSNIKETKCN GTDTKVKLIK QELDKYKNAV TELQLLMQNT PAANNRARRE APQYMNYTIN    120
TTKNLNVSIS KKRKRRFLGF LLGVGSAIAS GIAVSKVLHL EGEVNKIKNA LLSTNKAVVS    180
LSNGVSVLTS KVLDLKNYIN NQLLPIVNQQ SCRISTIETV IEFQQKNSRL LEINREFSVN    240
AGVTTPLSTY MLTNSELLSL INDMPITNDQ KKLMSSNVQI VRQQSYSIMS IIKEEVLAYV    300
VRLPIYGVID TPCWKLHTSP LCTTNIKEGS NICLTRTDRG WYCDNAGSVS FFPQADTCKV    360
QSNRVFCDTM NSLTLPSEVS LCNTDIFNSK YDCKIMTSKT DISSSVITSL GAIVSCYGKT    420
KCTASNKNRG IIKTFSNGCD YVSNKGVDTV SVGNTLYYVN KLEGKNLYVK GEPIINYYDP    480
LVFPSDEFDA SISQVNEKIN QSLAFIRRSD ELLHNVNTGK STTNIMITAI IIVIIVVLLS    540
LIAIGLLLYC KAKTTPVTLS KDQL                                           564

SEQ ID NO: 257          moltype = AA  length = 573
FEATURE                 Location/Qualifiers
REGION                  1..573
                        note = F protein of human RSV subtype B/AAS93665
source                  1..573
                        mol_type = protein
                        organism = Human respiratory syncytial virus
SEQUENCE: 257
MELLIHRSSA VFLTLAINAL YLTSSQNITE EFYQSTCSAV SRGYLSALRT GWYTSVITIE     60
LSNIKETKCN GTDTKVKLIK QELDKYKNAV TELQLLMQNT PAANNRARRE APQYMNYTIN    120
TTKNLNVSIS KKRKRRFLGF LLGVGSAIAS GIAVSKVLHL EGEVNKIKNA LLSTNKAVVS    180
LSNGVSVLTS KVLDLKNYIN NQLLPIVNQQ SCRISNIETV IEFQQKNSRL LEITREFSVN    240
AGVTTPLSTY MLTNSELLSL INDMPITNDQ KKLMSSNVQI VRQQSYSIMS IIKEEVLAYV    300
VQLPIYGVID TPCWKLHTSP LCTTNIKEGS NICLTRTDRG WYCDNAGSVS FFPQADTCKV    360
QSNRVFCDTM NSLTLPSEVS LCNTDIFNSK YDCKIMTSKT DISSSVITSL GAIVSCYGKT    420
KCTASNKNRG IIKTFSNGCD YVSNKGVDTV SVGNTLYYVN KLEGKNLYVK GEPIINYYDP    480
LVFPSDEFDA SISQVNEKIN QSLAFIRRSD ELLHNVNAGK STTNIMITAI IIVIIVVLLS    540
LIAIGLLLYC RAKNTPVTLS KDQLSGINNI AFR                                 573

SEQ ID NO: 258          moltype = AA  length = 574
FEATURE                 Location/Qualifiers
```

-continued

```
REGION                1..574
                      note = F protein of human RSV subtype B/AFD34264
source                1..574
                      mol_type = protein
                      organism = Human respiratory syncytial virus
SEQUENCE: 258
MELLIHRSSA ILLTLAINAL YLTSSQNITE EFYQSTCSAV SRGYFSALRT GWYTSVITIE  60
LSNIKETKCN GTDTKVKLIK QELDKYKNAV TELQLLMQNT PAANNRARRE APQYMNYTIN  120
TTKNLNVSIS KKRKRRFLGF LLGVGSAIAS GIAVSKVLHL EGEVNKIKNA LLSTNKAVVS  180
LSNGVSVLTS KVLDLKNYIN NQLLPIVNQQ SCRISNIETV IEFQQKNSRL LEITREFSVN  240
AGVTTPLSTY MLTNGELLSL INDMPITNDQ KKLMSSNAQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKNRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITAI IIVIIVVLLS  540
LIAIGLLLYC KAKNTPVTLS KEQLSGINNI AFSK                              574

SEQ ID NO: 259        moltype = AA  length = 574
FEATURE               Location/Qualifiers
REGION                1..574
                      note = F protein of human RSV subtype B/AGG39514
source                1..574
                      mol_type = protein
                      organism = Human respiratory syncytial virus
SEQUENCE: 259
MELLIHRSSA IFLTLAINAL YLTSSQNITE EFYQSTCSAV SRGYLSALRT GWYTSVITIE  60
LSNIKETKCN GTDTKVKLIK QELDKYKNAV TELQLLMQNT PVANNRARRE APQYMNYTIN  120
TTKNLNVSIS KKRKRRFLGF LLGVGSAIAS GIAVSKVLHL EGEVNKIKNA LLSTNKAVVS  180
LSNGVSVLTS KVLDLKNYIN NQLLPIVNQQ SCRISNIETV IEFQQKNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM YSLTLPSEVS LCNTDIFNSK YDCKIMTSKT DISSSVITSL GAIVSCYGKT  420
KCTASNKNRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITAI IIVIIVVLLS  540
LIAIGLLLYC KAKNTPVTLS KDQLSGINNI AFSK                              574

SEQ ID NO: 260        moltype = AA  length = 574
FEATURE               Location/Qualifiers
REGION                1..574
                      note = F protein of human RSV subtype B/AGG39487
source                1..574
                      mol_type = protein
                      organism = Human respiratory syncytial virus
SEQUENCE: 260
MELLIHRSSA IFLTLAVNAL YLTSSQNITE EFYQSTCSAV SRGYFSALRT GWYTSVITIE  60
LSNIKETKCN GTDTKVKLIK QELDKYKNAV TELQLLMQNT PAANNRARRE APQYMNYTIN  120
TTKNLNVSIS KKRKRRFLGF LLGVGSAIAS GMAVSKVLHL EGEVNKIKNA LLSTNKAVVS  180
LSNGISVLTS KVLDLKNYIN NRLLPIVNQQ SCRISNIETV IEFQQKNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKNRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITTI IIVIIVVLLS  540
LIAIGLLLYC KAKNTPVTLS KDQLSGINNI AFSK                              574

SEQ ID NO: 261        moltype = AA  length = 574
FEATURE               Location/Qualifiers
REGION                1..574
                      note = F protein of human RSV subtype B/AFI25251
source                1..574
                      mol_type = protein
                      organism = Human respiratory syncytial virus
SEQUENCE: 261
MELLIHRSSA IFLTLAINAL YLTSSQNITE EFYQSTCSAV SRGYFSALRT GWYTSVITIE  60
LSNIKETKCN GTDTKVKLIK QELDKYKNAV TELQLLMQNT PAANNRARRE APQYMNYTIN  120
TTKNLNVSIS KKRKRRFLGF LLGVGSAIAS GIAVSKVLHL EGEVNKIKNA LLSTNKAVVS  180
LSNGVSVLTS KVLDLKNYIN NQLLPIVNQQ SCRISNIETV IEFQQKNSRL LEITREFSVN  240
AGVTTPLSTY MLTNSELLSL INDMPITNDQ KKLMSSNVQI VRQQSYSIMS IMKEEVLAYV  300
VQLPIYGVID TPCWKLHTSP LCTTNTKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKNRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITVI IIVIIVVLLS  540
LIAIGLLLYC KAKNTPVTLS KDQLSGINNI AFSK                              574

SEQ ID NO: 262        moltype = AA  length = 574
FEATURE               Location/Qualifiers
REGION                1..574
                      note = F protein of human RSV subtype B/AGG39523
source                1..574
```

```
                         mol_type = protein
                         organism = Human respiratory syncytial virus
SEQUENCE: 262
MELLIHRSIA IFLTLAINAL YLTSSQNITE EFYQSTCSAV SRGYFSALRT GWYTSVITIE  60
LSNITETKCN GTDTKVKLIK QELDKYKNAV TELQLLMQNT PAANNRARRE APQYMNYTIN  120
TTKNLNVSIS KKRKRRFLGF LLGVGSAIAS GIAVSKVLHL EGEVNKIKNA LLSTNKAVVS  180
LSNGVSVLTS KVLDLKNYIN NQLLPIVNQQ SCRISNIETV IEFQQKNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKNRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNVGK STTNIMITAI IIVIIVVLLS  540
LIAIGLLLYC KAKNTPVTLS KDQLSGINNI AFSK                            574

SEQ ID NO: 263           moltype = AA  length = 574
FEATURE                  Location/Qualifiers
REGION                   1..574
                         note = F protein of human RSV subtype B/AGG39502
source                   1..574
                         mol_type = protein
                         organism = Human respiratory syncytial virus
SEQUENCE: 263
MELLVHRSSA IFLTLAINAL YLTSSQNITE EFYQSTCSAV SRGYFSALRT GWYTSVITIE  60
LSNIKETKCN GTDTKVKLIK QELDKYKNAV TELQLLMQNT PAANNRARRE APQYMNYTIN  120
TTNNLNVSIS KKRKRRFLGF LLGVGSAIAS GIAVSKVLHL EGEVNKIKNA LLSTNKAVVS  180
LSNGVSVLTS KVLDLKNYIN NQLLPIVNQQ SCRISNIETV IEFQQKNSRL LEIAREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKNRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITAI IIVIIVVLLS  540
LIAIGLLLYC KAKNTPVTLS KDQLSGINNI AFSK                            574

SEQ ID NO: 264           moltype = AA  length = 574
FEATURE                  Location/Qualifiers
REGION                   1..574
                         note = F protein of Bovine RSV/P22167
source                   1..574
                         mol_type = protein
                         organism = Bovine respiratory syncytial virus
SEQUENCE: 264
MAATAMRMII SIIFISTYMT HITLCQNITE EFYQSTCSAV SRGYLSALRT GWYTSVVTIE  60
LSKIQKNVCK STDSKVKLIK QELERYNNAV IELQSLMQNE PASFSRAKRG IPELIHYTRN  120
STKRFYGLMG KKRKRRFLGF LLGIGSAIAS GVAVSKVLHL EGEVNKIKNA LLSTNKAVVS  180
LSNGVSVLTS KVLDLKNYID KELLPKVNNH DCRISNIETV IEFQQKNNRL LEIAREFSVN  240
AGITTPLSTY MLTNSELLSL INDMPITNDQ KKLMSSNVQI VRQQSYSIMS VVKEEVIAYV  300
VQLPIYGVID TPCWKLHTSP LCTTDNKEGS NICLTRTDRG WYCDNAGSVS FFPQAETCKV  360
QSNRVFCDTM NSLTLPTDVN LCNTDIFNTK YDCKIMTSKT DISSSVITSI GAIVSCYGKT  420
KCTASNKNRG IIKTFSNGCD YVSNKGVDTV SVGNTLYYVN KLEGKALYIK GEPIINYYDP  480
LVFPSDEFDA SIAQVNAKIN QSLAFIRRSD ELLHSVDVGK STTNVVITTI IIVIVVVILM  540
LIAVGLLFYC KTRSTPIMLG KDQLSGINNL SFSK                            574

SEQ ID NO: 265           moltype = AA  length = 574
FEATURE                  Location/Qualifiers
REGION                   1..574
                         note = F protein of Bovine RSV/CAA76980
source                   1..574
                         mol_type = protein
                         organism = Bovine respiratory syncytial virus
SEQUENCE: 265
MATTAMTMII SIIFISTYVT HITLCQNITE EFYQSTCSAV SRGYLSALRT GWYTSVVTIE  60
LSKIQKNVCK STDSKVKLIK QELERYNNAV VELQSLMQNE PASFSRAKRS IPELIHYTRN  120
STKKFYGLMG KKRKRRFLGF LLGIGSAIAS GVAVSKVLHL EGEVNKIKNA LLSTNKAVVS  180
LSNGVSVLTS KVLDLKNYID KELLPKVNNH DCRISNIATV IEFQQKNNRL LEIAREFSVN  240
AGITTPLSTY MLTNSELLSL INDMPITNDQ KKLMSSNVQI VRQQSYSIMS VVKEEVIAYV  300
VQLPIYGVID TPCWKLHTSP LCTTDNKEGS NICLTRTDRG WYCDNAGSVS FFPQAETCKV  360
QSNRVFCDTM NSLTLPTDVN LCNTDIFNTK YDCKIMTSKT DISSSVITSI GAIVSCYGKT  420
KCTASNKNRG IIKTFSNGCD YVSNKGVDTV SVGNTLYYVN KLEGKALYIK GEPIINYYDP  480
LVFPSDEFDA SIAQVNAKIN QSLAFIRRSD ELLHSVDVGK STTNVVITTI IIVIVVVILM  540
LIAVGLLFYC KTRSTPIMLG KDQLSGINNL SFSK                            574

SEQ ID NO: 266           moltype = AA  length = 574
FEATURE                  Location/Qualifiers
REGION                   1..574
                         note = F protein of Bovine RSV/AAL49399
source                   1..574
                         mol_type = protein
                         organism = Bovine respiratory syncytial virus
SEQUENCE: 266
```

-continued

```
MATTAMRMII SIIFISTYVT HITLCQNITE EFYQSTCSAV SRGYLSALRT GWYTSVVTIE  60
LSKIQKNVCN STDSKVKLIK QELERYNNAV VELQSLMQNE PASFSRAKRG IPELIHYTRN  120
STKKFYGLMG KKRKRRFLGF LLGIGSAIAS GVAVSKVLHL EGEVNKIKNA LLSTNKAVVS  180
LSNGVSVLTS KVLDLKNYID KELLPKVNNH DCRISKIETV IEFQQKNNRL LEIAREFSVN  240
AGITTPLSTY MLTNSELLSL INDMPITNDQ KKLMSSNVQI VRQQSYSIMS VVKEEVIAYV  300
VQLPIYGVID TPCWKLHTSP LCTTDNKEGS NICLTRTDRG WYCDNAGSVS FFPQTETCKV  360
QSNRVFCDTM NSLTLPTDVN LCNTDIFNTK YDCKIMTSKT DISSSVITSI GAIVSCYGKT  420
KCTASNKNRG IIKTFSNGCD YVSNKGVDTV SVGNTLYYVN KLEGKALYIK GEPIINYYDP  480
LVFPSDEFDA SIAQVNAKIN QSLAFIRRSD ELLHSVDVGK STTNVVITTI IIVIVVVILM  540
LIAVGLLFYC KTKSTPIMLG KDQLSGINNL SFSK                            574

SEQ ID NO: 267         moltype = AA  length = 574
FEATURE                Location/Qualifiers
REGION                 1..574
                       note = F protein of Bovine RSV/NP_048055
source                 1..574
                       mol_type = protein
                       organism = Bovine respiratory syncytial virus
SEQUENCE: 267
MATTAMRMII SIIFISTYVT HITLCQNITE EFYQSTCSAV SRGYLSALRT GWYTSVVTIE  60
LSKIQKNVCK STDSKVKLIK QELERYNNAV VELQSLMQNE PASFSRAKRG IPELIHYTRN  120
STKKFYGLMG KKRKRRFLGF LLGIGSAVAS GVAVSKVLHL EGEVNKIKNA LLSTNKAVVS  180
LSNGVSVLTS KVLDLKNYID KELLPQVNNH DCRISNIETV IEFQQKNNRL LEIAREFSVN  240
AGITTPLSTY MLTNSELLSL INDMPITNDQ KKLMSSNVQI VRQQSYSIMS VVKEEVIAYV  300
VQLPIYGVID TPCWKLHTSP LCTTDNKEGS NICLTRTDRG WYCDNAGSVS FFPQTETCKV  360
QSNRVFCDTM NSLTLPTDVN LCNTDIFNTK YDCKIMTSKT DISSSVITSI GAIVSCYGKT  420
KCTASNKNRG IIKTFSNGCD YVSNKGVDTV SVGNTLYYVN KLEGKALYIK GEPIINYYDP  480
LVFPSDEFDA SIAQVNAKIN QSLAFIRRSD ELLHSVDVGK STTNVVITTI IIVIVVVILM  540
LIAVGLLFYC KTKSTPIMLG KDQLSGINNL SFSK                            574

SEQ ID NO: 268         moltype = AA  length = 574
FEATURE                Location/Qualifiers
REGION                 1..574
                       note = F protein of Bovine RSV/CAI96787
source                 1..574
                       mol_type = protein
                       organism = Bovine respiratory syncytial virus
SEQUENCE: 268
MATTAMRMII SIIFISTYVT HITLCQNITE EFYQSTCSAV SRGYLSALRT GWYTSVVTIE  60
LSKIQKNVCK STDSKVKLIK QELERYNNAV VELQSLMQNE PGSFSRAKRG IPELIHYTRN  120
STKKFYGHMG KKRKRRFLGF LLGIGSAIAS GVAVSKVLHL EGEVNKIKNA LLSTNKAVVS  180
LSNGVSVLTS KVLDLKNYID KELLPKVNNH DCRISNIETV IDFQQKNNRL LEIAREFSVN  240
AGITTPLSTY MLTNSELLSL INDMPITNDQ KKLMSSNVQI VRQQSYSIMS VVKEEVMAYV  300
VQLPIYGVID TPCWKLHTSP LCTTDNKEGS NICLTRTDRG WYCDNAGSVS FFPQAETCKV  360
QSNRVFCDTM NSLTLPTDVN LCNTDIFNAK YDCKIMTSKT DISSSVITSI GAIVSCYGKT  420
KCTASNKNRG IIKTFSNGCD YVSNKGVDTV SVGNTLYYVN KLEGKALYIK GEPIINYYDP  480
LVFPSDEFDA SIAQVNAKIN QSLAFIRRSD ELLHSVDVGK STTNVVITTI IIVIVVVILM  540
LIAVGLLFYC KTRSTPIMLG KDQLSGINNL SFSK                            574

SEQ ID NO: 269         moltype = AA  length = 574
FEATURE                Location/Qualifiers
REGION                 1..574
                       note = F protein of Bovine RSV/AAB28458
source                 1..574
                       mol_type = protein
                       organism = Bovine respiratory syncytial virus
SEQUENCE: 269
MGTTAMRMVI SIIFISTYVT HITLCQNITE EFYQSTCSAV SRGYLSALRT GWYTSVVTIE  60
LSKIQKNVCK STDSKVKLIK QELERYNNAV IELQSLMQNE PASFSRAKRG IPELIHYPRN  120
STKRFYGLMG KKRKRRFLGF LLGIGSAIAS GVAVSKVLHL EGEVNKIKNA LLSTNKAVVS  180
LSNGVSVLTS KVLDLKNYID KELLPKVNNH DCRISNIGTV IEFQQKNNRL LEIAREFSVN  240
AGITTPLSTY MLTNSELLSL INDMPITNDQ KKLMSSNVQI VRQQSYSIMS VVKEEVIAYE  300
VQLPIYGVID TPCWKIHTSP LCTTDNKEGS NICLTRTDRG WYCDNAGSVS FFPQAETCKV  360
QSNRVFCDTM NSLTLPTDVN LCNTDIFNTK YDCKIMTSKT DISSSVITSI GAIVSCYGKT  420
KCTASNKNRG IIKTFPIGCD YVSNKGVDTV SVGNTLYYVN KLEGKALYIK GEPIINYYDP  480
LVFPSDEFDA SIAQVNAKIN QSLAFIRRSD ELLHSVDVGK STTNVVITTI IIVIVVVILM  540
LIAVGLLFYC KTRSTPIMLG KDQLSGINNL SFSK                            574

SEQ ID NO: 270         moltype = AA  length = 569
FEATURE                Location/Qualifiers
REGION                 1..569
                       note = F protein of Bovine RSV/AAL49410
source                 1..569
                       mol_type = protein
                       organism = Bovine respiratory syncytial virus
SEQUENCE: 270
MRMIISIILI STYVPHITLC QNITEEFYQS TCSAVSRGYL SALRTGWYTS VVTIELSKIQ  60
KNVCNGTDSK VKLIKQELER YNNAVVELQS LMQNEPTSSS RAKRGIPESI HYTRNSTKKF  120
YGLMGKKRKR RFLGFLLGIG SAIASGVAVS KVLHLEGEVN KIKNALLSTN KAVVSLSNGV  180
```

-continued

```
SVLTSKVLDL KNYIDKELLP KVNNHDCRIS NIATVIEFQQ KNNRLLEIAR EFSVNAGITT  240
PLSTYMLTNS ELLSIINDMP ITNDQKKLMS SNVQIVRQQS YSIMSVVKEE VIAYVVQLPL  300
YGVIDTPCWK LHTSPLCTTD NEEGSNICLT RTDRGWYCDN AGSVSFFPQA ETCKVQSNRV  360
FCDTMNSLTL PTDVNLCNTD IFNAKYDCKI MTSKTDISSS VITSIGAIVS CYGKTKCTAS  420
NKNRGIIKTF SNGCDYVSNK GVDTVSVGNT LYYVNKLEGK ALYIKGEPII NYYNPLVFPS  480
DEFDASIAQV NAKINQSLAF IRRSDELLHS VDVGKSTTNV VITTIIIVIV VVILMLITVG  540
LLFYCKTRST PIMLGKDQLS SINNLSFSK                                    569

SEQ ID NO: 271          moltype = AA  length = 537
FEATURE                 Location/Qualifiers
REGION                  1..537
                        note = Synthetic
source                  1..537
                        mol_type = protein
                        organism = synthetic construct
SEQUENCE: 271
MELLILKANA ITTILTAVTF CFASGQNITE EFYQSTCSAV SKGYLSALRT GWYHCVITIE  60
LSNIKENKCN GTDAKVKLIK QELDKYKNAV TELQLLMQST PATNNRARRE LPRFMNYTLN  120
NAKKTNVTLS KKRKRRFLGF LLGVGSAIAS GVAVSKVLHL EGEVNKIKSA LLSTNKAVVS  180
LSNGVSVCTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSSEFDA SISQVNEKIN QSLAFIRKSD ELLGGLVPRG SHHHHHHGSW SHPQFEK     537

SEQ ID NO: 272          moltype = AA  length = 545
FEATURE                 Location/Qualifiers
REGION                  1..545
                        note = Synthetic
source                  1..545
                        mol_type = protein
                        organism = synthetic construct
SEQUENCE: 272
MELLILKANA ITTILTAVTF CFASGQNITE EFYQSTCSAV SKGYLSALRT GWYHCVITIE  60
LSNIKENKCN GTDAKVKLIK QELDKYKNAV TELQLLMQST PATGSAIASG VAVSKVLHLE  120
GEVNKIKSAL LSTNKAVVSL SNGVSVCTSK VLDLKNYIDK QLLPIVNKQS CSISNIETVI  180
EFQQKNNRLL EITREFSVNA GVTTPVSTYM LTNSELLSLI NDMPITNDQK KLMSNNVQIV  240
RQQSYSIMSI IKEEVLAYVV QLPLYGVIDT PCWKLHTSPL CTTNTKEGSN ICLTRTDRGW  300
YCDNAGSVSF FPQAETCKVQ SNRVFCDTMN SLTLPSEVNL CNVDIFNPKY DCKIMTSKTD  360
VSSSVITSLG AIVSCYGKTK CTASNKNRGI IKTFSNGCDY VSNKGVDTVS VGNTLYYVNK  420
QEGKSLYVKG EPIINFYDPL VFPSSEFDAS ISQVNEKINQ SLAFIRCCDE LLHNVNAGKS  480
TTNIMITTLV PRGSGGSAIG GYIPEAPRDG QAYVRKDGEW VLLSTFLGGH HHHHHGSWSH  540
PQFEK                                                              545

SEQ ID NO: 273          moltype = AA  length = 545
FEATURE                 Location/Qualifiers
REGION                  1..545
                        note = Synthetic
source                  1..545
                        mol_type = protein
                        organism = synthetic construct
SEQUENCE: 273
MELLILKANA ITTILTAVTF CFASGQNITE EFYQSTCSAV SKGYLSALRT GWYHCVITIE  60
LSNIKENKCN GTDAKVKLIK QELDKYKNAV TELQLLMQST PATGSAIASG VAVSKVLHLE  120
GEVNKIKSAL LSTNKAVVSL SNGVSVCTSK VLDLKNYIDK QLLPIVNKQS CSISNIETVI  180
EFQQKNNRLL EITREFSVNA GVTTPVSTYM LTNSELLSLI NDMPITNDQK KLMSNNVQIV  240
RQQSYSIMSI IKEEVLAYVV QLPLYGVIDT PCWKLHTSPL CTTNTKEGSN ICLTRTDRGW  300
YCDNAGSVSF FPQAETCKVQ SNRVFCDTMN SLTLPSEVNL CNVDIFNPKY DCKIMTSKTD  360
VSSSVITSLG AIVSCYGKTK CTASNKNRGI IKTFSNGCDY VSNKGVDTVS VGNTLYYVNK  420
QEGKSLYVKG EPIINFYDPL VFPSSEFDAS ISQVNEKINQ SLAFIRKSDE LLHCCNAGKS  480
TTNIMITTLV PRGSGGSAIG GYIPEAPRDG QAYVRKDGEW VLLSTFLGGH HHHHHGSWSH  540
PQFEK                                                              545

SEQ ID NO: 274          moltype = AA  length = 545
FEATURE                 Location/Qualifiers
REGION                  1..545
                        note = Synthetic
source                  1..545
                        mol_type = protein
                        organism = synthetic construct
SEQUENCE: 274
MELLILKANA ITTILTAVTF CFASGQNITE EFYQSTCSAV SKGYLSALRT GWYHCVITIE  60
LSNIKENKCN GTDAKVKLIK QELDKYKNAV TELQLLMQST PATGSAIASG VAVSKVLHLE  120
GEVNKIKSAL LSTNKAVVSL SNGVSVCTSK VLDLKNYIDK QLLPIVNKQS CSISNIETVI  180
EFQQKNNRLL EITREFSVNA GVTTPVSTYM LTNSELLSLI NDMPITNDQK KLMSNNVQIV  240
RQQSYSIMSI IKEEVLAYVV QLPLYGVIDT PCWKLHTSPL CTTNTKEGSN ICLTRTDRGW  300
YCDNAGSVSF FPQAETCKVQ SNRVFCDTMN SLTLPSEVNL CNVDIFNPKY DCKIMTSKTD  360
VSSSVITSLG AIVSCYGKTK CTASNKNRGI IKTFSNGCDY VSNKGVDTVS VGNTLYYVNK  420
```

-continued

```
QEGKSLYVKG EPIINFYDPL VFPSSEFDAS ISQVNEKINQ SLAFIRKSDE LLHNVNAGKS  480
CCNIMITTLV PRGSGGSAIG GYIPEAPRDG QAYVRKDGEW VLLSTFLGGH HHHHHGSWSH  540
PQFEK                                                              545

SEQ ID NO: 275         moltype = AA  length = 545
FEATURE                Location/Qualifiers
REGION                 1..545
                       note = Synthetic
source                 1..545
                       mol_type = protein
                       organism = synthetic construct
SEQUENCE: 275
MELLILKANA ITTILTAVTF CFASGQNITE EFYQSTCSAV SKGYLSALRT GWYHCVITIE  60
LSNIKENKCN GTDAKVKLIK QELDKYKNAV TELQLLMQST PATGSAIASG VAVSKVLHLE  120
GEVNKIKSAL LSTNKAVVSL SNGVSVCTSK VLDLKNYIDK QLLPIVNKQS CSISNIETVI  180
EFQQKNNRLL EITREFSVNA GVTTPVSTYM LTNSELLSLI NDMPITNDQK KLMSNNVQIV  240
RQQSYSIMSI IKEEVLAYVV QLPLYGVIDT PCWKLHTSPL CTTNTKEGSN ICLTRTDRGW  300
YCDNAGSVSF FPQAETCKVQ SNRVFCDTMN SLTLPSEVNL CNVDIFNPKY DCKIMTSKTD  360
VSSSVITSLG AIVSCYGKTK CTASNKNRGI IKTFSNGCDY VSNKGVDTVS VGNTLYYVNK  420
QEGKSLYVKG EPIINFYDPL VFPSSEFDAS ISQVNEKINQ SLAFIRCCDE LLHCCNAGKS  480
TTNIMITTLV PRGSGGSAIG GYIPEAPRDG QAYVRKDGEW VLLSTFLGGH HHHHHGSWSH  540
PQFEK                                                              545

SEQ ID NO: 276         moltype = AA  length = 545
FEATURE                Location/Qualifiers
REGION                 1..545
                       note = Synthetic
source                 1..545
                       mol_type = protein
                       organism = synthetic construct
SEQUENCE: 276
MELLILKANA ITTILTAVTF CFASGQNITE EFYQSTCSAV SKGYLSALRT GWYHCVITIE  60
LSNIKENKCN GTDAKVKLIK QELDKYKNAV TELQLLMQST PATGSAIASG VAVSKVLHLE  120
GEVNKIKSAL LSTNKAVVSL SNGVSVCTSK VLDLKNYIDK QLLPIVNKQS CSISNIETVI  180
EFQQKNNRLL EITREFSVNA GVTTPVSTYM LTNSELLSLI NDMPITNDQK KLMSNNVQIV  240
RQQSYSIMSI IKEEVLAYVV QLPLYGVIDT PCWKLHTSPL CTTNTKEGSN ICLTRTDRGW  300
YCDNAGSVSF FPQAETCKVQ SNRVFCDTMN SLTLPSEVNL CNVDIFNPKY DCKIMTSKTD  360
VSSSVITSLG AIVSCYGKTK CTASNKNRGI IKTFSNGCDY VSNKGVDTVS VGNTLYYVNK  420
QEGKSLYVKG EPIINFYDPL VFPSSEFDAS ISQVNEKINQ SLAFIRCCDE LLHNVNAGKS  480
CCNIMITTLV PRGSGGSAIG GYIPEAPRDG QAYVRKDGEW VLLSTFLGGH HHHHHGSWSH  540
PQFEK                                                              545

SEQ ID NO: 277         moltype = AA  length = 545
FEATURE                Location/Qualifiers
REGION                 1..545
                       note = Synthetic
source                 1..545
                       mol_type = protein
                       organism = synthetic construct
SEQUENCE: 277
MELLILKANA ITTILTAVTF CFASGQNITE EFYQSTCSAV SKGYLSALRT GWYHCVITIE  60
LSNIKENKCN GTDAKVKLIK QELDKYKNAV TELQLLMQST PATGSAIASG VAVSKVLHLE  120
GEVNKIKSAL LSTNKAVVSL SNGVSVCTSK VLDLKNYIDK QLLPIVNKQS CSISNIETVI  180
EFQQKNNRLL EITREFSVNA GVTTPVSTYM LTNSELLSLI NDMPITNDQK KLMSNNVQIV  240
RQQSYSIMSI IKEEVLAYVV QLPLYGVIDT PCWKLHTSPL CTTNTKEGSN ICLTRTDRGW  300
YCDNAGSVSF FPQAETCKVQ SNRVFCDTMN SLTLPSEVNL CNVDIFNPKY DCKIMTSKTD  360
VSSSVITSLG AIVSCYGKTK CTASNKNRGI IKTFSNGCDY VSNKGVDTVS VGNTLYYVNK  420
QEGKSLYVKG EPIINFYDPL VFPSSEFDAS ISQVNEKINQ SLAFIRKSDE LLHCCNAGKS  480
CCNIMITTLV PRGSGGSAIG GYIPEAPRDG QAYVRKDGEW VLLSTFLGGH HHHHHGSWSH  540
PQFEK                                                              545

SEQ ID NO: 278         moltype = AA  length = 545
FEATURE                Location/Qualifiers
REGION                 1..545
                       note = Synthetic
source                 1..545
                       mol_type = protein
                       organism = synthetic construct
SEQUENCE: 278
MELLILKANA ITTILTAVTF CFASGQNITE EFYQSTCSAV SKGYLSALRT GWYHCVITIE  60
LSNIKENKCN GTDAKVKLIK QELDKYKNAV TELQLLMQST PATGSAIASG VAVSKVLHLE  120
GEVNKIKSAL LSTNKAVVSL SNGVSVCTSK VLDLKNYIDK QLLPIVNKQS CSISNIETVI  180
EFQQKNNRLL EITREFSVNA GVTTPVSTYM LTNSELLSLI NDMPITNDQK KLMSNNVQIV  240
RQQSYSIMSI IKEEVLAYVV QLPLYGVIDT PCWKLHTSPL CTTNTKEGSN ICLTRTDRGW  300
YCDNAGSVSF FPQAETCKVQ SNRVFCDTMN SLTLPSEVNL CNVDIFNPKY DCKIMTSKTD  360
VSSSVITSLG AIVSCYGKTK CTASNKNRGI IKTFSNGCDY VSNKGVDTVS VGNTLYYVNK  420
QEGKSLYVKG EPIINFYDPL VFPSSEFDAS ISQVNEKINQ SLAFIRCCDE LLHCCNAGKS  480
CCNIMITTLV PRGSGGSAIG GYIPEAPRDG QAYVRKDGEW VLLSTFLGGH HHHHHGSWSH  540
PQFEK                                                              545
```

```
SEQ ID NO: 279          moltype = AA  length = 84
FEATURE                 Location/Qualifiers
REGION                  1..84
                        note = synthetic polypeptide
source                  1..84
                        mol_type = protein
                        organism = synthetic construct
SEQUENCE: 279
QNITEEFYQS TCSAVSKGYL SALRTGWYTS VITIELSNIK ENKCNGTDAK VKLIKQELDK  60
YKNAVTELQL LMQSTPACNN RARR                                         84

SEQ ID NO: 280          moltype = AA  length = 377
FEATURE                 Location/Qualifiers
REGION                  1..377
                        note = synthetic polypeptide
source                  1..377
                        mol_type = protein
                        organism = synthetic construct
SEQUENCE: 280
FLGFLLGVGS ACASGIAVSK VLHLEGEVNK IKSALLSTNK AVVSLSNGVS VLTIKVLDLK  60
NYIDKQLLPI VNKQSCSISN IETVIEFQQK NNRLLEITRE FSVNAGVTTP VSTYMLTNSE  120
LLSLINDMPI TNDQKKLMSN NVQIVRQQSY SIMSIIKEEV LAYVVQLPLY GVIDTPCWKL  180
HTSPLCTTNT KEGSNICLTR TDRGWYCDNA GSVSFFPQAE TCKVQSNRVF CDTMNSLTLP  240
SEVNLCNIDI FNPKYDCKIM TSKTDVSSSV ITSLGAIVSC YGKTKCTASN KNRGIIKTFS  300
NGCDYVSNKG VDTVSVGNTL YYVNKQEGKS LYVKGEPIIN FYDPLVFPSS EFDASISQVN  360
EKINQSLAFI RKSDELL                                                 377

SEQ ID NO: 281          moltype = AA  length = 84
FEATURE                 Location/Qualifiers
REGION                  1..84
                        note = synthetic polypeptide
source                  1..84
                        mol_type = protein
                        organism = synthetic construct
SEQUENCE: 281
QNITEEFYQS TCSAVSKGYL SALRTGWYTS VITIELSNIK ENKCNGTDAK VKLIKQELDK  60
YKNAVTELQL LMQSTPACNN RARR                                         84

SEQ ID NO: 282          moltype = AA  length = 377
FEATURE                 Location/Qualifiers
REGION                  1..377
                        note = synthetic polypeptide
source                  1..377
                        mol_type = protein
                        organism = synthetic construct
SEQUENCE: 282
FLGFLLGVGS ACASGIAVSK VLHLEGEVNK IKSALLSTNK AVVSLSNGVS VLTIKVLDLK  60
NYIDKQLLPI VNKQSCSISN IETVIEFQQK NNRLLEITRE FSVNAGVTTP VSTYMLTNSE  120
LLSLINDMPI TNDQKKLMSN NVQIVRQQSY SIMSIIKEEV LAYVVQLPLY GVIDTPCWKL  180
HTSPLCTTNT KEGSNICLTR TDRGWYCDNA GSVSFFPQAE TCKVQSNRVF CDTMNSLTLP  240
SEVNLCNIDI FNPKYDCKIM TSKTDVSSSV ITSLGAIVSC YGKTKCTASN KNRGIIKTFS  300
NGCDYVSNKG VDTVSVGNTL YYVNKQEGKS LYVKGEPIIN FYDPLVFPSS EFDASISQVN  360
EKINQSLAFI RKSDELL                                                 377

SEQ ID NO: 283          moltype = AA  length = 84
FEATURE                 Location/Qualifiers
REGION                  1..84
                        note = synthetic polypeptide
source                  1..84
                        mol_type = protein
                        organism = synthetic construct
SEQUENCE: 283
QNITEEFYQS TCSAVSKGYL SALRTGWYTS VITIELSNIK ENKCNGTDAK VKLIKQELDK  60
YKNAVTELQL LMQSTPACNN RARR                                         84

SEQ ID NO: 284          moltype = AA  length = 377
FEATURE                 Location/Qualifiers
REGION                  1..377
                        note = synthetic polypeptide
source                  1..377
                        mol_type = protein
                        organism = synthetic construct
SEQUENCE: 284
FLGFLLGVGS ACASGIAVSK VLHLEGEVNK IKSALLSTNK AVVSLSNGVS VLTIKVLDLK  60
NYIDKQLLPI VNKQSCSISN IETVIEFQQK NNRLLEITRE FSVNAGVTTP VSTYMLTNSE  120
LLSLINDMPI TNDQKKLMSN NVQIVRQQSY SIMSIIKEEV LAYVVQLPLY GVIDTPCWKL  180
HTSPLCTTNT KEGSNICLTR TDRGWYCDNA GSVSFFPQAE TCKVQSNRVF CDTMNSLTLP  240
SEVNLCNIDI FNPKYDCKIM TSKTDVSSSV ITSLGAIVSC YGKTKCTASN KNRGIIKTFS  300
```

-continued

```
NGCDYVSNKG VDTVSVGNTL YYVNKQEGKS LYVKGEPIIN FYDPLVFPSS EFDASISQVN  360
EKINQSLAFI RKSDELL                                                 377

SEQ ID NO: 285         moltype = AA  length = 84
FEATURE                Location/Qualifiers
REGION                 1..84
                       note = synthetic polypeptide
source                 1..84
                       mol_type = protein
                       organism = synthetic construct
SEQUENCE: 285
QNITEEFYQS TCSAVSRGYF SALRTGWYTS VITIELSNIK ETKCNGTDTK VKLIKQELDK  60
YKNAVTELQL LMQNTPACNN RARR                                         84

SEQ ID NO: 286         moltype = AA  length = 377
FEATURE                Location/Qualifiers
REGION                 1..377
                       note = synthetic polypeptide
source                 1..377
                       mol_type = protein
                       organism = synthetic construct
SEQUENCE: 286
FLGFLLGVGS ACASGIAVSK VLHLEGEVNK IKNALLSTNK AVVSLSNGVS VLTIKVLDLK  60
NYINNQLLPI VNKQSCRISN IETVIEFQQK NSRLLEITRE FSVNAGVTTP LSTYMLTNSE  120
LLSLINDMPI TNDQKKLMSS NVQIVRQQSY SIMSIIKEEV LAYVVQLPIY GVIDTPCWKL  180
HTSPLCTTNI KEGSNICLTR TDRGWYCDNA GSVSFFPQAD TCKVQSNRVF CDTMNSLTLP  240
SEVSLCNTDI FNSKYDCKIM TSKTDVSSSV ITSLGAIVSC YGKTKCTASN KNRGIIKTFS  300
NGCDYVSNKG VDTVSVGNTL YYVNKLEGKN LYVKGEPIIN YYDPLVFPSS EFDASISQVN  360
EKINQSLAFI RRSDELL                                                 377

SEQ ID NO: 287         moltype = AA  length = 84
FEATURE                Location/Qualifiers
REGION                 1..84
                       note = synthetic polypeptide
source                 1..84
                       mol_type = protein
                       organism = synthetic construct
SEQUENCE: 287
QNITEEFYQS TCSAVSRGYF SALRTGWYTS VITIELSNIK ETKCNGTDTK VKLIKQELDK  60
YKNAVTELQL LMQNTPACNN RARR                                         84

SEQ ID NO: 288         moltype = AA  length = 377
FEATURE                Location/Qualifiers
REGION                 1..377
                       note = synthetic polypeptide
source                 1..377
                       mol_type = protein
                       organism = synthetic construct
SEQUENCE: 288
FLGFLLGVGS ACASGIAVSK VLHLEGEVNK IKNALLSTNK AVVSLSNGVS VLTIKVLDLK  60
NYINNQLLPI VNQQSCRISN IETVIEFQQK NSRLLEITRE FSVNAGVTTP LSTYMLTNSE  120
LLSLINDMPI TNDQKKLMSS NVQIVRQQSY SIMSIMKEEV LAYVVQLPIY GVIDTPCWKL  180
HTSPLCTTNI KEGSNICLTR TDRGWYCDNA GSVSFFPQAD TCKVQSNRVF CDTMNSLTLP  240
SEVSLCNTDI FNSKYDCKIM TSKTDISSSV ITSLGAIVSC YGKTKCTASN KNRGIIKTFS  300
NGCDYVSNKG VDTVSVGNTL YYVNKLEGKN LYVKGEPIIN YYDPLVFPSS EFDASISQVN  360
EKINQSLAFI RRSDELL                                                 377

SEQ ID NO: 289         moltype = AA  length = 84
FEATURE                Location/Qualifiers
REGION                 1..84
                       note = synthetic polypeptide
source                 1..84
                       mol_type = protein
                       organism = synthetic construct
SEQUENCE: 289
QNITEEFYQS TCSAVSRGYL SALRTGWYTS VITIELSNIK ETKCNGTDTK VKLIKQELDK  60
YKNAVTELQL LMQNTPACNN RARR                                         84

SEQ ID NO: 290         moltype = AA  length = 377
FEATURE                Location/Qualifiers
REGION                 1..377
                       note = synthetic polypeptide
source                 1..377
                       mol_type = protein
                       organism = synthetic construct
SEQUENCE: 290
FLGFLLGVGS ACASGIAVSK VLHLEGEVNK IKNALLSTNK AVVSLSNGVS VLTIKVLDLK  60
NYINNQLLPI VNQQSCRISN IETVIEFQQK NSRLLEIARE FSVNAGVTTP LSTYMLTNSE  120
LLSLINDMPI TNDQKKLMSS NVQIVRQQSY SIMSIIKEEV LAYVVQLPIY GVIDTPCWKL  180
```

-continued

```
HTSPLCTTNI KEGSNICLTR TDRGWYCDNA GSVSFFPQAD TCKVQSNRVF CDTMNSLTLP  240
SEVSLCNTDI FNSKYDCKIM TSKTDISSSV ITSLGAIVSC YGKTKCTASN KNRGIIKTFS  300
NGCDYVSNKG VDTVSVGNTL YYVNKLEGKN LYVKGEPIIN YYDPLVFPSS EFDASISQVN  360
EKINQSLAFI RRSDELL                                                 377

SEQ ID NO: 291         moltype = AA  length = 84
FEATURE                Location/Qualifiers
REGION                 1..84
                       note = synthetic polypeptide
source                 1..84
                       mol_type = protein
                       organism = synthetic construct
SEQUENCE: 291
QNITEEFYQS TCSAVSKGYL SALRTGWYHS VITIELSNIK ENKCNGTDAK VKLIKQELDK  60
YKNAVTELQL LMQSTPACNN RARR                                         84

SEQ ID NO: 292         moltype = AA  length = 377
FEATURE                Location/Qualifiers
REGION                 1..377
                       note = synthetic polypeptide
source                 1..377
                       mol_type = protein
                       organism = synthetic construct
SEQUENCE: 292
FLGFLLGVGS ACASGIAVSK VLHLEGEVNK IKSALLSTNK AVVSLSNGVS VLTIKVLDLK  60
NYIDKQLLPI VNKQSCSISN IETVIEFQQK NNRLLEITRE FSVNAGVTTP VSTYMLTNSE  120
LLSLINDMPI TNDQKKLMSN NVQIVRQQSY SIMSIIKEEI LAYVVQLPLY GVIDTPCWKL  180
HTSPLCTTNT KEGSNICLTR TDRGWYCDNA GSVSFFPQAE TCKVQSNRVF CDTMNSLTLP  240
SEVNLCNIDI FNPKYDCKIM TSKTDVSSSV ITSLGAIVSC YGKTKCTASN KNRGIIKTFS  300
NGCDYVSNKG VDTVSVGNTL YYVNKQEGKS LYVKGEPIIN FYDPLVFPSS EFDASISQVN  360
EKINQSLAFI RKSDELL                                                 377

SEQ ID NO: 293         moltype = AA  length = 84
FEATURE                Location/Qualifiers
REGION                 1..84
                       note = synthetic polypeptide
source                 1..84
                       mol_type = protein
                       organism = synthetic construct
SEQUENCE: 293
QNITEEFYQS TCSAVSKGYL SALRTGWYHS VITIELSNIK ENKCNGTDAK VKLIKQELDK  60
YKNAVTELQL LMQSTPACNN RARR                                         84

SEQ ID NO: 294         moltype = AA  length = 377
FEATURE                Location/Qualifiers
REGION                 1..377
                       note = synthetic polypeptide
source                 1..377
                       mol_type = protein
                       organism = synthetic construct
SEQUENCE: 294
FLGFLLGVGS ACASGIAVSK VLHLEGEVNK IKSALLSTNK AVVSLSNGVS VLTIKVLDLK  60
NYIDKQLLPI VNKQSCSISN IETVIEFQQK NNRLLEITRE FSVNAGVTTP VSTYMLTNSE  120
LLSLINDMPI TNDQKKLMSN NVQIVRQQSY SIMSIIKEEI LAYVVQLPLY GVIDTPCWKL  180
HTSPLCTTNT KEGSNICLTR TDRGWYCDNA GSVSFFPQAE TCKVQSNRVF CDTMNSLTLP  240
SEVNLCNIDI FNPKYDCKIM TSKTDVSSSV ITSLGAIVSC YGKTKCTASN KNRGIIKTFS  300
NGCDYVSNKG VDTVSVGNTL YYVNKQEGKS LYVKGEPIIN FYDPLVFPSS EFDASISQVN  360
EKINQSLAFI RKSDELL                                                 377

SEQ ID NO: 295         moltype = AA  length = 84
FEATURE                Location/Qualifiers
REGION                 1..84
                       note = synthetic polypeptide
source                 1..84
                       mol_type = protein
                       organism = synthetic construct
SEQUENCE: 295
QNITEEFYQS TCSAVSKGYL SALRTGWYHS VITIELSNIK ENKCNGTDAK VKLIKQELDK  60
YKNAVTELQL LMQSTPACNN RARR                                         84

SEQ ID NO: 296         moltype = AA  length = 377
FEATURE                Location/Qualifiers
REGION                 1..377
                       note = synthetic polypeptide
source                 1..377
                       mol_type = protein
                       organism = synthetic construct
SEQUENCE: 296
FLGFLLGVGS ACASGIAVSK VLHLEGEVNK IKSALLSTNK AVVSLSNGVS VLTIKVLDLK  60
```

-continued

```
NYIDKQLLPI VNKQSCSISN IETVIEFQQK NNRLLEITRE FSVNAGVTTP VSTYMLTNSE  120
LLSLINDMPI TNDQKKLMSN NVQIVRQQSY SIMSIIKEEI LAYVVQLPLY GVIDTPCWKL  180
HTSPLCTTNT KEGSNICLTR TDRGWYCDNA GSVSFFPQAE TCKVQSNRVF CDTMNSLTLP  240
SEVNLCNIDI FNPKYDCKIM TSKTDVSSSV ITSLGAIVSC YGKTKCTASN KNRGIIKTFS  300
NGCDYVSNKG VDTVSVGNTL YYVNKQEGKS LYVKGEPIIN FYDPLVFPSS EFDASISQVN  360
EKINQSLAFI RKSDELL                                                 377

SEQ ID NO: 297         moltype = AA  length = 84
FEATURE                Location/Qualifiers
REGION                 1..84
                       note = synthetic polypeptide
source                 1..84
                       mol_type = protein
                       organism = synthetic construct
SEQUENCE: 297
QNITEEFYQS TCSAVSRGYF SALRTGWYHS VITIELSNIK ETKCNGTDTK VKLIKQELDK  60
YKNAVTELQL LMQNTPACNN RARR                                         84

SEQ ID NO: 298         moltype = AA  length = 377
FEATURE                Location/Qualifiers
REGION                 1..377
                       note = synthetic polypeptide
source                 1..377
                       mol_type = protein
                       organism = synthetic construct
SEQUENCE: 298
FLGFLLGVGS ACASGIAVSK VLHLEGEVNK IKNALLSTNK AVVSLSNGVS VLTIKVLDLK  60
NYINNQLLPI VNKQSCRISN IETVIEFQQK NSRLLEITRE FSVNAGVTTP LSTYMLTNSE  120
LLSLINDMPI TNDQKKLMSS NVQIVRQQSY SIMSIIKEEI LAYVVQLPIY GVIDTPCWKL  180
HTSPLCTTNI KEGSNICLTR TDRGWYCDNA GSVSFFPQAD TCKVQSNRVF CDTMNSLTLP  240
SEVSLCNTDI FNSKYDCKIM TSKTDVSSSV ITSLGAIVSC YGKTKCTASN KNRGIIKTFS  300
NGCDYVSNKG VDTVSVGNTL YYVNKLEGKN LYVKGEPIIN YYDPLVFPSS EFDASISQVN  360
EKINQSLAFI RRSDELL                                                 377

SEQ ID NO: 299         moltype = AA  length = 84
FEATURE                Location/Qualifiers
REGION                 1..84
                       note = synthetic polypeptide
source                 1..84
                       mol_type = protein
                       organism = synthetic construct
SEQUENCE: 299
QNITEEFYQS TCSAVSRGYF SALRTGWYHS VITIELSNIK ETKCNGTDTK VKLIKQELDK  60
YKNAVTELQL LMQNTPACNN RARR                                         84

SEQ ID NO: 300         moltype = AA  length = 377
FEATURE                Location/Qualifiers
REGION                 1..377
                       note = synthetic polypeptide
source                 1..377
                       mol_type = protein
                       organism = synthetic construct
SEQUENCE: 300
FLGFLLGVGS ACASGIAVSK VLHLEGEVNK IKNALLSTNK AVVSLSNGVS VLTIKVLDLK  60
NYINNQLLPI VNQQSCRISN IETVIEFQQK NSRLLEITRE FSVNAGVTTP LSTYMLTNSE  120
LLSLINDMPI TNDQKKLMSS NVQIVRQQSY SIMSIMKEEI LAYVVQLPIY GVIDTPCWKL  180
HTSPLCTTNI KEGSNICLTR TDRGWYCDNA GSVSFFPQAD TCKVQSNRVF CDTMNSLTLP  240
SEVSLCNTDI FNSKYDCKIM TSKTDISSSV ITSLGAIVSC YGKTKCTASN KNRGIIKTFS  300
NGCDYVSNKG VDTVSVGNTL YYVNKLEGKN LYVKGEPIIN YYDPLVFPSS EFDASISQVN  360
EKINQSLAFI RRSDELL                                                 377

SEQ ID NO: 301         moltype = AA  length = 84
FEATURE                Location/Qualifiers
REGION                 1..84
                       note = synthetic polypeptide
source                 1..84
                       mol_type = protein
                       organism = synthetic construct
SEQUENCE: 301
QNITEEFYQS TCSAVSRGYL SALRTGWYHS VITIELSNIK ETKCNGTDTK VKLIKQELDK  60
YKNAVTELQL LMQNTPACNN RARR                                         84

SEQ ID NO: 302         moltype = AA  length = 377
FEATURE                Location/Qualifiers
REGION                 1..377
                       note = synthetic polypeptide
source                 1..377
                       mol_type = protein
                       organism = synthetic construct
```

```
SEQUENCE: 302
FLGFLLGVGS ACASGIAVSK VLHLEGEVNK IKNALLSTNK AVVSLSNGVS VLTIKVLDLK  60
NYINNQLLPI VNQQSCRISN IETVIEFQQK NSRLLEIARE FSVNAGVTTP LSTYMLTNSE  120
LLSLINDMPI TNDQKKLMSS NVQIVRQQSY SIMSIIKEEI LAYVVQLPIY GVIDTPCWKL  180
HTSPLCTTNI KEGSNICLTR TDRGWYCDNA GSVSFFPQAD TCKVQSNRVF CDTMNSLTLP  240
SEVSLCNTDI FNSKYDCKIM TSKTDISSSV ITSLGAIVSC YGKTKCTASN KNRGIIKTFS  300
NGCDYVSNKG VDTVSVGNTL YYVNKLEGKN LYVKGEPIIN YYDPLVFPSS EFDASISQVN  360
EKINQSLAFI RRSDELL                                                377

SEQ ID NO: 303          moltype = AA  length = 84
FEATURE                 Location/Qualifiers
REGION                  1..84
                        note = synthetic polypeptide
source                  1..84
                        mol_type = protein
                        organism = synthetic construct
SEQUENCE: 303
QNITEEFYQS TCSAVSKGYL SALRTGWYHC VITIELSNIK ENKCNGTDAK VKLIKQELDK  60
YKNAVTELQL LMQSTPAANN RARR                                        84

SEQ ID NO: 304          moltype = AA  length = 377
FEATURE                 Location/Qualifiers
REGION                  1..377
                        note = synthetic polypeptide
source                  1..377
                        mol_type = protein
                        organism = synthetic construct
SEQUENCE: 304
FLGFLLGVGS AIASGIAVSK VLHLEGEVNK IKSALLSTNK AVVSLSNGVS VCTSKVLDLK  60
NYIDKQLLPI VNKQSCSISN IETVIEFQQK NNRLLEITRE FSVNAGVTTP VSTYMLTNSE  120
LLSLINDMPI TNDQKKLMSN NVQIVRQQSY SIMSIIKEEV LAYVVQLPLY GVIDTPCWKL  180
HTSPLCTTNT KEGSNICLTR TDRGWYCDNA GSVSFFPQAE TCKVQSNRVF CDTMNSLTLP  240
SEVNLCNIDI FNPKYDCKIM TSKTDVSSSV ITSLGAIVSC YGKTKCTASN KNRGIIKTFS  300
NGCDYVSNKG VDTVSVGNTL YYVNKQEGKS LYVKGEPIIN FYDPLVFPSS EFDASISQVN  360
EKINQSLAFI RKSDELL                                                377

SEQ ID NO: 305          moltype = AA  length = 84
FEATURE                 Location/Qualifiers
REGION                  1..84
                        note = synthetic polypeptide
source                  1..84
                        mol_type = protein
                        organism = synthetic construct
SEQUENCE: 305
QNITEEFYQS TCSAVSKGYL SALRTGWYHC VITIELSNIK ENKCNGTDAK VKLIKQELDK  60
YKNAVTELQL LMQSTPAANN RARR                                        84

SEQ ID NO: 306          moltype = AA  length = 377
FEATURE                 Location/Qualifiers
REGION                  1..377
                        note = synthetic polypeptide
source                  1..377
                        mol_type = protein
                        organism = synthetic construct
SEQUENCE: 306
FLGFLLGVGS AIASGIAVSK VLHLEGEVNK IKSALLSTNK AVVSLSNGVS VCTSKVLDLK  60
NYIDKQLLPI VNKQSCSISN IETVIEFQQK NNRLLEITRE FSVNAGVTTP VSTYMLTNSE  120
LLSLINDMPI TNDQKKLMSN NVQIVRQQSY SIMSIIKEEV LAYVVQLPLY GVIDTPCWKL  180
HTSPLCTTNT KEGSNICLTR TDRGWYCDNA GSVSFFPQAE TCKVQSNRVF CDTMNSLTLP  240
SEVNLCNIDI FNPKYDCKIM TSKTDVSSSV ITSLGAIVSC YGKTKCTASN KNRGIIKTFS  300
NGCDYVSNKG VDTVSVGNTL YYVNKQEGKS LYVKGEPIIN FYDPLVFPSS EFDASISQVN  360
EKINQSLAFI RKSDELL                                                377

SEQ ID NO: 307          moltype = AA  length = 84
FEATURE                 Location/Qualifiers
REGION                  1..84
                        note = synthetic polypeptide
source                  1..84
                        mol_type = protein
                        organism = synthetic construct
SEQUENCE: 307
QNITEEFYQS TCSAVSKGYL SALRTGWYHC VITIELSNIK ENKCNGTDAK VKLIKQELDK  60
YKNAVTELQL LMQSTPAANN RARR                                        84

SEQ ID NO: 308          moltype = AA  length = 377
FEATURE                 Location/Qualifiers
REGION                  1..377
                        note = synthetic polypeptide
source                  1..377
```

```
                         mol_type = protein
                         organism = synthetic construct
SEQUENCE: 308
FLGFLLGVGS AIASGIAVSK VLHLEGEVNK IKSALLSTNK AVVSLSNGVS VCTSKVLDLK  60
NYIDKQLLPI VNKQSCSISN IETVIEFQQK NNRLLEITRE FSVNAGVTTP VSTYMLTNSE  120
LLSLINDMPI TNDQKKLMSN NVQIVRQQSY SIMSIIKEEV LAYVVQLPLY GVIDTPCWKL  180
HTSPLCTTNT KEGSNICLTR TDRGWYCDNA GSVSFFPQAE TCKVQSNRVF CDTMNSLTLP  240
SEVNLCNIDI FNPKYDCKIM TSKTDVSSSV ITSLGAIVSC YGKTKCTASN KNRGIIKTFS  300
NGCDYVSNKG VDTVSVGNTL YYVNKQEGKS LYVKGEPIIN FYDPLVFPSS EFDASISQVN  360
EKINQSLAFI RKSDELL                                                377

SEQ ID NO: 309           moltype = AA  length = 84
FEATURE                  Location/Qualifiers
REGION                   1..84
                         note = synthetic polypeptide
source                   1..84
                         mol_type = protein
                         organism = synthetic construct
SEQUENCE: 309
QNITEEFYQS TCSAVSRGYF SALRTGWYHC VITIELSNIK ETKCNGTDTK VKLIKQELDK  60
YKNAVTELQL LMQNTPAANN RARR                                         84

SEQ ID NO: 310           moltype = AA  length = 377
FEATURE                  Location/Qualifiers
REGION                   1..377
                         note = synthetic polypeptide
source                   1..377
                         mol_type = protein
                         organism = synthetic construct
SEQUENCE: 310
FLGFLLGVGS AIASGIAVSK VLHLEGEVNK IKNALLSTNK AVVSLSNGVS VCTSKVLDLK  60
NYINNQLLPI VNKQSCRISN IETVIEFQQK NSRLLEITRE FSVNAGVTTP LSTYMLTNSE  120
LLSLINDMPI TNDQKKLMSS NVQIVRQQSY SIMSIIKEEV LAYVVQLPIY GVIDTPCWKL  180
HTSPLCTTNI KEGSNICLTR TDRGWYCDNA GSVSFFPQAD TCKVQSNRVF CDTMNSLTLP  240
SEVSLCNTDI FNSKYDCKIM TSKTDVSSSV ITSLGAIVSC YGKTKCTASN KNRGIIKTFS  300
NGCDYVSNKG VDTVSVGNTL YYVNKLEGKN LYVKGEPIIN YYDPLVFPSS EFDASISQVN  360
EKINQSLAFI RRSDELL                                                377

SEQ ID NO: 311           moltype = AA  length = 84
FEATURE                  Location/Qualifiers
REGION                   1..84
                         note = synthetic polypeptide
source                   1..84
                         mol_type = protein
                         organism = synthetic construct
SEQUENCE: 311
QNITEEFYQS TCSAVSRGYF SALRTGWYHC VITIELSNIK ETKCNGTDTK VKLIKQELDK  60
YKNAVTELQL LMQNTPAANN RARR                                         84

SEQ ID NO: 312           moltype = AA  length = 377
FEATURE                  Location/Qualifiers
REGION                   1..377
                         note = synthetic polypeptide
source                   1..377
                         mol_type = protein
                         organism = synthetic construct
SEQUENCE: 312
FLGFLLGVGS AIASGIAVSK VLHLEGEVNK IKNALLSTNK AVVSLSNGVS VCTSKVLDLK  60
NYINNQLLPI VNQQSCRISN IETVIEFQQK NSRLLEITRE FSVNAGVTTP LSTYMLTNSE  120
LLSLINDMPI TNDQKKLMSS NVQIVRQQSY SIMSIMKEEV LAYVVQLPIY GVIDTPCWKL  180
HTSPLCTTNI KEGSNICLTR TDRGWYCDNA GSVSFFPQAD TCKVQSNRVF CDTMNSLTLP  240
SEVSLCNTDI FNSKYDCKIM TSKTDISSSV ITSLGAIVSC YGKTKCTASN KNRGIIKTFS  300
NGCDYVSNKG VDTVSVGNTL YYVNKLEGKN LYVKGEPIIN YYDPLVFPSS EFDASISQVN  360
EKINQSLAFI RRSDELL                                                377

SEQ ID NO: 313           moltype = AA  length = 84
FEATURE                  Location/Qualifiers
REGION                   1..84
                         note = synthetic polypeptide
source                   1..84
                         mol_type = protein
                         organism = synthetic construct
SEQUENCE: 313
QNITEEFYQS TCSAVSRGYL SALRTGWYHC VITIELSNIK ETKCNGTDTK VKLIKQELDK  60
YKNAVTELQL LMQNTPAANN RARR                                         84

SEQ ID NO: 314           moltype = AA  length = 377
FEATURE                  Location/Qualifiers
REGION                   1..377
```

```
                        note = synthetic polypeptide
source                  1..377
                        mol_type = protein
                        organism = synthetic construct
SEQUENCE: 314
FLGFLLGVGS AIASGIAVSK VLHLEGEVNK IKNALLSTNK AVVSLSNGVS VCTSKVLDLK  60
NYINNQLLPI VNQQSCRISN IETVIEFQQK NSRLLEIARE FSVNAGVTTP LSTYMLTNSE  120
LLSLINDMPI TNDQKKLMSS NVQIVRQQSY SIMSIIKEEV LAYVVQLPIY GVIDTPCWKL  180
HTSPLCTTNI KEGSNICLTR TDRGWYCDNA GSVSFFPQAD TCKVQSNRVF CDTMNSLTLP  240
SEVSLCNTDI FNSKYDCKIM TSKTDISSSV ITSLGAIVSC YGKTKCTASN KNRGIIKTFS  300
NGCDYVSNKG VDTVSVGNTL YYVNKLEGKN LYVKGEPIIN YYDPLVFPSS EFDASISQVN  360
EKINQSLAFI RRSDELL                                                 377

SEQ ID NO: 315          moltype = AA  length = 84
FEATURE                 Location/Qualifiers
REGION                  1..84
                        note = synthetic polypeptide
source                  1..84
                        mol_type = protein
                        organism = synthetic construct
SEQUENCE: 315
QNITEEFYQS TCSAVSKGYL SALRTGWYHC VITIELSNIK ENKCNGTDAK VKLIKQELDK  60
YKNAVTELQL LMQSTPAANN RARR                                         84

SEQ ID NO: 316          moltype = AA  length = 377
FEATURE                 Location/Qualifiers
REGION                  1..377
                        note = synthetic polypeptide
source                  1..377
                        mol_type = protein
                        organism = synthetic construct
SEQUENCE: 316
FLGFLLGVGS AIASGIAVSK VLHLEGEVNK IKSALLSTNK AVVSLSNGVS VCTIKVLDLK  60
NYIDKQLLPI VNKQSCSISN IETVIEFQQK NNRLLEITRE FSVNAGVTTP VSTYMLTNSE  120
LLSLINDMPI TNDQKKLMSN NVQIVRQQSY SIMSIIKEEV LAYVVQLPLY GVIDTPCWKL  180
HTSPLCTTNT KEGSNICLTR TDRGWYCDNA GSVSFFPQAE TCKVQSNRVF CDTMNSLTLP  240
SEVNLCNIDI FNPKYDCKIM TSKTDVSSSV ITSLGAIVSC YGKTKCTASN KNRGIIKTFS  300
NGCDYVSNKG VDTVSVGNTL YYVNKQEGKS LYVKGEPIIN FYDPLVFPSS EFDASISQVN  360
EKINQSLAFI RKSDELL                                                 377

SEQ ID NO: 317          moltype = AA  length = 84
FEATURE                 Location/Qualifiers
REGION                  1..84
                        note = synthetic polypeptide
source                  1..84
                        mol_type = protein
                        organism = synthetic construct
SEQUENCE: 317
QNITEEFYQS TCSAVSKGYL SALRTGWYHC VITIELSNIK ENKCNGTDAK VKLIKQELDK  60
YKNAVTELQL LMQSTPAANN RARR                                         84

SEQ ID NO: 318          moltype = AA  length = 377
FEATURE                 Location/Qualifiers
REGION                  1..377
                        note = synthetic polypeptide
source                  1..377
                        mol_type = protein
                        organism = synthetic construct
SEQUENCE: 318
FLGFLLGVGS AIASGIAVSK VLHLEGEVNK IKSALLSTNK AVVSLSNGVS VCTIKVLDLK  60
NYIDKQLLPI VNKQSCSISN IETVIEFQQK NNRLLEITRE FSVNAGVTTP VSTYMLTNSE  120
LLSLINDMPI TNDQKKLMSN NVQIVRQQSY SIMSIIKEEV LAYVVQLPLY GVIDTPCWKL  180
HTSPLCTTNT KEGSNICLTR TDRGWYCDNA GSVSFFPQAE TCKVQSNRVF CDTMNSLTLP  240
SEVNLCNIDI FNPKYDCKIM TSKTDVSSSV ITSLGAIVSC YGKTKCTASN KNRGIIKTFS  300
NGCDYVSNKG VDTVSVGNTL YYVNKQEGKS LYVKGEPIIN FYDPLVFPSS EFDASISQVN  360
EKINQSLAFI RKSDELL                                                 377

SEQ ID NO: 319          moltype = AA  length = 84
FEATURE                 Location/Qualifiers
REGION                  1..84
                        note = synthetic polypeptide
source                  1..84
                        mol_type = protein
                        organism = synthetic construct
SEQUENCE: 319
QNITEEFYQS TCSAVSKGYL SALRTGWYHC VITIELSNIK ENKCNGTDAK VKLIKQELDK  60
YKNAVTELQL LMQSTPAANN RARR                                         84

SEQ ID NO: 320          moltype = AA  length = 377
```

```
FEATURE                Location/Qualifiers
REGION                 1..377
                       note = synthetic polypeptide
source                 1..377
                       mol_type = protein
                       organism = synthetic construct
SEQUENCE: 320
FLGFLLGVGS AIASGIAVSK VLHLEGEVNK IKSALLSTNK AVVSLSNGVS VCTIKVLDLK  60
NYIDKQLLPI VNKQSCSISN IETVIEFQQK NNRLLEITRE FSVNAGVTTP VSTYMLTNSE  120
LLSLINDMPI TNDQKKLMSN NVQIVRQQSY SIMSIIKEEV LAYVVQLPLY GVIDTPCWKL  180
HTSPLCTTNT KEGSNICLTR TDRGWYCDNA GSVSFFPQAE TCKVQSNRVF CDTMNSLTLP  240
SEVNLCNIDI FNPKYDCKIM TSKTDVSSSV ITSLGAIVSC YGKTKCTASN KNRGIIKTFS  300
NGCDYVSNKG VDTVSVGNTL YYVNKQEGKS LYVKGEPIIN FYDPLVFPSS EFDASISQVN  360
EKINQSLAFI RKSDELL                                                377

SEQ ID NO: 321         moltype = AA  length = 84
FEATURE                Location/Qualifiers
REGION                 1..84
                       note = synthetic polypeptide
source                 1..84
                       mol_type = protein
                       organism = synthetic construct
SEQUENCE: 321
QNITEEFYQS TCSAVSRGYF SALRTGWYHC VITIELSNIK ETKCNGTDTK VKLIKQELDK  60
YKNAVTELQL LMQNTPAANN RARR                                        84

SEQ ID NO: 322         moltype = AA  length = 377
FEATURE                Location/Qualifiers
REGION                 1..377
                       note = synthetic polypeptide
source                 1..377
                       mol_type = protein
                       organism = synthetic construct
SEQUENCE: 322
FLGFLLGVGS AIASGIAVSK VLHLEGEVNK IKNALLSTNK AVVSLSNGVS VCTIKVLDLK  60
NYINNQLLPI VNKQSCRISN IETVIEFQQK NSRLLEITRE FSVNAGVTTP LSTYMLTNSE  120
LLSLINDMPI TNDQKKLMSS NVQIVRQQSY SIMSIIKEEV LAYVVQLPIY GVIDTPCWKL  180
HTSPLCTTNI KEGSNICLTR TDRGWYCDNA GSVSFFPQAD TCKVQSNRVF CDTMNSLTLP  240
SEVSLCNTDI FNSKYDCKIM TSKTDVSSSV ITSLGAIVSC YGKTKCTASN KNRGIIKTFS  300
NGCDYVSNKG VDTVSVGNTL YYVNKLEGKN LYVKGEPIIN YYDPLVFPSS EFDASISQVN  360
EKINQSLAFI RRSDELL                                                377

SEQ ID NO: 323         moltype = AA  length = 84
FEATURE                Location/Qualifiers
REGION                 1..84
                       note = synthetic polypeptide
source                 1..84
                       mol_type = protein
                       organism = synthetic construct
SEQUENCE: 323
QNITEEFYQS TCSAVSRGYF SALRTGWYHC VITIELSNIK ETKCNGTDTK VKLIKQELDK  60
YKNAVTELQL LMQNTPAANN RARR                                        84

SEQ ID NO: 324         moltype = AA  length = 377
FEATURE                Location/Qualifiers
REGION                 1..377
                       note = synthetic polypeptide
source                 1..377
                       mol_type = protein
                       organism = synthetic construct
SEQUENCE: 324
FLGFLLGVGS AIASGIAVSK VLHLEGEVNK IKNALLSTNK AVVSLSNGVS VCTIKVLDLK  60
NYINNQLLPI VNQQSCRISN IETVIEFQQK NSRLLEITRE FSVNAGVTTP LSTYMLTNSE  120
LLSLINDMPI TNDQKKLMSS NVQIVRQQSY SIMSIMKEEV LAYVVQLPIY GVIDTPCWKL  180
HTSPLCTTNI KEGSNICLTR TDRGWYCDNA GSVSFFPQAD TCKVQSNRVF CDTMNSLTLP  240
SEVSLCNTDI FNSKYDCKIM TSKTDISSSV ITSLGAIVSC YGKTKCTASN KNRGIIKTFS  300
NGCDYVSNKG VDTVSVGNTL YYVNKLEGKN LYVKGEPIIN YYDPLVFPSS EFDASISQVN  360
EKINQSLAFI RRSDELL                                                377

SEQ ID NO: 325         moltype = AA  length = 84
FEATURE                Location/Qualifiers
REGION                 1..84
                       note = synthetic polypeptide
source                 1..84
                       mol_type = protein
                       organism = synthetic construct
SEQUENCE: 325
QNITEEFYQS TCSAVSRGYL SALRTGWYHC VITIELSNIK ETKCNGTDTK VKLIKQELDK  60
YKNAVTELQL LMQNTPAANN RARR                                        84
```

-continued

```
SEQ ID NO: 326          moltype = AA  length = 377
FEATURE                 Location/Qualifiers
REGION                  1..377
                        note = synthetic polypeptide
source                  1..377
                        mol_type = protein
                        organism = synthetic construct
SEQUENCE: 326
FLGFLLGVGS AIASGIAVSK VLHLEGEVNK IKNALLSTNK AVVSLSNGVS VCTIKVLDLK  60
NYINNQLLPI VNQQSCRISN IETVIEFQQK NSRLLEIARE FSVNAGVTTP LSTYMLTNSE  120
LLSLINDMPI TNDQKKLMSS NVQIVRQQSY SIMSIIKEEV LAYVVQLPIY GVIDTPCWKL  180
HTSPLCTTNI KEGSNICLTR TDRGWYCDNA GSVSFFPQAD TCKVQSNRVF CDTMNSLTLP  240
SEVSLCNTDI FNSKYDCKIM TSKTDISSSV ITSLGAIVSC YGKTKCTASN KNRGIIKTFS  300
NGCDYVSNKG VDTVSVGNTL YYVNKLEGKN LYVKGEPIIN YYDPLVFPSS EFDASISQVN  360
EKINQSLAFI RRSDELL                                                 377
```

RSV F PROTEIN MUTANTS

REFERENCE TO RELATED APPLICATIONS

This application is a divisional of application Ser. No. 17/060,944, filed Oct. 1, 2020, now abandoned, which is divisional of application Ser. No. 16/242,799 filed Jan. 8, 2019, now U.S. Pat. No. 10,821,171 issued Nov. 3, 2020, which is a divisional of application Ser. No. 15/896,871 filed Feb. 14, 2018, now U.S. Pat. No. 10,238,732 issued Mar. 26, 2019, which is a divisional of application Ser. No. 15/385,611 filed on Dec. 20, 2016, now U.S. Pat. No. 9,950,058 issued Apr. 24, 2018, which claim benefit of U.S. Provisional Application No. 62/387,270 filed on Dec. 23, 2015 and U.S. Provisional Application No. 62/421,184 filed on Nov. 11, 2016, all of which are hereby incorporated by referenced in their entireties.

REFERENCE TO SEQUENCE LISTING

This application is being filed electronically via EFS-Web and includes an electronically submitted sequence listing in .txt format. The .txt file contains a sequence listing entitled "PC72226A_SeqListing_ST25.txt" created on Oct. 1, 2020 and having a size of 1,286 KB. The sequence listing contained in this .txt file is part of the specification and is herein incorporated by reference in its entirety.

FIELD OF THE INVENTION

The present invention relates to vaccines in general and vaccines against respiratory syncytial viruses specifically.

BACKGROUND OF THE INVENTION

Respiratory syncytial virus, or RSV, is a respiratory virus that infects the lungs and breathing passages. RSV is the leading cause of serious viral lower respiratory tract illness in infants worldwide and an important cause of respiratory illness in the elderly. However, no vaccines have been approved for preventing RSV infection.

RSV is a member of the Paramyxoviridae family. Its genome consists of a single-stranded, negative-sense RNA molecule that encodes 11 proteins, including nine structural proteins (three glycoproteins and six internal proteins) and two non-structural proteins. The structural proteins include three transmembrane surface glycoproteins: the attachment protein G, fusion protein F, and the small hydrophobic SH protein. There are two subtypes of RSV, A and B. They differ primarily in the G glycoprotein, while the sequence of the F glycoprotein is more conserved between the two subtypes.

The mature F glycoprotein has three general domains: ectodomain (ED), transmembrane domain (TM), and a cytoplasmic tail (CT). CT contains a single palmitoylated cysteine residue.

The F glycoprotein of human RSV is initially translated from the mRNA as a single 574-amino acid polypeptide precursor (referred to "F0" or "F0 precursor"), which contains a signal peptide sequence (amino acids 1-25) at the N-terminus. Upon translation the signal peptide is removed by a signal peptidase in the endoplasmic reticulum. The remaining portion of the F0 precursor (i.e., residues 26-574) may be further cleaved at two polybasic sites (a.a. 109/110 and 136/137) by cellular proteases (in particular furin), removing a 27-amino acid intervening sequence designated pep27 (amino acids 110-136) and generating two linked fragments designated F1 (C-terminal portion; amino acids 137-574) and F2 (N-terminal portion; amino acids 26-109). F1 contains a hydrophobic fusion peptide at its N-terminus and two heptad-repeat regions (HRA and HRB). HRA is near the fusion peptide, and HRB is near the TM domain. The F1 and F2 fragments are linked together through two disulfide bonds. Either the uncleaved F0 protein without the signal peptide sequence or a F1-F2 heterodimer can form a RSV F protomer. Three such protomers assemble to form the final RSV F protein complex, which is a homotrimer of the three protomers.

The F proteins of subtypes A and B are about 90 percent identical in amino acid sequence. An example sequence of the F0 precursor polypeptide for the A subtype is provided in SEQ ID NO: 1 (A2 strain; GenBank GI: 138251; Swiss Prot P03420), and for the B subtype is provided in SEQ ID NO: 2 (18537 strain; GenBank GI: 138250; Swiss Prot P13843). SEQ ID NO: 1 and SEQ ID NO:2 are both 574 amino acid sequences. The signal peptide sequence for SEQ ID NO: 1 and SEQ ID NO:2 has also been reported as amino acids 1-25 (GenBank and UniProt). In both sequences the TM domain is from approximately amino acids 530 to 550, but has alternatively been reported as 525-548. The cytoplasmic tail begins at either amino acid 548 or 550 and ends at amino acid 574, with the palmitoylated cysteine residue located at amino acid 550.

One of the primary antigens explored for RSV subunit vaccines is the F protein. The RSV F protein trimer mediates fusion between the virion membrane and the host cellular membrane and also promotes the formation of syncytia. In the virion prior to fusion with the membrane of the host cell, the largest population of F molecules forms a lollipop-shaped structure, with the TM domain anchored in the viral envelope [Dormitzer, P. R., Grandi, G., Rappuoli, R., Nature Reviews Microbiol, 10, 807, 2012.]. This conformation is referred to as the pre-fusion conformation. Pre-fusion RSV F is recognized by monoclonal antibodies (mAbs) D25, AM22, and MPE8, without discrimination between oligomeric states. Pre-fusion F trimers are specifically recognized by mAb AM14 [Gilman M S, Moin S M, Mas V et al. Characterization of a prefusion-specific antibody that recognizes a quaternary, cleavage-dependent epitope on the RSV fusion glycoprotein. PLoS Pathogens, 11(7), 2015]. During RSV entry into cells, the F protein rearranges from the pre-fusion state (which may be referred to herein as "pre-F"), through an intermediate extended structure, to a post-fusion state ("post-F"). During this rearrangement, the C-terminal coiled-coil of the pre-fusion molecule dissociates into its three constituent strands, which then wrap around the globular head and join three additional helices to form the post-fusion six helix bundle. If a pre-fusion RSV F trimer is subjected to increasingly harsh chemical or physical conditions, such as elevated temperature, it undergoes structural changes. Initially, there is loss of trimeric structure (at least locally within the molecule), and then rearrangement to the post-fusion form, and then denaturation of the domains.

To prevent viral entry, F-specific neutralizing antibodies presumably must bind the pre-fusion conformation of F on the virion, or potentially the extended intermediate, before the viral envelope fuses with a cellular membrane. Thus, the pre-fusion form of the F protein is considered the preferred conformation as the desired vaccine antigen [Ngwuta, J. O., Chen, M., Modjarrad, K., Joyce, M. G., Kanekiyo, M., Kumar, A., Yassine, H. M., Moin, S. M., Killikelly, A. M., Chuang, G. Y., Druz, A., Georgiev, I. S., Rundlet, E. J., Sastry, M., Stewart-Jones, G. B., Yang. Y., Zhang, B., Nason, M. C., Capella, C., Peeples, M., Ledgerwood, J. E., Mclellan, J. S., Kwong, P. D., Graham, B. S., Science Translat.

Med., 14, 7, 309 (2015)]. Upon extraction from a membrane with surfactants such as Triton X-100, Triton X-114, NP-40, Brij-35, Brij-58, Tween 20, Tween 80, Octyl glucoside, Octyl thioglucoside, SDS, CHAPS, CHAPSO, or expression as an ectodomain, physical or chemical stress, or storage, the F glycoprotein readily converts to the post-fusion form [McLellan J S, Chen M, Leung S et al. Structure of RSV fusion glycoprotein trimer bound to a pre-fusion-specific neutralizing antibody. Science 340, 1113-1117 (2013); Chaiwatpongsakorn, S., Epand, R. F., Collins, P. L., Epand R. M., Peeples, M. E., J Virol. 85(8):3968-77 (2011); Yunus, A. S., Jackson T. P., Crisafi, K., Burimski, I., Kilgore, N. R., Zoumplis, D., Allaway, G. P., Wild, C. T., Salzwedel, K. Virology. 2010 Jan. 20; 396(2):226-37]. Therefore, the preparation of pre-fusion F as a vaccine antigen has remained a challenge. Since the neutralizing and protective antibodies function by interfering with virus entry, it is postulated that an F antigen that elicits only post-fusion specific antibodies is not expected to be as effective as an F antigen that elicits pre-fusion specific antibodies. Therefore, it is considered more desirable to utilize an F vaccine that contains a F protein immunogen in the pre-fusion form (or potentially the extended intermediate form). Efforts to date have not yielded an RSV vaccine that has been demonstrated in the clinic to elicit sufficient levels of protection to support licensure of an RSV vaccine. Therefore, there is a need for immunogens derived from a RSV F protein that have improved properties, such as enhanced immunogenicity or improved stability of the pre-fusion form, as compared with the corresponding native RSV F protein, as well as compositions comprising such an immunogen, such as a vaccine.

SUMMARY OF THE INVENTION

In some aspects, the present invention provides mutants of wild-type RSV F proteins, wherein the mutants display introduced mutations in the amino acid sequence relative to the amino acid sequence of the corresponding wild-type RSV F protein and are immunogenic against the wild-type RSV F protein or against a virus comprising the wild-type F protein. The amino acid mutations in the mutants include amino acid substitutions, deletions, or additions relative to a wild-type RSV F protein.

In some embodiments, the present disclosure provides mutants of a wild-type RSV F protein, wherein the introduced amino acid mutations are mutation of a pair of amino acid residues in a wild-type RSV F protein to a pair of cysteines ("engineered disulfide mutation"). The introduced pair of cysteine residues allows for formation of a disulfide bond between the cysteine residues that stabilize the protein's conformation or oligomeric state, such as the pre-fusion conformation. Examples of specific pairs of such mutations include: 55C and 188C; 155C and 290C; 103C and 148C; and 142C and 371C, such as S55C and L188C; S155C and S290C; T103C and I148C; and L142C and N371C.

In still other embodiments, the RSV F protein mutants comprise amino acid mutations that are one or more cavity filling mutations. Examples of amino acids that may be replaced with the goal of cavity filling include small aliphatic (e.g. Gly, Ala, and Val) or small polar amino acids (e.g. Ser and Thr) and amino acids that are buried in the pre-fusion conformation, but exposed to solvent in the post-fusion conformation. Examples of the replacement amino acids include large aliphatic amino acids (Ile, Leu and Met) or large aromatic amino acids (His, Phe, Tyr and Trp).

In some specific embodiments, the RSV F protein mutant comprises a cavity filling mutation selected from the group consisting of:

(1) substitution of S at position 55, 62, 155, 190, or 290 with I, Y, L, H, or M;
(2) substitution of T at position 54, 58, 189, 219, or 397 with I, Y, L, H, or M;
(3) substitution of G at position 151 with A or H;
(4) substitution of A at position 147 or 298 with I, L, H, or M;
(5) substitution of V at position 164, 187, 192, 207, 220, 296, 300, or 495 with I, Y, H; and
(6) substitution of R at position 106 with W.

In some particular embodiments, a RSV F protein mutant comprises at least one cavity filling mutation selected from the group consisting of: T54H, S190I, and V296I.

In still other embodiments, the present disclosure provides RSV F protein mutants, wherein the mutants comprise electrostatic mutations, which decrease ionic repulsion or increase ionic attraction between resides in a protein that are proximate to each other in the folded structure. In several embodiments, the RSV F protein mutant includes an electrostatic substitution that reduces repulsive ionic interactions or increases attractive ionic interactions with acidic residues of Glu487 and Asp489 from another protomer of RSV F trimer. In some specific embodiments, the RSV F protein mutant comprises an electrostatic mutation selected from the group consisting of:

(1) substitution of E at position 82, 92, or 487 by D, F, Q, T, S, L, or H;
(2) substitution of K at position 315, 394, or 399 by F, M, R, S, L, I, Q, or T;
(3) substitution of D at position 392, 486, or 489 by H, S, N, T, or and
(4) substitution of R at position 106 or 339 by F, Q, N, or W.

In still other embodiments, the present disclosure provides RSV F protein mutants, which comprise a combination of two or more different types of mutations selected from engineered disulfide mutations, cavity filling mutations, and electrostatic mutations. In some particular embodiments, the present invention provides a mutant of a wild-type RSV F protein, which comprises a combination of mutations relative to the corresponding wild-type RSV F protein, wherein the combination of mutations is selected from the group consisting of:

(1) combination of T103C, I148C, S190I, and D486S;
(2) combination of T54H S55C L188C D486S;
(3) combination of T54H, T103C, I148C, S190I, V296I, and D486S;
(4) combination of T54H, S55C, L142C, L188C, V296I, and N371C;
(5) combination of S55C, L188C, and D486S;
(6) combination of T54H, S55C, L188C, and S190I;
(7) combination of S55C, L188C, S190I, and D486S;
(8) combination of T54H, S55C, L188C, S190I, and D486S;
(9) combination of S155C, S190I, S290C, and D486S;
(10) combination of T54H, S55C, L142C, L188C, V296I, N371C, D486S, E487Q, and D489S; and
(11) combination of T54H, S155C, S190I, S290C, and V296I.

In another aspect, the present invention provides nucleic acid molecules that encode a RSV F protein mutant described herein. In some other specific embodiments, the present disclosure provides a nucleic acid molecule encoding a RSV F protein mutant, wherein the nucleic acid molecule comprises a nucleotide sequence selected from the group consisting of:

(1) a nucleotide sequence of SEQ ID NO:8;

(2) a nucleotide sequence of SEQ ID NO:9;

(3) a nucleotide sequence of SEQ ID NO:10;

(4) a nucleotide sequence of SEQ ID NO:11;

(5) a nucleotide sequence of SEQ ID NO:12;

(6) a nucleotide sequence of SEQ ID NO:13;

(7) a nucleotide sequence of SEQ ID NO:14;

(8) a nucleotide sequence of SEQ ID NO:15;

(9) a nucleotide sequence of SEQ ID NO:16;

(10) a nucleotide sequence of SEQ ID NO:17; and

(11) a nucleotide sequence of SEQ ID NO:18.

In another aspect, the invention provides compositions that comprise (1) a RSV F protein mutant described in the disclosure, or (2) a nucleic acid molecule or vector encoding such a RSV F protein mutant. In some particular embodiments, the compositions are pharmaceutical compositions, which comprise a RSV F protein mutant provided by the present disclosure and a pharmaceutically acceptable carrier. In still other particular embodiments, the pharmaceutical composition is a vaccine.

The present disclosure also relates to use of a RSV F protein mutant, nucleic acids encoding such as a RSV F protein mutant, or vectors for expressing such a RSV F protein mutant, or compositions comprising a RSV F protein mutant or nucleic acids. In some particular embodiments, the present disclosure provides a method of preventing RSV infection in a subject, comprising administering to the subject an effective amount of a pharmaceutical composition, such as a vaccine, comprising a RSV F protein mutant, a nucleic acid encoding a RSV F protein mutant, or a vector expressing a RSV F protein mutant.

BRIEF DESCRIPTION OF THE DRAWINGS

FIG. 1 depicts the amino acid sequence of the precursor polypeptide template (SEQ ID NO:3) used for the construction of some of the RSV F protein mutants described in the Examples. The precursor polypeptide includes a signal sequence (residues 1-25), F2 polypeptide (residues 26-109), pep27 sequence (residues 110-136), F1 polypeptide (residues 137-513), a T4 fibritin-derived trimerization domain (foldon; residues 518-544), a thrombin recognition sequence (residues 547-552), a histidine tag (residues 553-558), a Streptag II (561-568), and linker sequences (residues 514-517, 545-546, and 559-560). It also includes three naturally occurring substitutions (P102A, I379V, and M447V) relative to the native RSV F sequence set forth in SEQ ID NO:1. The furin cleavage sites are shown as RARR and KKRKRR.

DETAILED DESCRIPTION OF THE INVENTION

Figure 2A:
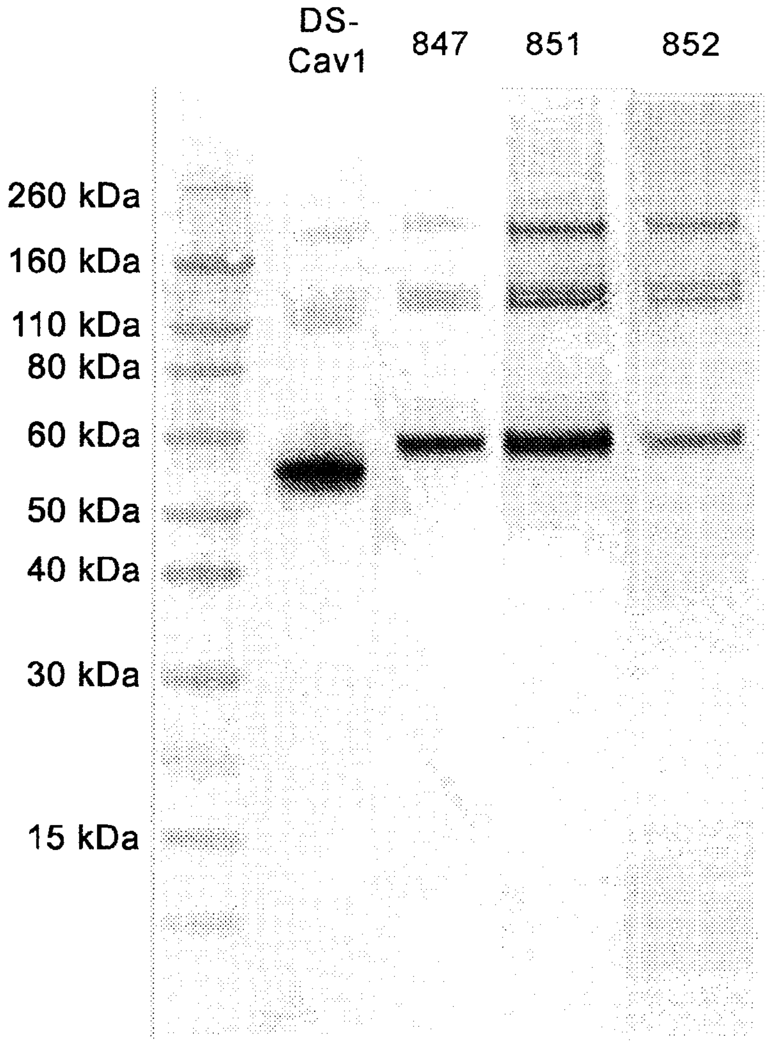
FIG. 2A depicts sodium dodecyl sulfate polyacrylamide gel electrophoresis (SDS-PAGE) and western blot analysis of selected pre-fusion F mutants (pXCS847, pXCS851 and pXCS852) under non-reducing conditions.

The present disclosure relates to RSV F protein mutants, immunogenic compositions comprising the RSV F protein mutants, methods for producing the RSV F protein mutants, compositions comprising the RSV F protein mutants, and nucleic acids that encode the RSV F protein mutants.

A. DEFINITIONS

The term "101F" refers to an antibody described in US 2006/0159695 A1, which has a heavy chain variable domain comprising an amino acid sequence of SEQ ID NO:30 and a light chain variable domain comprising an amino acid sequence of SEQ ID NO:31.

As used herein, the singular forms "a," "an," and "the," refer to both the singular as well as plural, unless the context clearly indicates otherwise. For example, the term "an antigen" includes single or plural antigens and can be considered equivalent to the phrase "at least one antigen."

The term "adjuvant" refers to a substance capable of enhancing, accelerating, or prolonging the body's immune response to an immunogen or immunogenic composition, such as a vaccine (although it is not immunogenic by itself). An adjuvant may be included in the immunogenic composition, such as a vaccine, or may be administered separately from the immunogenic composition.

The term "administration" refers to the introduction of a substance or composition into a subject by a chosen route. Administration can be local or systemic. For example, if the chosen route is intramuscular, the composition (such as a composition including a disclosed immunogen) is administered by introducing the composition into a muscle of the subject.

The term "AM14" refers to an antibody described in WO 2008/147196 A2, which has a heavy chain variable domain comprising an amino acid sequence of SEQ ID NO:24 and a light chain variable domain comprising an amino acid sequence of SEQ ID NO:25.

The term "AM22" refers to an antibody described in WO 2011/043643 A1, which has a heavy chain variable domain comprising an amino acid sequence of SEQ ID NO:26 and a light chain variable domain comprising an amino acid sequence of SEQ ID NO:27.

The term "antigen" refers to a molecule that can be recognized by an antibody. Examples of antigens include polypeptides, peptides, lipids, polysaccharides, and nucleic acids containing antigenic determinants, such as those recognized by an immune cell.

The term "conservative substitution" refers to the substitution of an amino acid with a chemically similar amino acid. Conservative amino acid substitutions providing functionally similar amino acids are well known in the art. The following six groups each contain amino acids that are conservative substitutions for one another:

1) alanine (A), serine (S), threonine (T);
2) aspartic acid (D), glutamic acid (E);
3) asparagine (N), glutamine (Q);
4) arginine (R), lysine (K);
5) isoleucine (I), leucine (L), methionine (M), valine (V); and
6) phenylalanine (F), tyrosine (Y), tryptophan (W).

The term "D25" refers to an antibody described in WO 2008/147196 A2, which has a heavy chain variable domain comprising an amino acid sequence of SEQ ID NO:22 and a light chain variable domain comprising an amino acid sequence of SEQ ID NO:23.

The term "degenerate variant" of a reference polynucleotide refers to a polynucleotide that differs in the nucleotide sequence from the reference polynucleotide but encodes the same polypeptide sequence as encoded by the reference polynucleotide. There are 20 natural amino acids, most of which are specified by more than one codon. For instance, the codons CGU, CGC, CGA, CGG, AGA, and AGG all encode the amino acid arginine. Thus, at every position where an arginine is specified within a protein encoding sequence, the codon can be altered to any of the corresponding codons described without altering the encoded protein. Because of the degeneracy of the genetic code, a large number of functionally identical nucleic acids encode any given polypeptide.

The term "DS-Cav1" refers to the recombinant RSV F protein having the amino acid sequence described in McLellan, et al., Science, 342(6158), 592-598, 2013. DS-Cav1 contains the following introduced amino acid substitutions: S155C, S290C, S190F, and V207L.

The term "effective amount" refers to an amount of agent that is sufficient to generate a desired response. For instance, this can be the amount necessary to inhibit viral replication or to measurably alter outward symptoms of the viral infection.

The term "epitope" (or "antigenic determinant" or "antigenic site") refers to the region of an antigen to which an antibody, B cell receptor, or T cell receptor binds or responds. Epitopes can be formed from contiguous amino acids or noncontiguous amino acids juxtaposed by secondary, tertiary, or quaternary folding of a protein. Epitopes formed from contiguous amino acids are typically retained on exposure to denaturing solvents whereas epitopes formed by higher order folding are typically lost on treatment with denaturing solvents.

The term "F0 polypeptide" (F0) refers to the precursor polypeptide of the RSV F protein, which is composed of a signal polypeptide sequence, a F1 polypeptide sequence, a pep27 polypeptide sequence, and a F2 polypeptide sequence. With rare exceptions the F0 polypeptides of the known RSV strains consist of 574 amino acids.

The term "F1 polypeptide" (F1) refers to a polypeptide chain of a mature RSV F protein. Native F1 includes approximately residues 137-574 of the RSV F0 precursor and is composed of (from N- to C-terminus) an extracellular region (approximately residues 137-524), a transmembrane domain (approximately residues 525-550), and a cytoplasmic domain (approximately residues 551-574). As used herein, the term encompasses both native F1 polypeptides and F1 polypeptides including modifications (e.g., amino acid substitutions, insertions, or deletion) from the native sequence, for example, modifications designed to stabilize a F mutant or to enhance the immunogenicity of a F mutant.

The term "F2 polypeptide" (F2) refers to the polypeptide chain of a mature RSV F protein. Native F2 includes approximately residues 26-109 of the RSV F0 precursor. As used herein, the term encompasses both native F2 polypeptides and F2 polypeptides including modifications (e.g., amino acid substitutions, insertions, or deletion) from the native sequence, for example, modifications designed to stabilize a F mutant or to enhance the immunogenicity of a F mutant. In native RSV F protein, the F2 polypeptide is linked to the F1 polypeptide by two disulfide bonds to form a F2-F1 heterodimer. The term "foldon" or "foldon domain" refers to an amino acid sequence that is capable of forming trimers. One example of such foldon domains is the peptide sequence derived from bacteriophage T4 fibritin, which has the sequence of GYIPEAPRDGQAYVRKDGEWVLLSTFL (SEQ ID NO:40).

The term "subject" refers to either a human or a non-human mammal. The term "mammal" refers to any animal species of the Mammalia class. Examples of mammals include: humans; non-human primates such as monkeys; laboratory animals such as rats, mice, guinea pigs; domestic animals such as cats, dogs, rabbits, cattle, sheep, goats, horses, and pigs; and captive wild animals such as lions, tigers, elephants, and the like.

The term "glycoprotein" refers to a protein that contains oligosaccharide chains (glycans) covalently attached to polypeptide side-chains. The carbohydrate is attached to the protein in a cotranslational or posttranslational modification known as glycosylation. The term "glycosylation site" refers to an amino acid sequence on the surface of a polypeptide, such as a protein, which accommodates the attachment of a glycan. An N-linked glycosylation site is triplet sequence of NX(S/T) in which N is asparagine, X is any residue except proline, and (S/T) is a serine or threonine residue. A glycan is a polysaccharide or oligosaccharide. Glycan may also be used to refer to the carbohydrate portion of a glycoconjugate, such as a glycoprotein, glycolipid, or a proteoglycan.

The term "host cells" refers to cells in which a vector can be propagated and its DNA or RNA expressed. The cell may be prokaryotic or eukaryotic.

The term "identical" or percent "identity," in the context of two or more nucleic acid or polypeptide sequences, refers to two or more sequences or subsequences that are the same or have a specified percentage of amino acid residues or nucleotides that are the same, when compared and aligned for maximum correspondence. Methods of alignment of sequences for comparison are well known in the art. Once aligned, the number of matches is determined by counting the number of positions where an identical nucleotide or amino acid residue is present in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a peptide sequence that has 1166 matches when aligned with a test sequence having 1554 amino acids is 75.0 percent identical to the test sequence (1166÷1554*100=75.0).

Optimal alignment of sequences for comparison can be conducted, e.g., by the local homology algorithm of Smith and Waterman, Adv. Appl. Math. 2:482, 1981, by the homology alignment algorithm of Needleman and Wunsch, Mol. Biol. 48:443, 1970, by the search for similarity method of Pearson and Lipman, Proc. Nat'l. Acad. Sci. USA 85:2444, 1988, by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., Sambrook et al. (Molecular Cloning: A Laboratory Manual, 4th ed, Cold Spring Harbor, New York, 2012) and Ausubel et al. (In Current Protocols in Molecular Biology, John Wiley and Sons, New York, through supplement 104, 2013).

The term "immunogen" refers to a compound, composition, or substance that is immunogenic as defined herein below.

The term "immunogenic" refers to the ability of a substance to cause, elicit, stimulate, or induce an immune response against a particular antigen, in a subject, whether in the presence or absence of an adjuvant.

The term "immune response" refers to any detectable response of a cell or cells of the immune system of a host mammal to a stimulus (such as an immunogen), including, but not limited to, innate immune responses (e.g., activation of Toll receptor signaling cascade), cell-mediated immune responses (e.g., responses mediated by T cells, such as antigen-specific T cells, and non-specific cells of the immune system), and humoral immune responses (e.g., responses mediated by B cells, such as generation and secretion of antibodies into the plasma, lymph, and/or tissue fluids). Examples of immune responses include an alteration (e.g., increase) in Toll-like receptor activation, lymphokine (e.g., cytokine (e.g., Th1, Th2 or Th17 type cytokines) or chemokine) expression or secretion, macrophage activation, dendritic cell activation, T cell (e.g., CD4+ or CD8+ T cell) activation, NK cell activation, B cell activation (e.g., antibody generation and/or secretion), binding of an immunogen (e.g., antigen (e.g., immunogenic polypeptide)) to an MHC molecule, induction of a cytotoxic T lymphocyte ("CTL") response, induction of a B cell response (e.g., antibody production), and, expansion (e.g., growth of a population of cells) of cells of the immune system (e.g., T cells and B cells), and increased processing and presentation of antigen by antigen presenting cells. The term "immune response" also encompasses any detectable response to a particular substance (such as an antigen or immunogen) by one or more components of the immune system of a vertebrate animal in vitro.

The term "immunogenic composition" refers to a composition comprising an immunogen.

The term "MPE8" refers to an antibody described in Corti et al. [Corti, D., Bianchi, S., Vanzetta, F., Minola, A., Perez, L., Agatic, G., Lanzavecchia, A. Cross-neutralization of four paramyxoviruses by a human monoclonal antibody. Nature, 501(7467), 439-443 (2013)], which has a heavy chain variable domain comprising an amino acid sequence of SEQ ID NO:28 and a light chain variable domain comprising an amino acid sequence of SEQ ID NO:29. The term "mutant" of a wild-type RSV F protein, "mutant" of a RSV F protein, "RSV F protein mutant," or "modified RSV F protein" refers to a polypeptide that displays introduced mutations relative to a wild-type F protein and is immunogenic against the wild-type F protein.

The term "mutation" refers to deletion, addition, or substitution of amino acid residues in the amino acid sequence of a protein or polypeptide as compared to the amino acid sequence of a reference protein or polypeptide. Throughout the specification and claims, the substitution of an amino acid at one particular location in the protein sequence is referred to using a notation "(amino acid residue in wild type protein)(amino acid position)(amino acid residue in engineered protein)". For example, a notation Y75A refers to a substitution of a tyrosine (Y) residue at the 75th position of the amino acid sequence of the reference protein by an alanine (A) residue (in a mutant of the reference protein). In cases where there is variation in the amino acid residue at the same position among different wild-type sequences, the amino acid code preceding the position number may be omitted in the notation, such as "75A."

The term "native" or "wild-type" protein, sequence, or polypeptide refers to a naturally existing protein, sequence, or polypeptide that has not been artificially modified by selective mutations.

The term "pep27 polypeptide" or "pep27" refers to a 27-amino acid polypeptide that is excised from the F0 precursor during maturation of the RSV F protein. The sequence of pep27 is flanked by two furin cleavage sites that are cleaved by a cellular protease during F protein maturation to generate the F1 and F2 polypeptides.

The term "pharmaceutically acceptable carriers" refers to a material or composition which, when combined with an active ingredient, is compatible with the active ingredient and does not cause toxic or otherwise unwanted reactions when administered to a subject, particularly a mammal. Examples of pharmaceutically acceptable carriers include solvents, surfactants, suspending agents, buffering agents, lubricating agents, emulsifiers, absorbants, dispersion media, coatings, and stabilizers.

The term "pre-fusion-specific antibody" refers to an antibody that specifically binds to the RSV F glycoprotein in a pre-fusion conformation, but does not bind to the RSV F protein in a post-fusion conformation. Exemplary pre-fusion-specific antibodies include the D25, AM22, 5C4, MPE8, and AM14 antibodies.

The term "pre-fusion trimer-specific antibody" refers to an antibody that specifically binds to the RSV F glycoprotein in a pre-fusion, trimeric conformation, but does not bind to the RSV F protein in a post-fusion conformation or in a pre-fusion conformation that is not also trimeric. An exemplary pre-fusion trimer-specific antibody is the AM14 antibody. "Pre-fusion trimer-specific antibodies" are a subset of "pre-fusion-specific antibodies."

The term "prime-boost vaccination" refers to an immunotherapy regimen that includes administration of a first immunogenic composition (the primer vaccine) followed by administration of a second immunogenic composition (the booster vaccine) to a subject to induce an immune response. The primer vaccine and the booster vaccine typically contain the same immunogen and are presented in the same or similar format. However, they may also be presented in different formats, for example one in the form of a vector and the other in the form of a naked DNA plasmid. The skilled artisan will understand a suitable time interval between administration of the primer vaccine and the booster vaccine. Further, the primer vaccine, the booster vaccine, or both primer vaccine and the booster vaccine additionally include an adjuvant.

The term "pre-fusion conformation" refers to a structural conformation adopted by an RSV F protein or mutant that can be specifically bound by (i) antibody D25 when the RSV F protein or mutant is in the form of a monomer or trimer, or (ii) by antibody AM14 when the RSV F protein mutant is in the form of a trimer. The pre-fusion trimer conformation is a subset of pre-fusion conformations.

The term "post-fusion conformation" refers to a structural conformation adopted by the RSV F protein that is not specifically bound by D25, AM22, or AM14. Native F protein adopts the post-fusion conformation subsequent to the fusion of the virus envelope with the host cellular membrane. RSV F protein may also assume the post-fusion conformation outside the context of a fusion event, for example, under stress conditions such as heat and low osmolality, when extracted from a membrane, when expressed as an ectodomain, or upon storage.

The term "soluble protein" refers to a protein capable of dissolving in aqueous liquid and remaining dissolved. The solubility of a protein may change depending on the concentration of the protein in the water-based liquid, the buffering condition of the liquid, the concentration of other solutes in the liquid, for example salt and protein concentrations, and the temperature of the liquid.

The term "specifically bind," in the context of the binding of an antibody to a given target molecule, refers to the binding of the antibody with the target molecule with higher affinity than its binding with other tested substances. For example, an antibody that specifically binds to the RSV F protein in pre-fusion conformation is an antibody that binds RSV F protein in pre-fusion conformation with higher affinity than it binds to the RSV F protein in the post-fusion conformation.

The term "therapeutically effective amount" refers to the amount of agent that is sufficient to prevent, treat (including prophylaxis), reduce and/or ameliorate the symptoms and/or underlying causes of a disorder.

The term "vaccine" refers to a pharmaceutical composition comprising an immunogen that is capable of eliciting a prophylactic or therapeutic immune response in a subject. Typically, a vaccine elicits an antigen-specific immune response to an antigen of a pathogen, for example a viral pathogen.

The term "vector" refers to a nucleic acid molecule capable of transporting or transferring a foreign nucleic acid molecule. The term encompasses both expression vectors and transcription vectors. The term "expression vector" refers to a vector capable of expressing the insert in the target cell, and generally contains control sequences, such as enhancer, promoter, and terminator sequences, that drive expression of the insert. The term "transcription vector" refers to a vector capable of being transcribed but not translated. Transcription vectors are used to amplify their insert. The foreign nucleic acid molecule is referred to as "insert" or "transgene." A vector generally consists of an insert and a larger sequence that serves as the backbone of the vector. Based on the structure or origin of vectors, major types of vectors include plasmid vectors, cosmid vectors, phage vectors such as lambda phage, viral vectors such as adenovirus (Ad) vectors, and artificial chromosomes.

B. RSV F PROTEIN MUTANTS

In some aspects, the present invention provides mutants of wild-type RSV F proteins, wherein the mutants display introduced mutations in the amino acid sequence relative to the amino acid sequence of the corresponding wild-type RSV F protein and are immunogenic against the wild-type RSV F protein or against a virus comprising the wild-type F protein. In certain embodiments, the RSV F mutants possess certain beneficial characteristics, such as increased immunogenic properties or improved stability in the pre-fusion conformation of the mutants or pre-fusion trimeric conformation of the mutant, as compared to the corresponding wild-type F protein. In still other embodiments, the present disclosure provide RSV F mutants that display one or more introduced mutations as described herein and bind to a pre-fusion specific antibody selected from antibody D25 or antibody AM14.

The introduced amino acid mutations in the RSV F protein mutants include amino acid substitutions, deletions, or additions. In some embodiments, the only mutations in the amino acid sequence of the mutants are amino acid substitutions relative to a wild-type RSV F protein.

The amino acid sequence of a large number of native RSV F proteins from different RSV subtypes, as well as nucleic acid sequences encoding such proteins, is known in the art. For example, the sequence of several subtype A, B and bovine RSV F0 precursor proteins are set forth in SEQ ID NOs:1, 2, 4, 6 and 81-270.

The native RSV F protein exhibits remarkable sequence conservation across RSV subtypes. For example, RSV subtypes A and B share 90% sequence identity, and RSV subtypes A and B each share 81% sequence identify with bovine RSV F protein, across the F0 precursor molecule. Within RSV subtypes the F0 sequence identity is even greater; for example within each of RSV A, B, and bovine subtypes, the RSV F0 precursor protein has about 98% sequence identity. Nearly all identified RSV F0 precursor sequences consist of 574 amino acids in length, with minor differences in length typically due to the length of the C-terminal cytoplasmic tail. Sequence identity across various native RSV F proteins is known in the art (see, for example, WO2014/160463). To further illustrate the level of the sequence conservation of F proteins, non-consensus amino acid residues among F0 precursor polypeptide sequences from representative RSV A strains and RSV B strains are provided in Tables A and B, respectively (where non-consensus amino acids were identified following alignment of selected F protein sequences from RSV A strains with ClustalX (v. 2)).

In view of the substantial conservation of RSV F sequences, a person of ordinary skill in the art can easily compare amino acid positions between different native RSV F sequences to identify corresponding RSV F amino acid positions between different RSV strains and subtypes. For example, across nearly all identified native RSV F0 precursor proteins, the furin cleavage sites fall in the same amino acid positions. Thus, the conservation of native RSV F protein sequences across strains and subtypes allows use of a reference RSV F sequence for comparison of amino acids at particular positions in the RSV F protein. For the purposes of this disclosure (unless context indicates otherwise), the RSV F protein amino acid positions are given with reference to the sequence of the F0 precursor polypeptide set forth in SEQ ID NO: 1 (the amino acid sequence of the full length native F precursor polypeptide of the RSV A2 strain; corresponding to GenInfo Identifier GI 138251 and Swiss Prot identifier P03420). However, it should be noted, and one of skill in the art will understand, that different RSV F0 sequences may have different numbering systems, for example, if there are additional amino acid residues added or removed as compared to SEQ ID NO:1. As such, it is to be understood that when specific amino acid residues are referred to by their number, the description is not limited to only amino acids located at precisely that numbered position when counting from the beginning of a given amino acid sequence, but rather that the equivalent/corresponding amino acid residue in any and all RSV F sequences is intended even if that residue is not at the same precise numbered position, for example if the RSV sequence is shorter or longer than SEQ ID NO:1, or has insertions or deletions as compared to SEQ ID NO: 1.

B-1. Structure of the RSV F Protein Mutants

The RSV F protein mutants provided by the present disclosure comprise a F1 polypeptide and a F2 polypeptide. In several embodiments, the mutants further comprise a trimerization domain. In some embodiments, either the F1 polypeptide or the F2 polypeptide includes at least one introduced modification (e.g., amino acid substitution) as described in detail herein below. In some other embodiments, each of the F1 polypeptide and F2 polypeptide includes at least one introduced modification (e.g., amino acid substitution) as described in detail herein below.

B-1(a). F1 Polypeptide and F2 Polypeptide of the RSV F Mutants

In some embodiments, the mutants are in the mature form of the RSV F protein, which comprises two separate polypeptide chains, namely the F1 polypeptide and F2 polypeptide. In some other embodiments, the F2 polypeptide is linked to the F1 polypeptide by one or two disulfide bonds to form a F2-F1 polypeptide heterodimer. In still other embodiments, the RSV F mutants are in the form a single chain protein, wherein the F2 polypeptide is linked to the F1 polypeptide by a peptide bond or peptide linker. Any suitable peptide linkers for joining two polypeptide chains together may be used. Examples of such linkers include G, GG, GGG, GS, and SAIG linker sequences. The linker may also be the full length pep27 sequence or a fragment thereof.

The F1 polypeptide chain of the mutant may be of the same length as the full length F1 polypeptide of the corresponding wild-type RSV F protein; however, it may also have deletions, such as deletions of 1 up to 60 amino acid residues from the C-terminus of the full-length F1 polypeptide. A full-length F1 polypeptide of the RSV F mutants corresponds to amino acid positions 137-574 of the native RSV F0 precursor, and includes (from N- to C-terminus) an extracellular region (residues 137-524), a transmembrane domain (residues 525-550), and a cytoplasmic domain (residues 551-574). It should be noted that amino acid residues 514 onwards in a native F1 polypeptide sequence are optional sequences in a F1 polypeptide of the RSV F mutants provided herein, and therefore may be absent from the F1 polypeptide of the mutant.

In some embodiments, the F1 polypeptide of the RSV F mutants lacks the entire cytoplasmic domain. In other embodiments, the F1 polypeptide lacks the cytoplasmic domain and a portion of or all entire transmembrane domain. In some specific embodiments, the mutant comprises a F1 polypeptide wherein the amino acid residues from position 510, 511, 512, 513, 514, 515, 520, 525, or 530 through 574 are absent. Typically, for mutants that are linked to trimerization domain, such as a foldon, amino acids 514 through 754 can be absent. Thus, in some specific embodiment, amino acid residues 514 through 574 are absent from the F1 polypeptide of the mutant. In still other specific embodiments, the F1 polypeptide of the RSV F mutants comprises or consists of amino acid residues 137-513 of a native F0 polypeptide sequence, such as any of the F0 precursor sequence set forth in SEQ ID Nos: 1, 2, 4, 6, and 81-270.

On the other hand, the F1 polypeptide of the RSV F mutant may include a C-terminal linkage to a trimerization domain, such as a foldon. Many of the sequences of the RSV F mutants disclosed herein include a sequence of protease cleavage site, such as thrombin cleavage site (LVPRGS), protein tags, such as 6× His-tag (HHHHHH) and Streptag II (WSHPGFEK), or linker sequences (such as GG and GS) (See FIG. 1) that are not essential for the function of the RSV F protein, such as for induction of an immune response. A person skilled in the art will recognize such sequences, and when appropriate, understand that these sequences are not included in a disclosed RSV F mutant.

In the RSV F mutants provided by the present disclosure, the F2 polypeptide chain may be of the same length as the full-length F2 polypeptide of the corresponding wild-type RSV F protein; it may also have deletions, such as deletions of 1, 2, 3, 4, 5, 6, 7, or 8 amino acid residues from the N-terminus or C-terminus of the F2 polypeptide.

The mutant in F0 form (i.e., a single chain polypeptide comprising the F2 polypeptide joined to the F1 polypeptide with or without partial or full length pep 27) or F1-F2 heterodimer form may form a protomer. The mutant may also be in the form of a trimer, which comprises three of the same protomer. Further, the mutants may be glycosylated proteins (i.e., glycoproteins) or non-glycosylated proteins. The mutant in F0 form may include, or may lack, the signal peptide sequence.

The F1 polypeptide and F2 polypeptide of the RSV F protein mutants to which one or more mutations are introduced can be from any wild-type RSV F proteins known in the art or discovered in the future, including, without limitations, the F protein amino acid sequence of RSV subtype A, and subtype B strains, including A2 Ontario and Buenos Aires, or any other subtype. In some embodiments, the RSV F mutant comprises a F1 and/or a F2 polypeptide from a RSV A virus, for example, a F1 and/or F2 polypeptide from a RSV F0 precursor protein set forth in any one of SEQ ID NOs: 1, 2, 4, 6, and 81-270 to which one or more mutations are introduced. In some other embodiments, the RSV F mutant comprises a F1 and/or a F2 polypeptide from a RSV B virus, for example, a F1 and/or F2 polypeptide from a RSV F0 precursor protein set forth in any one of SEQ ID NOs:2, and 211-263 to which one or more mutations are introduced. In still other embodiments, the RSV F mutant comprises a F1 and/or a F2 polypeptide from a RSV bovine virus, for example, a F1 and/or F2 polypeptide from a RSV F0 precursor protein set forth in any one of SEQ ID NOs:264-270 to which one or more mutations are introduced.

In some embodiments, the RSV F protein mutants comprise a F1-polypeptide, a F2 polypeptide, and one or more introduced amino acid mutations as described herein below, wherein the F1 polypeptide comprises 350 consecutive amino acids and is at least 90, 95, 98, or 99 percent identical to amino acids 137-513 of any of the sequences of SEQ ID NO:1, 4, and 81-210, wherein the F2 polypeptide comprises 70 consecutive amino acids and is at least 90, 95, 98, or 99 percent identical to amino acids 26-109 of any of the sequence of SEQ ID NO:1, 4, and 81-210 and wherein RSV F protein mutant is stabilized in pre-fusion conformation, whether as monomer or trimer. In some embodiments, the F1 polypeptide comprises 350 consecutive amino acids and is at least 90, 95, 98, or 99 percent identical to amino acids 137-513 of any of the sequence of SEQ ID NOs:2, 6, and 211-263, and the F2 polypeptide comprises 70 consecutive amino acids and is at least 90, 95, 98, or 99 percent identical to amino acids 26-109 of any of the sequence of SEQ ID NOs:2, 6, and 211-263. In some other embodiments, the RSV F protein mutant is stabilized in pre-fusion trimer conformation.

B-1(b) Trimerization Domains

In several embodiments, the RSV F mutant provided by the present disclosure is linked to a trimerization domain. In some embodiments, the trimerization domain promotes the formation of trimer of three F1/F2 heterodimers.

Several exogenous multimerization domains that promote formation of stable trimers of soluble proteins are known in the art. Examples of such multimerization domains that can be linked to a mutant provided by the present disclosure include: (1) the GCN4 leucine zipper (Harbury et al. 1993 Science 262: 1401-1407); (2) the trimerization motif from the lung surfactant protein (Hoppe et al. 1994 FEB S Lett 344: 191-195); (3) collagen (McAlinden et al. 2003 Biol Chem 278:42200-42207); and (4) the phage T4 fibritin foldon (Miroshnikov et al. 1998 Protein Eng 11:329-414). In some embodiments, a foldon domain is linked to a F mutant at the C-terminus of F1 polypeptide. In specific embodiments, the foldon domain is a T4 fibritin foldon domain, such as the amino acid sequence GYIPEAPRDGQAYVRKDGEWVLLSTFL (SEQ ID NO: 40).

Typically, the multimerization domain is positioned C-terminal to the F1 polypeptide. It may join directly to the F1 polypeptide chain. Optionally, the multimerization domain is connected to the F1 polypeptide via a linker, such as an amino acid linker, for example the sequence GG, GS, or SAIG. The linker can also be a longer linker (for example, including the repeat sequence GG). Numerous conformationally neutral linkers are known in the art that can be used in the mutants provided by the present disclosure. In some embodiments, the F mutant comprising a foldon domain include a protease cleavage site for removing the foldon domain from the F1 polypeptide, such as a thrombin site between the F1 polypeptide and the foldon domain.

B-2. Introduced Mutations in the RSV F Protein Mutants

The RSV F mutants provided by the present disclosure comprise a F1 polypeptide and a F2 polypeptide, wherein (1) either the F1 polypeptide or (2) the F2 polypeptide, or (3) both the F1 polypeptide and F2 polypeptide include one or more introduced amino acid mutations relative to the amino acid sequence of the corresponding native F protein. The introduction of such amino acid mutations in the RSV F mutants may confer a beneficial property to the mutants, such as enhanced immunogenicity, improved stability, or formation or improved stability of certain desired physical form or conformation of the mutants. Such introduced amino acid mutations are referred to as "engineered disulfide bond mutations," "cavity filling mutations," or "electrostatic mutations," and are described in detail herein below. RSV F mutants that include any additional mutations are also encompassed by the invention so long as the immunogenic property of the mutants is not substantially adversely affected by the additional mutations.

B-2(a) Engineered Disulfide Bond Mutations

In some embodiments, RSV F mutants provided by the present disclosure include one or more engineered disulfide bond mutations. The term "engineered disulfide bond mutation" or "engineered disulfide mutation" refers to mutation of a pair of amino acid residues in a wild-type RSV F protein to a pair of cysteine residues. The introduced pair of cysteine residues allows for formation of a disulfide bond between the introduced cysteine residues, which disulfide bond serves to stabilize the protein's conformation or oligomeric state, such as pre-fusion conformation. For stabilizing the pre-fusion conformation of the mutant, the residue pairs for mutation to cysteine should be in close proximity in the pre-fusion conformation but distant in the post-fusion conformation. Such residues can be identified by suitable methods known in the art, such as by visual inspection of a crystal structure of RSV F in a pre-fusion conformation, or more quantitative selection using computational protein design software (such as BioLuminate™ [BioLuminate, Schrodinger LLC, New York, 2015], Discovery Studio™ [Discovery Studio Modeling Environment, Accelrys, San Diego, 2015], MOE™ [Molecular Operating Environment, Chemical Computing Group Inc., Montreal, 2015], and Rosetta™ [Rosetta, University of Washington, Seattle, 2015]). Preferably, the distance between the pair of residues (e.g. the beta carbons) is less than 8 Å in a pre-fusion conformation, but more than 20 Å in a post-fusion conformation.

In some embodiments, the RSV F protein mutants comprise only one engineered disulfide mutation ("single engineered disulfide mutation"). In some other embodiments, the RSV F protein mutants comprise at least two engineered disulfide mutations, wherein each pair of the cysteine residues of the engineered disulfide mutations are appropriately positioned when RSV F protein mutant is in pre-fusion conformation ("double engineered disulfide mutation").

In some specific embodiments, the present disclosure provides a RSV F mutant comprising at least one engineered disulfide bond mutation, wherein the mutant comprises the same introduced mutations that are in any of the exemplary mutants provided in Tables 1 and 4-6. The exemplary RSV F mutants provided in Tables 1 and 4-6 are based on the same native F0 sequence of RSV A2 strain with three naturally-occurring substitutions at positions 102, 379, and 447 (SEQ ID NO:3). The same introduced mutations in each of the mutants can be made to a native F0 polypeptide sequence of any other RSV subtype or strain to arrive at different RSV F mutants, such as a native F0 polypeptide sequence set forth in any of the SEQ ID NOs: 1, 2, 4, 6, and 81-270. RSV F mutants that are based on a native F0 polypeptide sequence of any other RSV subtype or strain and comprise any of the engineered disulfide mutations are also within the scope of the invention. In some particular embodiments, a RSV F protein mutant comprises at least one engineered disulfide mutation selected from the group consisting of: 55C and 188C; 155C and 290C; 103C and 148C; and 142C and 371C, such as S55C and L188C, S155C and S290C, T103C and I148C, or L142C and N371C.

In some embodiments, the present disclosure provides RSV F protein mutants, wherein the amino acid mutations are mutation of a pair of amino acid residues in the HRB region (approximately amino acids 476-524) of a RSV F protein to a pair of cysteines. The introduced pair of cysteine residues allows for formation of a disulfide bond between the cysteine residues from two adjacent F2-F1 mutant protomers of a trimer. The disulfide linking two protomers in a trimer serves to stabilize the mutant in a trimeric state. Examples of specific pairs of such mutations include: 508C and 509C; 515C and 516C; 522C and 523C, such as K508C and S509C, N515C and V516C, or T522C and T523C. In some embodiments, the RSV F mutants comprise (1) at least one pair of cysteine mutations in the HRB region and (2) at least one introduced mutation outside of the HRB region selected from an engineered disulfide bond mutation as described herein above, a cavity filling mutation as described herein below, an electrostatic mutation as described herein below, or a combination of any of these mutations.

B-2(b) Cavity Filling Mutations.

In other embodiments, the present disclosure provides RSV F mutants that comprise one or more cavity filling mutations. The term "cavity filling mutation" refers to the substitution of an amino acid residue in the wild-type RSV F protein by an amino acid that is expected to fill an internal cavity of the mature RSV F protein. In one application, such cavity-filling mutations contribute to stabilizing the pre-fusion conformation of a RSV F protein mutant. The cavities in the pre-fusion conformation of the RSV F protein can be identified by methods known in the art, such as by visual inspection of a crystal structure of RSV F in a pre-fusion conformation, or by using computational protein design software (such as BioLuminate™ [BioLuminate, Schrodinger LLC, New York, 2015], Discovery Studio™ [Discovery Studio Modeling Environment, Accelrys, San Diego, 2015], MOE™ [Molecular Operating Environment, Chemical Computing Group Inc., Montreal, 2015], and Rosetta™ [Rosetta, University of Washington, Seattle, 2015]). The amino acids to be replaced for cavity-filling mutations typically include small aliphatic (e.g. Gly, Ala, and Val) or small polar amino acids (e.g. Ser and Thr). They may also include amino acids that are buried in the pre-fusion conformation, but exposed to solvent in the post-conformation. The replacement amino acids can be large aliphatic amino acids (Ile, Leu and Met) or large aromatic amino acids (His, Phe, Tyr and Trp). For example, in several embodiments, the RSV F protein mutant includes a T54H mutation.

In some specific embodiments, the present disclosure provides a RSV F protein mutant that comprises one or more cavity filling mutations selected from the group consisting of:

1) substitution of the amino acid at position 55, 62, 155, 190, or 290 with I, Y, L, H, or NA;
2) substitution of the amino acid at position 54, 58, 189, 219, or 397 with I, Y, L, H, or M;
3) substitution of the amino acid at position 151 with A or H;
4) substitution of the amino acid at position 147 or 298 with I, L, H, or M;
5) substitution of the amino acid at position 164, 187, 192, 207, 220, 296, 300, or 495 with I, Y, H; and
6) substitution of the amino acid at position 106 with W.

In some further specific embodiments, the RSV F protein mutant comprises one or more cavity filling mutations selected from the group consisting of:

1) substitution of S at position 55, 62, 155, 190, or 290 with I, Y, L, H, or M;
2) substitution of T at position 54, 58, 189, 219, or 397 with I, Y, L, H, or M;
3) substitution of G at position 151 with A or H;
4) substitution of A at position 147 or 298 with I, L, H, or M;
5) substitution of V at position 164, 187, 192, 207, 220, 296, 300, or 495 with I, Y, H; and
6) substitution of R at position 106 with W.

In some specific embodiments, the present disclosure provides a RSV F mutant comprising one or more cavity filling mutations, wherein the mutant comprises the cavity filling mutations in any of the mutants provided in Tables 2, 4, and 6. RSV F mutants provided in Tables 2, 4, and 6 are based on the same native F0 sequence of RSV A2 strain with three naturally occurring substitutions at positions 102, 379, and 447 (SEQ ID NO:3). The same introduced mutations in each of the mutants can be made to a native F0 polypeptide sequence of any other RSV subtype or strain to arrive at different RSV F mutants, such as a native F0 polypeptide sequence set forth in any of the SEQ ID NOs:1, 2, 4, 6, and 81-270. The RSV F mutants that are based on a native F0 polypeptide sequence of any other RSV subtype or strain and comprise any of the one or more cavity filling mutations are also within the scope of the invention. In some particular embodiments, a RSV F protein mutant provided by the present disclosure comprises at least one cavity filling mutation selected from the group consisting of: T54H, S190I, and V296I.

B-2 (c) Electrostatic Mutations.

In still other embodiments, the present disclosure provides RSV F protein mutants that include one or more electrostatic mutations. The term "electrostatic mutation" refers to an amino acid mutation introduced to a wild-type RSV F protein that decreases ionic repulsion or increase ionic attraction between residues in a protein that are proximate to each other in the folded structure. As hydrogen bonding is a special case of ionic attraction, electrostatic mutations may increase hydrogen bonding between such proximate residues. In one example, an electrostatic mutation may be introduced to improve trimer stability. In some embodiments, an electrostatic mutation is introduced to decrease repulsive ionic interactions or increase attractive ionic interactions (potentially including hydrogen bonds) between residues that are in close proximity in the RSV F glycoprotein in its pre-fusion conformation but not in its post-fusion conformation. For example, in the pre-fusion conformation, the acidic side chain of Asp486 from one protomer of the RSV F glycoprotein trimer is located at the trimer interface and structurally sandwiched between two other acidic side chains of Glu487 and Asp489 from another protomer. On the other hand, in the post-fusion conformation, the acidic side chain of Asp486 is located on the trimer surface and exposed to solvent. In several embodiments, the RSV F protein mutant includes an electrostatic D486S substitution that reduces repulsive ionic interactions or increases attractive ionic interactions with acidic residues of Glu487 and Asp489 from another protomer of RSV F trimer.

Introduction of an electrostatic mutation may increase the melting temperature (Tm) of the pre-fusion conformation or pre-fusion trimer conformation of the RSV F protein.

Unfavorable electrostatic interactions in a pre-fusion or pre-fusion trimer conformation can be identified by method known in the art, such as by visual inspection of a crystal structure of RSV F in a pre-fusion or pre-fusion trimer conformation, or by using computational protein design software (such as BioLuminate™ [BioLuminate, Schrodinger LLC, New York, 2015], Discovery Studio™ [Discovery Studio Modeling Environment, Accelrys, San Diego, 2015], MOE™ [Molecular Operating Environment, Chemical Computing Group Inc., Montreal, 2015.], and Rosetta™ [Rosetta, University of Washington, Seattle, 2015.])

In some specific embodiments, the RSV F protein mutant provided by the present disclosure comprises at least one electrostatic mutation selected from the group consisting of:

1) substitution of the amino acid at position 82, 92, or 487 by D, F, Q, T, S, L, or H;
2) substitution of the amino acid at position 315, 394, or 399 by F, M, R, S, L, I, Q, or T;
3) substitution of the amino acid at position 392, 486, or 489 by H, S, N, T, or P; and
4) substitution of the amino acid at position 106 or 339 by F, Q, N, or W.

In some further specific embodiments, the RSV F protein mutant comprises at least one electrostatic mutation selected from the group consisting of:

1) substitution of Eat position 82, 92, or 487 by D, F, Q, T, S, L, or H;
2) substitution of Kat position 315, 394, or 399 by F, M, R, S, L, I, Q, or T;
3) substitution of D at position 392, 486, or 489 by H, S, N, T, or P; and
4) substitution of R at position 106 or 339 by F, Q, N, or W.

In some specific embodiments, the present disclosure provides a RSV F mutant comprising one or more electrostatic mutations, wherein the mutant comprises the electrostatic mutations in any of the mutants provided in Tables 3, 5, and 6. RSV F mutants provided in Tables 3, 5, and 6 are based on the same native F0 sequence of RSV A2 strain with three naturally occurring substitutions at positions 102, 379, and 447 (SEQ ID NO:3). The same introduced mutations in each of the mutants can be made to a native F0 polypeptide sequence of any other RSV subtype or strain to arrive at different RSV F mutants, such as a native F0 polypeptide sequence set forth in any of the SEQ ID NOs:1, 2, 4, 6, and 81-270. RSV F mutants that are based on a native F0 polypeptide sequence of any other RSV subtype or strain and comprise any of the one or more electrostatic mutations are also within the scope of the invention. In some particular embodiments, the RSV F protein mutant comprises mutation D486S.

B-2 (d) Combination of Engineered Disulfide Bond Mutations, Cavity Filling Mutations, and Electrostatic Mutations.

In another aspect, the present disclosure provides RSV F protein mutants, which comprise a combination of two or more different types of mutations selected from engineered disulfide bond mutations, cavity filling mutations, and electrostatic mutations, each as described herein above.

In some embodiments, the mutants comprise at least one engineered disulfide bond mutation and at least one cavity filling mutation. In some specific embodiments, the RSV F mutants include a combination of mutations as noted in Table 4.

In some further embodiments, the RSV F protein mutants comprise at least one engineered disulfide mutation and at least one electrostatic mutation. In some specific embodiments, the RSV F mutants include a combination of mutations as noted in Table 5.

In still other embodiments, the RSV F protein mutants comprise at least one engineered disulfide mutation, at least one cavity filling mutation, and at least one electrostatic mutation. In some specific embodiments, the RSV F mutants include a combination of mutations as provided in Table 6.

In some particular embodiments, the present invention provides a RSV F mutant that comprises a combination of mutations selected from the group consisting of:

(1) combination of 103C, 148C, 190I, and 486S;
(2) combination of 54H, 55C, 188C, and 486S;
(3) combination of 54H, 103C, 148C, 190I, 296I, and 486S;
(4) combination of 54H, 55C, 142C, 188C, 296I, and 371C;
(5) combination of 55C, 188C, and 486S;
(6) combination of 54H, 55C, 188C, and 190I;
(7) combination of 55C, 188C, 190I, and 486S;
(8) combination of 54H, 55C, 188C, 190I, and 486S;
(9) combination of 155C, 190I, 290C, and 486S;
(10) combination of 54H, 55C, 142C, 188C, 296I, 371C, 486S, 487Q, and 489S; and
(11) combination of 54H, 155C, 190I, 290C, and 296I.

In some particular embodiments, the present invention provides a RSV F mutant that comprises a combination of mutations selected from the group consisting of:

(1) combination of T103C, I148C, S190I, and D486S;
(2) combination of T54H, S55C, L188C, and D486S;
(3) combination of T54H, T103C, I148C, S190I, V296I, and D486S;
(4) combination of T54H, S55C, L142C, L188C, V296I, and N371C;
(5) combination of S55C, L188C, and D486S;
(6) combination of T54H, S55C, L188C, and S190I;
(7) combination of S55C, L188C, S190I, and D486S;
(8) combination of T54H, S55C, L188C, S190I, and D486S;
(9) combination of S155C, S190I, S290C, and D486S;
(10) combination of T54H, S55C, L142C, L188C, V296I, N371C, D486S, E487Q, and D489S; and
(11) combination of T54H, S155C, S190I, S290C, and V296I.

In some specific embodiments, the present disclosure provides a RSV F mutant comprising a combination of introduced mutations, wherein the mutant comprises a combination of mutations in any of the mutants provided in Tables 4, 5, and 6. RSV F mutants provided in Tables 4, 5, and 6 are based on the same native F0 sequence of RSV A2 strain with three naturally occurring substitutions at positions 102, 379, and 447 (SEQ ID NO:3). The same introduced mutations in each of the mutants can be made to a native F0 polypeptide sequence of any other RSV subtype or strain to arrive at different RSV F mutants, such as a native F0 polypeptide sequence set forth in any of the SEQ ID NOs:1, 2, 4, 6, and 81-270. RSV F mutants that are based on a native F0 polypeptide sequence of any other RSV subtype or strain and comprise any of the combination of mutations are also within the scope of the invention.

In some other particular embodiments, the present invention provides a RSV F mutant, wherein the mutant comprises a cysteine (C) at position 103 (103C) and at position 148 (148C), an isoleucine (I) at position 190 (190I), and a serine (S) at position 486 (486S), and wherein the mutant comprises a F1 polypeptide and a F2 polypeptide selected from the group consisting of:

(1) a F2 polypeptide comprising the amino acid sequence of SEQ ID NO:41 and a F1 polypeptide comprising the amino acid sequence of SEQ ID NO:42;

(2) a F2 polypeptide comprising an amino acid sequence that is at least 97%, 98%, or 99% identical to the amino acid sequence of SEQ ID NO:41 and a F1 polypeptide comprising an amino acid sequence that is at least 97%, 98%, or 99% identical to the amino acid sequence of SEQ ID NO:42;

(3) a F2 polypeptide comprising the amino acid sequence of SEQ ID NO: 43 and a F1 polypeptide comprising the amino acid sequence of SEQ ID NO:44;

(4) a F2 polypeptide comprising an amino acid sequence that is at least 97%, 98%, or 99% identical to the amino acid sequence of SEQ ID NO:43 and a F1 polypeptide comprising an amino acid sequence that is at least 97%, 98%, or 99% identical to the amino acid sequence of SEQ ID NO:44;

(5) a F2 polypeptide comprising the amino acid sequence of SEQ ID NO: 45 and a F1 polypeptide comprising the amino acid sequence of SEQ ID NO:46;

(6) a F2 polypeptide comprising an amino acid sequence that is at least 97%, 98%, or 99% identical to the amino acid sequence of SEQ ID NO:45 and a F1 polypeptide comprising an amino acid sequence that is at least 97%, 98%, or 99% identical to the amino acid sequence of SEQ ID NO:46;

(7) a F2 polypeptide comprising the amino acid sequence of SEQ ID NO: 47 and a F1 polypeptide comprising the amino acid sequence of SEQ ID NO:48;

(8) a F2 polypeptide comprising an amino acid sequence that is at least 97%, 98%, or 99% identical to the amino acid sequence of SEQ ID NO:47 and a F1 polypeptide comprising an amino acid sequence that is at least 97%, 98%, or 99% identical to the amino acid sequence of SEQ ID NO:48;

(9) a F2 polypeptide comprising the amino acid sequence of SEQ ID NO: 49 and a F1 polypeptide comprising the amino acid sequence of SEQ ID NO:50;

(10) a F2 polypeptide comprising an amino acid sequence that is at least 97%, 98%, or 99% identical to the amino acid sequence of SEQ ID NO:49 and a F1 polypeptide comprising an amino acid sequence that is at least 97%, 98%, or 99% identical to the amino acid sequence of SEQ ID NO:50.

(11) a F2 polypeptide comprising the amino acid sequence of SEQ ID NO:279 and a F1 polypeptide comprising the amino acid sequence of SEQ ID NO:280;

(12) a F2 polypeptide comprising an amino acid sequence that is at least 97%, 98%, or 99% identical to the amino acid sequence of SEQ ID NO:279 and a F1 polypeptide comprising an amino acid sequence that is at least 97%, 98%, or 99% identical to the amino acid sequence of SEQ ID NO:280;

(13) a F2 polypeptide comprising the amino acid sequence of SEQ ID NO:281 and a F1 polypeptide comprising the amino acid sequence of SEQ ID NO:282;

(14) a F2 polypeptide comprising an amino acid sequence that is at least 97%, 98% or 99% identical to the amino acid sequence of SEQ ID NO:281 and a F1 polypeptide comprising an amino acid sequence that is at least 97%, 98%, or 99% identical to the amino acid sequence of SEQ ID NO:282;

(15) a F2 polypeptide comprising the amino acid sequence of SEQ ID NO:283 and a F1 polypeptide comprising the amino acid sequence of SEQ ID NO:284;

(16) a F2 polypeptide comprising an amino acid sequence that is at least 97%, 98%, or 99% identical to the amino acid sequence of SEQ ID NO:283 and a F1 polypeptide comprising an amino acid sequence that is at least 97%, 98%, or 99% identical to the amino acid sequence of SEQ ID NO:284;

(17) a F2 polypeptide comprising the amino acid sequence of SEQ ID NO:285 and a F1 polypeptide comprising the amino acid sequence of SEQ ID NO:286;

(18) a F2 polypeptide comprising an amino acid sequence that is at least 97%, 98%, or 99% identical to the amino acid sequence of SEQ ID NO:285 and a F1 polypeptide comprising an amino acid sequence that is at least 97%, 98%, or 99% identical to the amino acid sequence of SEQ ID NO:286;

(19) a F2 polypeptide comprising the amino acid sequence of SEQ ID NO:287 and a F1 polypeptide comprising the amino acid sequence of SEQ ID NO:288;

(20) a F2 polypeptide comprising an amino acid sequence that is at least 97%, 98%, or 99% identical to the amino acid sequence of SEQ ID NO:287 and a F1 polypeptide comprising an amino acid sequence that is at least 97%, 98%, or 99% identical to the amino acid sequence of SEQ ID NO:288;

(21) a F2 polypeptide comprising the amino acid sequence of SEQ ID NO:289 and a F1 polypeptide comprising the amino acid sequence of SEQ ID NO:290; and

(22) a F2 polypeptide comprising an amino acid sequence that is at least 97%, 98%, or 99% identical to the amino acid sequence of SEQ ID NO:289 and a F1 polypeptide comprising an amino acid sequence that is at least 97%, 98%, or 99% identical to the amino acid sequence of SEQ ID NO:290.

In some other particular embodiments, the present invention provides a RSV F mutant, wherein the mutant comprises a histidine (H) at position 54, a cysteine (C) at positions 103 and 148, a isoleucine (I) at positions 190 and 296, and a serine (S) at position 486, and wherein the mutant comprises a F1 polypeptide and a F2 polypeptide selected from the group consisting of:

(1) F2 polypeptide comprising the amino acid sequence of SEQ ID NO: 51 and a F1 polypeptide comprising the amino acid sequence of SEQ ID NO:52;

(2) a F2 polypeptide comprising an amino acid sequence that is at least 97%, 98%, or 99% identical to the amino acid sequence of SEQ ID NO:51 and a F1 polypeptide comprising an amino acid sequence that is at least 97%, 98%, or 99% identical to the amino acid sequence of SEQ ID NO:52;

(3) a F2 polypeptide comprising the amino acid sequence of SEQ ID NO:53 and a F1 polypeptide comprising the amino acid sequence of SEQ ID NO:54;

(4) a F2 polypeptide comprising an amino acid sequence that is at least 97%, 98%, or 99% identical to the amino acid sequence of SEQ ID NO:53 and a F1 polypeptide comprising an amino acid sequence that is at least 97%, 98%, or 99% identical to the amino acid sequence of SEQ ID NO:54;

(5) a F2 polypeptide comprising the amino acid sequence of SEQ ID NO:55 and a F1 polypeptide comprising the amino acid sequence of SEQ ID NO:56;

(6) a F2 polypeptide comprising an amino acid sequence that is at least 97%, 98%, or 99% identical to the amino acid sequence of SEQ ID NO:55 and a F1 polypeptide comprising an amino acid sequence that is at least 97%, 98%, or 99% identical to the amino acid sequence of SEQ ID NO:56;

(7) a F2 polypeptide comprising the amino acid sequence of SEQ ID NO:57 and a F1 polypeptide comprising the amino acid sequence of SEQ ID NO:58;

(8) a F2 polypeptide comprising an amino acid sequence that is at least 97%, 98%, or 99% identical to the amino acid sequence of SEQ ID NO:57 and a F1 polypeptide comprising an amino acid sequence that is at least 97%, 98%, or 99% identical to the amino acid sequence of SEQ ID NO:58;

(9) a F2 polypeptide comprising the amino acid sequence of SEQ ID NO:59 and a F1 polypeptide comprising the amino acid sequence of SEQ ID NO:60;

(10) a F2 polypeptide comprising an amino acid sequence that is at least 97%, 98%, or 99% identical to the amino acid sequence of SEQ ID NO:59 and a F1 polypeptide comprising an amino acid sequence that is at least 97%, 98%, or 99% identical to the amino acid sequence of SEQ ID NO:60;

(11) a F2 polypeptide comprising the amino acid sequence of SEQ ID NO:291 and a F1 polypeptide comprising the amino acid sequence of SEQ ID NO:292;

(12) a F2 polypeptide comprising an amino acid sequence that is at least 97%, 98%, or 99% identical to the amino acid sequence of SEQ ID NO:291 and a F1 polypeptide comprising an amino acid sequence that is at least 97%, 98%, or 99% identical to the amino acid sequence of SEQ ID NO:292;

(13) a F2 polypeptide comprising the amino acid sequence of SEQ ID NO:293 and a F1 polypeptide comprising the amino acid sequence of SEQ ID NO:294;

(14) a F2 polypeptide comprising an amino acid sequence that is at least 97%, 98%, or 99% identical to the amino acid sequence of SEQ ID NO:293 and a F1 polypeptide comprising an amino acid sequence that is at least 97%, 98%, or 99% identical to the amino acid sequence of SEQ ID NO:294;

(15) a F2 polypeptide comprising the amino acid sequence of SEQ ID NO:295 and a F1 polypeptide comprising the amino acid sequence of SEQ ID NO:296;

(16) a F2 polypeptide comprising an amino acid sequence that is at least 97%, 98%, or 99% identical to the amino acid sequence of SEQ ID NO:295 and a F1 polypeptide comprising an amino acid sequence that is at least 97%, 98%, or 99% identical to the amino acid sequence of SEQ ID NO:296;

(17) a F2 polypeptide comprising the amino acid sequence of SEQ ID NO:297 and a F1 polypeptide comprising the amino acid sequence of SEQ ID NO:298;

(18) a F2 polypeptide comprising an amino acid sequence that is at least 97%, 98%, or 99% identical to the amino acid sequence of SEQ ID NO:297 and a F1 polypeptide comprising an amino acid sequence that is at least 97%, 98%, or 99% identical to the amino acid sequence of SEQ ID NO:298;

(19) a F2 polypeptide comprising the amino acid sequence of SEQ ID NO:299 and a F1 polypeptide comprising the amino acid sequence of SEQ ID NO:300;

(20) a F2 polypeptide comprising an amino acid sequence that is at least 97%, 98%, or 99% identical to the amino acid sequence of SEQ ID NO:299 and a F1 polypeptide comprising an amino acid sequence that is at least 97%, 98%, or 99% identical to the amino acid sequence of SEQ ID NO:300;

(21) a F2 polypeptide comprising the amino acid sequence of SEQ ID NO:301 and a F1 polypeptide comprising the amino acid sequence of SEQ ID NO:302; and

(22) a F2 polypeptide comprising an amino acid sequence that is at least 97%, 98%, or 99% identical to the amino acid sequence of SEQ ID NO:301 and a F1 identical to the amino acid sequence of SEQ ID NO:302.

In some other particular embodiments, the present invention provides a RSV F mutant, wherein the mutant comprises a histidine (H) at position 54, a cysteine (C) at positions 55 and 188, and a serine (S) at position 486, and wherein the mutant comprises a F1 polypeptide and a F2 polypeptide selected from the group consisting of:

(1) a F2 polypeptide comprising the amino acid sequence of SEQ ID NO:61 and a F1 polypeptide comprising the amino acid sequence of SEQ ID NO:62;

(2) a F2 polypeptide comprising an amino acid sequence that is at least 97%, 98% or 99% identical to the amino acid sequence of SEQ ID NO:61 and a F1 polypeptide comprising an amino acid sequence that is at least 97%, 98%, or 99% identical to the amino acid sequence of SEQ ID NO:62;

(3) a F2 polypeptide comprising the amino acid sequence of SEQ ID NO:63 and a F1 polypeptide comprising the amino acid sequence of SEQ ID NO:64;

(4) a F2 polypeptide comprising an amino acid sequence that is at least 97%, 98%, or 99% identical to the amino acid sequence of SEQ ID NO:63 and a F1 polypeptide comprising an amino acid sequence that is at least 97%, 98%, or 99% identical to the amino acid sequence of SEQ ID NO:64;

(5) a F2 polypeptide comprising the amino acid sequence of SEQ ID NO:65 and a F1 polypeptide comprising the amino acid sequence of SEQ ID NO:66;

(6) a F2 polypeptide comprising an amino acid sequence that is at least 97%, 98%, or 99% identical to the amino acid sequence of SEQ ID NO:65 and a F1 polypeptide comprising an amino acid sequence that is at least 97%, 98%, or 99% identical to the amino acid sequence of SEQ ID NO:66;

(7) a F2 polypeptide comprising the amino acid sequence of SEQ ID NO:67 and a F1 polypeptide comprising the amino acid sequence of SEQ ID NO:68;

(8) a F2 polypeptide comprising an amino acid sequence that is at least 97%, 98%, or 99% identical to the amino acid sequence of SEQ ID NO:67 and a F1 polypeptide comprising an amino acid sequence that is at least 97%, 98%, or 99% identical to the amino acid sequence of SEQ ID NO:68;

(9) a F2 polypeptide comprising the amino acid sequence of SEQ ID NO:69 and a F1 polypeptide comprising the amino acid sequence of SEQ ID NO:70;

(10) a F2 polypeptide comprising an amino acid sequence that is at least 97%, 98%, or 99% identical to the amino acid sequence of SEQ ID NO:69 and a F1 polypeptide comprising an amino acid sequence that is at least 97%, 98%, or 99% identical to the amino acid sequence of SEQ ID NO:70;

(11) a F2 polypeptide comprising the amino acid sequence of SEQ ID NO:303 and a F1 polypeptide comprising the amino acid sequence of SEQ ID NO:304;

(12) a F2 polypeptide comprising an amino acid sequence that is at least 97%, 98%, or 99% identical to the amino acid sequence of SEQ ID NO:303 and a F1 polypeptide comprising an amino acid sequence that is at least 97%, 98%, or 99% identical to the amino acid sequence of SEQ ID NO:304;

(13) a F2 polypeptide comprising the amino acid sequence of SEQ ID NO:305 and a F1 polypeptide comprising the amino acid sequence of SEQ ID NO:306;

(14) a F2 polypeptide comprising an amino acid sequence that is at least 97%, 98%, or 99% identical to the amino acid sequence of SEQ ID NO:305 and a F1 polypeptide comprising an amino acid sequence that is at least 97%, 98%, or 99% identical to the amino acid sequence of SEQ ID NO:306;

(15) a F2 polypeptide comprising the amino acid sequence of SEQ ID NO:307 and a F1 polypeptide comprising the amino acid sequence of SEQ ID NO:308;

(16) a F2 polypeptide comprising an amino acid sequence that is at least 97%, 98%, or 99% identical to the amino acid sequence of SEQ ID NO:307 and a F1 polypeptide comprising an amino acid sequence that is at least 97%, 98%, or 99% identical to the amino acid sequence of SEQ ID NO:308;

(17) a F2 polypeptide comprising the amino acid sequence of SEQ ID NO:309 and a F1 polypeptide comprising the amino acid sequence of SEQ ID NO:310;

(18) a F2 polypeptide comprising an amino acid sequence that is at least 97%, 98%, or 99% identical to the amino acid sequence of SEQ ID NO:309 and a F1 polypeptide comprising an amino acid sequence that is at least 97%, 98%, or 99% identical to the amino acid sequence of SEQ ID NO:310;

(19) a F2 polypeptide comprising the amino acid sequence of SEQ ID NO:311 and a F1 polypeptide comprising the amino acid sequence of SEQ ID NO:312;

(20) a F2 polypeptide comprising an amino acid sequence that is at least 97%, 98%, or 99% identical to the amino acid sequence of SEQ ID NO:311 and a F1 identical to the amino acid sequence of SEQ ID NO:312.

(21) a F2 polypeptide comprising the amino acid sequence of SEQ ID NO:313 and a F1 polypeptide comprising the amino acid sequence of SEQ ID NO:314; and

(22) a F2 polypeptide comprising an amino acid sequence that is at least 97%, 98%, or 99% identical to the amino acid sequence of SEQ ID NO:313 and a F1 polypeptide comprising an amino acid sequence that is at least 97%, 98%, or 99% identical to the amino acid sequence of SEQ ID NO:314.

In some other particular embodiments, the present invention provides a RSV F mutant, wherein the mutant comprises a histidine (H) at position 54, a cysteine (C) at positions 55 and 188, an isoleucine (I) at position 190 (190I), and a serine (S) at position 486, and wherein the mutant comprises a F1 polypeptide and a F2 polypeptide selected from the group consisting of:

(1) a F2 polypeptide comprising the amino acid sequence of SEQ ID NO:71 and a F1 polypeptide comprising the amino acid sequence of SEQ ID NO:72;

(2) a F2 polypeptide comprising an amino acid sequence that is at least 97%, 98%, or 99% identical to the amino acid sequence of SEQ ID NO:71 and a F1 polypeptide comprising an amino acid sequence that is at least 97%, 98%, or 99% identical to the amino acid sequence of SEQ ID NO:72;

(3) a F2 polypeptide comprising the amino acid sequence of SEQ ID NO:73 and a F1 polypeptide comprising the amino acid sequence of SEQ ID NO:74;

(4) a F2 polypeptide comprising an amino acid sequence that is at least 97%, 98%, or 99% identical to the amino acid sequence of SEQ ID NO:73 and a F1 polypeptide comprising an amino acid sequence that is at least 97%, 98%, or 99% identical to the amino acid sequence of SEQ ID NO:74;

(5) a F2 polypeptide comprising the amino acid sequence of SEQ ID NO:75 and a F1 polypeptide comprising the amino acid sequence of SEQ ID NO:76;

(6) a F2 polypeptide comprising an amino acid sequence that is at least 97%, 98%, or 99% identical to the amino acid sequence of SEQ ID NO:75 and a F1 polypeptide comprising an amino acid sequence that is at least 97%, 98%, or 99% identical to the amino acid sequence of SEQ ID NO:76;

(7) a F2 polypeptide comprising the amino acid sequence of SEQ ID NO:77 and a F1 polypeptide comprising the amino acid sequence of SEQ ID NO:78;

(8) a F2 polypeptide comprising an amino acid sequence that is at least 97%, 98%, or 99% identical to the amino acid sequence of SEQ ID NO:77 and a F1 polypeptide comprising an amino acid sequence that is at least 97%, 98%, or 99% identical to the amino acid sequence of SEQ ID NO:78;

(9) a F2 polypeptide comprising the amino acid sequence of SEQ ID NO:79 and a F1 polypeptide comprising the amino acid sequence of SEQ ID NO:80;

(10) a F2 polypeptide comprising an amino acid sequence that is at least 97%, 98%, or 99% identical to the amino acid sequence of SEQ ID NO:79 and a F1 polypeptide comprising an amino acid sequence that is at least 97%, 98%, or 99% identical to the amino acid sequence of SEQ ID NO:80;

(11) a F2 polypeptide comprising the amino acid sequence of SEQ ID NO:315 and a F1 polypeptide comprising the amino acid sequence of SEQ ID NO:316;

(12) a F2 polypeptide comprising an amino acid sequence that is at least 97%, 98%, or 99% identical to the amino acid sequence of SEQ ID NO:315 and a F1 polypeptide comprising an amino acid sequence that is at least 97%, 98%, or 99% identical to the amino acid sequence of SEQ ID NO:316;

(13) a F2 polypeptide comprising the amino acid sequence of SEQ ID NO:317 and a F1 polypeptide comprising the amino acid sequence of SEQ ID NO:318;

(14) a F2 polypeptide comprising an amino acid sequence that is at least 97%, 98%, or 99% identical to the amino acid sequence of SEQ ID NO:317 and a F1 polypeptide comprising an amino acid sequence that is at least 97%, 98%, or 99% identical to the amino acid sequence of SEQ ID NO:318;

(15) a F2 polypeptide comprising the amino acid sequence of SEQ ID NO:319 and a F1 polypeptide comprising the amino acid sequence of SEQ ID NO:320;

(16) a F2 polypeptide comprising an amino acid sequence that is at least 97%, 98%, or 99% identical to the amino acid sequence of SEQ ID NO:319 and a F1 polypeptide comprising an amino acid sequence that is at least 97%, 98%, or 99% identical to the amino acid sequence of SEQ ID NO:320;

(17) a F2 polypeptide comprising the amino acid sequence of SEQ ID NO:321 and a F1 polypeptide comprising the amino acid sequence of SEQ ID NO:322;

(18) a F2 polypeptide comprising an amino acid sequence that is at least 97%, 98%, or 99% identical to the amino acid sequence of SEQ ID NO:321 and a F1 identical to the amino acid sequence of SEQ ID NO:322;

(19) a F2 polypeptide comprising the amino acid sequence of SEQ ID NO:323 and a F1 polypeptide comprising the amino acid sequence of SEQ ID NO:324;

(20) a F2 polypeptide comprising an amino acid sequence that is at least 97%, 98%, or 99% identical to the amino acid sequence of SEQ ID NO:323 and a F1 polypeptide comprising an amino acid sequence that is at least 97%, 98%, or 99% identical to the amino acid sequence of SEQ ID NO:324.

(21) a F2 polypeptide comprising the amino acid sequence of SEQ ID NO:325 and a F1 polypeptide comprising the amino acid sequence of SEQ ID NO:326; and

(22) a F2 polypeptide comprising an amino acid sequence that is at least 97%, 98%, or 99% identical to the amino acid sequence of SEQ ID NO:325 and a F1 polypeptide comprising an amino acid sequence that is at least 97%, 98%, or 99% identical to the amino acid sequence of SEQ ID NO:326.

The amino acid sequence of the F2 polypeptide and F1 polypeptide of exemplary RSV F mutants provided by the present disclosure is provided in Tables C-F.

In several embodiments, a foldon domain is linked to a RSV F mutant described herein above, wherein the foldon domain is linked to the C-terminus of the F1 polypeptide and comprises the amino acid sequence of SEQ ID NO:40.

The RSV F protein mutants provided by the present disclosure can be prepared by routine methods known in the art, such as by expression in a recombinant host system using a suitable vector. Suitable recombinant host cells include, for example, insect cells, mammalian cells, avian cells, bacteria, and yeast cells. Examples of suitable insect cells include, for example, Sf9 cells, Sf21 cells, Tn5 cells, Schneider S2 cells, and High Five cells (a clonal isolate derived from the parental Trichoplusia ni BTI-TN-5B1-4 cell line (Invitrogen)). Examples of suitable mammalian cells include Chinese hamster ovary (CHO) cells, human embryonic kidney cells (HEK293 or Expi 293 cells, typically transformed by sheared adenovirus type 5 DNA), NIH-3T3 cells, 293-T cells, Vero cells, and HeLa cells. Suitable avian cells include, for example, chicken embryonic stem cells (e.g., EBx® cells), chicken embryonic fibroblasts, chicken embryonic germ cells, quail fibroblasts (e.g. ELL-O), and duck cells. Suitable insect cell expression systems, such as baculovirus-vectored systems, are known to those of skill in the art and described in, e.g., Summers and Smith, Texas Agricultural Experiment Station Bulletin No. 1555 (1987). Materials and methods for baculovirus/insect cell expression systems are commercially available in kit form from, inter alia, Invitrogen, San Diego Calif. Avian cell expression systems are also known to those of skill in the art and described in, e.g., U.S. Pat. Nos. 5,340,740; 5,656,479; 5,830,510; 6,114,168; and 6,500,668. Similarly, bacterial and mammalian cell expression systems are also known in the art and described in, e.g., Yeast Genetic Engineering (Barr et al., eds., 1989) Butterworths, London.

A number of suitable vectors for expression of recombinant proteins in insect or mammalian cells are well-known and conventional in the art. Suitable vectors can contain a number of components, including, but not limited to one or more of the following: an origin of replication; a selectable marker gene; one or more expression control elements, such as a transcriptional control element (e.g., a promoter, an enhancer, a terminator), and/or one or more translation signals; and a signal sequence or leader sequence for targeting to the secretory pathway in a selected host cell (e.g., of mammalian origin or from a heterologous mammalian or non-mammalian species). For example, for expression in insect cells a suitable baculovirus expression vector, such as pFastBac (Invitrogen), is used to produce recombinant baculovirus particles. The baculovirus particles are amplified and used to infect insect cells to express recombinant protein. For expression in mammalian cells, a vector that will drive expression of the construct in the desired mammalian host cell (e.g., Chinese hamster ovary cells) is used.

The RSV F protein mutant polypeptides can be purified using any suitable methods. For example, methods for purifying RSV F protein mutant polypeptides by immunoaffinity chromatography are known in the art. Ruiz-Arguello et al., J. Gen. Virol., 85:3677-3687 (2004). Suitable methods for purifying desired proteins including precipitation and various types of chromatography, such as hydrophobic interaction, ion exchange, affinity, chelating and size exclusion are well-known in the art. Suitable purification schemes can be created using two or more of these or other suitable methods. If desired, the RSV F protein mutant polypeptides can include a "tag" that facilitates purification, such as an epitope tag or a histidine (HIS) tag. Such tagged polypeptides can conveniently be purified, for example from conditioned media, by chelating chromatography or affinity chromatography.

C. NUCLEIC ACIDS ENCODING RSV F PROTEIN MUTANTS

In another aspect, the present invention provides nucleic acid molecules that encode a RSV F protein mutant described herein above. These nucleic acid molecules include DNA, cDNA, and RNA sequences. Nucleic acid molecules that encode only a F2 polypeptide or only a F1 polypeptide of a RSV F mutant are also encompassed by the invention. The nucleic acid molecule can be incorporated into a vector, such as an expression vector.

In some embodiments, the nucleic acid molecule encodes a precursor F0 polypeptide that, when expressed in an appropriate cell, is processed into a disclosed RSV F mutant. In some embodiments, the nucleic acid molecule encodes a precursor F0 polypeptide that, when expressed in an appropriate cell, is processed into a disclosed RSV F mutant, wherein the precursor F0 polypeptide includes, from N- to C-terminus, a signal peptide, a F2 polypeptide, a Pep27 polypeptide, and a F1 polypeptide. In some embodiments, the Pep27 polypeptide comprises the amino acid sequence set forth at positions 110-136 of any of the amino acid sequences of SEQ ID NOs:1, 2, 4, 6, and 81-270, wherein the amino acid positions correspond to the amino acid sequence of SEQ ID NO:1. In some embodiments, the signal peptide comprises the amino acid sequence set forth at positions 1-25 of any one of the amino acid sequences of SEQ ID NOs: 1, 2, 4, 6, and 81-270, wherein the amino acid positions correspond to the amino acid sequence of a reference of SEQ ID NO:1.

In some embodiments, the nucleic acid molecule encodes a mutant selected from the group consisting of:

(1) a mutant comprising at least one engineered disulfide mutation;
(2) a mutant comprising at least one cavity filing mutation;
(3) a mutant comprising at least one electrostatic mutation;
(4) a mutant comprising at least one engineered disulfide mutation and at least one cavity filing mutation;
(5) a mutant comprising at least one engineered disulfide mutation and at least one electrostatic mutation;
(6) a mutant comprising at least one cavity filing mutation and at least one electrostatic mutation; and
(7) a mutant comprising at least one engineered disulfide mutation and at least one electrostatic mutation, at least one cavity filing mutation, and at least one electrostatic mutation.

In some specific embodiments, the present disclosure provides a nucleic acid molecule which encodes a mutant selected from the group consisting of:

(1) a mutant comprising a combination of substitutions 103C, 148C, 190I, and 486S;
(2) a mutant comprising a combination of substitutions 54H, 55C, 188C, and 486S;
(3) a mutant comprising a combination of substitutions 54H, 103C, 148C, 190I, 296I, and 486S;
(4) a mutant comprising a combination of substitutions 54H, 55C, 142C, 188C, 296I, and 371C,
(5) a mutant comprising a combination of amino acid substitutions 55C, 188C, and 486S;
(6) a mutant comprising a combination of amino acid substitutions 54H, 55C, 188C, and 190I;
(7) a mutant comprising a combination of amino acid substitutions 55C, 188C, 190I, and 486S;
(8) a mutant comprising a combination of amino acid substitutions 54H, 55C, 188C, 190I, and 486S;
(9) a mutant comprising a combination of amino acid substitutions 155C, 190I, 290C, and 486S;
(10) a mutant comprising a combination of amino acid substitutions 54H, 55C, 142C, 188C, 296I, 371C, 486S, 487Q, and 489S; and
(11) a mutant comprising a combination of amino acid substitutions 54H, 155C, 190I, 290C, and 296I.

In some particular embodiments, the nucleic acid molecule encodes a RSV F mutant, wherein the mutant comprises a cysteine (C) at position 103 (103C) and at position 148 (148C), an isoleucine (1) at position 190 (190I), and a serine (S) at position 486 (486S), and wherein the mutant comprises a F1 polypeptide and a F2 polypeptide selected from the group consisting of:

(1) a F2 polypeptide comprising the amino acid sequence of SEQ ID NO:41 and a F1 polypeptide comprising the amino acid sequence of SEQ ID NO:42;
(2) a F2 polypeptide comprising an amino acid sequence that is at least 97%, 98%, or 99% identical to the amino acid sequence of SEQ ID NO:41 and a F1 polypeptide comprising an amino acid sequence that is at least 97%, 98%, or 99% identical to the amino acid sequence of SEQ ID NO:42;
(3) a F2 polypeptide comprising the amino acid sequence of SEQ ID NO: 43 and a F1 polypeptide comprising the amino acid sequence of SEQ ID NO:44;
(4) a F2 polypeptide comprising an amino acid sequence that is at least 97%, 98%, or 99% identical to the amino acid sequence of SEQ ID NO:43 and a F1 polypeptide comprising an amino acid sequence that is at least 97%, 98%, or 99% identical to the amino acid sequence of SEQ ID NO:44;
(5) a F2 polypeptide comprising the amino acid sequence of SEQ ID NO: 45 and a F1 polypeptide comprising the amino acid sequence of SEQ ID NO:46;
(6) a F2 polypeptide comprising an amino acid sequence that is at least 97%, 98%, or 99% identical to the amino acid sequence of SEQ ID NO:45 and a F1 polypeptide comprising an amino acid sequence that is at least 97%, 98%, or 99% identical to the amino acid sequence of SEQ ID NO:46;
(7) a F2 polypeptide comprising the amino acid sequence of SEQ ID NO: 47 and a F1 polypeptide comprising the amino acid sequence of SEQ ID NO:48;
(8) a F2 polypeptide comprising an amino acid sequence that is at least 97%, 98%, or 99% identical to the amino acid sequence of SEQ ID NO:47 and a F1 polypeptide comprising an amino acid sequence that is at least 97%, 98%, or 99% identical to the amino acid sequence of SEQ ID NO:48;
(9) a F2 polypeptide comprising the amino acid sequence of SEQ ID NO: 49 and a F1 polypeptide comprising the amino acid sequence of SEQ ID NO:50;
(10) a F2 polypeptide comprising an amino acid sequence that is at least 97%, 98%, or 99% identical to the amino acid sequence of SEQ ID NO:49 and a F1 polypeptide comprising an amino acid sequence that is at least 97%, 98%, or 99% identical to the amino acid sequence of SEQ ID NO:50.
(11) a F2 polypeptide comprising the amino acid sequence of SEQ ID NO:279 and a F1 polypeptide comprising the amino acid sequence of SEQ ID NO:280;
(12) a F2 polypeptide comprising an amino acid sequence that is at least 97%, 98%, or 99% identical to the amino acid sequence of SEQ ID NO:279 and a F1 identical to the amino acid sequence of SEQ ID NO:280;
(13) a F2 polypeptide comprising the amino acid sequence of SEQ ID NO:281 and a F1 polypeptide comprising the amino acid sequence of SEQ ID NO:282;
(14) a F2 polypeptide comprising an amino acid sequence that is at least 97%, 98%, or 99% identical to the amino acid sequence of SEQ ID NO:281 and a F1 polypeptide comprising an amino acid sequence that is at least 97%, 98%, or 99% identical to the amino acid sequence of SEQ ID NO:282;
(15) a F2 polypeptide comprising the amino acid sequence of SEQ ID NO:283 and a F1 polypeptide comprising the amino acid sequence of SEQ ID NO:284;
(16) a F2 polypeptide comprising an amino acid sequence that is at least 97%, 98%, or 99% identical to the amino acid sequence of SEQ ID NO:283 and a F1 polypeptide comprising an amino acid sequence that is at least 97%, 98%, or 99% identical to the amino acid sequence of SEQ ID NO:284;
(17) a F2 polypeptide comprising the amino acid sequence of SEQ ID NO:285 and a F1 polypeptide comprising the amino acid sequence of SEQ ID NO:286;

(18) a F2 polypeptide comprising an amino acid sequence that is at least 97%, 98%, or 99% identical to the amino acid sequence of SEQ ID NO:285 and a F1 polypeptide comprising an amino acid sequence that is at least 97%, 98%, or 99% identical to the amino acid sequence of SEQ ID NO:286;

(19) a F2 polypeptide comprising the amino acid sequence of SEQ ID NO:287 and a F1 polypeptide comprising the amino acid sequence of SEQ ID NO:288;

(20) a F2 polypeptide comprising an amino acid sequence that is at least 97%, 98%, or 99% identical to the amino acid sequence of SEQ ID NO:287 and a F1 polypeptide comprising an amino acid sequence that is at least 97%, 98%, or 99% identical to the amino acid sequence of SEQ ID NO:288;

(21) a F2 polypeptide comprising the amino acid sequence of SEQ ID NO:289 and a F1 polypeptide comprising the amino acid sequence of SEQ ID NO:290; and

(22) a F2 polypeptide comprising an amino acid sequence that is at least 97%, 98%, or 99% identical to the amino acid sequence of SEQ ID NO:289 and a F1 polypeptide comprising an amino acid sequence that is at least 97%, 98%, or 99% identical to the amino acid sequence of SEQ ID NO:290.

In some other particular embodiments, the nucleic acid molecule encodes a RSV F mutant, wherein the mutant comprises a histidine (H) at position 54, a cysteine (C) at positions 103 and 148, a isoleucine (I) at positions 190 and 296, and a serine (S) at position 486, and wherein the mutant comprises a F1 polypeptide and a F2 polypeptide selected from the group consisting of:

(1) F2 polypeptide comprising the amino acid sequence of SEQ ID NO: 51 and a F1 polypeptide comprising the amino acid sequence of SEQ ID NO:52;

(2) a F2 polypeptide comprising an amino acid sequence that is at least 97%, 98%, or 99% identical to the amino acid sequence of SEQ ID NO:51 and a F1 polypeptide comprising an amino acid sequence that is at least 97%, 98%, or 99% identical to the amino acid sequence of SEQ ID NO:52;

(3) a F2 polypeptide comprising the amino acid sequence of SEQ ID NO:53 and a F1 polypeptide comprising the amino acid sequence of SEQ ID NO:54;

(4) a F2 polypeptide comprising an amino acid sequence that is at least 97%, 98%, or 99% identical to the amino acid sequence of SEQ ID NO:53 and a F1 polypeptide comprising an amino acid sequence that is at least 97%, 98%, or 99% identical to the amino acid sequence of SEQ ID NO:54;

(5) a F2 polypeptide comprising the amino acid sequence of SEQ ID NO:55 and a F1 polypeptide comprising the amino acid sequence of SEQ ID NO:56;

(6) a F2 polypeptide comprising an amino acid sequence that is at least 97%, 98%, or 99% identical to the amino acid sequence of SEQ ID NO:55 and a F1 polypeptide comprising an amino acid sequence that is at least 97%, 98%, or 99% identical to the amino acid sequence of SEQ ID NO:56;

(7) a F2 polypeptide comprising the amino acid sequence of SEQ ID NO:57 and a F1 polypeptide comprising the amino acid sequence of SEQ ID NO:58;

(8) a F2 polypeptide comprising an amino acid sequence that is at least 97%, 98%, or 99% identical to the amino acid sequence of SEQ ID NO:57 and a F1 polypeptide comprising an amino acid sequence that is at least 97%, 98%, or 99% identical to the amino acid sequence of SEQ ID NO:58;

(9) a F2 polypeptide comprising the amino acid sequence of SEQ ID NO:59 and a F1 polypeptide comprising the amino acid sequence of SEQ ID NO:60;

(10) a F2 polypeptide comprising an amino acid sequence that is at least 97%, 98%, or 99% identical to the amino acid sequence of SEQ ID NO:59 and a F1 identical to the amino acid sequence of SEQ ID NO:60;

(11) a F2 polypeptide comprising the amino acid sequence of SEQ ID NO:291 and a F1 polypeptide comprising the amino acid sequence of SEQ ID NO:292;

(12) a F2 polypeptide comprising an amino acid sequence that is at least 97%, 98%, or 99% identical to the amino acid sequence of SEQ ID NO:291 and a F1 polypeptide comprising an amino acid sequence that is at least 97%, 98%, or 99% identical to the amino acid sequence of SEQ ID NO:292;

(13) a F2 polypeptide comprising the amino acid sequence of SEQ ID NO:293 and a F1 polypeptide comprising the amino acid sequence of SEQ ID NO:294;

(14) a F2 polypeptide comprising an amino acid sequence that is at least 97%, 98%, or 99% identical to the amino acid sequence of SEQ ID NO:293 and a F1 polypeptide comprising an amino acid sequence that is at least 97%, 98%, or 99% identical to the amino acid sequence of SEQ ID NO:294;

(15) a F2 polypeptide comprising the amino acid sequence of SEQ ID NO:295 and a F1 polypeptide comprising the amino acid sequence of SEQ ID NO:296;

(16) a F2 polypeptide comprising an amino acid sequence that is at least 97%, 98%, or 99% identical to the amino acid sequence of SEQ ID NO:295 and a F1 polypeptide comprising an amino acid sequence that is at least 97%, 98%, or 99% identical to the amino acid sequence of SEQ ID NO:296;

(17) a F2 polypeptide comprising the amino acid sequence of SEQ ID NO:297 and a F1 polypeptide comprising the amino acid sequence of SEQ ID NO:298;

(18) a F2 polypeptide comprising an amino acid sequence that is at least 97%, 98%, or 99% identical to the amino acid sequence of SEQ ID NO:297 and a F1 polypeptide comprising an amino acid sequence that is at least 97%, 98%, or 99% identical to the amino acid sequence of SEQ ID NO:298;

(19) a F2 polypeptide comprising the amino acid sequence of SEQ ID NO:299 and a F1 polypeptide comprising the amino acid sequence of SEQ ID NO:300;

(20) a F2 polypeptide comprising an amino acid sequence that is at least 97%, 98%, or 99% identical to the amino acid sequence of SEQ ID NO:299 and a F1 polypeptide comprising an amino acid sequence that is at least 97%, 98%, or 99% identical to the amino acid sequence of SEQ ID NO:300;

(21) a F2 polypeptide comprising the amino acid sequence of SEQ ID NO:301 and a F1 polypeptide comprising the amino acid sequence of SEQ ID NO:302; and

(22) a F2 polypeptide comprising an amino acid sequence that is at least 97%, 98% or 99% identical to the amino acid sequence of SEQ ID NO:301 and a F1 polypeptide comprising an amino acid sequence that is at least 97%, 98%, or 99% identical to the amino acid sequence of SEQ ID NO:302.

In some other particular embodiments, the nucleic acid molecule encodes a RSV F mutant, wherein the mutant comprises a histidine (H) at position 54, a cysteine (C) at positions 55 and 188, and a serine (S) at position 486, and wherein the mutant comprises a F1 polypeptide and a F2 polypeptide selected from the group consisting of:

(1) a F2 polypeptide comprising the amino acid sequence of SEQ ID NO:61 and a F1 polypeptide comprising the amino acid sequence of SEQ ID NO:62;

(2) a F2 polypeptide comprising an amino acid sequence that is at least 97%, 98%, or 99% identical to the amino acid sequence of SEQ ID NO:61 and a F1 polypeptide comprising an amino acid sequence that is at least 97%, 98%, or 99% identical to the amino acid sequence of SEQ ID NO:62;

(3) a F2 polypeptide comprising the amino acid sequence of SEQ ID NO:63 and a F1 polypeptide comprising the amino acid sequence of SEQ ID NO:64;

(4) a F2 polypeptide comprising an amino acid sequence that is at least 97%, 98%, or 99% identical to the amino acid sequence of SEQ ID NO:63 and a F1 polypeptide comprising an amino acid sequence that is at least 97%, 98%, or 99% identical to the amino acid sequence of SEQ ID NO:64;

(5) a F2 polypeptide comprising the amino acid sequence of SEQ ID NO:65 and a F1 polypeptide comprising the amino acid sequence of SEQ ID NO:66;

(6) a F2 polypeptide comprising an amino acid sequence that is at least 97%, 98%, or 99% identical to the amino acid sequence of SEQ ID NO:65 and a F1 polypeptide comprising an amino acid sequence that is at least 97%, 98%, or 99% identical to the amino acid sequence of SEQ ID NO:66;

(7) a F2 polypeptide comprising the amino acid sequence of SEQ ID NO:67 and a F1 polypeptide comprising the amino acid sequence of SEQ ID NO:68;

(8) a F2 polypeptide comprising an amino acid sequence that is at least 97%, 98%, or 99% identical to the amino acid sequence of SEQ ID NO:67 and a F1 polypeptide comprising an amino acid sequence that is at least 97%, 98%, or 99% identical to the amino acid sequence of SEQ ID NO:68;

(9) a F2 polypeptide comprising the amino acid sequence of SEQ ID NO:69 and a F1 polypeptide comprising the amino acid sequence of SEQ ID NO:70;

(10) a F2 polypeptide comprising an amino acid sequence that is at least 97%, 98%, or 99% identical to the amino acid sequence of SEQ ID NO:69 and a F1 polypeptide comprising an amino acid sequence that is at least 97%, 98%, or 99% identical to the amino acid sequence of SEQ ID NO:70;

(11) a F2 polypeptide comprising the amino acid sequence of SEQ ID NO:303 and a F1 polypeptide comprising the amino acid sequence of SEQ ID NO:304;

(12) a F2 polypeptide comprising an amino acid sequence that is at least 97%, 98% or 99% identical to the amino acid sequence of SEQ ID NO:303 and a F1 polypeptide comprising an amino acid sequence that is at least 97%, 98%, or 99% identical to the amino acid sequence of SEQ ID NO:304;

(13) a F2 polypeptide comprising the amino acid sequence of SEQ ID NO:305 and a F1 polypeptide comprising the amino acid sequence of SEQ ID NO:306;

(14) a F2 polypeptide comprising an amino acid sequence that is at least 97%, 98%, or 99% identical to the amino acid sequence of SEQ ID NO:305 and a F1 polypeptide comprising an amino acid sequence that is at least 97%, 98%, or 99% identical to the amino acid sequence of SEQ ID NO:306;

(15) a F2 polypeptide comprising the amino acid sequence of SEQ ID NO:307 and a F1 polypeptide comprising the amino acid sequence of SEQ ID NO:308;

(16) a F2 polypeptide comprising an amino acid sequence that is at least 97%, 98%, or 99% identical to the amino acid sequence of SEQ ID NO:307 and a F1 polypeptide comprising an amino acid sequence that is at least 97%, 98%, or 99% identical to the amino acid sequence of SEQ ID NO:308;

(17) a F2 polypeptide comprising the amino acid sequence of SEQ ID NO:309 and a F1 polypeptide comprising the amino acid sequence of SEQ ID NO:310;

(18) a F2 polypeptide comprising an amino acid sequence that is at least 97%, 98%, or 99% identical to the amino acid sequence of SEQ ID NO:309 and a F1 polypeptide comprising an amino acid sequence that is at least 97%, 98%, or 99% identical to the amino acid sequence of SEQ ID NO:310;

(19) a F2 polypeptide comprising the amino acid sequence of SEQ ID NO:311 and a F1 polypeptide comprising the amino acid sequence of SEQ ID NO:312;

(20) a F2 polypeptide comprising an amino acid sequence that is at least 97%, 98%, or 99% identical to the amino acid sequence of SEQ ID NO:311 and a F1 polypeptide comprising an amino acid sequence that is at least 97%, 98%, or 99% identical to the amino acid sequence of SEQ ID NO:312.

(21) a F2 polypeptide comprising the amino acid sequence of SEQ ID NO:313 and a F1 polypeptide comprising the amino acid sequence of SEQ ID NO:314; and

(22) a F2 polypeptide comprising an amino acid sequence that is at least 97%, 98%, or 99% identical to the amino acid sequence of SEQ ID NO:313 and a F1 polypeptide comprising an amino acid sequence that is at least 97%, 98%, or 99% identical to the amino acid sequence of SEQ ID NO:314.

In some other particular embodiments, the nucleic acid molecule encodes a RSV F mutant, wherein the mutant comprises a histidine (H) at position 54, a cysteine (C) at positions 55 and 188, an isoleucine (I) at position 190 (190I), and a serine (S) at position 486, and wherein the mutant comprises a F1 polypeptide and a F2 polypeptide selected from the group consisting of:

(1) a F2 polypeptide comprising the amino acid sequence of SEQ ID NO:71 and a F1 polypeptide comprising the amino acid sequence of SEQ ID NO:72;

(2) a F2 polypeptide comprising an amino acid sequence that is at least 97%, 98%, or 99% identical to the amino acid sequence of SEQ ID NO:71 and a F1 polypeptide comprising an amino acid sequence that is at least 97%, 98%, or 99% identical to the amino acid sequence of SEQ ID NO:72;

(3) a F2 polypeptide comprising the amino acid sequence of SEQ ID NO:73 and a F1 polypeptide comprising the amino acid sequence of SEQ ID NO:74;

(4) a F2 polypeptide comprising an amino acid sequence that is at least 97%, 98%, or 99% identical to the amino acid sequence of SEQ ID NO:73 and a F1 polypeptide comprising an amino acid sequence that is at least 97%, 98%, or 99% identical to the amino acid sequence of SEQ ID NO:74;

(5) a F2 polypeptide comprising the amino acid sequence of SEQ ID NO:75 and a F1 polypeptide comprising the amino acid sequence of SEQ ID NO:76;

(6) a F2 polypeptide comprising an amino acid sequence that is at least 97%, 98%, or 99% identical to the amino acid sequence of SEQ ID NO:75 and a F1 polypeptide comprising an amino acid sequence that is at least 97%, 98%, or 99% identical to the amino acid sequence of SEQ ID NO:76;

(7) a F2 polypeptide comprising the amino acid sequence of SEQ ID NO:77 and a F1 polypeptide comprising the amino acid sequence of SEQ ID NO:78;

(8) a F2 polypeptide comprising an amino acid sequence that is at least 97%, 98%, or 99% identical to the amino acid sequence of SEQ ID NO:77 and a F1 polypeptide comprising an amino acid sequence that is at least 97%, 98%, or 99% identical to the amino acid sequence of SEQ ID NO:78;

(9) a F2 polypeptide comprising the amino acid sequence of SEQ ID NO:79 and a F1 polypeptide comprising the amino acid sequence of SEQ ID NO:80;

(10) a F2 polypeptide comprising an amino acid sequence that is at least 97%, 98%, or 99% identical to the amino acid sequence of SEQ ID NO:79 and a F1 polypeptide comprising an amino acid sequence that is at least 97%, 98%, or 99% identical to the amino acid sequence of SEQ ID NO:80;

(11) a F2 polypeptide comprising the amino acid sequence of SEQ ID NO:315 and a F1 polypeptide comprising the amino acid sequence of SEQ ID NO:316;

(12) a F2 polypeptide comprising an amino acid sequence that is at least 97%, 98%, or 99% identical to the amino acid sequence of SEQ ID NO:315 and a F1 polypeptide comprising an amino acid sequence that is at least 97%, 98%, or 99% identical to the amino acid sequence of SEQ ID NO:316;

(13) a F2 polypeptide comprising the amino acid sequence of SEQ ID NO:317 and a F1 polypeptide comprising the amino acid sequence of SEQ ID NO:318;

(14) a F2 polypeptide comprising an amino acid sequence that is at least 97%, 98%, or 99% identical to the amino acid sequence of SEQ ID NO:317 and a F1 polypeptide comprising an amino acid sequence that is at least 97%, 98%, or 99% identical to the amino acid sequence of SEQ ID NO:318;

(15) a F2 polypeptide comprising the amino acid sequence of SEQ ID NO:319 and a F1 polypeptide comprising the amino acid sequence of SEQ ID NO:320;

(16) a F2 polypeptide comprising an amino acid sequence that is at least 97%, 98%, or 99% identical to the amino acid sequence of SEQ ID NO:319 and a F1 polypeptide comprising an amino acid sequence that is at least 97%, 98%, or 99% identical to the amino acid sequence of SEQ ID NO:320;

(17) a F2 polypeptide comprising the amino acid sequence of SEQ ID NO:321 and a F1 polypeptide comprising the amino acid sequence of SEQ ID NO:322;

(18) a F2 polypeptide comprising an amino acid sequence that is at least 97%, 98%, or 99% identical to the amino acid sequence of SEQ ID NO:321 and a F1 polypeptide comprising an amino acid sequence that is at least 97%, 98%, or 99% identical to the amino acid sequence of SEQ ID NO:322;

(19) a F2 polypeptide comprising the amino acid sequence of SEQ ID NO:323 and a F1 polypeptide comprising the amino acid sequence of SEQ ID NO:324;

(20) a F2 polypeptide comprising an amino acid sequence that is at least 97%, 98%, or 99% identical to the amino acid sequence of SEQ ID NO:323 and a F1 polypeptide comprising an amino acid sequence that is at least 97%, 98%, or 99% identical to the amino acid sequence of SEQ ID NO:324.

(21) a F2 polypeptide comprising the amino acid sequence of SEQ ID NO:325 and a F1 polypeptide comprising the amino acid sequence of SEQ ID NO:326; and

(22) a F2 polypeptide comprising an amino acid sequence that is at least 97%, 98%, or 99% identical to the amino acid sequence of SEQ ID NO:325 and a F1 polypeptide comprising an amino acid sequence that is at least 97%, 98%, or 99% identical to the amino acid sequence of SEQ ID NO:326.

In some specific embodiments, the present disclosure provides a nucleic acid molecule, which encodes a mutant selected from the group consisting of:

(1) a mutant comprising amino acids 26-513 of SEQ ID NO:19;

(2) a mutant comprising amino acids 26-513 of SEQ ID NO:20; and (3) a mutant comprising amino acids 26-513 of SEQ ID NO:21.

In some other specific embodiments, the present disclosure provides a nucleic acid molecule encoding a RSV F protein mutant, or a degenerate variant thereof, wherein the nucleic acid molecule comprises a nucleotide sequence selected from the group consisting of:

(1) a nucleotide sequence comprising nucleotides 76-1539 of SEQ ID NO:8;

(2) a nucleotide sequence comprising nucleotides 76-1539 of SEQ ID NO:9;

(3) a nucleotide sequence comprising nucleotides 76-1539 of SEQ ID NO:10;

(4) a nucleotide sequence comprising nucleotides 76-1539 of SEQ ID NO:11;

(5) a nucleotide sequence comprising nucleotides 76-1539 of SEQ ID NO:12;

(6) a nucleotide sequence comprising nucleotides 76-1539 of SEQ ID NO:13;

(7) a nucleotide sequence comprising nucleotides 76-1539 of SEQ ID NO:14;

(8) a nucleotide sequence comprising nucleotides 76-1539 of SEQ ID NO:15;

(9) a nucleotide sequence comprising nucleotides 76-1539 of SEQ ID NO:16;

(10) a nucleotide sequence comprising nucleotides 76-1539 of SEQ ID NO:17; and

(11) a nucleotide sequence comprising nucleotides 76-1539 of SEQ ID NO:18.

D. COMPOSITIONS COMPRISING A RSV F PROTEIN MUTANT; COMPOSITIONS COMPRISING A NUCLEIC ACID ENCODING A RSV F PROTEIN MUTANT

In another aspect, the invention provides compositions that comprise (1) a RSV F protein mutant described in the disclosure, or (2) a nucleic acid molecule or vector encoding such a RSV F protein mutant.

In some embodiments, the composition is an immunogenic composition capable of eliciting an immune response against the F protein of RSV in a subject. In some particular embodiments, the immunogenic composition is a pharmaceutical composition, which comprises a RSV F protein mutant provided by the present disclosure and a pharmaceutically acceptable carrier.

In still other embodiments, the pharmaceutical composition is a vaccine. The immunogenic component in the vaccine may be (1) a RSV F protein mutant described herein, (2) a nucleic acid encoding such as a RSV F protein mutant, or (3) a vector for expressing such a RSV F protein mutant.

In some particular embodiments, the vaccine comprises a RSV F protein mutant, wherein the mutant comprises a cysteine (C) at position 103 (103C) and at position 148 (148C), an isoleucine (I) at position 190 (190I), and a serine (S) at position 486 (486S), and wherein the mutant comprises a F1 polypeptide and a F2 polypeptide selected from the group consisting of:

(1) a F2 polypeptide comprising the amino acid sequence of SEQ ID NO:41 and a F1 polypeptide comprising the amino acid sequence of SEQ ID NO:42;

(2) a F2 polypeptide comprising an amino acid sequence that is at least 97%, 98%, or 99% identical to the amino acid sequence of SEQ ID NO:41 and a F1 polypeptide comprising an amino acid sequence that is at least 97%, 98%, or 99% identical to the amino acid sequence of SEQ ID NO:42;

(3) a F2 polypeptide comprising the amino acid sequence of SEQ ID NO: 43 and a F1 polypeptide comprising the amino acid sequence of SEQ ID NO:44;

(4) a F2 polypeptide comprising an amino acid sequence that is at least 97%, 98%, or 99% identical to the amino acid sequence of SEQ ID NO:43 and a F1 polypeptide comprising an amino acid sequence that is at least 97%, 98%, or 99% identical to the amino acid sequence of SEQ ID NO:44;

(5) a F2 polypeptide comprising the amino acid sequence of SEQ ID NO: 45 and a F1 polypeptide comprising the amino acid sequence of SEQ ID NO:46;

(6) a F2 polypeptide comprising an amino acid sequence that is at least 97%, 98%, or 99% identical to the amino acid sequence of SEQ ID NO:45 and a F1 polypeptide comprising an amino acid sequence that is at least 97%, 98%, or 99% identical to the amino acid sequence of SEQ ID NO:46;

(7) a F2 polypeptide comprising the amino acid sequence of SEQ ID NO: 47 and a F1 polypeptide comprising the amino acid sequence of SEQ ID NO:48;

(8) a F2 polypeptide comprising an amino acid sequence that is at least 97%, 98%, or 99% identical to the amino acid sequence of SEQ ID NO:47 and a F1 polypeptide comprising an amino acid sequence that is at least 97%, 98%, or 99% identical to the amino acid sequence of SEQ ID NO:48;

(9) a F2 polypeptide comprising the amino acid sequence of SEQ ID NO: 49 and a F1 polypeptide comprising the amino acid sequence of SEQ ID NO:50;

(10) a F2 polypeptide comprising an amino acid sequence that is at least 97%, 98%, or 99% identical to the amino acid sequence of SEQ ID NO:49 and a F1 polypeptide comprising an amino acid sequence that is at least 97%, 98%, or 99% identical to the amino acid sequence of SEQ ID NO:50.

(11) a F2 polypeptide comprising the amino acid sequence of SEQ ID NO:279 and a F1 polypeptide comprising the amino acid sequence of SEQ ID NO:280;

(12) a F2 polypeptide comprising an amino acid sequence that is at least 97%, 98%, or 99% identical to the amino acid sequence of SEQ ID NO:279 and a F1 polypeptide comprising an amino acid sequence that is at least 97%, 98%, or 99% identical to the amino acid sequence of SEQ ID NO:280;

(13) a F2 polypeptide comprising the amino acid sequence of SEQ ID NO:281 and a F1 polypeptide comprising the amino acid sequence of SEQ ID NO:282;

(14) a F2 polypeptide comprising an amino acid sequence that is at least 97%, 98%, or 99% identical to the amino acid sequence of SEQ ID NO:281 and a F1 polypeptide comprising an amino acid sequence that is at least 97%, 98%, or 99% identical to the amino acid sequence of SEQ ID NO:282;

(15) a F2 polypeptide comprising the amino acid sequence of SEQ ID NO:283 and a F1 polypeptide comprising the amino acid sequence of SEQ ID NO:284;

(16) a F2 polypeptide comprising an amino acid sequence that is at least 97%, 98%, or 99% identical to the amino acid sequence of SEQ ID NO:283 and a F1 polypeptide comprising an amino acid sequence that is at least 97%, 98%, or 99% identical to the amino acid sequence of SEQ ID NO:284;

(17) a F2 polypeptide comprising the amino acid sequence of SEQ ID NO:285 and a F1 polypeptide comprising the amino acid sequence of SEQ ID NO:286;

(18) a F2 polypeptide comprising an amino acid sequence that is at least 97%, 98%, or 99% identical to the amino acid sequence of SEQ ID NO:285 and a F1 polypeptide comprising an amino acid sequence that is at least 97%, 98%, or 99% identical to the amino acid sequence of SEQ ID NO:286;

(19) a F2 polypeptide comprising the amino acid sequence of SEQ ID NO:287 and a F1 polypeptide comprising the amino acid sequence of SEQ ID NO:288;

(20) a F2 polypeptide comprising an amino acid sequence that is at least 97%, 98%, or 99% identical to the amino acid sequence of SEQ ID NO:287 and a F1 polypeptide comprising an amino acid sequence that is at least 97%, 98%, or 99% identical to the amino acid sequence of SEQ ID NO:288;

(21) a F2 polypeptide comprising the amino acid sequence of SEQ ID NO:289 and a F1 polypeptide comprising the amino acid sequence of SEQ ID NO:290; and

(22) a F2 polypeptide comprising an amino acid sequence that is at least 97%, 98%, or 99% identical to the amino acid sequence of SEQ ID NO:289 and a F1 polypeptide comprising an amino acid sequence that is at least 97%, 98%, or 99% identical to the amino acid sequence of SEQ ID NO:290.

In some other particular embodiments, the vaccine comprises a RSV F mutant, wherein the mutant comprises a histidine (H) at position 54, a cysteine (C) at positions 103 and 148, a isoleucine (I) at positions 190 and 296, and a serine (S) at position 486, and wherein the mutant comprises a F1 polypeptide and a F2 polypeptide selected from the group consisting of:

(1) F2 polypeptide comprising the amino acid sequence of SEQ ID NO: 51 and a F1 polypeptide comprising the amino acid sequence of SEQ ID NO:52;

(2) a F2 polypeptide comprising an amino acid sequence that is at least 97%, 98%, or 99% identical to the amino acid sequence of SEQ ID NO:51 and a F1 polypeptide comprising an amino acid sequence that is at least 97%, 98%, or 99% identical to the amino acid sequence of SEQ ID NO:52;

(3) a F2 polypeptide comprising the amino acid sequence of SEQ ID NO:53 and a F1 polypeptide comprising the amino acid sequence of SEQ ID NO:54;

(4) a F2 polypeptide comprising an amino acid sequence that is at least 97%, 98%, or 99% identical to the amino acid sequence of SEQ ID NO:53 and a F1 polypeptide comprising an amino acid sequence that is at least 97%, 98%, or 99% identical to the amino acid sequence of SEQ ID NO:54;

(5) a F2 polypeptide comprising the amino acid sequence of SEQ ID NO:55 and a F1 polypeptide comprising the amino acid sequence of SEQ ID NO:56;

(6) a F2 polypeptide comprising an amino acid sequence that is at least 97%, 98%, or 99% identical to the amino acid sequence of SEQ ID NO:55 and a F1 polypeptide comprising an amino acid sequence that is at least 97%, 98%, or 99% identical to the amino acid sequence of SEQ ID NO:56;

(7) a F2 polypeptide comprising the amino acid sequence of SEQ ID NO:57 and a F1 polypeptide comprising the amino acid sequence of SEQ ID NO:58;

(8) a F2 polypeptide comprising an amino acid sequence that is at least 97%, 98%, or 99% identical to the amino acid sequence of SEQ ID NO:57 and a F1 polypeptide comprising an amino acid sequence that is at least 97%, 98%, or 99% identical to the amino acid sequence of SEQ ID NO:58;

(9) a F2 polypeptide comprising the amino acid sequence of SEQ ID NO:59 and a F1 polypeptide comprising the amino acid sequence of SEQ ID NO:60;

(10) a F2 polypeptide comprising an amino acid sequence that is at least 97%, 98%, or 99% identical to the amino acid sequence of SEQ ID NO:59 and a F1 polypeptide comprising an amino acid sequence that is at least 97%, 98%, or 99% identical to the amino acid sequence of SEQ ID NO:60;

(11) a F2 polypeptide comprising the amino acid sequence of SEQ ID NO:291 and a F1 polypeptide comprising the amino acid sequence of SEQ ID NO:292;

(12) a F2 polypeptide comprising an amino acid sequence that is at least 97%, 98%, or 99% identical to the amino acid sequence of SEQ ID NO:291 and a F1 polypeptide comprising an amino acid sequence that is at least 97%, 98%, or 99% identical to the amino acid sequence of SEQ ID NO:292;

(13) a F2 polypeptide comprising the amino acid sequence of SEQ ID NO:293 and a F1 polypeptide comprising the amino acid sequence of SEQ ID NO:294;

(14) a F2 polypeptide comprising an amino acid sequence that is at least 97%, 98%, or 99% identical to the amino acid sequence of SEQ ID NO:293 and a F1 polypeptide comprising an amino acid sequence that is at least 97%, 98%, or 99% identical to the amino acid sequence of SEQ ID NO:294;

(15) a F2 polypeptide comprising the amino acid sequence of SEQ ID NO:295 and a F1 polypeptide comprising the amino acid sequence of SEQ ID NO:296;

(16) a F2 polypeptide comprising an amino acid sequence that is at least 97%, 98%, or 99% identical to the amino acid sequence of SEQ ID NO:295 and a F1 polypeptide comprising an amino acid sequence that is at least 97%, 98%, or 99% identical to the amino acid sequence of SEQ ID NO:296;

(17) a F2 polypeptide comprising the amino acid sequence of SEQ ID NO:297 and a F1 polypeptide comprising the amino acid sequence of SEQ ID NO:298;

(18) a F2 polypeptide comprising an amino acid sequence that is at least 97%, 98%, or 99% identical to the amino acid sequence of SEQ ID NO:297 and a F1 polypeptide comprising an amino acid sequence that is at least 97%, 98%, or 99% identical to the amino acid sequence of SEQ ID NO:298;

(19) a F2 polypeptide comprising the amino acid sequence of SEQ ID NO:299 and a F1 polypeptide comprising the amino acid sequence of SEQ ID NO:300;

(20) a F2 polypeptide comprising an amino acid sequence that is at least 97%, 98%, or 99% identical to the amino acid sequence of SEQ ID NO:299 and a F1 polypeptide comprising an amino acid sequence that is at least 97%, 98%, or 99% identical to the amino acid sequence of SEQ ID NO:300;

(21) a F2 polypeptide comprising the amino acid sequence of SEQ ID NO:301 and a F1 polypeptide comprising the amino acid sequence of SEQ ID NO:302; and

(22) a F2 polypeptide comprising an amino acid sequence that is at least 97%, 98%, or 99% identical to the amino acid sequence of SEQ ID NO:301 and a F1 polypeptide comprising an amino acid sequence that is at least 97%, 98%, or 99% identical to the amino acid sequence of SEQ ID NO:302.

In some other particular embodiments, the vaccine comprises a RSV F mutant, wherein the mutant comprises a histidine (H) at position 54, a cysteine (C) at positions 55 and 188, and a serine (S) at position 486, and wherein the mutant comprises a F1 polypeptide and a F2 polypeptide selected from the group consisting of:

(1) a F2 polypeptide comprising the amino acid sequence of SEQ ID NO:61 and a F1 polypeptide comprising the amino acid sequence of SEQ ID NO:62;

(2) a F2 polypeptide comprising an amino acid sequence that is at least 97%, 98%, or 99% identical to the amino acid sequence of SEQ ID NO:61 and a F1 polypeptide comprising an amino acid sequence that is at least 97%, 98%, or 99% identical to the amino acid sequence of SEQ ID NO:62;

(3) a F2 polypeptide comprising the amino acid sequence of SEQ ID NO:63 and a F1 polypeptide comprising the amino acid sequence of SEQ ID NO:64;

(4) a F2 polypeptide comprising an amino acid sequence that is at least 97%, 98%, or 99% identical to the amino acid sequence of SEQ ID NO:63 and a F1 polypeptide comprising an amino acid sequence that is at least 97%, 98%, or 99% identical to the amino acid sequence of SEQ ID NO:64;

(5) a F2 polypeptide comprising the amino acid sequence of SEQ ID NO:65 and a F1 polypeptide comprising the amino acid sequence of SEQ ID NO:66;

(6) a F2 polypeptide comprising an amino acid sequence that is at least 97%, 98%, or 99% identical to the amino acid sequence of SEQ ID NO:65 and a F1 polypeptide comprising an amino acid sequence that is at least 97%, 98%, or 99% identical to the amino acid sequence of SEQ ID NO:66;

(7) a F2 polypeptide comprising the amino acid sequence of SEQ ID NO:67 and a F1 polypeptide comprising the amino acid sequence of SEQ ID NO:68;

(8) a F2 polypeptide comprising an amino acid sequence that is at least 97%, 98%, or 99% identical to the amino acid sequence of SEQ ID NO:67 and a F1 polypeptide comprising an amino acid sequence that is at least 97%, 98%, or 99% identical to the amino acid sequence of SEQ ID NO:68;

(9) a F2 polypeptide comprising the amino acid sequence of SEQ ID NO:69 and a F1 polypeptide comprising the amino acid sequence of SEQ ID NO:70;

(10) a F2 polypeptide comprising an amino acid sequence that is at least 97%, 98%, or 99% identical to the amino acid sequence of SEQ ID NO:69 and a F1 polypeptide comprising an amino acid sequence that is at least 97%, 98%, or 99% identical to the amino acid sequence of SEQ ID NO:70;

(11) a F2 polypeptide comprising the amino acid sequence of SEQ ID NO:303 and a F1 polypeptide comprising the amino acid sequence of SEQ ID NO:304;

(12) a F2 polypeptide comprising an amino acid sequence that is at least 97%, 98%, or 99% identical to the amino acid sequence of SEQ ID NO:303 and a F1 polypeptide comprising an amino acid sequence that is at least 97%, 98%, or 99% identical to the amino acid sequence of SEQ ID NO:304;

(13) a F2 polypeptide comprising the amino acid sequence of SEQ ID NO:305 and a F1 polypeptide comprising the amino acid sequence of SEQ ID NO:306;

(14) a F2 polypeptide comprising an amino acid sequence that is at least 97%, 98%, or 99% identical to the amino acid sequence of SEQ ID NO:305 and a F1 polypeptide comprising an amino acid sequence that is at least 97%, 98%, or 99% identical to the amino acid sequence of SEQ ID NO:306;

(15) a F2 polypeptide comprising the amino acid sequence of SEQ ID NO:307 and a F1 polypeptide comprising the amino acid sequence of SEQ ID NO:308;

(16) a F2 polypeptide comprising an amino acid sequence that is at least 97%, 98%, or 99% identical to the amino acid sequence of SEQ ID NO:307 and a F1 polypeptide comprising an amino acid sequence that is at least 97%, 98%, or 99% identical to the amino acid sequence of SEQ ID NO:308;

(17) a F2 polypeptide comprising the amino acid sequence of SEQ ID NO:309 and a F1 polypeptide comprising the amino acid sequence of SEQ ID NO:310;

(18) a F2 polypeptide comprising an amino acid sequence that is at least 97%, 98%, or 99% identical to the amino acid sequence of SEQ ID NO:309 and a F1 polypeptide comprising an amino acid sequence that is at least 97%, 98%, or 99% identical to the amino acid sequence of SEQ ID NO:310;

(19) a F2 polypeptide comprising the amino acid sequence of SEQ ID NO:311 and a F1 polypeptide comprising the amino acid sequence of SEQ ID NO:312;

(20) a F2 polypeptide comprising an amino acid sequence that is at least 97%, 98%, or 99% identical to the amino acid sequence of SEQ ID NO:311 and a F1 polypeptide comprising an amino acid sequence that is at least 97%, 98%, or 99% identical to the amino acid sequence of SEQ ID NO:312.

(21) a F2 polypeptide comprising the amino acid sequence of SEQ ID NO:313 and a F1 polypeptide comprising the amino acid sequence of SEQ ID NO:314; and

(22) a F2 polypeptide comprising an amino acid sequence that is at least 97%, 98%, or 99% identical to the amino acid sequence of SEQ ID NO:313 and a F1 polypeptide comprising an amino acid sequence that is at least 97%, 98%, or 99% identical to the amino acid sequence of SEQ ID NO:314.

In some other particular embodiments, the vaccine comprises a RSV F mutant, wherein the mutant comprises a histidine (H) at position 54, a cysteine (C) at positions 55 and 188, an isoleucine (I) at position 190 (190I), and a serine (S) at position 486, and wherein the mutant comprises a F1 polypeptide and a F2 polypeptide selected from the group consisting of:

(1) a F2 polypeptide comprising the amino acid sequence of SEQ ID NO:71 and a F1 polypeptide comprising the amino acid sequence of SEQ ID NO:72;

(2) a F2 polypeptide comprising an amino acid sequence that is at least 97%, 98%, or 99% identical to the amino acid sequence of SEQ ID NO:71 and a F1 polypeptide comprising an amino acid sequence that is at least 97%, 98%, or 99% identical to the amino acid sequence of SEQ ID NO:72;

(3) a F2 polypeptide comprising the amino acid sequence of SEQ ID NO:73 and a F1 polypeptide comprising the amino acid sequence of SEQ ID NO:74;

(4) a F2 polypeptide comprising an amino acid sequence that is at least 97%, 98%, or 99% identical to the amino acid sequence of SEQ ID NO:73 and a F1 polypeptide comprising an amino acid sequence that is at least 97%, 98%, or 99% identical to the amino acid sequence of SEQ ID NO:74;

(5) a F2 polypeptide comprising the amino acid sequence of SEQ ID NO:75 and a F1 polypeptide comprising the amino acid sequence of SEQ ID NO:76;

(6) a F2 polypeptide comprising an amino acid sequence that is at least 97%, 98%, or 99% identical to the amino acid sequence of SEQ ID NO:75 and a F1 polypeptide comprising an amino acid sequence that is at least 97%, 98%, or 99% identical to the amino acid sequence of SEQ ID NO:76;

(7) a F2 polypeptide comprising the amino acid sequence of SEQ ID NO:77 and a F1 polypeptide comprising the amino acid sequence of SEQ ID NO:78;

(8) a F2 polypeptide comprising an amino acid sequence that is at least 97%, 98%, or 99% identical to the amino acid sequence of SEQ ID NO:77 and a F1 polypeptide comprising an amino acid sequence that is at least 97%, 98%, or 99% identical to the amino acid sequence of SEQ ID NO:78;

(9) a F2 polypeptide comprising the amino acid sequence of SEQ ID NO:79 and a F1 polypeptide comprising the amino acid sequence of SEQ ID NO:80;

(10) a F2 polypeptide comprising an amino acid sequence that is at least 97%, 98% or 99% identical to the amino acid sequence of SEQ ID NO:79 and a F1 polypeptide comprising an amino acid sequence that is at least 97%, 98%, or 99% identical to the amino acid sequence of SEQ ID NO:80;

(11) a F2 polypeptide comprising the amino acid sequence of SEQ ID NO:315 and a F1 polypeptide comprising the amino acid sequence of SEQ ID NO:316;

(12) a F2 polypeptide comprising an amino acid sequence that is at least 97%, 98%, or 99% identical to the amino acid sequence of SEQ ID NO:315 and a F1 polypeptide comprising an amino acid sequence that is at least 97%, 98%, or 99% identical to the amino acid sequence of SEQ ID NO:316;

(13) a F2 polypeptide comprising the amino acid sequence of SEQ ID NO:317 and a F1 polypeptide comprising the amino acid sequence of SEQ ID NO:318;

(14) a F2 polypeptide comprising an amino acid sequence that is at least 97%, 98%, or 99% identical to the amino acid sequence of SEQ ID NO:317 and a F1 polypeptide comprising an amino acid sequence that is at least 97%, 98%, or 99% identical to the amino acid sequence of SEQ ID NO:318;

(15) a F2 polypeptide comprising the amino acid sequence of SEQ ID NO:319 and a F1 polypeptide comprising the amino acid sequence of SEQ ID NO:320;

(16) a F2 polypeptide comprising an amino acid sequence that is at least 97%, 98%, or 99% identical to the amino acid sequence of SEQ ID NO:319 and a F1 polypeptide comprising an amino acid sequence that is at least 97%, 98%, or 99% identical to the amino acid sequence of SEQ ID NO:320;

(17) a F2 polypeptide comprising the amino acid sequence of SEQ ID NO:321 and a F1 polypeptide comprising the amino acid sequence of SEQ ID NO:322;

(18) a F2 polypeptide comprising an amino acid sequence that is at least 97%, 98%, or 99% identical to the amino acid sequence of SEQ ID NO:321 and a F1 polypeptide comprising an amino acid sequence that is at least 97%, 98%, or 99% identical to the amino acid sequence of SEQ ID NO:322;

(19) a F2 polypeptide comprising the amino acid sequence of SEQ ID NO:323 and a F1 polypeptide comprising the amino acid sequence of SEQ ID NO:324;

(20) a F2 polypeptide comprising an amino acid sequence that is at least 97%, 98%, or 99% identical to the amino acid sequence of SEQ ID NO:323 and a F1 polypeptide comprising an amino acid sequence that is at least 97%, 98%, or 99% identical to the amino acid sequence of SEQ ID NO:324.

(21) a F2 polypeptide comprising the amino acid sequence of SEQ ID NO:325 and a F1 polypeptide comprising the amino acid sequence of SEQ ID NO:326; and

(22) a F2 polypeptide comprising an amino acid sequence that is at least 97%, 98%, or 99% identical to the amino acid sequence of SEQ ID NO:325 and a F1 polypeptide comprising an amino acid sequence that is at least 97%, 98%, or 99% identical to the amino acid sequence of SEQ ID NO:326.

In some embodiments, a composition, such as a pharmaceutical composition or a vaccine, comprises two or more different RSV F mutants. The two or more different RSV F mutants may comprise the same introduced amino acid mutations but comprise a F1 polypeptide and F2 polypeptide from different RSV strains or subtypes. The two or more different RSV F mutants may comprise different introduced amino acid mutations.

In some embodiments, the composition comprises two different mutants comprising the same introduced amino acid mutations, wherein one of the mutant comprises a F1 polypeptide and F2 polypeptide from RSV subtype A and wherein the other mutant comprises a F1 polypeptide and F2 polypeptide from RSV subtype B. In some specific embodiments, the two different mutants comprise the same combination of amino acid substitutions selected from the group consisting of:

(1) a combination of amino acid substitutions 103C, 148C, 190I, and 486S;

(2) a combination of amino acid substitutions 54H, 55C, 188C, and 486S;

(3) a combination of amino acid substitutions 54H, 103C, 148C, 190I, 296I, and 486S;

(4) a combination of amino acid substitutions 54H, 55C, 142C, 188C, 296I, and 371C;

(5) a combination of amino acid substitutions 55C, 188C, and 486S;

(6) a combination of amino acid substitutions 54H, 55C, 188C, and 190I;

(7) a combination of amino acid substitutions 55C, 188C, 190I, and 486S;

(8) a combination of amino acid substitutions 54H, 55C, 188C, 190I, and 486S;

(9) a combination of amino acid substitutions 155C, 190I, 290C, and 486S;

(10) a combination of amino acid substitutions 54H, 55C, 142C, 188C, 296I, 371C, 486S, 487Q, and 489S; and

(11) a combination of amino acid substitutions 54H, 155C, 190I, 290C, and 296I.

In addition to the immunogenic component, the vaccine may further comprise an immunomodulatory agent, such as an adjuvant. Examples of suitable adjuvants include aluminum salts such as aluminum hydroxide and/or aluminum phosphate; oil-emulsion compositions (or oil-in-water compositions), including squalene-water emulsions, such as MF59 (see e.g., WO 90/14837); saponin formulations, such as, for example, QS21 and Immunostimulating Complexes (ISCOMS) (see e.g., U.S. Pat. No. 5,057,540; WO 90/03184, WO 96/11711, WO 2004/004762, WO 2005/002620); bacterial or microbial derivatives, examples of which are monophosphoryl lipid A (MPL), 3-O-deacylated MPL (3dMPL), CpG-motif containing oligonucleotides, ADP-ribosylating bacterial toxins or mutants thereof, such as *E. coli* heat labile enterotoxin LT, cholera toxin CT, and the like. It is also possible to use vector-encoded adjuvant, e.g., by using heterologous nucleic acid that encodes a fusion of the oligomerization domain of C4-binding protein (C4 bp) to the antigen of interest (e.g., Solabomi et al., 2008, Infect Immun 76: 3817-23). In certain embodiments the compositions hereof comprise aluminum as an adjuvant, e.g., in the form of aluminum hydroxide, aluminum phosphate, aluminum potassium phosphate, or combinations thereof, in concentrations of 0.05-5 mg, e.g., from 0.075-1.0 mg, of aluminum content per dose.

E. USES OF THE RSV F PROTEIN MUTANTS, NUCLEIC ACID MOLECULES, AND COMPOSITIONS

The present disclosure also relates to use of a RSV F protein mutant, nucleic acids encoding a RSV F protein mutant, or vectors for expressing a RSV F protein mutant, or compositions comprising a RSV F protein mutant or nucleic acids.

In one aspect, the disclosure provides use of a RSV F protein mutant, nucleic acids encoding a RSV F protein mutant, or vectors for expressing a RSV F protein mutant, or compositions comprising a RSV F protein mutant or nucleic acids as a medicament, or in the manufacture of a medicament, for eliciting an immune response against RSV or for preventing or elevating RSV infection in a subject.

In other aspects, the present disclosure provides a method of eliciting an immune response against RSV in a subject, such as a human, comprising administering to the subject an effective amount of a RSV F protein mutant, a nucleic acid molecule encoding a RSV F protein mutant, or a composition comprising a RSV F protein mutant or nucleic acid molecule. The present disclosure also provides a method of preventing RSV infection in a subject, comprising administering to the subject an effective amount of a pharmaceutical composition, such as a vaccine, comprising a RSV F protein mutant, a nucleic acid encoding a RSV F protein mutant, or a vector expressing a RSV F protein mutant. In some particular embodiments, the pharmaceutical composition comprises a RSV F protein mutant. In some embodiments of the methods provided herein above, the subject is a human. In some particular embodiments, the human is a child, such as an infant. In some other particular embodiments, the human is a woman, particularly a pregnant woman.

The composition may be administered to the subject with or without administration of an adjuvant. The effective amount administered to the subject is an amount that is sufficient to elicit an immune response against an RSV antigen, such as RSV F protein, in the subject. Subjects that can be selected for treatment include those that are at risk for developing an RSV infection because of exposure or the possibility of exposure to RSV. Because nearly all humans are infected with RSV by the age of 2, the entire birth cohort is included as a relevant population for immunization. This could be done, for example, by beginning an immunization regimen anytime from birth to 6 months of age, from 6 months of age to 5 years of age, in pregnant women (or women of child-bearing age) to protect their infants by passive transfer of antibody, family members of newborn infants or those still in utero, and subjects greater than 50 years of age. Subjects at greatest risk of RSV infection with severe symptoms (e.g. requiring hospitalization) include children with prematurity, bronchopulmonary dysplasia, and congenital heart disease.

Administration of the compositions provided by the present disclosure, such as pharmaceutical compositions, can be carried out using standard routes of administration. Non-limiting embodiments include parenteral administration, such as intradermal, intramuscular, subcutaneous, transcutaneous, mucosal, or oral administration.

The total dose of the composition provided to a subject during one administration can be varied as is known to the skilled practitioner.

It is also possible to provide one or more booster administrations of one or more of the vaccine compositions. If a boosting vaccination is performed, typically, such a boosting vaccination will be administered to the same subject at a moment between one week and 10 years, preferably between two weeks and six months, after administering the composition to the subject for the first time (which is in such cases referred to as "priming vaccination"). In alternative boosting regimens, it is also possible to administer different vectors, e.g., one or more adenovirus, or other vectors such as modified vaccinia virus of Ankara (MVA), or DNA, or protein, to the subject after the priming vaccination. It is, for instance, possible to administer to the subject a recombinant viral vector hereof as a prime, and boosting with a composition comprising RSV F protein.

In certain embodiments, the administration comprises a priming administration and at least one booster administration. In certain other embodiments, the administration is provided annually. In still other embodiments, the administration is provided annually together with an influenza vaccine.

The vaccines provided by the present disclosure may be used together with one or more other vaccines. For example, in adults they may be used together with an influenza vaccine, Prevnar, tetanus vaccine, diphtheria vaccine, and pertussis vaccine. For pediatric use, vaccines provided by the present disclosure may be used with any other vaccine indicated for pediatric patients.

TABLE A

Non-consensus amino acid residues among F protein sequences from selected RSV A strains.

| | Strain Name (GenBank) | | | | | | | | |
|---|---|---|---|---|---|---|---|---|---|
| Amino Acid Position | A2 (138251) | RSVA/*Homo sapiens*/USA/LA2_21/2013 (AHX57185) | A/WI/629-4071/98 (AEQ63520) | TX-79223 (AGG39418) | BE08-5146 (AFM55563) | Tracy (AGG39397) | RSV-4 (AEO45850) | 06-000827 (AFM55442) | RSVA/*Homo sapiens*/USA/90I-226A-01/1990 (AHY21463) |
| 4 | L | P | P | P | P | P | P | P | P |
| 6 | L | L | L | L | L | I | L | L | L |
| 8 | A | T | T | T | T | A | T | T | T |
| 15 | L | L | L | L | L | L | L | F | F |
| 16 | T | A | A | A | A | I | T | A | A |
| 20 | F | L | L | L | L | F | F | L | L |
| 25 | G | S | S | S | S | S | S | S | S |
| 59 | I | I | I | I | I | I | I | I | V |
| 101 | P | P | P | P | Q | T | P | P | P |
| 102 | P | A | A | A | A | A | A | A | A |
| 103 | T | A | A | A | A | A | A | A | A |
| 105 | N | S | N | N | S | N | N | N | N |
| 122 | A | T | T | T | T | A | T | T | T |
| 124 | K | N | N | T | N | K | N | N | N |
| 125 | T | T | T | T | T | T | N | N | T |
| 129 | L | L | V | L | L | L | L | L | L |

TABLE A-continued

| Non-consensus amino acid residues among F protein sequences from selected RSV A strains. | | | | | | | | | |
|---|---|---|---|---|---|---|---|---|---|
| | Strain Name (GenBank) | | | | | | | | |
| Amino Acid Position | A2 (138251) | RSVA/*Homo sapiens*/USA/LA2_21/2013 (AHX57185) | A/WI/629-4071/98 (AEQ63520) | TX-79223 (AGG39418) | BE08-5146 (AFM55563) | Tracy (AGG39397) | RSV-4 (AEO45850) | 06-000827 (AFM55442) | RSVA/*Homo sapiens*/USA/90I-226A-01/1990 (AHY21463) |
| 152 | V | I | I | I | I | I | I | I | I |
| 276 | N | S | N | N | N | N | N | N | N |
| 356 | E | E | E | E | E | D | E | E | E |
| 379 | I | V | V | V | V | V | V | V | V |
| 384 | V | I | I | T | I | I | V | I | I |
| 447 | M | V | V | V | V | V | V | V | V |
| 518 | A | A | A | A | A | A | V | V | A |
| 540 | S | A | S | S | S | S | L | L | S |
| 547 | L | L | L | L | L | L | L | F | L |
| 562 | D | D | D | D | D | D | D | E | D |
| 574 | N | N | N | S | N | N | N | N | N |

TABLE B

| Non-consensus amino acid residues among F protein sequences from selected RSV B strains. | | | | | | | | |
|---|---|---|---|---|---|---|---|---|
| | Strain Name (GenBank) | | | | | | | |
| Amino Acid Position | 18537 (138250) | RSVB/*Homo sapiens*/PER/FPP00592/2011 (AHV80758) | NH1144 (AFD34260) | TX-79247 (AGG39514) | CH-18537 (AGG39487) | NH1125 (AFI25251) | TX-79222 (AGG39523) | TX-60567 (AGG39502) |
| 5 | I | I | I | I | I | I | I | V |
| 9 | S | S | S | S | S | S | I | S |
| 17 | V | I | I | I | V | I | I | I |
| 45 | F | F | F | L | F | F | F | F |
| 65 | K | K | K | K | K | K | T | K |
| 102 | A | A | A | V | A | A | A | A |
| 123 | K | K | K | K | K | K | K | N |
| 152 | I | I | I | I | M | I | I | I |
| 185 | V | V | V | V | I | V | V | V |
| 202 | R | Q | Q | Q | R | Q | Q | Q |
| 209 | Q | Q | K | Q | Q | Q | Q | Q |
| 226 | M | K | K | K | K | K | K | K |
| 234 | T | T | T | T | T | T | T | A |
| 292 | I | I | I | I | I | M | I | I |
| 326 | I | I | I | T | I | I | I | I |
| 371 | N | N | N | Y | N | N | N | N |
| 402 | I | I | V | I | I | I | I | I |
| 518 | T | T | T | T | T | T | V | T |
| 529 | T | A | A | A | T | V | A | A |

TABLE C

| Variants of Mutant pXCS847 Comprising Introduced Mutations T103C, I148C, S190I, and D486S | | | | |
|---|---|---|---|---|
| | F2 Polypeptide | | F1 Polypeptide | |
| | | Amino Acid Sequence | | |
| Mutant ID | SEQ ID | (residues 26-109) | SEQ ID | Amino Acid Sequence (residues 137-513) |
| pXCS847 | 41 | QNITEEFYQSTCSAVSK<br>GYLSALRTGWYTSVITI<br>ELSNIKENKCNGTDAK<br>VKLIKQELDKYKNAVT<br>ELQLLMQSTPACNNRA<br>RR | 42 | FLGFLLGVGSACASGVAVSKVLHLEGEVNKIKSALLSTNKA<br>VSLSNGVSVLT ***I*** KVLDLKNYIDKQLLPIVNKQSCSISNIETV<br>IEFQQKNNRLLEITREFSVNAGVTTPVSTYMLTNSELLSLIND<br>MPITNDQKKLMSNNVQIVRQQSYSIMSIIKEEVLAYVVQLPL<br>YGVIDTPCWKLHTSPLCTTNTKEGSNICLTRTDRGWYCDNA<br>GSVSFFPQAETCKVQSNRVFCDTMNSLTLPSEVNLCNVDIFN<br>PKYDCKIMTSKTDVSSSVITSLGAIVSCYGKTKCTASNKNRG<br>IIKTFSNGCDYVSNKGVDTVSVGNTLYYVNKQEGKSLYVK<br>GEPIINFYDPLVFPS ***S*** EFDASISQVNEKINQSLAFIRKSDELL |
| 847-138251<br>(A2) | 43 | QNITEEFYQSTCSAVSK<br>GYLSALRTGWYTSVITI<br>ELSNIKENKCNGTDAK | 44 | FLGFLLGVGSACASGVAVSKVLHLEGEVNKIKSALLSTNKA<br>VVSLSNGVSVLT ***I*** KVLDLKNYIDKQLLPIVNKQSCSISNIETV<br>IEFQQKNNRLLEITREFSVNAGVTTPVSTYMLTNSELLSLIND |

TABLE C-continued

Variants of Mutant pXCS847 Comprising Introduced Mutations T103C, I148C, S190I, and D486S

| Mutant ID | F2 Polypeptide SEQ ID | F2 Polypeptide Amino Acid Sequence (residues 26-109) | F1 Polypeptide SEQ ID | F1 Polypeptide Amino Acid Sequence (residues 137-513) |
|---|---|---|---|---|
| | | VKLIKQELDKYKNAVT<br>ELQLLMQSTPPCNNRA<br>RR | | MPITNDQKKLMSNNVQIVRQQSYSIMSIIKEEVLAYVVQLPL<br>YGVIDTPCWKLHTSPLCTTNTKEGSNICLTRTDRGWYCDNA<br>GSVSFFPQAETCKVQSNRVFCDTMNSLTLPSEINLCNVDIFN<br>PKYDCKIMTSKTDVSSSVITSLGAIVSCYGKTKCTASNKNRG<br>IIKTFSNGCDYVSNKGMDTVSVGNTLYYVNKQEGKSLYVK<br>GEPIINFYDPLVFPS***S***EFDASISQVNEKINQSLAFIRKSDELL |
| 847-57185 (A)<br>(Ontario) | 45 | QNITEEFYQSTCSAVSK<br>GYLSALRTGWYTSVITI<br>ELSNIKENKCNGTDAK<br>VKLIKQELDKYKNAVT<br>ELQLLMQSTPACNSRA<br>RR | 46 | FLGFLLGVGSA***C***ASGIAVSKVLHLEGEVNKIKSALLSTNKAV<br>VSLSNGVSVLT***I***KVLDLKNYIDKQLLPIVNKQSCSISNIETVIE<br>FQQKNNRLLEITREFSVNAGVTTPVSTYMLTNSELLSLINDM<br>PITNDQKKLMSSNVQIVRQQSYSIMSIIKEEVLAYVVQLPLY<br>GVIDTPCWKLHTSPLCTTNTKEGSNICLTRTDRGWYCDNAG<br>SVSFFPQAETCKVQSNRVFCDTMNSLTLPSEVNLCNIDIFNP<br>KYDCKIMTSKTDVSSSVITSLGAIVSCYGKTKCTASNKNRGII<br>KTFSNGCDYVSNKGVDTVSVGNTLYYVNKQEGKSLYVKGE<br>PIINFYDPLVFPS***S***EFDASISQVNEKINQSLAFIRKSDELL |
| 847-138250 (B) | 47 | QNITEEFYQSTCSAVSR<br>GYFSALRTGWYTSVITI<br>ELSNIKETKCNGTDTKV<br>KLIKQELDKYKNAVTE<br>LQLLMQNTPACNNRAR<br>R | 48 | FLGFLLGVGSA*C*ASGIAVSKVLHLEGEVNKIKNALLSTNKA<br>VVSLSNGVSVLT***I***KVLDLKNYINNRLLPIVNQQSCRISNIETV<br>IEFQQMNSRLLEITREFSVNAGVTTPLSTYMLTNSELLSLIND<br>MPITNDQKKLMSSNVQIVRQQSYSIMSIIKEEVLAYVVQLPI<br>YGVIDTPCWKLHTSPLCTTNTKEGSNICLTRTDRGWYCDNA<br>GSVSFFPQADTCKVQSNRVFCDTMNSLTLPSEVSLCNTDIFN<br>SKYDCKIMTSKTDISSSVITSLGAIVSCYGKTKCTASNKNRGI<br>IKTFSNGCDYVSNKGVDTVSVGNTLYYVNKLEGKNLYVKG<br>EPIINYYDPLVFPS***S***EFDASISQVNEKINQSLAFIRRSDELL |
| 847-80758 (B)<br>(Buenos Aires) | 49 | QNITEEFYQSTCSAVSR<br>GYFSALRTGWYTSVITI<br>ELSNIKETKCNGTDTKV<br>KLIKQELDKYKNAVTE<br>LQLLMQNTPACNNRAR<br>R | 50 | FLGFLLGVGSA*C*ASGIAVSKVLHLEGEVNKIKNALLSTNKA<br>VVSLSNGVSVLT***I***KVLDLKNYINNQLLPIVNQQSCRISNIETV<br>IEFQQKNSRLLEITREFSVNAGVTTPLSTYMLTNSELLSLIND<br>MPITNDQKKLMSSNVQIVRQQSYSIMSIIKEEVLAYVVQLPI<br>YGVIDTPCWKLHTSPLCTTNTKEGSNICLTRTDRGWYCDNA<br>GSVSFFPQADTCKVQSNRVFCDTMNSLTLPSEVSLCNTDIFN<br>SKYDCKIMTSKTDISSSVITSLGAIVSCYGKTKCTASNKNRGI<br>IKTFSNGCDYVSNKGVDTVSVGNTLYYVNKLEGKNLYVKG<br>EPIINYYDPLVFPS***S***EFDASISQVNEKINQSLAFIRRSDELL |
| 847-AFM55442<br>(A) | 279 | QNITEEFYQSTCSAVSK<br>GYLSALRTGWYTSVITI<br>ELSNIKENKCNGTDAK<br>VKLIKQELDKYKNAVT<br>ELQLLMQSTPACNNRA<br>RR | 280 | FLGFLLGVGSA**C**ASGIAVSKVLHLEGEVNKIKSALLSTNKA<br>VVSLSNGVSVLT**I**KVLDLKNYIDKQLLPIVNKQSCSISNIETV<br>IEFQQKNNRLLEITREFSVNAGVTTPVSTYMLTNSELLSLIND<br>MPITNDQKKLMSNNVQIVRQQSYSIMSIIKEEVLAYVVQLPL<br>YGVIDTPCWKLHTSPLCTTNTKEGSNICLTRTDRGWYCDNA<br>GSVSFFPQAETCKVQSNRVFCDTMNSLTLPSEVNLCNIDIFN<br>PKYDCKIMTSKTDVSSSVITSLGAIVSCYGKTKCTASNKNRG<br>IIKTFSNGCDYVSNKGVDTVSVGNTLYYVNKQEGKSLYVK<br>GEPIINFYDPLVFPS**S**EFDASISQVNEKINQSLAFIRKSDELL |
| 847-AFM95376<br>(A) | 281 | QNITEEFYQSTCSAVSK<br>GYLSALRTGWYTSVITI<br>ELSNIKENKCNGTDAK<br>VKLIKQELDKYKNAVT<br>ELQLLMQSTPACNNRA<br>RR | 282 | FLGFLLGVGSA**C**ASGIAVSKVLHLEGEVNKIKSALLSTNKA<br>VVSLSNGVSVLT**I**KVLDLKNYIDKQLLPIVNKQSCSISNIETV<br>IEFQQKNNRLLEITREFSVNAGVTTPVSTYMLTNSELLSLIND<br>MPITNDQKKLMSNNVQIVRQQSYSIMSIIKEEVLAYVVQLPL<br>YGVIDTPCWKLHTSPLCTTNTKEGSNICLTRTDRGWYCDNA<br>GSVSFFPQAETCKVQSNRVFCDTMNSLTLPSEVNLCNIDIFN<br>PKYDCKIMTSKTDVSSSVITSLGAIVSCYGKTKCTASNKNRG<br>IIKTFSNGCDYVSNKGVDTVSVGNTLYYVNKQEGKSLYVK<br>GEPIINFYDPLVFPS**S**EFDASISQVNEKINQSLAFIRKSDELL |
| 847-AEQ63520<br>(A) | 283 | QNITEEFYQSTCSAVSK<br>GYLSALRTGWYTSVITI<br>ELSNIKENKCNGTDAK<br>VKLIKQELDKYKNAVT<br>ELQLLMQSTPACNNRA<br>RR | 284 | FLGFLLGVGSA**C**ASGIAVSKVLHLEGEVNKIKSALLSTNKA<br>VVSLSNGVSVLT**I**KVLDLKNYIDKQLLPIVNKQSCSISNIETV<br>IEFQQKNNRLLEITREFSVNAGVTTPVSTYMLTNSELLSLIND<br>MPITNDQKKLMSNNVQIVRQQSYSIMSIIKEEVLAYVVQLPL<br>YGVIDTPCWKLHTSPLCTTNTKEGSNICLTRTDRGWYCDNA<br>GSVSFFPQAETCKVQSNRVFCDTMNSLTLPSEVNLCNIDIFN<br>PKYDCKIMTSKTDVSSSVITSLGAIVSCYGKTKCTASNKNRG<br>IIKTFSNGCDYVSNKGVDTVSVGNTLYYVNKQEGKSLYVK<br>GEPIINFYDPLVFPS**S**EFDASISQVNEKINQSLAFIRKSDELL |
| 847-AFD34260<br>(B) | 285 | QNITEEFYQSTCSAVSR<br>GYFSALRTGWYTSVITI<br>ELSNIKETKCNGTDTKV | 286 | FLGFLLGVGSA**C**ASGIAVSKVLHLEGEVNKIKNALLSTNKA<br>VVSLSNGVSVLT**I**KVLDLKNYINNQLLPIVNKQSCRISNIETV<br>IEFQQKNSRLLEITREFSVNAGVTTPLSTYMLTNSELLSLIND |

TABLE C-continued

Variants of Mutant pXCS847 Comprising Introduced Mutations T103C, I148C, S190I, and D486S

| Mutant ID | F2 Polypeptide SEQ ID | F2 Polypeptide Amino Acid Sequence (residues 26-109) | F1 Polypeptide SEQ ID | F1 Polypeptide Amino Acid Sequence (residues 137-513) |
|---|---|---|---|---|
| | | KLIKQELDKYKNAVTE<br>LQLLMQNTPACNNRAR<br>R | | MPITNDQKKLMSSNVQIVRQQSYSIMSIIKEEVLAYVVQLPI<br>YGVIDTPCWKLHTSPLCTTNIKEGSNICLTRTDRGWYCDNA<br>GSVSFFPQADTCKVQSNRVFCDTMNSLTLPSEVSLCNTDIFN<br>SKYDCKIMTSKTDVSSSVITSLGAIVSCYGKTKCTASNKNRG<br>IIKTFSNGCDYVSNKGVDTVSVGNTLYYVNKLEGKNLYVK<br>GEPIINYYDPLVFPSSEFDASISQVNEKINQSLAFIRRSDELL |
| 847-BAE96918<br>(B) | 287 | QNITEEFYQSTCSAVSR<br>GYFSALRTGWYTSVITI<br>ELSNIKETKCNGTDTKV<br>KLIKQELDKYKNAVTE<br>LQLLMQNTPACNNRAR<br>R | 288 | FLGFLLGVGSACASGIAVSKVLHLEGEVNKIKNALLSTNKA<br>VVSLSNGVSVLTIKVLDLKNYINNQLLPIVNQQSCRISNIETV<br>IEFQQKNSRLLEITREFSVNAGVTTPLSTYMLTNSELLSLIND<br>MPITNDQKKLMSSNVQIVRQQSYSIMSIMKEEVLAYVVQLPI<br>YGVIDTPCWKLHTSPLCTTNIKEGSNICLTRTDRGWYCDNA<br>GSVSFFPQADTCKVQSNRVFCDTMNSLTLPSEVSLCNTDIFN<br>SKYDCKIMTSKTDISSSVITSLGAIVSCYGKTKCTASNKNRGI<br>IKTFSNGCDYVSNKGVDTVSVGNTLYYVNKLEGKNLYVKG<br>EPIINYYDPLVFPSSEFDASISQVNEKINQSLAFIRRSDELL |
| 847-AFD34265<br>(B) | 289 | QNITEEFYQSTCSAVSR<br>GYLSALRTGWYTSVITI<br>ELSNIKETKCNGTDTKV<br>KLIKQELDKYKNAVTE<br>LQLLMQNTPACNNRAR<br>R | 290 | FLGFLLGVGSACASGIAVSKVLHLEGEVNKIKNALLSTNKA<br>VVSLSNGVSVLTIKVLDLKNYINNQLLPIVNQQSCRISNIETV<br>IEFQQKNSRLLEIAREFSVNAGVTTPLSTYMLTNSELLSLIND<br>MPITNDQKKLMSSNVQIVRQQSYSIMSIIKEEVLAYVVQLPI<br>YGVIDTPCWKLHTSPLCTTNIKEGSNICLTRTDRGWYCDNA<br>GSVSFFPQADTCKVQSNRVFCDTMNSLTLPSEVSLCNTDIFN<br>SKYDCKIMTSKTDISSSVITSLGAIVSCYGKTKCTASNKNRGI<br>IKTFSNGCDYVSNKGVDTVSVGNTLYYVNKLEGKNLYVKG<br>EPIINYYDPLVFPSSEFDASISQVNEKINQSLAFIRRSDELL |

TABLE D

Variant of Mutant pXCS851 Comprising Introduced Mutations T54H, T103C, I148C, S190I, V296I, D486S

| Mutant ID | F2 Polypeptide SEQ ID | F2 Polypeptide Amino Acid Sequence (residues 26-109) | F1 Polypeptide SEQ ID | F1 Polypeptide Amino Acid Sequence (residues 137-513) |
|---|---|---|---|---|
| pXCS851 | 51 | QNITEEFYQSTCSAVSKG<br>YLSALRTGWYHSVITIEL<br>SNIKENKCNGTDAKVKLI<br>KQELDKYKNAVTELQLL<br>MQSTPACNNRARR | 52 | FLGFLLGVGSACASGVAVSKVLHLEGEVNKIKSALLST<br>NKAVVSLSNGVSVLTIKVLDLKNYIDKQLLPIVNKQSC<br>SISNIETVIEFQQKNNRLLEITREFSVNAGVTTPVSTYML<br>TNSELLSLINDMPITNDQKKLMSNNVQIVRQQSYSIMSI<br>IKEEILAYVVQLPLYGVIDTPCWKLHTSPLCTTNTKEGS<br>NICLTRTDRGWYCDNAGSVSFFPQAETCKVQSNRVFC<br>DTMNSLTLPSEVNLCNVDIFNPKYDCKIMTSKTDVSSS<br>VITSLGAIVSCYGKTKCTASNKNRGIIKTFSNGCDYVSN<br>KGVDTVSVGNTLYYVNKQEGKSLYVKGEPIINFYDPL<br>VFPSSEFDASISQVNEKINQSLAFIRKSDELL |
| GI-138251 (A2) | 53 | QNITEEFYQSTCSAVSKG<br>YLSALRTGWYHSVITIEL<br>SNIKENKCNGTDAKVKLI<br>KQELDKYKNAVTELQLL<br>MQSTPPCNNRARR | 54 | FLGFLLGVGSACASGVAVSKVLHLEGEVNKIKSALLST<br>NKAVVSLSNGVSVLTIKVLDLKNYIDKQLLPIVNKQSC<br>SISNIETVIEFQQKNNRLLEITREFSVNAGVTTPVSTYML<br>TNSELLSLINDMPITNDQKKLMSNNVQIVRQQSYSIMSI<br>IKEEILAYVVQLPLYGVIDTPCWKLHTSPLCTTNTKEGS<br>NICLTRTDRGWYCDNAGSVSFFPQAETCKVQSNRVFC<br>DTMNSLTLPSEINLCNVDIFNPKYDCKIMTSKTDVSSSV<br>ITSLGAIVSCYGKTKCTASNKNRGIIKTFSNGCDYVSNK<br>GMDTVSVGNTLYYVNKQEGKSLYVKGEPIINFYDPLV<br>FPSSEFDASISQVNEKINQSLAFIRKSDELL |
| GI-57185 (A)<br>(Ontario) | 55 | QNITEEFYQSTCSAVSKG<br>YLSALRTGWYHSVITIEL<br>SNIKENKCNGTDAKVKLI<br>KQELDKYKNAVTELQLL<br>MQSTPACNSRARR | 56 | FLGFLLGVGSACASGIAVSKVLHLEGEVNKIKSALLST<br>NKAVVSLSNGVSVLTIKVLDLKNYIDKQLLPIVNKQSC<br>SISNIETVIEFQQKNNRLLEITREFSVNAGVTTPVSTYML<br>TNSELLSLINDMPITNDQKKLMSSNVQIVRQQSYSIMSII<br>KEEILAYVVQLPLYGVIDTPCWKLHTSPLCTTNTKEGS<br>NICLTRTDRGWYCDNAGSVSFFPQAETCKVQSNRVFC<br>DTMNSLTLPSEVNLCNIDIFNPKYDCKIMTSKTDVSSSV<br>ITSLGAIVSCYGKTKCTASNKNRGIIKTFSNGCDYVSNK<br>GVDTVSVGNTLYYVNKQEGKSLYVKGEPIINFYDPLVF<br>PSSEFDASISQVNEKINQSLAFIRKSDELL |

TABLE D-continued

Variant of Mutant pXCS851 Comprising Introduced Mutations T54H, T103C, I148C, S190I, V296I, D486S

| Mutant ID | F2 Polypeptide SEQ ID | F2 Polypeptide Amino Acid Sequence (residues 26-109) | F1 Polypeptide SEQ ID | F1 Polypeptide Amino Acid Sequence (residues 137-513) |
|---|---|---|---|---|
| GI-138250 (B) | 57 | QNITEEFYQSTCSAVSRG<br>YFSALRTGWYHSVITIEL<br>SNIKETKCNGTDTKVKLI<br>KQELDKYKNAVTELQLL<br>MQNTPACNNRARR | 58 | FLGFLLGVGSACASGIAVSKVLHLEGEVNKIKNALLST<br>NKAVVSLSNGVSVLTIKVLDLKNYINNRLLPIVNQQSC<br>RISNIETVIEFQQMNSRLLEITREFSVNAGVTTPLSTYML<br>TNSELLSLINDMPITNDQKKLMSSNVQIVRQQSYSIMSII<br>KEEILAYVVQLPIYGVIDTPCWKLHTSPLCTTNIKEGSN<br>ICLTRTDRGWYCDNAGSVSFFPQADTCKVQSNRVFCD<br>TMNSLTLPSEVSLCNTDIFNSKYDCKIMTSKTDISSSVIT<br>SLGAIVSCYGKTKCTASNKNRGIIKTFSNGCDYVSNKG<br>VDTVSVGNTLYYVNKLEGKNLYVKGEPIINYYDPLVFP<br>SSEFDASISQVNEKINQSLAFIRRSDELL |
| GI-80758 (B)<br>(Buenos Aires) | 59 | QNITEEFYQSTCSAVSRG<br>YFSALRTGWYHSVITIEL<br>SNIKETKCNGTDTKVKLI<br>KQELDKYKNAVTELQLL<br>MQNTPACNNRARR | 60 | FLGFLLGVGSACASGIAVSKVLHLEGEVNKIKNALLST<br>NKAVVSLSNGVSVLTIKVLDLKNYINNQLLPIVNQQSC<br>RISNIETVIEFQQKNSRLLEITREFSVNAGVTTPLSTYML<br>TNSELLSLINDMPITNDQKKLMSSNVQIVRQQSYSIMSII<br>KEEILAYVVQLPIYGVIDTPCWKLHTSPLCTTNIKEGSN<br>ICLTRTDRGWYCDNAGSVSFFPQADTCKVQSNRVFCD<br>TMNSLTLPSEVSLCNTDIFNSKYDCKIMTSKTDISSSVIT<br>SLGAIVSCYGKTKCTASNKNRGIIKTFSNGCDYVSNKG<br>VDTVSVGNTLYYVNKLEGKNLYVKGEPIINYYDPLVFP<br>SSEFDASISQVNEKINQSLAFIRRSDELL |
| 851-AFM55442<br>(A) | 291 | QNITEEFYQSTCSAVSKG<br>YLSALRTGWYHSVITIEL<br>SNIKENKCNGTDAKVKLI<br>KQELDKYKNAVTELQLL<br>MQSTPACNNRARR | 292 | FLGFLLGVGSACASGIAVSKVLHLEGEVNKIKSALLST<br>NKAVVSLSNGVSVLTIKVLDLKNYIDKQLLPIVNKQSC<br>SISNIETVIEFQQKNNRLLEITREFSVNAGVTTPVSTYML<br>TNSELLSLINDMPITNDQKKLMSNNVQIVRQQSYSIMSI<br>IKEEILAYVVQLPLYGVIDTPCWKLHTSPLCTTNTKEGS<br>NICLTRTDRGWYCDNAGSVSFFPQAETCKVQSNRVFC<br>DTMNSLTLPSEVNLCNIDIFNPKYDCKIMTSKTDVSSSV<br>ITSLGAIVSCYGKTKCTASNKNRGIIKTFSNGCDYVSNK<br>GVDTVSVGNTLYYVNKQEGKSLYVKGEPIINFYDPLVF<br>PSSEFDASISQVNEKINQSLAFIRKSDELL |
| 851-AFM95376<br>(A) | 293 | QNITEEFYQSTCSAVSKG<br>YLSALRTGWYHSVITIEL<br>SNIKENKCNGTDAKVKLI<br>KQELDKYKNAVTELQLL<br>MQSTPACNNRARR | 294 | FLGFLLGVGSACASGIAVSKVLHLEGEVNKIKSALLST<br>NKAVVSLSNGVSVLTIKVLDLKNYIDKQLLPIVNKQSC<br>SISNIETVIEFQQKNNRLLEITREFSVNAGVTTPVSTYML<br>TNSELLSLINDMPITNDQKKLMSNNVQIVRQQSYSIMSI<br>IKEEILAYVVQLPLYGVIDTPCWKLHTSPLCTTNTKEGS<br>NICLTRTDRGWYCDNAGSVSFFPQAETCKVQSNRVFC<br>DTMNSLTLPSEVNLCNIDIFNPKYDCKIMTSKTDVSSSV<br>ITSLGAIVSCYGKTKCTASNKNRGIIKTFSNGCDYVSNK<br>GVDTVSVGNTLYYVNKQEGKSLYVKGEPIINFYDPLVF<br>PSSEFDASISQVNEKINQSLAFIRKSDELL |
| 851-AEQ63520<br>(A) | 295 | QNITEEFYQSTCSAVSKG<br>YLSALRTGWYHSVITIEL<br>SNIKENKCNGTDAKVKLI<br>KQELDKYKNAVTELQLL<br>MQSTPACNNRARR | 296 | FLGFLLGVGSACASGIAVSKVLHLEGEVNKIKSALLST<br>NKAVVSLSNGVSVLTIKVLDLKNYIDKQLLPIVNKQSC<br>SISNIETVIEFQQKNNRLLEITREFSVNAGVTTPVSTYML<br>TNSELLSLINDMPITNDQKKLMSNNVQIVRQQSYSIMSI<br>IKEEILAYVVQLPLYGVIDTPCWKLHTSPLCTTNTKEGS<br>NICLTRTDRGWYCDNAGSVSFFPQAETCKVQSNRVFC<br>DTMNSLTLPSEVNLCNIDIFNPKYDCKIMTSKTDVSSSV<br>ITSLGAIVSCYGKTKCTASNKNRGIIKTFSNGCDYVSNK<br>GVDTVSVGNTLYYVNKQEGKSLYVKGEPIINFYDPLVF<br>PSSEFDASISQVNEKINQSLAFIRKSDELL |
| 851-AFD34260<br>(B) | 297 | QNITEEFYQSTCSAVSRG<br>YFSALRTGWYHSVITIEL<br>SNIKETKCNGTDTKVKLI<br>KQELDKYKNAVTELQLL<br>MQNTPACNNRARR | 298 | FLGFLLGVGSACASGIAVSKVLHLEGEVNKIKNALLST<br>NKAVVSLSNGVSVLTIKVLDLKNYINNQLLPIVNKQSC<br>RISNIETVIEFQQKNSRLLEITREFSVNAGVTTPLSTYML<br>TNSELLSLINDMPITNDQKKLMSSNVQIVRQQSYSIMSII<br>KEEILAYVVQLPIYGVIDTPCWKLHTSPLCTTNIKEGSN<br>ICLTRTDRGWYCDNAGSVSFFPQADTCKVQSNRVFCD<br>TMNSLTLPSEVSLCNTDIFNSKYDCKIMTSKTDVSSSVI<br>TSLGAIVSCYGKTKCTASNKNRGIIKTFSNGCDYVSNK<br>GVDTVSVGNTLYYVNKLEGKNLYVKGEPIINYYDPLV<br>FPSSEFDASISQVNEKINQSLAFIRRSDELL |
| 851-BAE96918<br>(B) | 299 | QNITEEFYQSTCSAVSRG<br>YFSALRTGWYHSVITIEL<br>SNIKETKCNGTDTKVKLI<br>KQELDKYKNAVIELQLL<br>MQNTPACNNRARR | 300 | FLGFLLGVGSACASGIAVSKVLHLEGEVNKIKNALLST<br>NKAVVSLSNGVSVLTIKVLDLKNYINNQLLPIVNQQSC<br>RISNIETVIEFQQKNSRLLEITREFSVNAGVTTPLSTYML<br>TNSELLSLINDMPIINDQKKLMSSNVQIVRQQSYSIMSI<br>MKEEILAYVVQLPIYGVIDTPCWKLHTSPLCTTNIKEGS |

TABLE D-continued

Variant of Mutant pXCS851 Comprising Introduced Mutations T54H, T103C, I148C, S190I, V296I, D486S

| Mutant ID | F2 Polypeptide SEQ ID | F2 Polypeptide Amino Acid Sequence (residues 26-109) | F1 Polypeptide SEQ ID | F1 Polypeptide Amino Acid Sequence (residues 137-513) |
|---|---|---|---|---|
| | | | | NICLTRTDRGWYCDNAGSVSFFPQADTCKVQSNRVFC<br>DTMNSLTLPSEVSLCNTDIFNSKYDCKIMTSKTDISSSVI<br>TSLGAIVSCYGKTKCTASNKNRGIIKTFSNGCDYVSNK<br>GVDTVSVGNTLYYVNKLEGKNLYVKGEPIINYYDPLV<br>FPS**S**EFDASISQVNEKINQSLAFIRRSDELL |
| 851-AFD34265<br>(B) | 301 | QNITEEFYQSTCSAVSRG<br>YLSALRTGWY**H**SVITIEL<br>SNIKETKCNGTDTKVKLI<br>KQELDKYKNAVIELQLL<br>MQNTPA**C**NNRARR | 302 | FLGFLLGVGSA**C**ASGIAVSKVLHLEGEVNKIKNALLST<br>NKAVVSLSNGVSVLT**I**KVLDLKNYINNQLLPIVNQQSC<br>RISNIETVIEFQQKNSRLLEIAREFSVNAGVTTPLSTYML<br>TNSELLSLINDMPITNDQKKLMSSNVQIVRQQSYSIMSII<br>KEE**I**LAYVVQLPIYGVIDTPCWKLHTSPLCTTNIKEGSN<br>ICLTRTDRGWYCDNAGSVSFFPQADTCKVQSNRVFCD<br>TMNSLTLPSEVSLCNTDIFNSKYDCKIMTSKTDISSSVIT<br>SLGAIVSCYGKTKCTASNKNRGIIKTFSNGCDYVSNKG<br>VDTVSVGNTLYYVNKLEGKNLYVKGEPIINYYDPLVFP<br>S**S**EFDASISQVNEKINQSLAFIRRSDELL |

TABLE E

Variant of Mutants pXCS852 Comprising Introduced Mutations T54H, S55C, L188C, D486S

| Mutant ID | F2 Polypeptide SEQ ID | F2 Polypeptide Amino Acid Sequence (residues 26-109) | F1 Polypeptide SEQ ID | F1 Polypeptide Amino Acid Sequence (residues 137-513) |
|---|---|---|---|---|
| pXCS852 | 61 | QNITEEFYQSTCSAVSKGY<br>LSALRTGWY**H**CVITIELSN<br>IKENKCNGTDAKVKLIKQ<br>ELDKYKNAVTELQLLMQS<br>TPATNNRARR | 62 | FLGFLLGVGSAIASGVAVSKVLHLEGEVNKIKSALLS<br>TNKAVVSLSNGVSV**C**TSKVLDLKNYIDKQLLPIVNK<br>QSCSISNIETVIEFQQKNNRLLEITREFSVNAGVTTPVS<br>TYMLTNSELLSLINDMPITNDQKKLMSNNVQIVRQQS<br>YSIMSIIKEEVLAYVVQLPLYGVIDTPCWKLHTSPLCT<br>TNTKEGSNICLTRTDRGWYCDNAGSVSFFPQAETCK<br>VQSNRVFCDTMNSLTLPSEVNLCNVDIFNPKYDCKI<br>MTSKTDVSSSVITSLGAIVSCYGKTKCTASNKNRGIIK<br>TFSNGCDYVSNKGVDTVSVGNTLYYVNKQEGKSLY<br>VKGEPIINFYDPLVFPS**S**EFDASISQVNEKINQSLAFIR<br>KSDELL |
| GI-138251 (A2) | 63 | QNITEEFYQSTCSAVSKGY<br>LSALRTGWY**H**CVITIELSN<br>IKENKCNGTDAKVKLIKQ<br>ELDKYKNAVTELQLLMQS<br>TPPTNNRARR | 64 | FLGFLLGVGSAIASGVAVSKVLHLEGEVNKIKSALLS<br>TNKAVVSLSNGVSV**C**TSKVLDLKNYIDKQLLPIVNK<br>QSCSISNIETVIEFQQKNNRLLEITREFSVNAGVTTPVS<br>TYMLTNSELLSLINDMPITNDQKKLMSNNVQIVRQQS<br>YSIMSIIKEEVLAYVVQLPLYGVIDTPCWKLHTSPLCT<br>TNTKEGSNICLTRTDRGWYCDNAGSVSFFPQAETCK<br>VQSNRVFCDTIVINSLTLPSEINLCNVDIFNPKYDCKIM<br>TSKTDVSSSVITSLGAIVSCYGKTKCIASNKNRGIIKT<br>FSNGCDYVSNKGMDTVSVGNTLYYVNKQEGKSLYV<br>KGEPIINFYDPLVFPS**S**EFDASISQVNEKINQSLAFIRKS<br>DELL |
| GI-57185 (A)<br>(Ontario) | 65 | QNITEEFYQSTCSAVSKGY<br>LSALRTGWY**H**CVITIELSN<br>IKENKCNGTDAKVKLIKQ<br>ELDKYKNAVTELQLLMQS<br>TPAANSRARR | 66 | FLGFLLGVGSAIASGIAVSKVLHLEGEVNKIKSALLST<br>NKAVVSLSNGVSV**C**TSKVLDLKNYIDKQLLPIVNKQ<br>SCSISNIETVIEFQQKNNRLLEITREFSVNAGVTTPVST<br>YMLTNSELLSLINDMPITNDQKKLMSSNVQIVRQQSY<br>SIMSIIKEEVLAYVVQLPLYGVIDTPCWKLHTSPLCTT<br>NTKEGSNICLTRTDRGWYCDNAGSVSFFPQAETCKV<br>QSNRVFCDTMNSLTLPSEVNLCNIDIFNPKYDCKIMT<br>SKTDVSSSVITSLGAIVSCYGKTKCTASNKNRGIIKTF<br>SNGCDYVSNKGVDTVSVGNTLYYVNKQEGKSLYVK<br>GEPIINFYDPLVFPS**S**EFDASISQVNEKINQSLAFIRKSD<br>ELL |
| GI-138250 (B) | 67 | QNITEEFYQSTCSAVSRGY<br>FSALRTGWY**H**CVITIELSN<br>IKETKCNGTDTKVKLIKQE<br>LDKYKNAVTELQLLMQN<br>TPAANNRARR | 68 | FLGFLLGVGSAIASGIAVSKVLHLEGEVNKIKNALLST<br>NKAVVSLSNGVSV**C**TSKVLDLKNYINNRLLPIVNQQS<br>CRISNIETVIEFQQMNSRLLEITREFSVNAGVTTPLSTY<br>MLTNSELLSLINDMPITNDQKKLMSSNVQIVRQQSYS<br>IMSIIKEEVLAYVVQLPIYGVIDTPCWKLHTSPLCTTNI<br>KEGSNICLTRTDRGWYCDNAGSVSFFPQADTCKVQS |

TABLE E-continued

| Variant of Mutants pXCS852 Comprising Introduced Mutations T54H, S55C, L188C, D486S | | | | |
|---|---|---|---|---|
| | F2 Polypeptide | | F1 Polypeptide | |
| Mutant ID | SEQ ID | Amino Acid Sequence (residues 26-109) | SEQ ID | Amino Acid Sequence (residues 137-513) |
| | | | | NRVFCDTMNSLTLPSEVSLCNTDIFNSKYDCKIMTSK<br>TDISSSVITSLGAIVSCYGKTKCTASNKNRGIIKTFSNG<br>CDYVSNKGVDTVSVGNTLYYVNKLEGKNLYVKGEP<br>IINYYDPLVFPS**S**EFDASISQVNEKINQSLAFIRRSDEL<br>L |
| GI-80758 (B)<br>(Buenos Aires) | 69 | QNITEEFYQSTCSAVSRGY<br>FSALRTGWY**H**CVITIELSN<br>IKETKCNGTDTKVKLIKQE<br>LDKYKNAVTELQLLMQN<br>TPAANNRARR | 70 | FLGFLLGVGSAIASGIAVSKVLHLEGEVNKIKNALLST<br>NKAVVSLSNGVSV**C**TSKVLDLKNYINNQLLPIVNQQ<br>SCRISNIETVIEFQQKNSRLLEITREFSVNAGVTTPLST<br>YMLTNSELLSLINDMPITNDQKKLMSSNVQIVRQQSY<br>SIMSIIKEEVLAYVVQLPIYGVIDTPCWKLHTSPLCTT<br>NTKEGSNICLTRTDRGWYCDNAGSVSFFPQADTCKV<br>QSNRVFCDTMNSLTLPSEVSLCNTDIFNSKYDCKIMT<br>SKTDISSSVITSLGAIVSCYGKTKCTASNKNRGIIKTFS<br>NGCDYVSNKGVDTVSVGNTLYYVNKLEGKNLYVKG<br>EPIINYYDPLVFPS**S**EFDASISQVNEKINQSLAFIRRSDE<br>LL |
| 852-AFM55442<br>(A) | 303 | QNITEEFYQSTCSAVSKGY<br>LSALRTGWY**H**CVITIELSN<br>IKENKCNGTDAKVKLIKQ<br>ELDKYKNAVTELQLLMQS<br>TPAANNRARR | 304 | FLGFLLGVGSAIASGIAVSKVLHLEGEVNKIKSALLST<br>NKAVVSLSNGVSV**C**TSKVLDLKNYIDKQLLPIVNKQ<br>SCSISNIETVIEFQQKNNRLLEITREFSVNAGVTTPVST<br>YMLTNSELLSLINDMPITNDQKKLMSNNVQIVRQQS<br>YSIMSIIKEEVLAYVVQLPLYGVIDTPCWKLHTSPLCT<br>TNTKEGSNICLTRTDRGWYCDNAGSVSFFPQAETCK<br>VQSNRVFCDTMNSLTLPSEVNLCNIDIFNPKYDCKIM<br>TSKTDVSSSVITSLGAIVSCYGKTKCTASNKNRGIIKT<br>FSNGCDYVSNKGVDTVSVGNTLYYVNKQEGKSLYV<br>KGEPIINFYDPLVFPS**S**EFDASISQVNEKINQSLAFIRKS<br>DELL |
| 852-AFM95376<br>(A) | 305 | QNITEEFYQSTCSAVSKGY<br>LSALRTGWY**H**CVITIELSN<br>IKENKCNGTDAKVKLIKQ<br>ELDKYKNAVTELQLLMQS<br>TPAANNRARR | 306 | FLGFLLGVGSAIASGIAVSKVLHLEGEVNKIKSALLST<br>NKAVVSLSNGVSV**C**TSKVLDLKNYIDKQLLPIVNKQ<br>SCSISNIETVIEFQQKNNRLLEITREFSVNAGVTTPVST<br>YMLTNSELLSLINDMPITNDQKKLMSNNVQIVRQQS<br>YSIMSIIKEEVLAYVVQLPLYGVIDTPCWKLHTSPLCT<br>TNTKEGSNICLTRTDRGWYCDNAGSVSFFPQAETCK<br>VQSNRVFCDTMNSLTLPSEVNLCNIDIFNPKYDCKIM<br>TSKTDVSSSVITSLGAIVSCYGKTKCTASNKNRGIIKT<br>FSNGCDYVSNKGVDTVSVGNTLYYVNKQEGKSLYV<br>KGEPIINFYDPLVFPS**S**EFDASISQVNEKINQSLAFIRKS<br>DELL |
| 852-AEQ63520<br>(A) | 307 | QNITEEFYQSTCSAVSKGY<br>LSALRTGWY**H**CVITIELSN<br>IKENKCNGTDAKVKLIKQ<br>ELDKYKNAVTELQLLMQS<br>TPAANNRARR | 308 | FLGFLLGVGSAIASGIAVSKVLHLEGEVNKIKSALLST<br>NKAVVSLSNGVSV**C**TSKVLDLKNYIDKQLLPIVNKQ<br>SCSISNIETVIEFQQKNNRLLEITREFSVNAGVTTPVST<br>YMLTNSELLSLINDMPITNDQKKLMSNNVQIVRQQS<br>YSIMSIIKEEVLAYVVQLPLYGVIDTPCWKLHTSPLCT<br>TNTKEGSNICLTRTDRGWYCDNAGSVSFFPQAETCK<br>VQSNRVFCDTMNSLTLPSEVNLCNIDIFNPKYDCKIM<br>TSKTDVSSSVITSLGAIVSCYGKTKCTASNKNRGIIKT<br>FSNGCDYVSNKGVDTVSVGNTLYYVNKQEGKSLYV<br>KGEPIINFYDPLVFPS**S**EFDASISQVNEKINQSLAFIRKS<br>DELL |
| 852-AFD34260<br>(B) | 309 | QNITEEFYQSTCSAVSRGY<br>FSALRTGWY**H**CVITIELSN<br>IKETKCNGTDTKVKLIKQE<br>LDKYKNAVTELQLLMQN<br>TPAANNRARR | 310 | FLGFLLGVGSAIASGIAVSKVLHLEGEVNKIKNALLST<br>NKAVVSLSNGVSV**C**TSKVLDLKNYINNQLLPIVNKQ<br>SCRISNIETVIEFQQKNSRLLEITREFSVNAGVTTPLST<br>YMLTNSELLSLINDMPITNDQKKLMSSNVQIVRQQSY<br>SIMSIIKEEVLAYVVQLPIYGVIDTPCWKLHTSPLCTT<br>NIKEGSNICLTRTDRGWYCDNAGSVSFFPQADTCKV<br>QSNRVFCDTMNSLTLPSEVSLCNTDIFNSKYDCKIMT<br>SKTDVSSSVITSLGAIVSCYGKTKCTASNKNRGIIKTF<br>SNGCDYVSNKGVDTVSVGNTLYYVNKLEGKNLYVK<br>GEPIINYYDPLVFPS**S**EFDASISQVNEKINQSLAFIRRS<br>DELL |
| 852-BAE96918<br>(B) | 311 | QNITEEFYQSTCSAVSRGY<br>FSALRTGWY**H**CVITIELSN<br>IKETKCNGTDTKVKLIKQE<br>LDKYKNAVTELQLLMQN<br>TPAANNRARR | 312 | FLGFLLGVGSAIASGIAVSKVLHLEGEVNKIKNALLST<br>NKAVVSLSNGVSV**C**TSKVLDLKNYINNQLLPIVNQQ<br>SCRISNIETVIEFQQKNSRLLEITREFSVNAGVTTPLST<br>YMLTNSELLSLINDMPITNDQKKLMSSNVQIVRQQSY<br>SIMSIMKEEVLAYVVQLPIYGVIDTPCWKLHTSPLCTT<br>NIKEGSNICLTRTDRGWYCDNAGSVSFFPQADTCKV |

TABLE E-continued

Variant of Mutants pXCS852 Comprising Introduced Mutations T54H, S55C, L188C, D486S

| | F2 Polypeptide | | F1 Polypeptide | |
|---|---|---|---|---|
| Mutant ID | SEQ ID | Amino Acid Sequence (residues 26-109) | SEQ ID | Amino Acid Sequence (residues 137-513) |
| | | | | QSNRVFCDTMNSLTLPSEVSLCNTDIFNSKYDCKIMT<br>SKTDISSSVITSLGAIVSCYGKTKCTASNKNRGIIKTFS<br>NGCDYVSNKGVDTVSVGNTLYYVNKLEGKNLYVKG<br>EPIINYYDPLVFPS**S**EFDASISQVNEKINQSLAFIRRSDE<br>LL |
| 852-AFD34265<br>(B) | 313 | QNITEEFYQSTCSAVSRGY<br>LSALRTGWY**H**CVITIELSN<br>IKETKCNGTDTKVKLIKQE<br>LDKYKNAVTELQLLMQN<br>TPAANNRARR | 314 | FLGFLLGVGSAIASGIAVSKVLHLEGEVNKIKNALLST<br>NKAVVSLSNGVSV**C**TSKVLDLKNYINNQLLPIVNQQ<br>SCRISNIETVIEFQQKNSRLLEIAREFSVNAGVTTPLST<br>YMLTNSELLSLINDMPITNDQKKLMSSNVQIVRQQSY<br>SIMSIIKEEVLAYVVQLPIYGVIDTPCWKLHTSPLCTT<br>NIKEGSNICLTRTDRGWYCDNAGSVSFFPQADTCKV<br>QSNRVFCDTMNSLTLPSEVSLCNTDIFNSKYDCKIMT<br>SKTDISSSVITSLGAIVSCYGKTKCTASNKNRGIIKTFS<br>NGCDYVSNKGVDTVSVGNTLYYVNKLEGKNLYVKG<br>EPIINYYDPLVFPS**S**EFDASISQVNEKINQSLAFIRRSDE<br>LL |

TABLE F

Variant of Mutant pXCS855 Comprising Introduced Mutations T54H, S55C, L188C, S190I, D486S

| | F2 Polypeptide | | F1 Polypeptide | |
|---|---|---|---|---|
| Mutant ID | SEQ ID | Amino Acid Sequence (residues 26-109) | SEQ ID | Amino Acid Sequence (residues 137-513) |
| pXCS855 | 71 | QNITEEFYQSTCSAVSKGY<br>LSALRTGWY**H**CVITIELSN<br>IKENKCNGTDAKVKLIKQ<br>ELDKYKNAVTELQLLMQS<br>TPATNNRARR | 72 | FLGFLLGVGSAIASGVAVSKVLHLEGEVNKIKSALLST<br>NKAVVSLSNGVSV**C**T**I**KVLDLKNYIDKQLLPIVNKQSC<br>SISNIETVIEFQQKNNRLLEITREFSVNAGVTTPVSTYML<br>TNSELLSLINDMPITNDQKKLMSNNVQIVRQQSYSIMSI<br>IKEEVLAYVVQLPLYGVIDTPCWKLHTSPLCTTNTKEG<br>SNICLTRTDRGWYCDNAGSVSFFPQAETCKVQSNRVF<br>CDTMNSLTLPSEVNLCNVDIFNPKYDCKIMTSKTDVSS<br>SVITSLGAIVSCYGKTKCTASNKNRGIIKTFSNGCDYVS<br>NKGVDTVSVGNTLYYVNKQEGKSLYVKGEPIINFYDP<br>LVFPS**S**EFDASISQVNEKINQSLAFIRKSDELL |
| 855-GI138251<br>(A2) | 73 | QNITEEFYQSTCSAVSKGY<br>LSALRTGWY**H**CVITIELSN<br>IKENKCNGTDAKVKLIKQ<br>ELDKYKNAVTELQLLMQS<br>TPPTNNRARR | 74 | FLGFLLGVGSAIASGVAVSKVLHLEGEVNKIKSALLST<br>NKAVVSLSNGVSV**C**T**I**KVLDLKNYIDKQLLPIVNKQSC<br>SISNIETVIEFQQKNNRLLEITREFSVNAGVTTPVSTYML<br>TNSELLSLINDMPITNDQKKLMSNNVQIVRQQSYSIMSI<br>IKEEVLAYVVQLPLYGVIDTPCWKLHTSPLCTTNTKEG<br>SNICLTRTDRGWYCDNAGSVSFFPQAETCKVQSNRVF<br>CDTMNSLTLPSEINLCNVDIFNPKYDCKIMTSKTDVSSS<br>VITSLGAIVSCYGKTKCTASNKNRGIIKTFSNGCDYVSN<br>KGMDTVSVGNTLYYVNKQEGKSLYVKGEPIINFYDPL<br>VFPS**S**EFDASISQVNEKINQSLAFIRKSDELL |
| 855-GI57185<br>(A) (Ontario) | 75 | QNITEEFYQSTCSAVSKGY<br>LSALRTGWY**H**CVITIELSN<br>IKENKCNGTDAKVKLIKQ<br>ELDKYKNAVTELQLLMQS<br>TPAANSRARR | 76 | FLGFLLGVGSAIASGIAVSKVLHLEGEVNKIKSALLSIN<br>KAVVSLSNGVSV**C**T**I**KVLDLKNYIDKQLLPIVNKQSCSI<br>SNIETVIEFQQKNNRLLEITREFSVNAGVTTPVSTYMLT<br>NSELLSLINDMPITNDQKKLMSSNVQIVRQQSYSIMSII<br>KEEVLAYVVQLPLYGVIDTPCWKLHTSPLCTTNTKEGS<br>NICLTRTDRGWYCDNAGSVSFFPQAETCKVQSNRVFC<br>DTMNSLTLPSEVNLCNIDIFNPKYDCKIMTSKTDVSSSV<br>ITSLGAIVSCYGKTKCTASNKNRGIIKTFSNGCDYVSNK<br>GVDTVSVGNTLYYVNKQEGKSLYVKGEPIINFYDPLVF<br>PS**S**EFDASISQVNEKINQSLAFIRKSDELL |
| 855-GI138250<br>(B) | 77 | QNITEEFYQSTCSAVSRGY<br>FSALRTGWY**H**CVITIELSN<br>IKETKCNGTDTKVKLIKQE<br>LDKYKNAVTELQLLMQN<br>TPAANNRARR | 78 | FLGFLLGVGSAIASGIAVSKVLHLEGEVNKIKNALLSIN<br>KAVVSLSNGVSV**C**T**I**KVLDLKNYINNRLLPIVNQQSCR<br>ISNIETVIEFQQMNSRLLEITREFSVNAGVTTPLSTYMLT<br>NSELLSLINDMPITNDQKKLMSSNVQIVRQQSYSIMSII<br>KEEVLAYVVQLPIYGVIDTPCWKLHTSPLCTTNIKEGS<br>NICLTRTDRGWYCDNAGSVSFFPQADTCKVQSNRVFC<br>DTMNSLTLPSEVSLCNTDIFNSKYDCKIMTSKTDISSSVI<br>TSLGAIVSCYGKTKCTASNKNRGIIKTFSNGCDYVSNK |

TABLE F-continued

Variant of Mutant pXCS855 Comprising Introduced Mutations T54H, S55C, L188C, S190I, D486S

| | F2 Polypeptide | | F1 Polypeptide | |
|---|---|---|---|---|
| | | Amino Acid Sequence | | |
| Mutant ID | SEQ ID | (residues 26-109) | SEQ ID | Amino Acid Sequence (residues 137-513) |
| | | | | GVDTVSVGNTLYYVNKLEGKNLYVKGEPIINYYDPLV<br>FPS**S**EFDASISQVNEKINQSLAFIRRSDELL |
| 855-GI80758<br>(B)<br>(Buenos Aires) | 79 | QNITEEFYQSTCSAVSRGY<br>FSALRTGWY**H**CVITIELSN<br>IKETKCNGTDTKVKLIKQE<br>LDKYKNAVTELQLLMQN<br>TPAANNRARR | 80 | FLGFLLGVGSAIASGIAVSKVLHLEGEVNKIKNALLSIN<br>KAVVSLSNGVSV**C**T**I**KVLDLKNYINNQLLPIVNQQSCR<br>ISNIETVIEFQQKNSRLLEITREFSVNAGVTTPLSTYMLT<br>NSELLSLINDMPITNDQKKLMSSNVQIVRQQSYSIMSII<br>KEEVLAYVVQLPIYGVIDTPCWKLHTSPLCTTNIKEGS<br>NICLTRTDRGWYCDNAGSVSFFPQADTCKVQSNRVFC<br>DININSLTLPSEVSLCNTDIFNSKYDCKIMTSKTDISSSVI<br>TSLGAIVSCYGKTKCTASNKNRGIIKTFSNGCDYVSNK<br>GVDTVSVGNTLYYVNKLEGKNLYVKGEPIINYYDPLV<br>FPS**S**EFDASISQVNEKINQSLAFIRRSDELL |
| 855-AFM55442<br>(A) | 315 | QNITEEFYQSTCSAVSKGY<br>LSALRTGWY**H**CVITIELSN<br>IKENKCNGTDAKVKLIKQ<br>ELDKYKNAVTELQLLMQS<br>TPAANNRARR | 316 | FLGFLLGVGSAIASGIAVSKVLHLEGEVNKIKSALLSIN<br>KAVVSLSNGVSV**C**T**I**KVLDLKNYIDKQLLPIVNKQSCSI<br>SNIETVIEFQQKNNRLLEITREFSVNAGVTTPVSTYMLT<br>NSELLSLINDMPITNDQKKLMSNNVQIVRQQSYSIMSII<br>KEEVLAYVVQLPLYGVIDTPCWKLHTSPLCTTNTKEGS<br>NICLTRTDRGWYCDNAGSVSFFPQAETCKVQSNRVFC<br>DTMNSLTLPSEVNLCNIDIFNPKYDCKIMTSKTDVSSSV<br>ITSLGAIVSCYGKTKCTASNKNRGIIKTFSNGCDYVSNK<br>GVDTVSVGNTLYYVNKQEGKSLYVKGEPIINFYDPLVF<br>PS**S**EFDASISQVNEKINQSLAFIRKSDELL |
| 855-AFM95376<br>(A) | 317 | QNITEEFYQSTCSAVSKGY<br>LSALRTGWY**H**CVITIELSN<br>IKENKCNGTDAKVKLIKQ<br>ELDKYKNAVTELQLLMQS<br>TPAANNRARR | 318 | FLGFLLGVGSAIASGIAVSKVLHLEGEVNKIKSALLSIN<br>KAVVSLSNGVSV**C**T**I**KVLDLKNYIDKQLLPIVNKQSCSI<br>SNIETVIEFQQKNNRLLEITREFSVNAGVTTPVSTYMLT<br>NSELLSLINDMPITNDQKKLMSNNVQIVRQQSYSIMSII<br>KEEVLAYVVQLPLYGVIDTPCWKLHTSPLCTTNTKEGS<br>NICLTRTDRGWYCDNAGSVSFFPQAETCKVQSNRVFC<br>DTMNSLTLPSEVNLCNIDIFNPKYDCKIMTSKTDVSSSV<br>ITSLGAIVSCYGKTKCTASNKNRGIIKTFSNGCDYVSNK<br>GVDTVSVGNTLYYVNKQEGKSLYVKGEPIINFYDPLVF<br>PS**S**EFDASISQVNEKINQSLAFIRKSDELL |
| 855-AEQ63520<br>(A) | 319 | QNITEEFYQSTCSAVSKGY<br>LSALRTGWY**H**CVITIELSN<br>IKENKCNGTDAKVKLIKQ<br>ELDKYKNAVTELQLLMQS<br>TPAANNRARR | 320 | FLGFLLGVGSAIASGIAVSKVLHLEGEVNKIKSALLSIN<br>KAVVSLSNGVSV**C**T**I**KVLDLKNYIDKQLLPIVNKQSCSI<br>SNIETVIEFQQKNNRLLEITREFSVNAGVTTPVSTYMLT<br>NSELLSLINDMPITNDQKKLMSNNVQIVRQQSYSIMSII<br>KEEVLAYVVQLPLYGVIDTPCWKLHTSPLCTTNTKEGS<br>NICLTRTDRGWYCDNAGSVSFFPQAETCKVQSNRVFC<br>DTMNSLTLPSEVNLCNIDIFNPKYDCKIMTSKTDVSSSV<br>ITSLGAIVSCYGKTKCTASNKNRGIIKTFSNGCDYVSNK<br>GVDTVSVGNTLYYVNKQEGKSLYVKGEPIINFYDPLVF<br>PS**S**EFDASISQVNEKINQSLAFIRKSDELL |
| 855-AFD34260<br>(B) | 321 | QNITEEFYQSTCSAVSRGY<br>FSALRTGWY**H**CVITIELSN<br>IKETKCNGTDTKVKLIKQE<br>LDKYKNAVTELQLLMQN<br>TPAANNRARR | 322 | FLGFLLGVGSAIASGIAVSKVLHLEGEVNKIKNALLSIN<br>KAVVSLSNGVSV**C**T**I**KVLDLKNYINNQLLPIVNKQSCR<br>ISNIETVIEFQQKNSRLLEITREFSVNAGVTTPLSTYMLT<br>NSELLSLINDMPITNDQKKLMSSNVQIVRQQSYSIMSII<br>KEEVLAYVVQLPIYGVIDTPCWKLHTSPLCTTNIKEGS<br>NICLTRTDRGWYCDNAGSVSFFPQADTCKVQSNRVFC<br>DTMNSLTLPSEVSLCNTDIFNSKYDCKIMTSKTDVSSSV<br>ITSLGAIVSCYGKTKCTASNKNRGIIKTFSNGCDYVSNK<br>GVDTVSVGNTLYYVNKLEGKNLYVKGEPIINYYDPLV<br>FPS**S**EFDASISQVNEKINQSLAFIRRSDELL |
| 855-BAE96918<br>(B) | 323 | QNITEEFYQSTCSAVSRGY<br>FSALRTGWY**H**CVITIELSN<br>IKETKCNGTDTKVKLIKQE<br>LDKYKNAVTELQLLMQN<br>TPAANNRARR | 324 | FLGFLLGVGSAIASGIAVSKVLHLEGEVNKIKNALLSIN<br>KAVVSLSNGVSV**C**T**I**KVLDLKNYINNQLLPIVNQQSCR<br>ISNIETVIEFQQKNSRLLEITREFSVNAGVTTPLSTYMLT<br>NSELLSLINDMPITNDQKKLMSSNVQIVRQQSYSIMSIM<br>KEEVLAYVVQLPIYGVIDTPCWKLHTSPLCTTNIKEGS<br>NICLTRTDRGWYCDNAGSVSFFPQADTCKVQSNRVFC<br>DTMNSLTLPSEVSLCNTDIFNSKYDCKIMTSKTDISSSVI<br>TSLGAIVSCYGKTKCIASNKNRGIIKTFSNGCDYVSNK<br>GVDTVSVGNTLYYVNKLEGKNLYVKGEPIINYYDPLV<br>FPS**S**EFDASISQVNEKINQSLAFIRRSDELL |
| 855-AFD34265<br>(B) | 325 | QNITEEFYQSTCSAVSRGY<br>LSALRTGWY**H**CVITIELSN<br>IKETKCNGTDTKVKLIKQE | 326 | FLGFLLGVGSAIASGIAVSKVLHLEGEVNKIKNALLSIN<br>KAVVSLSNGVSV**C**T**I**KVLDLKNYINNQLLPIVNQQSCR<br>ISNIETVIEFQQKNSRLLEIAREFSVNAGVTTPLSTYMLT |

TABLE F-continued

| Variant of Mutant pXCS855 Comprising Introduced Mutations T54H, S55C, L188C, S190I, D486S | | | | |
|---|---|---|---|---|
| | F2 Polypeptide | | F1 Polypeptide | |
| Mutant ID | SEQ ID | Amino Acid Sequence (residues 26-109) | SEQ ID | Amino Acid Sequence (residues 137-513) |
| | | LDKYKNAVTELQLLMQN<br>TPAANNRARR | | NSELLSLINDMPITNDQKKLMSSNVQIVRQQSYSIMSII<br>KEEVLAYVVQLPIYGVIDTPCWKLHTSPLCTTNIKEGS<br>NICLTRTDRGWYCDNAGSVSFFPQADTCKVQSNRVFC<br>DTMNSLTLPSEVSLCNTDIFNSKYDCKIMTSKTDISSSVI<br>TSLGAIVSCYGKTKCIASNKNRGIIKTFSNGCDYVSNK<br>GVDTVSVGNTLYYVNKLEGKNLYVKGEPIINYYDPLV<br>FPS**S**EFDASISQVNEKINQSLAFIRRSDELL |

TABLE G

| Sequence Index | |
|---|---|
| SEQ ID NO | Description |
| 1, 4, 81-210 | Amino acid sequence of F0 precursor polypeptide of representative RSV subtype A |
| 2, 6, 211-263 | Amino acid sequence of F0 precursor polypeptide of representative RSV subtype B |
| 264-270 | Amino acid sequence of F0 precursor polypeptide of representative bovine RSV |
| 3 | Amino acid sequence of the ectodomain (with foldon) of RSV A2, |
| 5 | Amino acid sequence of the ectodomain (with foldon) of RSV A (Ontario) |
| 7 | Amino acid sequence of the ectodomain (with foldon) of a RSV B strain |
| 8-18 | Nucleotide sequence encoding the precursor polypeptide of representative RSV F mutants |
| 19-21, 32-39, 271-278 | Amino acid sequence of F precursor polypeptide of representative RSV F mutants |
| 22-31 | Amino acid sequences of the light chain variable domain and heavy chain variable domain of RSV F antibodies |
| 40 | Amino acid sequence of T4 Fibritin foldon |
| 41-80, 279-326 | Amino acid sequence of F2 polypeptide and F1 polypeptide of representative RSV F mutants |

F. EXAMPLES

The invention is further described by the following illustrative examples. The examples do not limit the invention in any way. They merely serve to clarify the invention.

Example 1: Design and Preparation of RSV F Protein Mutants

1A: RSV F Mutants with Foldon Domain

This example illustrates the design and preparation of various RSV F protein mutants, which include a fibritin foldon trimerization domain and introduced amino acid mutations, such as engineered disulfide bond mutations, cavity-filling mutations, electrostatic mutations, or a combination thereof. Exemplary RSV F mutants, each of which is identified by an unique identifier, such as pXCS501, pXCS601, etc., are provided in Tables 1-6. Each of these mutants was designed and prepared based on the amino acid sequence set forth in SEQ ID NO:3, which is also illustrated in FIG. 1. Amino acid residues 1-513 of the sequence of SEQ ID NO:3 are identical to amino acid residues 1-513 of the F0 precursor polypeptide of native RSV A2 as set forth in SEQ ID NO:1, except for the three naturally occurring substitutions, P102A, I379V and M447V, in the sequence of SEQ ID NO:3. Therefore, the amino acid sequences of these exemplary F mutants are identical except for the introduced amino acid mutations as noted for each mutant listed in Tables 1-6. Each of these RSV F protein mutants comprises two separate polypeptide chains. One of the polypeptide chains, the F2 polypeptide, comprises amino acids 26-109 of SEQ ID NO:3 except for the introduced mutations as noted. The other polypeptide chain comprises the F1 polypeptide (residues 137-513) linked to a foldon trimerization domain (residues 518-544) via a SAIG linker (residues 514-517). The signal peptide (residues 1-25) and pep27 (residues 110-136) of SEQ ID NO:3 were cleaved from the F0 precursor during the expression process. The process for expression and purification of these exemplary RSV F mutants is described in Examples 2 and 3.

1B: RSV F Mutants without Foldon Domain

RSV F mutant, pXCS899, which was devoid of foldon domain, was prepared in the same method described in Example 1A above, except that amino acids 514-544 of the F0 precursor sequence of SEQ ID NO:3 were deleted. The amino acid sequence of the precursor polypeptide of pXCS899 is set forth in SEQ ID NO:271.

TABLE 1

| Exemplary RSV F Protein Mutants Comprising Engineered Disulfide Mutations | |
|---|---|
| Mutant ID | Mutations |
| pXCS501 | I28C, G464C |
| pXCS502 | E30C, S466C |
| pXCS503 | Q34C, G471C |
| pXCS504 | S35C, G471C |
| pXCS505 | W52C, S150C |
| pXCS506 | T54C, G151C |
| pXCS507 | S55C, L188C |
| pXCS508 | V56C, V187C |
| pXCS509 | V56C, T189C |
| pXCS510 | I57C, S190C |
| pXCS511 | T58C, K191C |
| pXCS512 | I59C, L193C |
| pXCS513 | E60C, K196C |
| pXCS514 | L61C, L195C |
| pXCS515 | S62C, K196C |
| pXCS516 | S62C, I199C |
| pXCS518 | T103C, A147C |
| pXCS519 | T103C, I148C |
| pXCS520 | R106C, V144C |
| pXCS521 | L138C, T337C |
| pXCS522 | G139C, P353C |
| pXCS523 | G139C, Q354C |
| pXCS524 | L142C, N371C |
| pXCS525 | G145C, M370C |
| pXCS526 | I148C, Y286C |
| pXCS527 | G151C, V300C |

TABLE 1-continued

Exemplary RSV F Protein Mutants Comprising Engineered Disulfide Mutations

| Mutant ID | Mutations |
|---|---|
| pXCS528 | G151C, Q302C |
| pXCS529 | V154C, V300C |
| pXCS531 | S155C, V300C |
| pXCS532 | L158C, S290C |
| pXCS534 | V164C, K293C |
| pXCS535 | V164C, E294C |
| pXCS536 | T397C, P484C |
| pXCS537 | T397C, E487C |
| pXCS538 | K399C, S485C |
| pXCS539 | L410C, G464C |
| pXCS540 | L410C, S466C |
| pXCS541 | S443C, S466C |
| pXCS542 | L138C, P353C |
| pXCS543 | G151C, I288C |
| pXCS544 | S155C, S290C |
| pXCS545 | S155C, S290C; I28C, G464C |
| pXCS546 | S155C, S290C; E30C, S466C |
| pXCS547 | S155C, S290C; Q34C, G471C |
| pXCS548 | S155C, S290C; S35C, G471C |
| pXCS549 | S155C, S290C; T397C, P484C |
| pXCS550 | S155C, S290C; T397C, E487C |
| pXCS551 | S155C, S290C; K399C, S485C |
| pXCS553 | S155C, S290C; L410C, S466C |
| pXCS554 | S155C, S290C; S443C, S466C |
| pXCS556 | R106C, V144C; S443C, S466C |
| pXCS557 | R106C, V144C; L142C, N371C |
| pXCS558 | R106C, V144C; T397C, P484C |
| pXCS596 | S55C, L188C; T103C, I148C |
| pXCS597 | S55C, L188C; R106C, V1440C |
| pXCS598 | S55C, L188C; L142C, N371C |
| pXCS599 | S55C, L188C; T397C, P484C |
| pXCS600 | S55C, L188C; Q34C, G471C |
| pXCS601 | S55C, L188C; T397C, E487C |
| pXCS602 | S55C, L188C; S443C, S466C |
| pXCS603 | S55C, L188C; L410C, S466C |
| pXCS604 | S55C, L188C; S35C, G471C |
| pXCS605 | S55C, L188C; S62C, I199C |
| pXCS606 | T103C, I148C; Q34C, G471C |
| pXCS607 | T103C, I148C; S35C, G471C |
| pXCS608 | T103C, I148C; S62C, I199C |
| pXCS609 | T103C, I148C; L142C, N371C |
| pXCS610 | T103C, I148C; T397C, P484C |
| pXCS611 | T103C, I148C; T397C, E487C |
| pXCS612 | T103C, I148C; L410C, S466C |
| pXCS613 | T103C, I148C; S443C, S466C |
| pXCS614 | Q34C, G471C; S62C, I199C |
| pXCS615 | Q34C, G471C; R106C, V144C |
| pXCS616 | Q34C, G471C; L138C, T337C |
| pXCS617 | Q34C, G471C; L142C, N371C |
| pXCS618 | L142C, N371C; S35C, G471C |
| pXCS619 | L142C, N371C; S62C, I199C |
| pXCS620 | L142C, N371C; S155C, S290C |
| pXCS621 | L142C, N371C; T397C, P484C |
| pXCS622 | L142C, N371C; T397C, E487C |
| pXCS623 | L142C, N371C; L410C, S466C |
| pXCS624 | L142C, N371C; S443C, S466C |
| pXCS625 | R106C, V144C; S62C, I199C |
| pXCS626 | R106C, V144C; T397C, E487C |
| pXCS627 | R106C, V144C; L410C, S466C |
| pXCS628 | S55C, L188C; L138C, T337C |
| pXCS629 | S55C, L188C; G145C, M370C |
| pXCS630 | T103C, I148C; L138C, T337C |
| pXCS712 | S55C, L188C; R106C, V144C; L142C, N371C |
| pXCS517 | S62C, D200C |
| pXCS530 | S155C, I288C |
| pXCS533 | L158C, I291C |
| pXCS552 | S155C, S290C; L410C, G464C |
| pXCS555 | S155C, S290C; R106C, V144C |

TABLE 2

Exemplary RSV F Protein Mutants Comprising Cavity Filling Mutations

| Mutant ID | Mutations |
|---|---|
| pXCS559 | S55I |
| pXCS560 | S55Y |
| pXCS561 | S62L |
| pXCS562 | S62Y |
| pXCS563 | S155H |
| pXCS564 | S155Y |
| pXCS565 | S190I |
| pXCS566 | S190M |
| pXCS567 | S190Y |
| pXCS568 | S290H |
| pXCS569 | S290M |
| pXCS570 | S290Y |
| pXCS571 | T54H |
| pXCS572 | T54I |
| pXCS573 | T58L |
| pXCS574 | T58M |
| pXCS575 | T189I |
| pXCS577 | T219I |
| pXCS578 | T219M |
| pXCS579 | T397I |
| pXCS580 | T397Y |
| pXCS581 | G151A |
| pXCS582 | G151H |
| pXCS583 | A147H |
| pXCS584 | A147I |
| pXCS585 | A298L |
| pXCS586 | A298M |
| pXCS587 | V164I |
| pXCS588 | V187I |
| pXCS589 | V192H |
| pXCS590 | V207I |
| pXCS591 | V220I |
| pXCS592 | V296I |
| pXCS593 | V300I |
| pXCS594 | V495Y |
| pXCS595 | R106W |
| pXCS666 | S190F, V207L |
| pXCS691 | V495Y, S62L |
| pXCS692 | V495Y, T219M |
| pXCS693 | V495Y, T54H |
| pXCS694 | V495Y, T58L |
| pXCS695 | V495Y, V164I |
| pXCS696 | V495Y, V187I |
| pXCS697 | V495Y, V296I |
| pXCS698 | V296I, S62L |
| pXCS699 | V296I, T219M |
| pXCS700 | V296I, T54H |
| pXCS701 | T54H, S62L |
| pXCS702 | T54H, T219M |
| pXCS711 | F488W |
| pXCS576 | T189Y |

TABLE 3

Exemplary RSV F Protein Mutants Comprising Electrostatic Mutations

| Mutant ID | Mutations |
|---|---|
| pXCS631 | E82Q |
| pXCS632 | E82S |
| pXCS633 | E82L |
| pXCS634 | E92D |
| pXCS635 | E92T |
| pXCS636 | E92Q |
| pXCS637 | E92F |
| pXCS638 | R106Q |
| pXCS639 | R106N |
| pXCS640 | R106F |
| pXCS641 | K315F |
| pXCS642 | K315L |
| pXCS643 | K315I |

TABLE 3-continued

Exemplary RSV F Protein Mutants Comprising Electrostatic Mutations

| Mutant ID | Mutations |
|---|---|
| pXCS644 | K315Q |
| pXCS645 | R339Q |
| pXCS646 | R339W |
| pXCS647 | R339F |
| pXCS648 | D392N |
| pXCS649 | D392S |
| pXCS650 | D392P |
| pXCS651 | K394M |
| pXCS652 | K394T |
| pXCS653 | K394F |
| pXCS654 | K399R |
| pXCS655 | K399M |
| pXCS656 | K399S |
| pXCS657 | D486H |
| pXCS658 | D486S |
| pXCS659 | D486T |
| pXCS660 | E487Q |
| pXCS661 | E487H |
| pXCS662 | E487D |
| pXCS663 | D489H |
| pXCS664 | D489S |
| pXCS665 | D489N |

TABLE 4

Exemplary RSV F Protein Mutants Comprising Engineered Disulfide Mutations and Cavity Filling Mutations

| Mutant ID | Mutations |
|---|---|
| pXCS667 | R106C-V144C; S443C-S466C; S55I |
| pXCS668 | R106C-V144C; L142C-N371C; S55I |
| pXCS669 | R106C-V144C; T397C-P484C; S55I |
| pXCS670 | R106C-V144C; S443C-S466C; T54H |
| pXCS671 | R106C-V144C; L142C-N371C; T54H |
| pXCS672 | R106C-V144C; T397C-P484C; T54H |
| pXCS674 | R106C-V144C; L142C-N371C; T54H, S190Y |
| pXCS679 | S62C-I199C; L142C-N371C; S55I |
| pXCS680 | S62C-I199C; L142C-N371C; T54H |
| pXCS683 | Q34C-G471C; L142C-N371C; S62L |
| pXCS684 | Q34C-G471C; L142C-N371C; T219M |
| pXCS685 | Q34C-G471C; L142C-N371C; T54H |
| pXCS686 | Q34C-G471C; L142C-N371C; V164I |
| pXCS687 | Q34C-G471C; L142C-N371C; V187I |
| pXCS688 | Q34C-G471C; L142C-N371C; V296I |
| pXCS689 | Q34C-G471C; L142C-N371C; T397Y |
| pXCS690 | Q34C-G471C; L142C-N371C; V495Y |
| pXCS713 | Q34C-G471C; S155C-S290C; T54H |
| pXCS714 | Q34C-G471C; S155C-S290C; V296I |
| pXCS715 | Q34C-G471C; S155C-S290C; V495Y |
| pXCS716 | Q34C-G471C; S155C-S290C; T54H, V495Y |
| pXCS717 | Q34C-G471C; S155C-S290C; T54H, V296I |
| pXCS718 | Q34C-G471C; S155C-S290C; T54H, V296I, V495Y |
| pXCS719 | Q34C-G471C; S155C-S290C; S190I |
| pXCS720 | S155C-S290C; L410C-S466C; T54H |
| pXCS721 | S155C-S290C; L410C-S466C; V296I |
| pXCS722 | S155C-S290C; L410C-S466C; V495Y |
| pXCS723 | S155C-S290C; L410C-5466C; T54H, V495Y |
| pXCS724 | S155C-S290C; L410C-5466C; T54H, V296I |
| pXCS725 | S155C-S290C; L410C-S466C; T54H, V296I, V495Y |
| pXCS726 | S155C-S290C; L410C-S466C; S190I |
| pXCS727 | R106C-V144C; L142C-N371C; T54H |
| pXCS728 | R106C-V144C; L142C-N371C; V296I |
| pXCS729 | R106C-V144C; L142C-N371C; V495Y |
| pXCS730 | R106C-V144C; L142C-N371C; T54H, V495Y |
| pXCS731 | R106C-V144C; L142C-N371C; T54H, V296I |
| pXCS732 | R106C-V144C; L142C-N371C; T54H, V296I, V495Y |
| pXCS733 | R106C-V144C; L142C-N371C; S190I |
| pXCS734 | S55C-L188C; L142C-N371C; T54H |
| pXCS735 | S55C-L188C; L142C-N371C; V296I |
| pXCS736 | S55C-L188C; L142C-N371C; V495Y |
| pXCS737 | S55C-L188C; L142C-N371C; T54H, V495Y |

TABLE 4-continued

Exemplary RSV F Protein Mutants Comprising Engineered Disulfide Mutations and Cavity Filling Mutations

| Mutant ID | Mutations |
|---|---|
| pXCS738 | S55C-L188C; L142C-N371C; T54H, V296I |
| pXCS739 | S55C-L188C; L142C-N371C; T54H, V296I, V495Y |
| pXCS740 | S55C-L188C; L142C-N371C; S190I |
| pXCS741 | Q34C-G471C; S55C-L188C; T54H |
| pXCS742 | Q34C-G471C; S55C-L188C; V296I |
| pXCS743 | Q34C-G471C; S55C-L188C; V495Y |
| pXCS744 | Q34C-G471C; S55C-L188C; T54H, V495Y |
| pXCS745 | Q34C-G471C; S55C-L188C; T54H, V296I |
| pXCS746 | Q34C-G471C; S55C-L188C; T54H, V296I, V495Y |
| pXCS747 | Q34C-G471C; S55C-L188C; S190I |
| pXCS748 | T103C-I148C; T54H |
| pXCS749 | T103C-I148C; V296I |
| pXCS750 | T103C-I148C; V495Y |
| pXCS751 | T103C-I148C; T54H, V495Y |
| pXCS752 | T103C-I148C; T54H, V296I |
| pXCS753 | T103C-I148C; T54H, V296I, V495Y |
| pXCS754 | T103C-I148C; S190I |
| pXCS781 | S55C-L188C; T54H |
| pXCS782 | S55C-L188C; V296I |
| pXCS783 | S55C-L188C; V495Y |
| pXCS784 | S55C-L188C; T54H, V495Y |
| pXCS785 | S55C-L188C; T54H, V296I |
| pXCS786 | S55C-L188C; T54H, V296I, V495Y |
| pXCS787 | S55C-L188C; S190I |
| pXCS789 | R106C-V144C; T54H |
| pXCS790 | R106C-V144C; V296I |
| pXCS791 | R106C-V144C; V495Y |
| pXCS792 | R106C-V144C; T54H, V495Y |
| pXCS793 | R106C-V144C; T54H, V296I |
| pXCS794 | R106C-V144C; T54H, V296I, V495Y |
| pXCS795 | R106C-V144C; S190I |
| pXCS797 | L142C-N371C; T54H |
| pXCS798 | L142C-N371C; V296I |
| pXCS799 | L142C-N371C; V495Y |
| pXCS800 | L142C-N371C; T54H, V495Y |
| pXCS801 | L142C-N371C; T54H, V296I |
| pXCS802 | L142C-N371C; T54H, V296I, V495Y |
| pXCS803 | L142C-N371C; S190I |
| pXCS805 | S155C-S290C; T54H |
| pXCS806 | S155C-S290C; V296I |
| pXCS807 | S155C-S290C; V495Y |
| pXCS808 | S155C-S290C; T54H, V495Y |
| pXCS809 | S155C-S290C; T54H, V296I |
| pXCS810 | S155C-S290C; T54H, V296I, V495Y |
| pXCS811 | S155C-S290C; S190I |
| pXCS812 | Q34C-G471C; S155C-S290C; T54H, S190I |
| pXCS815 | S155C-S290C; L410C-S466C; T54H, S190I |
| pXCS818 | R106C-V144C; L142C-N371C; T54H, S190I |
| pXCS821 | S55C-L188C; L142C-N371C; T54H, S190I |
| pXCS827 | T103C-I148C; T54H, S190I |
| pXCS828 | T103C-I148C; S190I, V495Y |
| pXCS830 | S55C-L188C; T54H, S190I |
| pXCS831 | S55C-L188C; S190I, V495Y |
| pXCS833 | R106C-V144C; T54H, S190I |
| pXCS834 | R106C-V144C; S190I, V495Y |
| pXCS836 | L142C-N371C; T54H, S190I |
| pXCS837 | L142C-N371C; S190I, V495Y |
| pXCS839 | S155C-S290C; T54H, S190I |
| pXCS840 | S155C-S290C; S190I, V495Y |
| pXCS889 | T103C-I148C; S190I, V296I |
| pXCS890 | T103C-I148C; T54H, S190I, V296I |
| pXCS891 | S55C-L188C; S190I, V296I |
| pXCS892 | S55C-L188C; T54H, S190I, V296I |
| pXCS893 | R106C-V144C; S190I, V296I |
| pXCS894 | R106C-V144C; T54H, S190I, V296I |
| pXCS895 | L142C-N371C; S190I, V296I |
| pXCS896 | L142C-N371C; T54H, S190I, V296I |
| pXCS897 | S155C-S290C; S190I, V296I |
| pXCS898 | S155C-S290C; T54H, S190I, V296I |

TABLE 5

Exemplary RSV F Protein Mutants Comprising Engineered Disulfide Mutations and Electrostatic Mutations.

| Mutant ID | Mutations |
|---|---|
| pXCS755 | Q34C-G471C; S155C-S290C; D486S |
| pXCS756 | S155C-S290C; L410C-S466C; D486S |
| pXCS757 | R106C-V144C; L142C-N371C; D486S |
| pXCS758 | S55C-L188C; L142C-N371C; D486S |
| pXCS759 | Q34C-G471C; S55C-L188C; D486S |
| pXCS760 | T103C-I148C; D486S |
| pXCS770 | Q34C-G471C; S155C-S290C; D486S, E487Q |
| pXCS771 | Q34C-G471C; S155C-S290C; D486S, D489S |
| pXCS772 | Q34C-G471C; S155C-S290C; D486S, E487Q, D489S |
| pXCS776 | T103C-I148C; D486S, E487Q |
| pXCS777 | T103C-I148C; D486S, D489S |
| pXCS778 | T103C-I148C; D486S, E487Q, D489S |
| pXCS779 | T103C-I148C; E92D |
| pXCS780 | S55C-L188C; D486S |
| pXCS788 | R106C-V144C; D486S |
| pXCS796 | L142C-N371C; D486S |
| pXCS804 | S155C-S290C; D486S |
| pXCS883 | S55C-L188C; L142C-N371C; D486S, E487Q |
| pXCS884 | S55C-L188C; L142C-N371C; D486S, D489S |
| pXCS885 | S55C-L188C; L142C-N371C; D486S, E487Q, D489S |

TABLE 6

Exemplary RSV F Protein Mutants Comprising a Combination of Engineered Disulfide Mutations, Cavity Filling Mutations, and Electrostatic Mutations.

| Mutant ID | Mutations |
|---|---|
| pXCS761 | Q34C-G471C; S155C-S290C; T54H, D486S, E487Q, D489S, V495Y |
| pXCS762 | Q34C-G471C; S155C-S290C; T54H, V296I, D486S, E487Q, D489S |
| pXCS763 | Q34C-G471C; S155C-S290C; T54H, V296I, D486S, E487Q, D489S, V495Y |
| pXCS764 | Q34C-G471C; S55C-L188C; T54H, D486S, E487Q, D489S, V495Y |
| pXCS765 | Q34C-G471C; S55C-L188C; T54H, V296I, D486S, E487Q, D489S |
| pXCS766 | Q34C-G471C; S55C-L188C; T54H, V296I, D486S, E487Q, D489S, V495Y |
| pXCS767 | R106C-V144C; L142C-N371C; T54H, D486S, E487Q, D489S, V495Y |
| pXCS768 | R106C-V144C; L142C-N371C; T54H, V296I, D486S, E487Q, D489S |
| pXCS769 | R106C-V144C; L142C-N371C; T54H, V296I, D486S, E487Q, D489S, V495Y |
| pXCS773 | T103C-I148C; T54H, D486S, E487Q, D489S, V495Y |
| pXCS774 | T103C-I148C; T54H, V296I, D486S, E487Q, D489S |
| pXCS775 | T103C-I148C; T54H, V296I, D486S, E487Q, D489S, V495Y |
| pXCS842 | T103C-I148C; T54H, S190I, D486S |
| pXCS843 | T103C-I148C; S190I, D486S, V495Y |
| pXCS844 | T103C-I148C; T54H, S190I, D486S, V495Y |
| pXCS845 | T103C-I148C; T54H, D486S |
| pXCS846 | T103C-I148C; D486S, V495Y |
| pXCS847 | T103C-I148C; S190I, D486S |
| pXCS848 | T103C-I148C; V296I, D486S |
| pXCS849 | T103C-I148C; T54H, V296I, D486S |
| pXCS850 | T103C-I148C; S190I, V296I, D486S |
| pXCS851 | T103C-I148C; T54H, S190I, V296I, D486S |
| pXCS852 | S55C-L188C; T54H, D486S |
| pXCS853 | S55C-L188C; S190I, D486S |
| pXCS854 | S55C-L188C; V296I, D486S |
| pXCS855 | S55C-L188C; T54H, S190I, D486S |
| pXCS856 | S55C-L188C; T54H, V296I, D486S |
| pXCS857 | S55C-L188C; S190I, V296I, D486S |
| pXCS858 | S55C-L188C; T54H, S190I, V296I, D486S |
| pXCS859 | R106C-V144C; T54H, D486S |
| pXCS860 | R106C-V144C; S190I, D486S |
| pXCS861 | R106C-V144C; V296I, D486S |
| pXCS862 | R106C-V144C; T54H, S190I, D486S |
| pXCS863 | R106C-V144C; T54H, V296I, D486S |
| pXCS864 | R106C-V144C; S190I, V296I, D486S |
| pXCS865 | R106C-V144C; T54H, S190I, V296I, D486S |
| pXCS866 | L142C-N371C; T54H, D486S |
| pXCS867 | L142C-N371C; S190I, D486S |
| pXCS868 | L142C-N371C; V296I, D486S |
| pXCS869 | L142C-N371C; T54H, S190I, D486S |
| pXCS870 | L142C-N371C; T54H, V296I, D486S |
| pXCS871 | L142C-N371C; S190I, V296I, D486S |
| pXCS872 | L142C-N371C; T54H, S190I, V296I, D486S |
| pXCS873 | S155C-S290C; T54H, D486S |
| pXCS874 | S155C-S290C; S190I, D486S |
| pXCS875 | S155C-S290C; V296I, D486S |
| pXCS876 | S155C-S290C; T54H, S190I, D486S |
| pXCS877 | S155C-S290C; T54H, V296I, D486S |
| pXCS878 | S155C-S290C; S190I, V296I, D486S |
| pXCS879 | S155C-S290C; T54H, S190I, V296I, D486S |
| pXCS880 | S55C-L188C; L142C-N371C; T54H, S190I, D486S, E487Q, D489S |
| pXCS881 | S55C-L188C; L142C-N371C; T54H, V296I, D486S, E487Q, D489S |
| pXCS882 | S55C-L188C; L142C-N371C; T54H, S190I, V296I, D486S, E487Q, D489S |
| pXCS886 | T103C-I148C; T54H, S190I, D486S, E487Q, D489S |
| pXCS888 | T103C-I148C; T54H, S190I, V296I, D486S, E487Q, D489S |

Example 2. RSV F Mutant Expression Vector Construction

A nucleic acid molecule encoding the native RSV A2 F0 polypeptide set forth in SEQ ID NO:1 having the naturally-occurring substitutions P102A, I379V and M447V was mutated using standard molecular biology techniques to encode a precursor polypeptide for a RSV F mutant having desired introduced amino acid mutations. The structure and components of the precursor polypeptide are set forth in FIG. 1 and SEQ ID NO:3. The precursor polypeptide comprises a signal peptide (residues 1-25), F2 polypeptide (residues 26-109), pep27 polypeptide (residues 110-136), F1 polypeptide (residues 137-513), T4 fibritin foldon (residues 518-544), thrombin recognition sequence (547-552), purification tags (HIS-tag (residues 553-558)), Strep tag II (residues 561-568), and linker sequences (residues 514-517, 545, 546, 559, and 560).

The protein sequence of SEQ ID NO:3 was submitted for mammalian codon optimization and synthesis by DNA2.0 (Menlo Park, CA). The synthesized gene product was introduced into a commercially available expression vector, pcDNA3.1/Zeo(+) (ThermoFisher Scientific, Waltham, MA) that had been modified to encode kanamycin resistance instead of ampicillin resistance and to encode the CAG promoter [Niwa, H., Yamamura, K., & Miyazaki, J., Efficient selection for high-expression transfectants with a novel eukaryotic vector. Gene, 108(2), 193-199, 1991] in place of the CMV promoter. Mutagenic oligonucleotides were designed with the QuikChange Primer Design algorithm (Agilent Technologies, Santa Clara, CA), and all oligonucleotides were purchased from Integrated DNA Technologies (Coralville, IA). Nucleotide substitutions, insertions, and deletions were incorporated with the QuikChange Lightning Multi Site-Directed Mutagenesis Kit (Agilent Technologies). Following digestion of the original plasmid template with DpnI, the mutagenized F allele was re-amplified by polymerase chain reaction (PCR) with high-fidelity Q5 DNA polymerase (New England Biolabs, Ipswich, MA) or PrimeSTAR HS (Premix) DNA polymerase (Takara/Clontech, Mountain View, CA), and the resulting product was inserted into a mammalian expression vector with the NEBuilder HiFi DNA Assembly Kit (New England Biolabs) or with Gibson Assembly Master Mix (New England Biolabs). The presence of the intended sequence was confirmed by DNA sequencing. Plasmid DNA for transfection into Expi293 cells was purified with the QIAprep Spin MiniPrep Kit (Qiagen, Valencia, CA), or with the EndoFree Plasmid Mega Kit (Qiagen). For all commercial kits or reagents, procedures were performed according to the manufacturer's protocol.

Example 3. Expression and Purification of RSV F Protein Mutants

Protein for RSV F protein mutant evaluation was produced by transient transfection of Expi293F cells (ThermoFisher, Waltham, MA) with DNA constructs assembled and prepared as described in Example 2. Transient transfections were carried out according to the manufacturer's protocol.

Clarified cell culture was concentrated 5-10 fold using tangential flow filtration, followed by buffer exchange into a buffer suitable for capture on a Ni-IMAC column. The conditioned cell culture medium containing soluble F protein was loaded onto a Ni-IMAC column. The product was eluted using increasing concentrations of imidazole. The fractions containing product were pooled and then loaded on a Strep-Tactin column (IBA Life Sciences, Goettingen, Germany). The product was eluted from the Strep-Tactin column using increasing concentrations of desthiobiotin. Fractions containing product were pooled and dialysed into the final storage buffer. The crude culture supernatants and purified proteins were used for in vitro and in vivo assays described herein.

Example 4: Stability of RSV F Protein Mutants

The stability of the designed RSV F protein mutants was evaluated by stress testing and storage stability experiments. During thermal stress testing, crude culture supernatants of the designed mutants were incubated for 1 hour at 50° C. or 60° C. and probed with the pre-fusion specific monoclonal antibody D25 and the pre-fusion trimer-specific antibody AM14 in ELISA assays. The ratio of the antibody reactivity of the stressed versus unstressed sample is defined as the stress resistance parameter. More stable mutants are expected to have higher stress resistance. During storage stability assays, pre-fusion antibody reactivity in crude culture supernatants after 1 week of storage at 4° C. was compared to the reactivity of the fresh culture supernatants. The activity ratio is defined as storage stability of the mutant.

Results are presented in Tables 7A-7C and 8A-8C. Stress resistance was calculated as fractional pre-fusion specific mAb reactivity remaining after stress ("NR"—No Reactivity was detected, "ND"—Not Determined). The most stabilizing amino acid substitutions identified from screens of the individual engineered disulfide mutants, cavity filling mutants and electrostatic mutants (pre-fusion stability defined by D25 reactivity remaining after thermal stress) were combined into the combination mutants. These combination mutants were also subjected to the thermal stress and probed with two monoclonal antibodies—D25 (pre-fusion-specific) and AM14 (pre-fusion trimer-specific). The pre-fusion trimer-specific quaternary epitope recognized by the AM14 antibody is significantly more sensitive to thermal stress than the D25 epitope (Table 8B). No significant AM14 reactivity was retained after 60° C. stress by any of the combination mutants, yet most of the mutants retained D25 reactivity after the 60° C. thermal stress. This observation provides important evidence that the AM14 antibody is a much more precise indicator of pre-fusion structure loss, and particularly loss of the pre-fusion trimeric state.

TABLE 7A

Thermal and storage stability for mutants containing engineered disulfides

| Mutant ID | 50° C. stress resistance, D25 | 60° C. stress resistance, D25 | Storage stability |
|---|---|---|---|
| pXCS507 | 0.45 ± 0.09 | <0.05 | 0.58 |
| pXCS519 | 1.07 ± 0.18 | NR | 0.75 |
| pXCS524 | 0.64 ± 0.08 | NR | 1.00 |
| pXCS544 | 0.52 ± 0.04 | NR | 0.76 |
| pXCS545 | 0.97 ± 0.12 | 0.52 ± 0.13 | low expression |
| pXCS546 | 1.11 ± 0.09 | 0.43 ± 0.09 | low expression |
| pXCS547 | 1.00 ± 0.04 | 0.49 ± 0.11 | 0.96 |
| pXCS548 | 1.04 ± 0.08 | 0.45 ± 0.10 | low expression |
| pXCS549 | 0.66 ± 0.09 | 0.24 ± 0.07 | 1.03 |
| pXCS550 | 0.83 ± 0.02 | 0.19 ± 0.04 | 1.06 |
| pXCS551 | 0.72 ± 0.08 | NR | low expression |
| pXCS553 | 1.12 ± 0.08 | 0.33 ± 0.03 | 1.31 |
| pXCS554 | 2.08 ± 0.19 | 0.41 ± 0.08 | low expression |
| pXCS596 | 0.86 ± 0.09 | 0.02 | 0.80 |
| pXCS597 | 0.50 ± 0.05 | 0.05 | 1.07 |
| pXCS598 | 0.75 ± 0.03 | 0.13 ± 0.03 | 1.09 |
| pXCS599 | 0.68 ± 0.10 | 0.02 | 0.95 |
| pXCS600 | 0.87 ± 0.09 | 0.15 ± 0.04 | 0.90 |
| pXCS601 | 0.71 ± 0.08 | 0.04 | 0.57 |
| pXCS602 | 0.75 ± 0.03 | 0.06 ± 0.01 | 0.58 |
| pXCS603 | 0.67 ± 0.06 | 0.12 ± 0.02 | 0.40 |
| pXCS604 | 0.74 ± 0.03 | ND | low expression |
| pXCS605 | 0.71 ± 0.04 | 0.16 ± 0.03 | 0.00 |
| pXCS606 | 0.76 ± 0.06 | NR | low expression |
| pXCS607 | NR | NR | low expression |
| pXCS608 | 0.62 ± 0.14 | NR | 0.00 |
| pXCS609 | 0.76 ± 0.08 | 0.08 ± 0.01 | 0.28 |
| pXCS610 | 0.34 ± 0.06 | NR | 0.00 |
| pXCS611 | 0.35 ± 0.11 | NR | low expression |
| pXCS612 | NR | NR | low expression |
| pXCS613 | 0.3 | NR | 0.00 |
| pXCS617 | 1.04 ± 0.04 | 0.43 ± 0.04 | 0.50 |
| pXCS618 | 1.01 ± 0.07 | 0.30 ± 0.08 | low expression |
| pXCS619 | 1.04 ± 0.08 | 0.34 ± 0.07 | 0.57 |
| pXCS620 | ND | ND | low expression |
| pXCS621 | 0.87 ± 0.03 | 0.14 ± 0.02 | 0.62 |
| pXCS622 | ND | ND | low expression |
| pXCS623 | 0.91 ± 0.03 | 0.26 ± 0.03 | low expression |
| pXCS624 | 0.87 ± 0.06 | 0.18 ± 0.04 | 0.67 |
| pXCS628 | 0.83 ± 0.04 | 0.16 ± 0.02 | 0.71 |

TABLE 7A-continued

Thermal and storage stability for mutants containing engineered disulfides

| Mutant ID | 50° C. stress resistance, D25 | 60° C. stress resistance, D25 | Storage stability |
|---|---|---|---|
| pXCS629 | 1.01 ± 0.06 | 0.04 ± 0.03 | 1.00 |
| pXCS630 | 0.61 ± 0.04 | NR | 0.00 |

TABLE 7B

Thermal and storage stability of mutants containing cavity filling mutations

| Mutant ID | 50° C. stress resistance, D25 | 60° C. stress resistance, D25 | Storage stability |
|---|---|---|---|
| pXCS565 | 0.61 ± 0.06 | 0.03 ± 0.01 | 0.74 |
| pXCS571 | 0.46 ± 0.05 | NR | 0.81 |
| pXCS592 | 0.38 ± 0.07 | NR | 0.025 |

TABLE 7C

Thermal and storage stability of mutants containing electrostatic mutations

| Mutant ID | 50° C. stress resistance, D25 | 60° C. stress resistance, D25 | Storage stability |
|---|---|---|---|
| pXCS658 | 1.05 ± 0.05 | 0.30 ± 0.03 | 0.71 |
| pXCS660 | 1.03 ± 0.03 | NR | 0.94 |
| pXCS664 | 0.87 ± 0.03 | NR | 0.76 |

TABLE 8A

Thermal and storage stability of mutants containing double combination mutations

| Mutant ID | 50° C. stress resistance, D25 | 60° C. stress resistance, D25 | Storage stability |
|---|---|---|---|
| pXCS674 | 0.73 ± 0.09 | 0.53 ± 0.07 | 1.47 |
| pXCS683 | 1.10 ± 0.02 | 0.4 | low expression |
| pXCS684 | 1.05 ± 0.01 | 0.46 ± 0.04 | low expression |
| pXCS685 | 1.10 ± 0.02 | 0.70 ± 0.06 | low expression |
| pXCS686 | 1.17 ± 0.08 | 0.63 ± 0.05 | low expression |
| pXCS687 | 1.10 ± 0.04 | 0.50 ± 0.03 | low expression |
| pXCS688 | 1.09 ± 0.03 | 0.56 ± 0.08 | low expression |
| pXCS689 | 1.06 ± 0.02 | 0.44 ± 0.07 | low expression |
| pXCS690 | 1.06 ± 0.06 | 0.50 ± 0.03 | 0.27 |
| pXCS693 | 0.70 ± 0.05 | 0.08 ± 0.01 | 0.54 |
| pXCS697 | 0.49 ± 0.04 | 0.06 | low expression |
| pXCS698 | NR | NR | low expression |
| pXCS699 | 0.31 ± 0.05 | NR | low expression |
| pXCS700 | 0.65 ± 0.05 | 0.03 | 0.67 |

TABLE 8A-continued

Thermal and storage stability of mutants containing double combination mutations

| Mutant ID | 50° C. stress resistance, D25 | 60° C. stress resistance, D25 | Storage stability |
|---|---|---|---|
| pXCS701 | 0.36 | NR | low expression |
| pXCS702 | 0.48 ± 0.02 | NR | low expression |

TABLE 8B

Thermal and storage stability for mutants containing triple combination mutations

| Mutant ID | 50° C. resistance, AM14 | 60° C. stress resistance, D25 | Storage stability |
|---|---|---|---|
| pXCS734 | 0.61 | 0.31 ± 0.00 | 1.09 ± 0.06 |
| pXCS735 | 0.70 | 0.37 ± 0.04 | 0.73 ± 0.13 |
| pXCS738 | 0.72 | 0.37 | 0.58 ± 0.10 |
| pXCS740 | 0.69 | 0.41 ± 0.06 | 1.03 ± 0.11 |
| pXCS749 | ND | 0.00 ± 0.10 | 0.65 ± 0.15 |
| pXCS752 | ND | 0.00 ± 0.10 | 0.62 ± 0.05 |
| pXCS754 | ND | 0.00 ± 0.10 | 1.19 ± 0.06 |
| pXCS758 | 0.70 | 0.22 ± 0.04 | 1.32 ± 0.03 |
| pXCS760 | ND | 0.82 ± 0.04 | 0.66 ± 0.22 |
| pXCS774 | 1.00 ± 0.16 | 0.74 ± 0.03 | 0.74 ± 0.10 |
| pXCS776 | 1.40 ± 0.21 | 1.08 ± 0.09 | 0.30 ± 0.16 |
| pXCS777 | 1.03 ± 0.17 | 1.17 ± 0.05 | 0.54 ± 0.21 |
| pXCS778 | 1.14 ± 0.18 | 0.36 ± 0.07 | 0.34 ± 0.06 |
| pXCS779 | 0.85 ± 0.15 | 0.00 ± 0.00 | 0.51 ± 0.08 |
| pXCS780 | 0.70 ± 0.17 | 0.11 ± 0.00 | 0.82 ± 0.08 |
| pXCS781 | 0.88 ± 0.17 | 0.00 ± 0.10 | 0.94 ± 0.05 |
| pXCS782 | 0.55 ± 0.18 | 0.07 ± 0.01 | 0.67 ± 0.13 |
| pXCS785 | 1.01 ± 0.18 | 0.00 ± 0.10 | 1.08 ± 0.18 |
| pXCS787 | 0.82 ± 0.17 | 0.14 ± 0.01 | 0.82 ± 0.19 |
| pXCS804 | 0.79 ± 0.11 | 0.19 ± 0.01 | 0.98 ± 0.08 |
| pXCS805 | 0.72 ± 0.15 | 0.24 ± 0.01 | 0.78 ± 0.24 |
| pXCS806 | 0.40 ± 0.13 | 0.16 ± 0.03 | 0.79 ± 0.13 |
| pXCS809 | 0.84 ± 0.12 | 0.29 ± 0.04 | 0.82 ± 0.11 |
| pXCS811 | 0.67 ± 0.10 | 0.30 ± 0.04 | 1.03 ± 0.16 |
| pXCS827 | 0.88 ± 0.07 | 0.06 | 0.50 ± 0.10 |
| pXCS830 | 1.01 ± 0.15 | 0.14 ± 0.02 | 0.53 ± 0.10 |
| pXCS839 | 0.82 ± 0.06 | 0.55 ± 0.03 | 0.57 ± 0.14 |
| pXCS842 | 0.87 ± 0.14 | 0.88 ± 0.02 | 0.57 ± 0.10 |
| pXCS845 | 1.00 ± 0.11 | 1.11 ± 0.11 | 0.50 ± 0.20 |
| pXCS847 | 0.92 ± 0.14 | 0.74 ± 0.01 | 0.54 ± 0.11 |
| pXCS848 | 1.24 ± 0.12 | 1.00 ± 0.03 | 0.15 ± 0.29 |
| pXCS849 | 0.92 ± 0.30 | 1.08 ± 0.10 | 0.59 ± 0.14 |
| pXCS850 | 0.88 ± 0.22 | 0.70 ± 0.01 | 0.75 ± 0.16 |
| pXCS851 | 0.95 ± 0.09 | 0.84 ± 0.05 | 0.79 ± 0.10 |
| pXCS852 | 0.86 ± 0.13 | 0.78 ± 0.02 | 0.89 ± 0.03 |
| pXCS853 | 0.98 ± 0.10 | 0.10 ± 0.01 | 0.53 ± 0.11 |
| pXCS854 | 0.93 ± 0.08 | 0.08 ± 0.01 | 0.55 ± 0.14 |
| pXCS855 | 0.94 ± 0.10 | 0.81 ± 0.07 | 0.53 ± 0.10 |
| pXCS856 | 0.97 ± 0.10 | 0.78 ± 0.00 | 0.59 ± 0.12 |
| pXCS857 | 0.90 ± 0.14 | 0.11 | 0.91 ± 0.07 |
| pXCS858 | 0.95 ± 0.10 | 0.78 ± 0.08 | 0.94 ± 0.06 |
| pXCS873 | 0.77 ± 0.22 | 1.11 ± 0.01 | 0.36 ± 0.13 |
| pXCS874 | 0.93 ± 0.20 | 0.46 ± 0.01 | 0.78 ± 0.19 |
| pXCS875 | 0.62 ± 0.16 | 0.23 ± 0.00 | 0.50 ± 0.10 |
| pXCS876 | 0.90 ± 0.20 | 1.06 ± 0.04 | 0.52 ± 0.10 |
| pXCS877 | 0.49 ± 0.20 | 1.09 ± 0.00 | 0.41 ± 0.09 |
| pXCS878 | 0.66 ± 0.16 | 0.40 ± 0.04 | 0.47 ± 0.16 |
| pXCS879 | 0.82 ± 0.20 | 0.84 ± 0.04 | 0.50 ± 0.20 |
| pXCS880 | 0.68 ± 0.20 | 0.87 ± 0.07 | 0.46 ± 0.15 |
| pXCS881 | 0.68 ± 0.23 | 0.92 ± 0.03 | 0.47 ± 0.26 |
| pXCS882 | 0.75 ± 0.21 | 0.94 ± 0.01 | 0.44 ± 0.16 |
| pXCS883 | 0.81 ± 0.13 | 0.40 ± 0.01 | 0.47 ± 0.24 |
| pXCS884 | 0.69 ± 0.15 | 0.43 ± 0.05 | 0.45 ± 0.17 |
| pXCS885 | 0.60 ± 0.21 | 0.47 ± 0.01 | 0.45 ± 0.13 |
| pXCS886 | 0.89 ± 0.13 | 0.70 ± 0.02 | 0.45 ± 0.14 |
| pXCS888 | 0.86 ± 0.14 | 0.81 ± 0.05 | 0.43 ± 0.10 |

TABLE 8B-continued

Thermal and storage stability for mutants containing triple combination mutations

| Mutant ID | 50° C. resistance, AM14 | 60° C. stress resistance, D25 | Storage stability |
|---|---|---|---|
| pXCS889 | 0.99 ± 0.14 | 0.00 ± 0.10 | 0.86 ± 0.10 |
| pXCS890 | 0.72 ± 0.34 | 0.10 ± 0.03 | 1.08 ± 0.05 |
| pXCS891 | 0.93 ± 0.06 | 0.08 ± 0.01 | 1.08 ± 0.06 |
| pXCS892 | 0.95 ± 0.13 | 0.18 ± 0.01 | 1.09 ± 0.04 |
| pXCS897 | 0.60 ± 0.28 | 0.42 ± 0.04 | 0.67 ± 0.37 |
| pXCS898 | 0.94 ± 0.46 | 0.48 ± 0.05 | 0.81 ± 0.19 |
| DS-Cav1 | 0.60 | 0.22 | 0.90 |

TABLE 8C

Thermal stability of a mutant devoid of a foldon trimerization domain (pXCS899)

| Mutant ID | 50° C. resistance, AM14 | 60° C. stress resistance, AM14 | 50° C. resistance, D25 | 60° C. stress resistance, D25 |
|---|---|---|---|---|
| pXCS899 | 0.684 | 0.323 | 0.906 | 0.287 |

Example 5: Conformational Integrity of RSV F Protein Mutants Evaluated with a Panel of Monoclonal Antibodies The purpose of the study was to identify RSV F protein mutants that maintain the structural integrity of a RSV-F pre-fusion conformation, including a pre-fusion trimer conformation and association. Each mutant was tested against a panel of reference mAbs that includes two site ø- and pre-fusion-specific mAbs (AM22 and D25), one mAb that binds an epitope close to site II is also pre-fusion-specific (MPE8), one site II-specific mAb that binds both pre-fusion and post-fusion F (palivizumab, Synagis®), one pre-fusion trimer-specific mAb (AM14) and a site IV-specific antibody that binds both pre-fusion and post-fusion F (101F). RSV F protein mutants maintained in a pre-fusion conformation were expected to bind all the reference antibodies tested.

The OCTET HTX (ForteBio, Pall Corporation, Port Washington, NY) instrument, which measures kinetics of real-time biomolecular interactions, was used to evaluate the antibody reactivity for each mutant. Experiments were conducted with 1000 rpm agitation, at 30° C. temperature in 96-well black plates (Greiner Bio-One, Monroe, NC) with a final volume of 200 μL per well. Anti-HIS biosensor tips were equilibrated in phosphate-buffered saline (PBS), 2% bovine serum albumin (BSA), 0.05% Tween 20 (PBT) for 10 min before commencing binding measurements. HIS-tagged mutant proteins were captured by anti-HIS biosensors for 5 min. Baseline was established in PBT for 3 min before the association step with 20 nM antibodies in PBT for 10 min. Dissociation of all antibodies was allowed for 20 min in the same wells used to establish baseline. OCTET data analysis software (version 8.2, Pall Corp.) was used for kinetic analysis, based on curve fitting of association and dissociation steps, and assuming 1:1 reversible binding interaction. Binding responses (nm shift) for each of the mutants with various reference monoclonal antibodies are presented in Tables 9A and 9B. A response value <0.10 was considered negative and is the limit of detection (LOD) for this assay. Values ≥0.10 were considered positive and indicated antibody binding to individual mutants. Varying degrees of binding were observed across the mutants and with each antibody. However, the majority of combination mutants were bound by 101F and Synagis whereas mutants such as pXCS735 and pXCS776 for example showed loss of binding to at least one pre-fusion-specific mAb. Loss of binding indicated lack of an intact pre-fusion conformation.

TABLE 9A

OCTET Results for Pre-Fusion-Specific Antibodies

| Mutant ID | Response (nm shift) AM22 | D25 | MPE8 | AM14 |
|---|---|---|---|---|
| pXCS734 | 0.284 | 0.590 | 0.818 | 0.931 |
| pXCS735 | LoD | 0.302 | 0.375 | 0.442 |
| pXCS738 | 0.273 | 0.545 | 0.741 | 0.899 |
| pXCS740 | 0.172 | 0.422 | 0.546 | 0.524 |
| pXCS749 | LoD | 0.153 | 0.206 | 0.178 |
| pXCS752 | 0.234 | 0.463 | 0.703 | 0.641 |
| pXCS754 | 0.298 | 0.562 | 0.676 | 0.816 |
| pXCS758 | 0.273 | 0.589 | 0.816 | 0.772 |
| pXCS760 | 0.121 | 0.176 | 0.151 | 0.203 |
| pXCS774 | 0.340 | 0.595 | 0.795 | 0.738 |
| pXCS776 | LoD | LoD | 0.127 | LoD |
| pXCS777 | 0.121 | 0.201 | 0.270 | 0.285 |
| pXCS778 | LoD | LoD | LoD | 0.121 |
| pXCS779 | 0.125 | 0.200 | 0.232 | 0.329 |
| pXCS780 | 0.290 | 0.495 | 0.608 | 0.684 |
| pXCS781 | 0.423 | 0.666 | 0.876 | 1.053 |
| pXCS782 | 0.222 | 0.378 | 0.513 | 0.580 |
| pXCS785 | 0.465 | 0.727 | 0.937 | 0.955 |
| pXCS787 | 0.225 | 0.464 | 0.621 | 0.445 |
| pXCS804 | 0.267 | 0.432 | 0.605 | 0.522 |
| pXCS805 | 0.173 | 0.282 | 0.443 | 0.355 |
| pXCS806 | 0.152 | 0.252 | 0.347 | 0.330 |
| pXCS809 | 0.185 | 0.281 | 0.392 | 0.444 |
| pXCS811 | 0.322 | 0.490 | 0.638 | 0.714 |
| pXCS827 | 0.450 | 0.692 | 0.880 | 0.881 |
| pXCS830 | 0.465 | 0.707 | 0.923 | 0.878 |
| pXCS839 | 0.390 | 0.593 | 0.782 | 0.731 |
| pXCS842 | 0.493 | 0.780 | 0.932 | 0.930 |
| pXCS845 | 0.314 | 0.495 | 0.699 | 0.653 |
| pXCS847 | 0.484 | 0.732 | 0.871 | 0.935 |
| pXCS848 | 0.109 | 0.188 | 0.266 | 0.235 |
| pXCS849 | 0.430 | 0.668 | 0.908 | 0.886 |
| pXCS850 | 0.517 | 0.839 | 1.038 | 1.018 |
| pXCS851 | 0.508 | 0.824 | 1.025 | 1.027 |
| pXCS852 | 0.565 | 0.881 | 1.126 | 1.144 |
| pXCS853 | 0.484 | 0.746 | 0.905 | 0.883 |
| pXCS854 | 0.453 | 0.693 | 0.886 | 0.884 |
| pXCS855 | 0.523 | 0.778 | 0.982 | 0.992 |
| pXCS856 | 0.568 | 0.827 | 1.063 | 1.094 |
| pXCS857 | 0.563 | 0.890 | 1.091 | 1.110 |
| pXCS858 | 0.547 | 0.840 | 1.061 | 1.097 |
| pXCS873 | 0.192 | 0.398 | 0.537 | 0.434 |
| pXCS874 | 0.444 | 0.681 | 0.851 | 0.771 |
| pXCS875 | 0.205 | 0.459 | 0.623 | 0.540 |
| pXCS876 | 0.268 | 0.523 | 0.702 | 0.600 |
| pXCS877 | 0.213 | 0.419 | 0.573 | 0.525 |
| pXCS878 | 0.324 | 0.666 | 0.812 | 0.833 |
| pXCS879 | 0.351 | 0.680 | 0.826 | 0.804 |
| pXCS880 | 0.213 | 0.563 | 0.684 | 0.505 |
| pXCS881 | 0.178 | 0.556 | 0.763 | 0.623 |
| pXCS882 | 0.219 | 0.516 | 0.691 | 0.463 |
| pXCS883 | 0.233 | 0.553 | 0.704 | 0.484 |
| pXCS884 | 0.323 | 0.576 | 0.784 | 0.714 |
| pXCS885 | 0.105 | 0.327 | 0.408 | 0.239 |
| pXCS886 | 0.443 | 0.715 | 0.863 | 0.872 |
| pXCS888 | 0.434 | 0.726 | 0.878 | 0.875 |
| pXCS889 | 0.477 | 0.720 | 0.889 | 0.870 |
| pXCS890 | 0.538 | 0.778 | 0.999 | 0.994 |
| pXCS891 | 0.461 | 0.719 | 0.920 | 0.828 |
| pXCS892 | 0.542 | 0.756 | 1.032 | 1.000 |

TABLE 9A-continued

OCTET Results for Pre-Fusion-Specific Antibodies

| | Response (nm shift) | | | |
|---|---|---|---|---|
| Mutant ID | AM22 | D25 | MPE8 | AM14 |
| pXCS897 | 0.406 | 0.605 | 0.745 | 0.740 |
| pXCS898 | 0.416 | 0.614 | 0.816 | 0.795 |
| DS Cav1 | 0.469 | 0.714 | 0.810 | 0.842 |

Note:
LoD = limit of detection,
ND = not determined

TABLE 9B

OCTET Results for Antibodies 101F and Synagis

| | Response (nm shift) | |
|---|---|---|
| Mutant ID | 101F | Synagis |
| pXCS734 | 0.843 | 0.653 |
| pXCS735 | 0.813 | 0.560 |
| pXCS738 | 0.774 | 0.519 |
| pXCS740 | 0.759 | 0.611 |
| pXCS749 | 0.629 | 0.480 |
| pXCS752 | 0.739 | 0.520 |
| pXCS754 | 0.665 | 0.394 |
| pXCS758 | 0.743 | 0.431 |
| pXCS760 | 0.345 | 0.334 |
| pXCS774 | 0.742 | 0.530 |
| pXCS776 | 0.139 | 0.123 |
| pXCS777 | 0.389 | 0.329 |
| pXCS778 | 0.118 | 0.124 |
| pXCS779 | 0.340 | 0.286 |
| pXCS780 | 0.623 | 0.471 |
| pXCS781 | 0.786 | 0.536 |
| pXCS782 | 0.615 | 0.468 |
| pXCS785 | 0.763 | 0.580 |
| pXCS787 | 0.615 | 0.547 |
| pXCS804 | 0.788 | 0.574 |
| pXCS805 | 0.810 | 0.598 |
| pXCS806 | 0.865 | 0.621 |
| pXCS809 | 0.687 | 0.554 |
| pXCS811 | 0.768 | 0.606 |
| pXCS827 | 0.973 | 0.898 |
| pXCS830 | 0.901 | 0.839 |
| pXCS839 | 0.900 | 0.880 |
| pXCS842 | 0.942 | 0.853 |
| pXCS845 | 0.798 | 0.782 |
| pXCS847 | 0.941 | 0.960 |
| pXCS848 | 0.400 | 0.394 |
| pXCS849 | 0.999 | 0.991 |
| pXCS850 | 1.040 | 1.076 |
| pXCS851 | 0.991 | 1.002 |
| pXCS852 | 1.072 | 1.014 |
| pXCS853 | 0.842 | 0.878 |
| pXCS854 | 0.851 | 0.857 |
| pXCS855 | 0.914 | 0.894 |
| pXCS856 | 0.957 | 0.935 |
| pXCS857 | 1.016 | 1.056 |
| pXCS858 | 0.981 | 1.010 |
| pXCS873 | 0.809 | 0.798 |
| pXCS874 | 0.881 | 0.844 |
| pXCS875 | 0.912 | 0.833 |
| pXCS876 | 0.820 | 0.727 |
| pXCS877 | 0.842 | 0.823 |
| pXCS878 | 0.832 | 0.776 |
| pXCS879 | 0.838 | 0.725 |
| pXCS880 | 0.693 | 0.735 |
| pXCS881 | 0.812 | 0.786 |
| pXCS882 | 0.651 | 0.714 |
| pXCS883 | 0.719 | 0.807 |
| pXCS884 | 0.798 | 0.792 |
| pXCS885 | 0.666 | 0.737 |
| pXCS886 | 0.807 | 0.853 |
| pXCS888 | 0.839 | 0.873 |

TABLE 9B-continued

OCTET Results for Antibodies 101F and Synagis

| | Response (nm shift) | |
|---|---|---|
| Mutant ID | 101F | Synagis |
| pXCS889 | 1.020 | 0.946 |
| pXCS890 | 0.999 | 0.949 |
| pXCS891 | 0.919 | 0.851 |
| pXCS892 | 0.960 | 0.889 |
| pXCS897 | 0.939 | 0.901 |
| pXCS898 | 0.802 | 0.773 |
| DS Cav1 | 0.821 | 0.704 |

Example 6. Molecular Weight and Size Distribution Analysis of Selected Pre-Fusion RSV F Mutants Stabilized pre-fusion F mutants were analyzed by SDS-PAGE followed by western blotting with the RSV F-specific monoclonal antibody L4 [Walsh E E, Cote P T, Fernie B F et al. Analysis of the Respiratory Syncytial Virus Fusion Protein Using Monoclonal and Polyclonal Antibodies. J. Gen. Virol. 76: 505-513, 1986.]. FIG. 2A shows SDS-PAGE mobility profiles for representative mutants pXCS847, pXCS851, pXCS852, and DS-Cav1. In all cases a major band with an apparent molecular weight between 55 and 60 kDa, as expected for the monomeric RSV F mutants, was present under non-reducing conditions. The observed slight change in mobility between DS-Cav1 and mutants pXCS847, pXCS851, and pXCS852 could be due to the nature of the individual disulfide bonds and the resulting effect on the overall compactness of the protein in the unfolded state and accessibility to SDS.

Figure 2B:
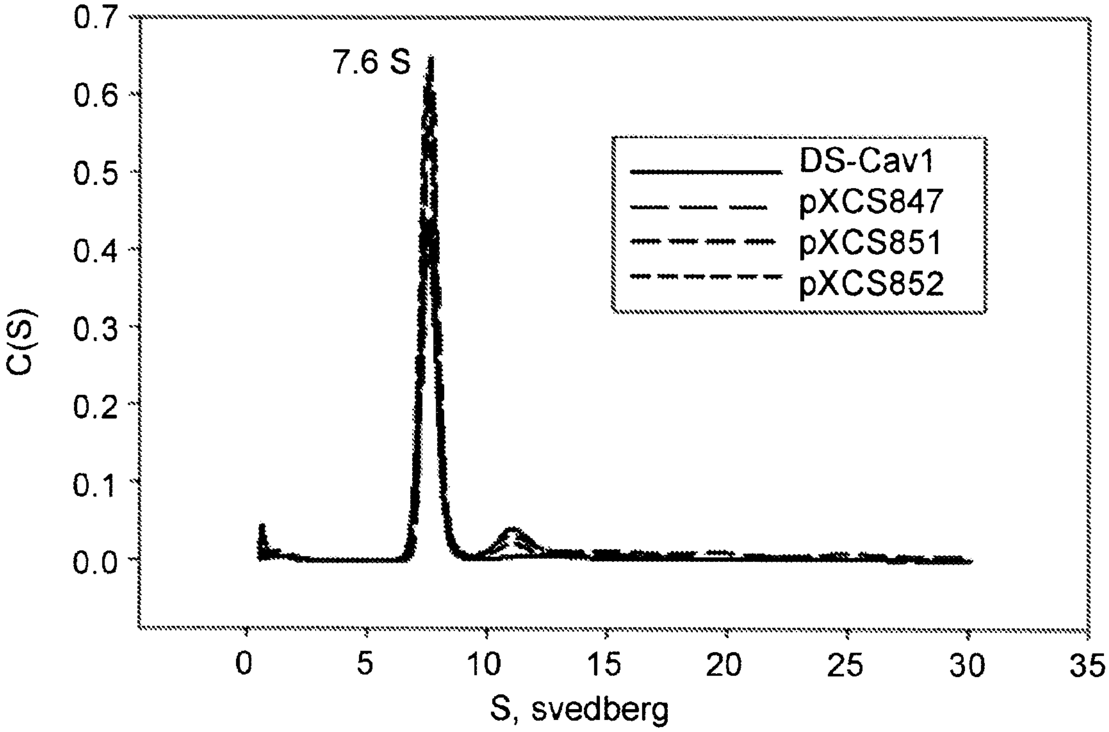
FIG. 2B shows sedimentation coefficient distributions of selected mutants (pXCS847, pXCS851 and pXCS852) calculated from sedimentation velocity experiments using an analytical ultracentrifuge.

FIG. 2B describes molecular weights and size distributions of the mutants pXCS847, pXCS851, pXCS852, and DS-Cav1 in solution under native conditions. The molecular weights and size distributions were estimated from sedimentation velocity analysis using the analytical ultracentrifuge. Purified protein was centrifuged at 35,000 rpm, at 20° C., and UV absorbance across the sample cells was monitored at 280 nm. Data were fit to the continuous c(s) distributions, assuming the same frictional ratio for all of the sedimenting species in the cell. All proteins sedimented with sedimentation coefficient of ~7.6 S and apparent molecular weight of ~180 kDa, indicating that purified proteins are trimeric in solution. The expected molecular weight of the RSV F trimer, calculated from its amino acid composition is 171 kDa.

Example 7. Circular Dichroism Spectroscopy to Characterize Secondary and Tertiary Structure Integrity of the Designed RSV F Protein Mutants Both far- and near-UV CD spectra were recorded on a Jasco J-810 automated recording spectropolarimeter, equipped with a Peltier-type 6-position temperature-controlled cell holder. Far-UV CD spectra were recorded at 0.10-0.12 mg/ml protein concentration in 1×PBS, pH 7.4, in 1 mm rectangular quartz cells between 200 and 260 nm every 0.1 nm at 100 nm/min, with 3 nm band width. Five spectra were collected and averaged for each sample. Near-UV CD spectra were recorded at 0.4-0.5 mg/ml protein concentration in 1×PBS, pH 7.4, in 1 cm rectangular quartz cells between 250 and 320 nm every 0.1 nm at 100 nm/min, with 3 nm band width. Five spectra were collected and averaged for each sample as well. Data were corrected for the buffer baseline contributions and normalized to either mean residue ellipticity (far-UV CD) or molar ellipticity (near-UV CD), using established relationships.

Figure 3A:
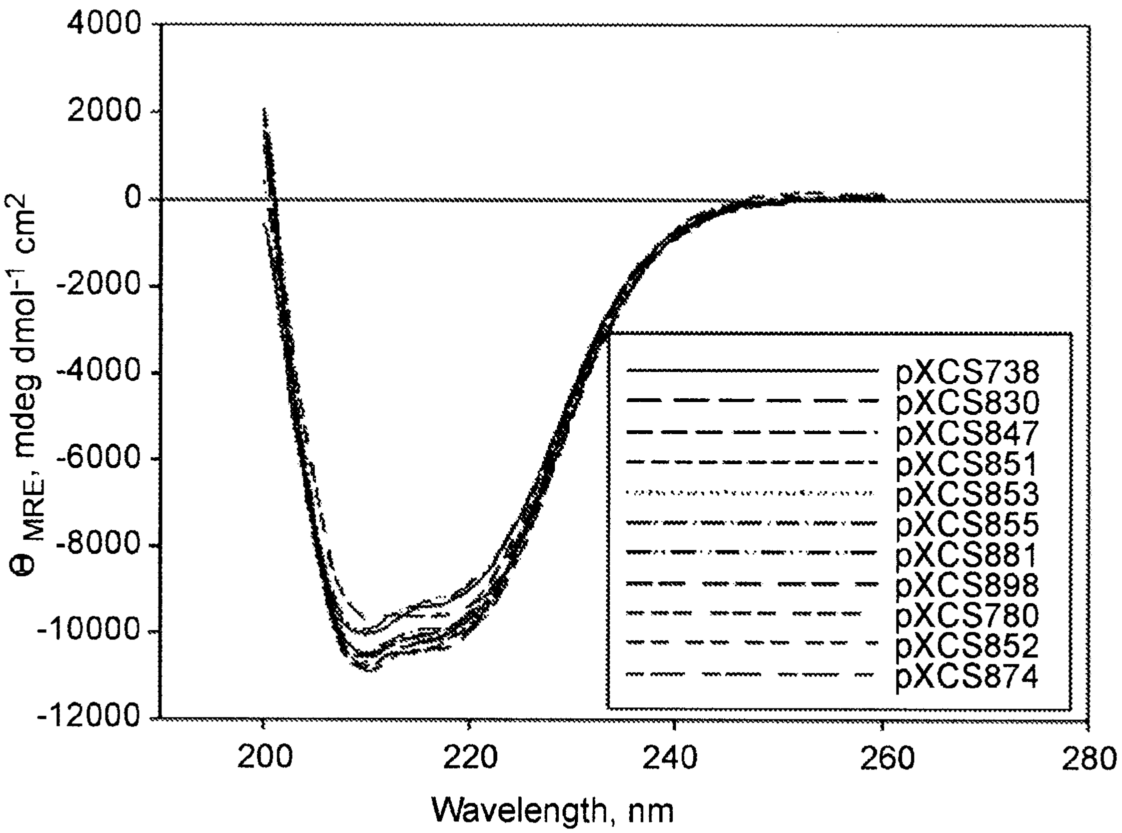
FIGS. 3A and 3B depict the circular dichroism spectroscopy (CD) spectra of exemplary modified RSV F proteins with specific site mutations. The far-ultraviolet (UV) CD spectra of the designed mutants confirm secondary structure integrity, and the near-UV CD spectra confirm tertiary structure integrity.
Figure 3B:
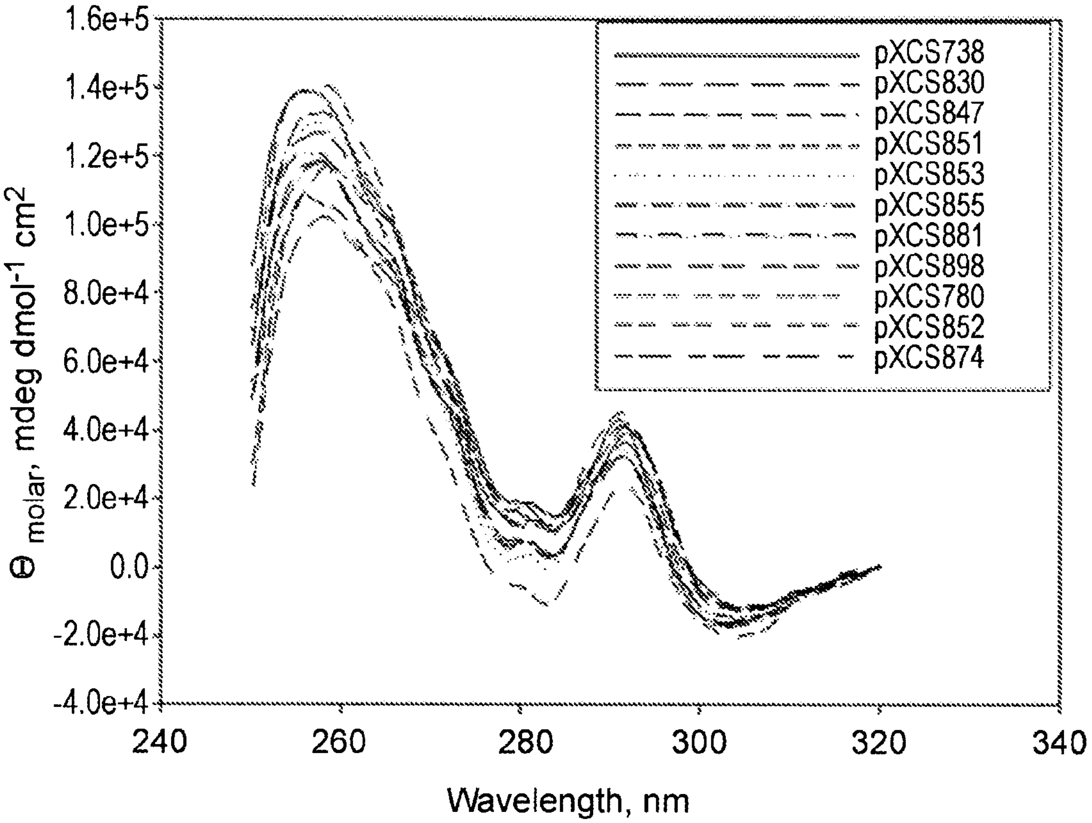

The results are shown in FIGS. 3A and 3B. Both far- and near-UV CD data show that all proteins retain well defined secondary and tertiary structure. Furthermore, obvious similarity of the far- and near-UV CD spectra indicates that overall secondary and tertiary structures of the mutants are similar, and structural integrity of the proteins is preserved.

Example 8. Structural Stability of the Designed RSV F Protein Mutants

The structural stability of the purified RSV F protein mutants was characterized using differential scanning calorimetry (DSC). DSC experiments were conducted on a VP-DSC microcalorimeter (MicroCal, Northampton, MA). Protein concentration was determined spectrophotometrically and corrected for light scattering contribution. Protein samples in 1×PBS, pH 7.4 at 0.2-0.5 mg/mL (1.0-2.4 micromolar trimer concentration) were scanned from 10° C. to 80° C. at 90° C./hr, with a response time of 8 seconds and pre-scan equilibration time of 5 minutes. Depending on the number of the observed transitions in thermograms, heat capacity profiles were fit to the 2- or 3-state unfolding models using Origin 7.0 software provided by the DSC manufacturer. Melting temperatures of the first observable transitions are given as melting temperatures of each mutant.

DSC data show almost all of the designed mutants are more stable than DS-Cav1 (Table 10). Melting temperatures (defined as DSC maxima of the first observable DSC peak in each experiment, Table 10) of all mutants (with the exception of pXCS738) are higher than DS-Cav1 by up to 18° C. DSC data show that computational protein design described in Example 1 succeeded in producing significantly more stable RSV F mutants that also retain a pre-fusion conformation (Octet data, Example 5).

TABLE 10

Melting temperatures of RSV F protein mutants. Melting temperatures were calculated from the DSC experiments (as described in Example 8).

| Mutant ID | $T_{m1}$, ° C. |
|---|---|
| DS-Cav1 | 52.9 ± 0.0 |
| pXCS738 | 52.5 ± 0.1 |
| pXCS780 | 65.2 ± 0.0 |
| pXCS830 | 58.3 ± 0.0 |
| pXCS847 | 68.4 ± 0.0 |
| pXCS851 | 70.4 ± 0.0 |
| pXCS852 | 69.2 ± 0.0 |
| pXCS853 | 65.2 ± 0.0 |
| pXCS855 | 69.3 ± 0.0 |
| pXCS874 | 54.8 ± 1.0 |
| pXCS881 | 70.6 ± 0.0 |
| pXCS898 | 59.6 ± 0.5 |

Example 9. Mechanism of the Pre-Fusion Trimer Conformation Loss

Figure 5:
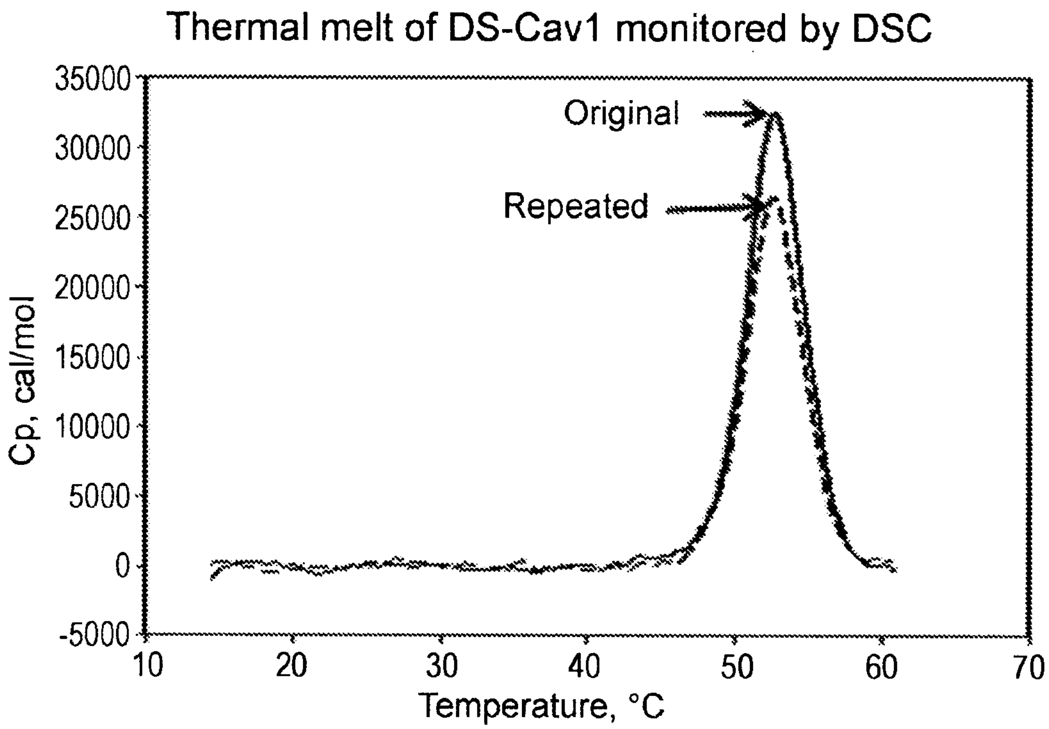
FIG. 5 depicts differential scanning calorimetry (DSC) experiments with purified DS-Cav1 (Example 8). The experiments were done as described for the designed pre-fusion F mutants. Solid line—initial DSC scan of the sample, dashed line—repeated scan of the same sample that was used in the initial scan. The DSC peak largely recovers during the repeated scan, indicating that conformational transition detected by the DSC is reversible.
Figure 6A:
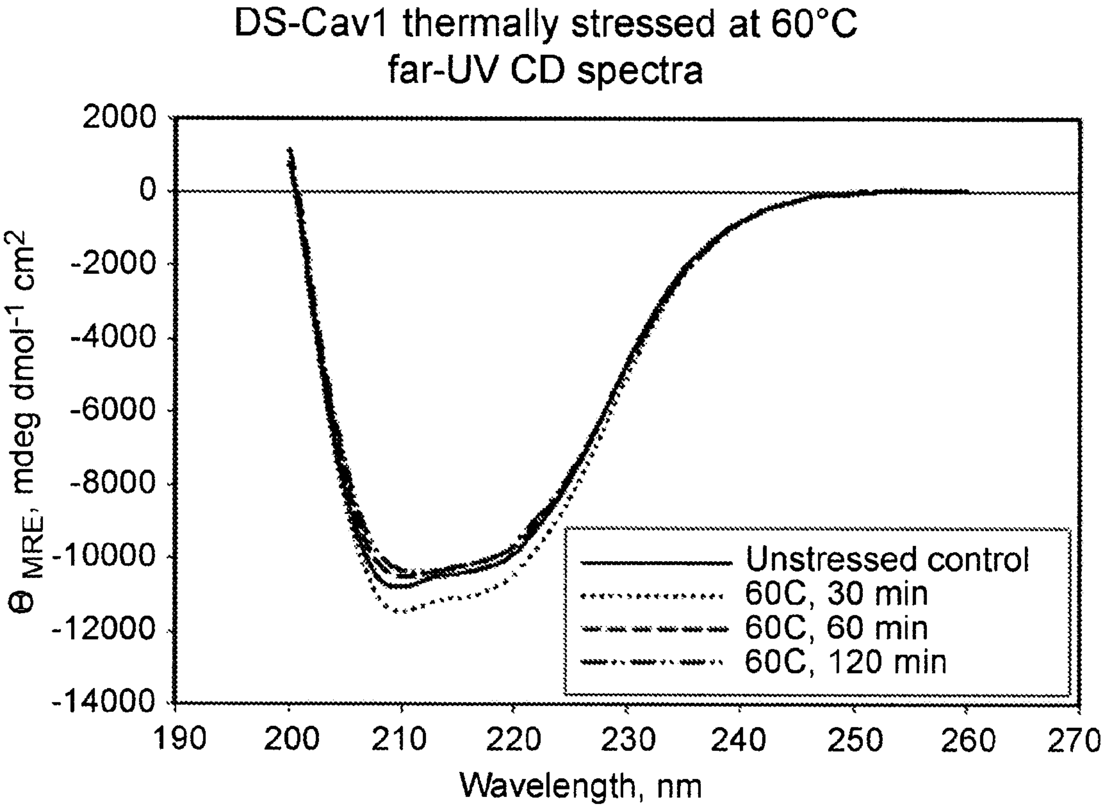
FIG. 6A depicts far-UV CD spectra of DS-Cav1 stressed at 60° C. (Example 8). CD spectra were recorded as described above for the designed pre-fusion RSV F mutants (Example 6). DS-Cav1 retains defined far-UV CD spectrum after up to 2 hours of incubation at 60° C., indicating that no global protein unfolding is taking place during that time.
Figure 6B:
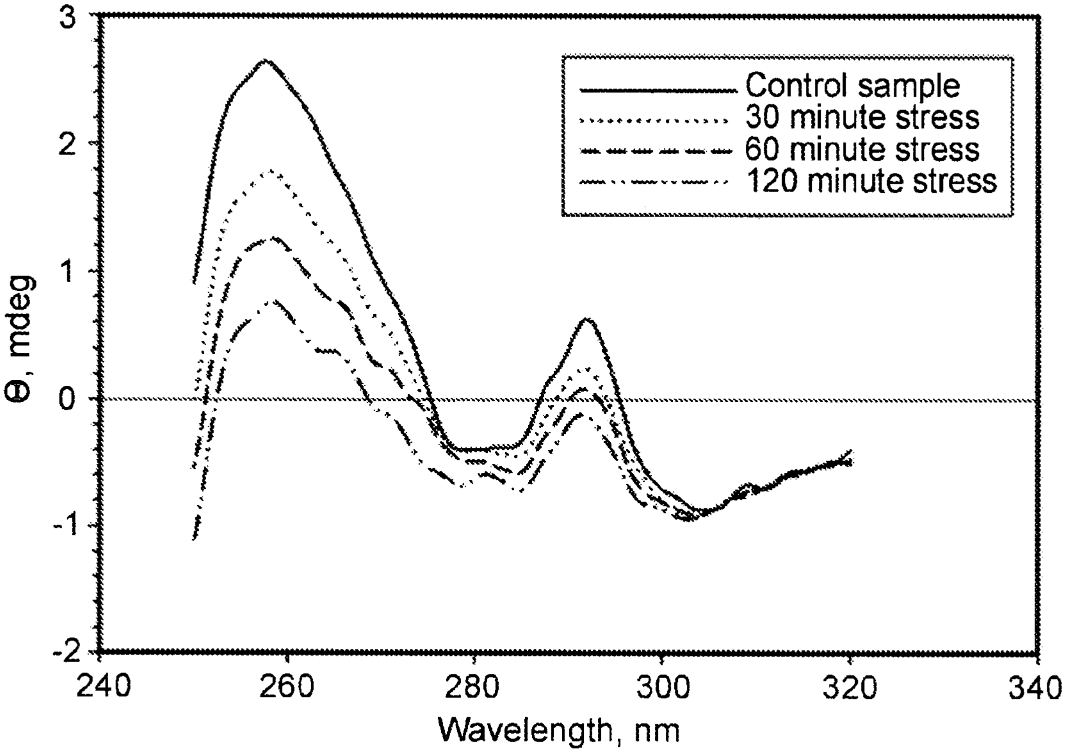
FIG. 6B depicts near-UV CD spectra of DS-Cav1 stressed at 60° C. (Example 8). CD spectra were recorded as described above for the designed pre-fusion RSV F mutants (Example 6).

In order to characterize a specific structural pathway leading to loss of the pre-fusion conformation, we subjected purified DS-Cav1 to thermal stress testing. The purified glycoprotein (0.5 mg/ml in 1×PBS, pH 7.4) was incubated at 50° C. and 60° C. for 30, 60 and 120 minutes. Binding of the pre-fusion-specific mAb D25 and the pre-fusion trimer-specific mAb AM14 to the stressed protein was assessed via ELISA experiments as described in Example 4). The structural integrity of the protein was characterized via CD and DSC as described in Examples 7 and 8, respectively. The results are shown in FIGS. 4-6.

Figure 4:
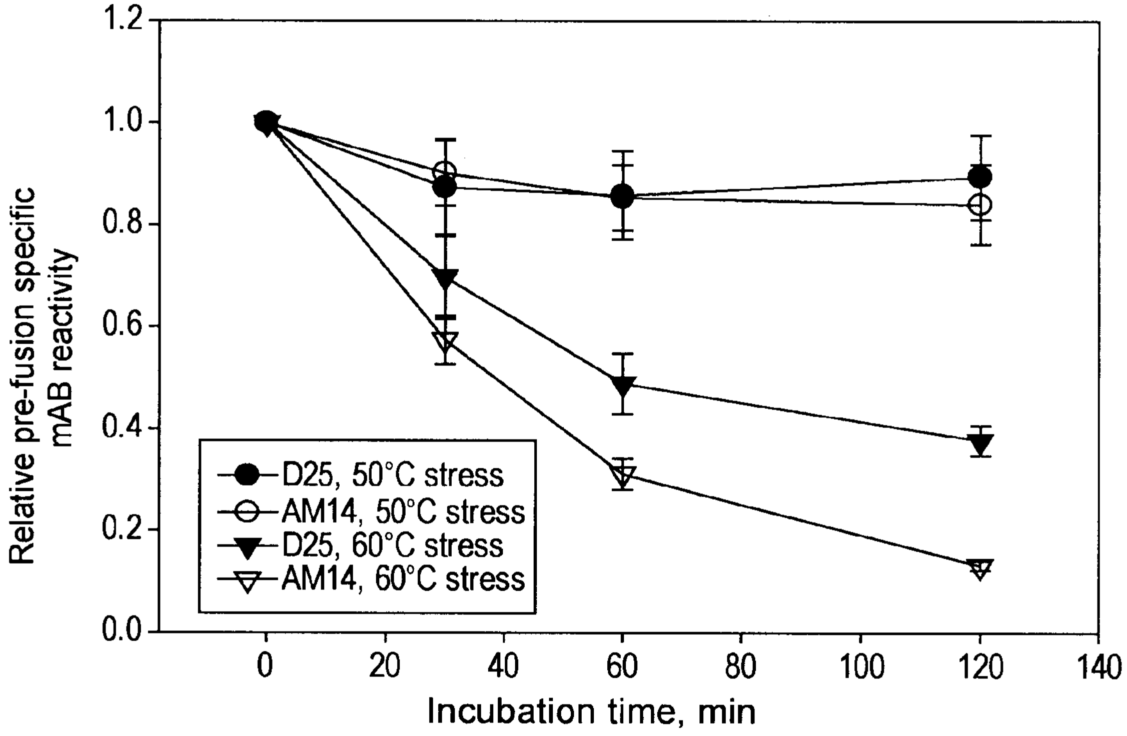
FIG. 4 depicts the time-dependent stress testing of purified DS-Cav1 using two different monoclonal antibodies (mAbs) D25 and AM14 at two temperatures (50° C. and 60° C.).

The relative AM14 and D25 reactivities of the stressed samples are shown in FIG. 4. Both D25 and AM14 reactivity of DS-Cav1 remain largely unchanged after up to 2 hours of incubation at 50° C. In contrast, reactivity to both pre-fusion specific antibodies is progressively lost during 60° C. treatment. Furthermore, AM14 reactivity is lost more quickly than D25 reactivity, indicating that the quaternary pre-fusion AM14 epitope is disrupted earlier than the D25 epitope. The result highlights an advantage of the AM14 antibody as a probe for the detection of the pre-fusion trimer conformation loss.

DSC assessment of the unstressed DS-Cav1 (FIG. 5) shows that the protein undergoes a reversible conformational transition between 50° C. and 60° C. This transition does not correspond to the loss of the pre-fusion conformation, which is irreversible. Furthermore, this transition does not result from the global unfolding of the protein as DS-Cav1 retains defined far- and near-UV CD spectra (FIGS. 6A and 6B), indicating that the protein remains folded under these conditions. The most likely explanation of the observed DSC transition is reversible loss of the quaternary structure of the protein, i.e., at least local dissociation of the pre-fusion trimer. This dissociation is required for the initial steps toward loss of the pre-fusion conformation, since neither AM14 nor D25 reactivity is appreciably lost before that transition takes place (FIG. 4, ELISA data). These data emphasize the importance of trimer integrity for the stability of the pre-fusion conformation. Trimer integrity can only be confirmed by the reactivity against quaternary epitope-specific antibody AM14, but not the site Ø specific antibody D25

These data suggest that the loss of the pre-fusion conformation occurs via the following pathway:

$$N_3 \leftrightarrow 3N \rightarrow 3U \rightarrow U_n$$

Figure 7A:
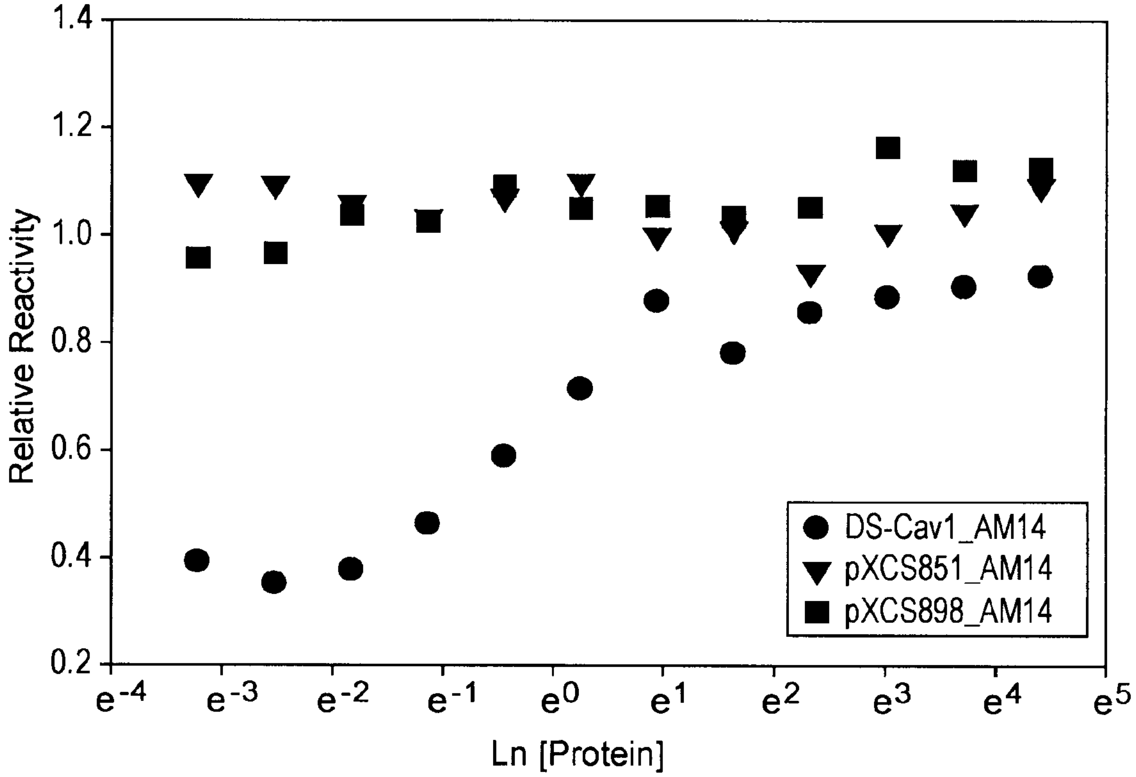
FIG. 7A depicts the protein concentration dependence of thermal stress resistance, as determined by the preservation of the pre-fusion F trimer-specific AM14 epitope (Example 8).
Figure 7B:
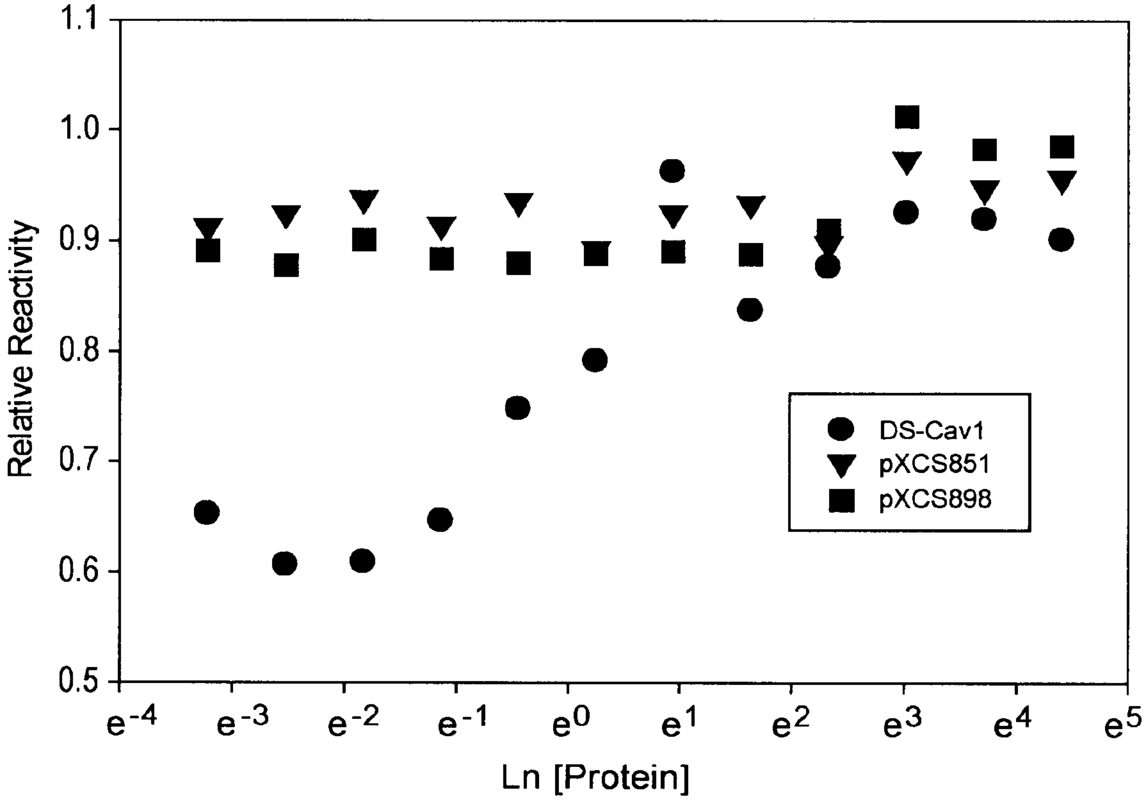
FIG. 7B depicts the protein concentration dependence of thermal stress resistance, as determined by the preservation of the pre-fusion F-specific D25 epitope (Example 8). Protein samples were serially diluted and subjected to the 50° C. stress for 1 hour. D25 reactivity remaining after the stress in relation to the control (unstressed) samples was assessed in ELISA assays.

Native trimer ($N_3$) reversibly dissociates into native monomers (3N), which slowly and irreversibly lose pre-fusion conformation (3U) and ultimately aggregate, forming high molecular mass species ($U_n$). The trimer dissociation, in turn, means that DS-Cav1 will display protein concentration-dependent resistance against thermal stress: a decrease in total protein concentration will promote trimer dissociation, which, in turn, will accelerate pre-fusion conformation loss. In contrast, stabilized pre-fusion F mutants (e.g. 851) should show little to no concentration dependence of their stress resistance, provided they were made sufficiently stable. FIGS. 7A and 7B provide further experimental evidence to support this hypothesis. Protein samples were serially diluted and subjected to 50° C. stress for one hour. AM14 and D25 reactivities remaining after stress in relation to the control (unstressed) samples were assessed in ELISA assays. Stress resistance of DS-Cav1 shows pronounced dependence on protein concentration, as determined by either AM14 (FIG. 7A) or D25 (FIG. 7B) antibody reactivity. In contrast, stress resistance of the stabilized mutants pXCS851 and pXCS898 remains largely unchanged over the same protein concentration range.

Example 10: Stabilized RSV F Protein Mutants in Pre-Fusion Conformation Elicit Neutralizing Antibody Responses in Mice Female Balb/c mice were immunized with either 0.025 μg or 0.25 μg of either DS-Cav1, wild-type F, F mutants pXCS738, pXCS780, pXCS830, pXCS847, pXCS851, pXCS852, pXCS853, pXCS855, pXCS874, pXCS881, or pXCS898, or, with or without 0.1 mg per dose aluminum phosphate (AlPO4) as adjuvant. Immunizations were given intramuscularly at weeks 0 and 3 (Table 11). Pre (week 0) and post-dose 2 (PD2, week 5) sera were evaluated in an RSV subfamily A neutralization assay as described with minor modifications [Eyles J E, Johnson J E, Megati S, et al. Nonreplicating vaccines can protect african green monkeys from the Memphis 37 strain of respiratory syncytial virus. J Inf Dis. 208(2):319-29, 2013.]. Briefly, neutralizing antibody titers were determined as the serum dilution factor resulting in a 50% reduction in infectious units. Results are reported as the geometric mean titer from 10 mice per group. Sera with no detectable virus neutralization were assigned a titer of 20. Fold rise in geometric mean titers are reported as the ratio of post-dose 2 (PD2) to pre-immunization titers within each group.

TABLE 11

Immunization schedule of the murine immunogenicity study comparing pre-fusion F mutants.

| Pre-fusion F Ag dose | 0.025 μg and 0.25 μg with and without AlPO4 (0.1 mg/mL) |
|---|---|
| Vaccination | Weeks 0, 3 |
| Bleed | Weeks 0 (Pre)<br>3 (PD1)<br>5 (PD2) |

Figure 8:
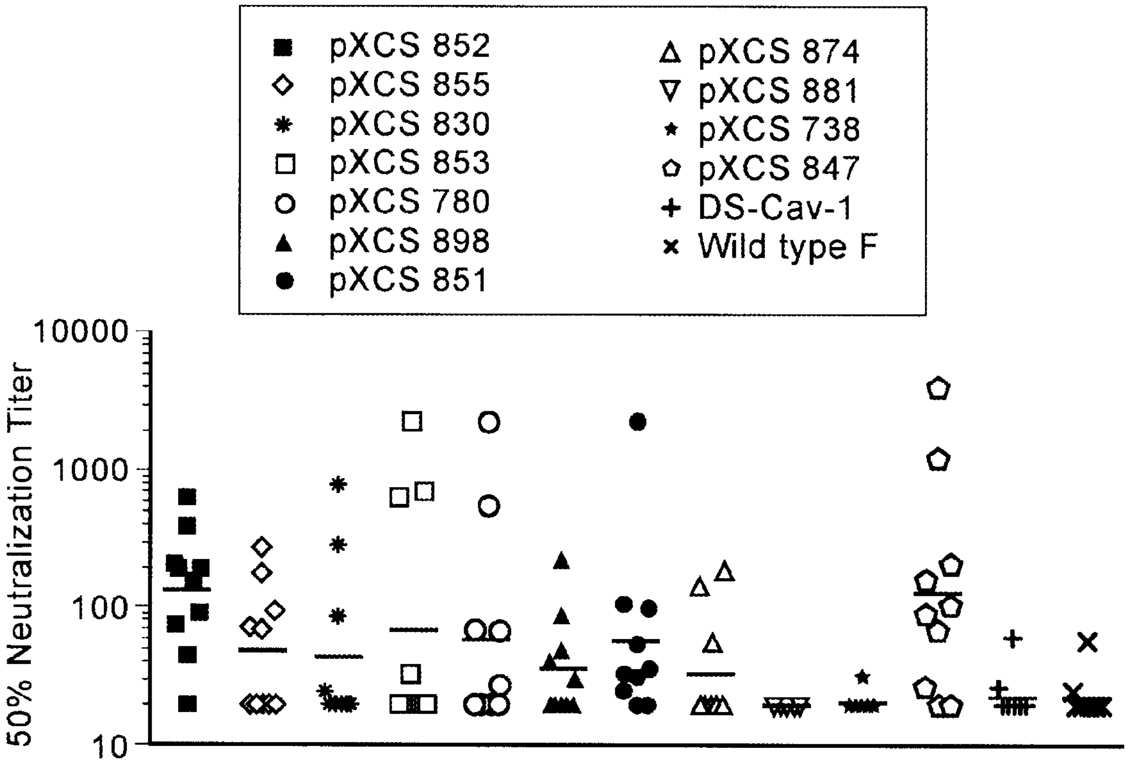
FIG. 8 shows neutralizing antibody responses from mice immunized with DS-Cav1; wild-type F; or mutants pXCS852, pXCS855, pXCS830, pXCS853, pXCS780, pXCS898, pXCS851, pXCS874, pXCS881, pXCS738, or pXCS847; with or without aluminum phosphate as adjuvant. Results are reported as the 50% geometric mean titer (GMT) from 10 mice per group. Each scatter plot reflects the response of individual mice with 10 animals total per group. The line within each group indicates the geometric mean 50% neutralizing antibody titer. "Wild-type F" refers to a wild-type F ectodomain recombinant construct.
Figure 9A:
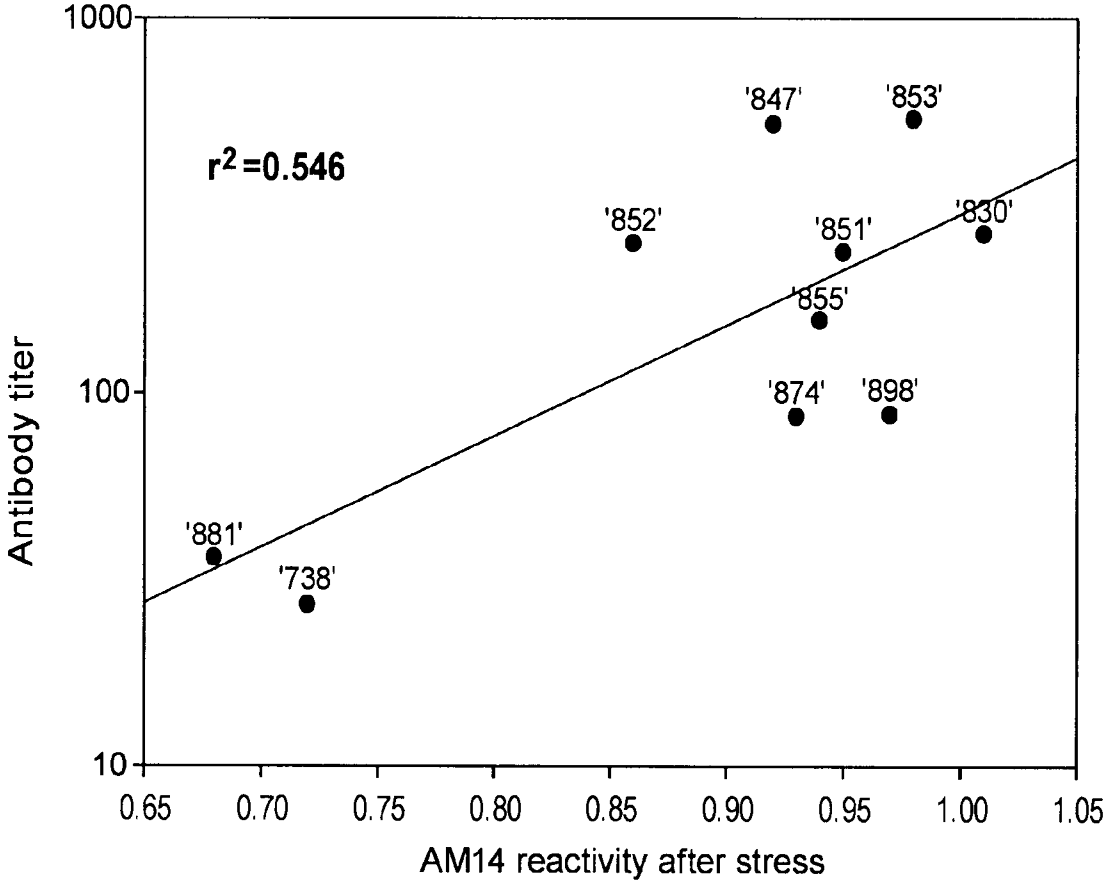
FIGS. 9A and 9B describe correlations between the neutralizing antibody titers elicited by and the stabilities of the engineered pre-fusion F protein mutants. Y-axis—neutralizing antibody titers elicited by immunization of the mice with 0.25 μg antigen and no adjuvant or 0.025 μg antigen with 0.1 mg/ml $AlPO_4$ adjuvant. (Data are shown in Table 12.) X-axis—stability of the engineered mutants, as defined by the residual AM14 reactivity after thermal stress. (Data are shown in Table 8B.)
Figure 9B:
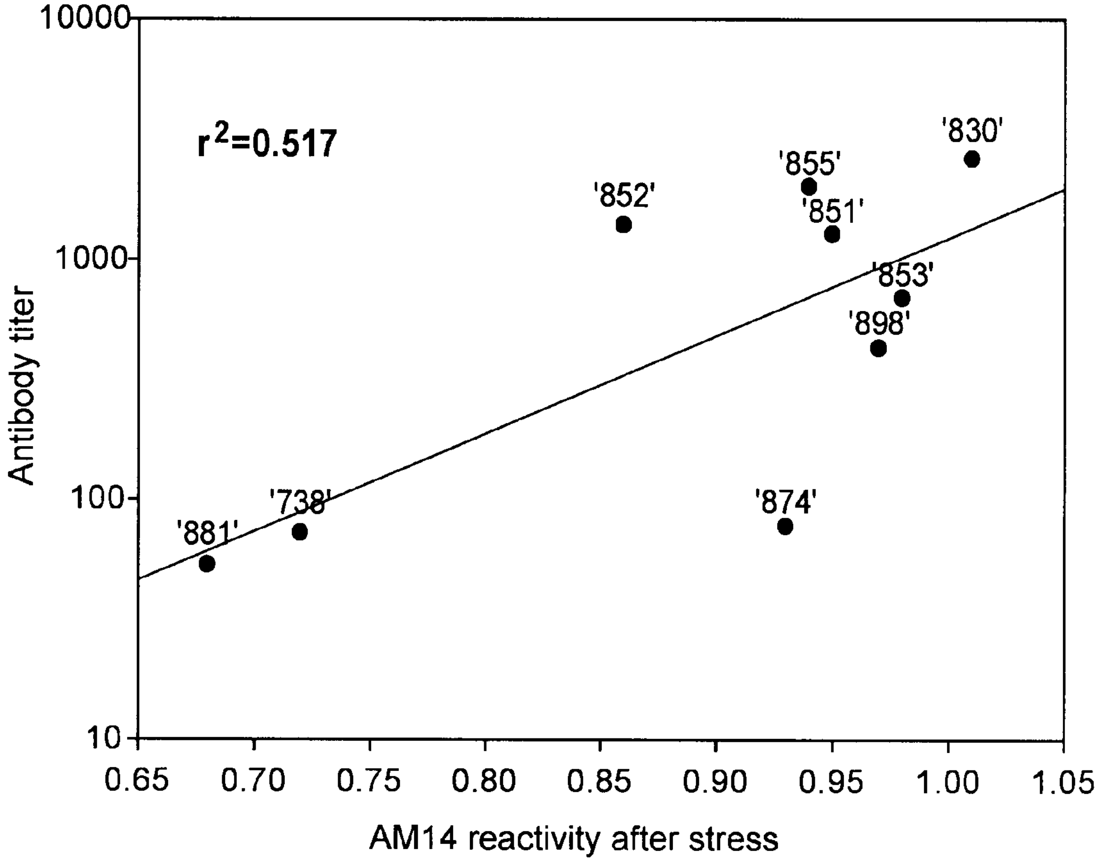

All mutants tested elicited a neutralizing antibody response following two immunizations in mice (Table 12). Overall, antibody titers were consistently higher at both antigen doses for mutants, pXCS830, pXCS847, pXCS851, and pXCS852, demonstrating that these mutants were the more immunogenic forms of a stabilized RSV pre-fusion F glycoprotein (Table 12 and 13, FIG. 8). Comparison of the PD2 50% neutralizing antibody titers with their corresponding mutants' in vitro characterization data shows correlation between the PD2 neutralizing antibody titer and the AM14 thermal stress resistance (FIG. 9). This result suggests that AM14 binding, which is specific for the pre-fusion trimeric state, correlates with the mutants' immunogenicity.

TABLE 12

Geometric mean neutralizing antibody titers of Balb/c mice following immunization with RSV F mutants.

| | 0.025 μg + AlPO4 | | 0.25 μg + AlPO4 | | 0.25 μg + No adjuvant | | 0.25 μg + No adjuvant | |
|---|---|---|---|---|---|---|---|---|
| Mutant ID | Pre | PD2 | Pre | PD2 | Pre | PD2 | Pre | PD2 |
| pXCS738 | 20 | 72 | 20 | 632 | 20 | 21 | 20 | 27 |
| pXCS780 | 20 | 2373 | 20 | 1311 | 20 | 59 | 20 | 108 |
| pXCS830 | 20 | 2615 | 20 | 3219 | 20 | 45 | 20 | 265 |
| pXCS847 | 20 | ND | 20 | ND | 20 | 129 | 20 | 518 |
| pXCS851 | 20 | 1275 | 20 | 4393 | 20 | 59 | 20 | 237 |
| pXCS852 | 20 | 1388 | 20 | 5100 | 20 | 135 | 20 | 331 |
| pXCS853 | 20 | 690 | 20 | 1225 | 20 | 69 | 20 | 535 |
| pXCS855 | 20 | 2004 | 20 | 1232 | 20 | 49 | 20 | 156 |
| pXCS874 | 20 | 77 | 20 | 2929 | 20 | 34 | 20 | 86 |
| pXCS881 | 20 | 53 | 20 | 2391 | 20 | 20 | 20 | 36 |
| pXCS898 | 20 | 427 | 20 | 2642 | 20 | 39 | 20 | 87 |
| DS-Cav1 | 20 | 271 | 20 | 2319 | 20 | 23 | 20 | 87 |
| Wild type F | 20 | 326 | 20 | 948 | 20 | 23 | 20 | 50 |

ND, not done.

TABLE 13

Fold rise in neutralizing antibody titers of Balb/c mice following immunization with RSV F mutants.

| | 0.025 mg + AlPO4 | 0.25 mg + AlPO4 | 0.025 mg No adjuvant | 0.25 mg No adjuvant |
|---|---|---|---|---|
| pXCS738 | 3.6 | 31.6 | 1.1 | 1.4 |
| pXCS780 | 118.7 | 65.6 | 3.0 | 5.4 |
| pXCS830 | 130.8 | 161.0 | 2.3 | 13.3 |
| pXCS847 | N/A | N/A | 6.5 | 25.9 |
| pXCS851 | 63.8 | 219.7 | 3.0 | 11.9 |
| pXCS852 | 69.4 | 255.0 | 6.8 | 16.6 |
| pXCS853 | 34.5 | 61.3 | 3.5 | 26.8 |
| pXCS855 | 100.2 | 61.6 | 2.5 | 7.8 |
| pXCS874 | 3.9 | 146.5 | 1.7 | 4.3 |
| pXCS881 | 2.7 | 119.6 | 1.0 | 1.8 |
| pXCS898 | 21.4 | 132.1 | 2.0 | 4.4 |
| DS-Cav1 | 13.6 | 116.0 | 1.2 | 4.4 |
| Wild type F | 16.3 | 47.4 | 1.2 | 2.5 |

N/A, not available.

Example 11. RSV F Mutants Comprising Introduced Cysteine Mutations in the HRB Region 11A. Preparation of RSV F Mutants Comprising Introduced Mutations in the HRB Region Representative RSV F mutants that comprise introduced cysteine mutations in the HRB region (approximately amino acids 476-524 of the F0 polypeptide) are provided in Table 14, where the specific mutations in this region in each mutant are noted. In addition to the mutations in the HRB region, each of these mutants also includes introduced mutations S55C, L188C, T54H, and D486S. These mutants were prepared by methods similar to those described in Examples 1-3. In brief, a precursor polypeptide consisting of 545 amino acids was prepared for each mutant, which comprises: (1) amino acids 1-529 of the sequence of SEQ ID NO:1 except fora deletion of 41 amino acids between residues 104 and 144; (2) the introduced mutations (S55C, L188C, T54H, and D486S) outside of the HRB region, (3) a thrombin protease recognition sequence; (4) a foldon domain; (5) a HIS-tag; (6) a Streptag II; (7) linker sequences; and (8) the introduced cysteine mutations as noted. The signal peptide, which comprises amino acids 1-25, was cleaved from the precursor during the expression process. The foldon domain was also cleaved from the mutants, which was achieved by digestion with 500 ug/ml bovine alpha-thrombin (HTI) overnight at room temperature after the expression process.

TABLE 14

Exemplary RSV F protein mutants comprising engineered disulfide mutations in the HRB region

| Mutant ID | Mutations in HRB Region | SEQ ID NO of Amino Acid Sequence of Precursor Polypeptide |
|---|---|---|
| pXCS1106 | K508C, S509C | 272 |
| pXCS1107 | N515C, V516C | 273 |
| pXCS1108 | T522C, T523C | 274 |
| pXCS1109 | K508C, S509C, N515C, V516C | 275 |
| pXCS1110 | K508C, S509C, T522C, T523C | 276 |
| pXCS1111 | N515C, V516C, T522C, T523C | 277 |
| pXCS1112 | K508C, S509C, N515C, V516C, T522C, T523C | 278 |

11B. Stability of RSV F Mutants Comprising Introduced Cysteine Mutations in the HRB Region Stability of RSV F Mutants provided in Table 14 was assessed according to the method described in Example 8 and Example 4. For thermal stability assessment for mutant pXCS1106, purified pXCS1106 protein, from which the foldon had been cleaved, was diluted into conditioned medium at a concentration of 12 μg/mL. Stress resistance for pXC1106 was calculated as fractional pre-fusion specific mAb reactivity remaining after stress. Results are presented in Tables 15 and 16, respectively.

TABLE 15

Melting temperatures of RSV F protein mutants

| Mutant ID | $T_{m1}$, ° C. |
|---|---|
| pXCS1106 | 66.3 |
| pXCS1108 | 66.7 |
| pXCS1109 | 66.5 |
| pXCS1110 | 67.0 |
| pXCS1111 | 66.5 |
| pXCS1112 | 67.2 |

TABLE 16

Thermal stability of RSV F Mutant pXCS1106

| Mutant ID | 50° C. resistance, AM14 | 60° C. stress resistance, AM14 | 50° C. resistance, D25 | 60° C. stress resistance, D25 |
|---|---|---|---|---|
| pXCS1106 | 1.041 | 0.720 | 1.080 | 1.019 |

Listing of Raw Sequences

SEQ ID NO: 1. Amino Acid Sequence of the Full Length F0 of Native RSV A2 (GenBank GI: 138251; Swiss Prot P03420)

MELLILKANAITTILTAVTFCFASGQNITEEFYQSTCSAVSKGYLSALRTGWYTSVITIE
LSNIKENKCNGTDAKVKLIKQELDKYKNAVTELQLLMQSTPPTNNRARRELPRFMNYT
LNNAKKTNVTLSKKRKRRFLGFLLGVGSAIASGVAVSKVLHLEGEVNKIKSALLSTNKA
VVSLSNGVSVLTSKVLDLKNYIDKQLLPIVNKQSCSISNIETVIEFQQKNNRLLEITREFS
VNAGVTTPVSTYMLTNSELLSLINDMPITNDQKKLMSNNVQIVRQQSYSIMSIIKEEVLA
YVVQLPLYGVIDTPCWKLHTSPLCTTNTKEGSNICLTRTDRGWYCDNAGSVSFFPQAE
TCKVQSNRVFCDTMNSLTLPSEINLCNVDIFNPKYDCKIMTSKTDVSSSVITSLGAIVSC
YGKTKCTASNKNRGIIKTFSNGCDYVSNKGMDTVSVGNTLYYVNKQEGKSLYVKGEPI
INFYDPLVFPSDEFDASISQVNEKINQSLAFIRKSDELLHNVNAGKSTTNIMITTIIIVIIVILL
S LIAVGLLLYCKARSTPVTLSKDQLSGINNIAFSN

SEQ ID NO: 2. Amino Acid Sequence of the Full Length F0 of Native RSV B (18537 strain; GenBank GI: 138250; Swiss Prot P13843)

MELLIHRSSAIFLTLAVNALYLTSSQNITEEFYQSTCSAVSRGYFSALRTGWYTSVITIE
LSNIKETKCNGTDTKVKLIKQELDKYKNAVTELQLLMQNTPAANNRARREAPQYMNYTI
NTTKNLNVSISKKRKRRFLGFLLGVGSAIASGIAVSKVLHLEGEVNKIKNALLSTNKAVV
SLSNGVSVLTSKVLDLKNYINNRLLPIVNQQSCRISNIETVIEFQQMNSRLLEITREFSVN
AGVTTPLSTYMLTNSELLSLINDMPITNDQKKLMSSNVQIVRQQSYSIMSIIKEEVLAYV
VQLPIYGVIDTPCWKLHTSPLCTTNIKEGSNICLTRTDRGWYCDNAGSVSFFPQADTC
KVQSNRVFCDTMNSLTLPSEVSLCNTDIFNSKYDCKIMTSKTDISSSVITSLGAIVSCYG
KTKCTASNKNRGIIKTFSNGCDYVSNKGVDTVSVGNTLYYVNKLEGKNLYVKGEPIINY
YDPLVFPSDEFDASISQVNEKINQSLAFIRRSDELLHNVNTGKSTTNIMITTIIIVIIVVLLS
LIAIGLLLYCKAKNTPVTLSKDQLSGINNIAFSK

SEQ ID NO: 3. RSV A2 F Ectodomain with foldon

MELLILKANAITTILTAVTFCFASGQNITEEFYQSTCSAVSKGYLSALRTGWYTSVITIELS
NiKENKCNGTDAKVKLIKQELDKYKNAVTELQLLMQSTPATNNRARRELPRFMNYTLN
NAKKTNVTLSKKRKRRFLGFLLGVGSAIASGVAVSKVLHLEGEVNKIKSALLSTNKAVV
SLSNGVSVLTSKVLDLKNYIDKQLLPIVNKQSCSISNIETVIEFQQKNNRLLEITREFSVN
AGVTTPVSTYMLTNSELLSLINDMPITNDQKKLMSNNVQIVRQQSYSIMSIIKEEVLAYV
VQLPLYGVIDTPCWKLHTSPLCTTNTKEGSNICLTRTDRGWYCDNAGSVSFFPQAETC
KVQSNRVFCDTMNSLTLPSEVNLCNVDIFNPKYDCKIMTSKTDVSSSVITSLGAIVSCY
GKTKCTASNKNRGIIKTFSNGCDYVSNKGVDTVSVGNTLYYVNKQEGKSLYVKGEPIIN
FYDPLVFPSDEFDASISQVNEKINQSLAFIRKSDELLSAIGGYIPEAPRDGQAYVRKDGE
WVLLSTFLGGLVPRGSHHHHHHGSWSHPQFEK

SEQ ID NO: 4: RSV RSVA/*Homo sapiens*/USA/LA2_21/2013 F (Ontario) Native Amino Acid Sequence (GenBank GI: AHX57185):

MELPILKTNAITTILAAVTLCFASSQNITEEFYQSTCSAVSKGYLSALRTGWYTSVITIELS
NIKENKCNGTDAKVKLIKQELDKYKNAVTELQLLMQSTPAANSRARRELPRFMNYTLN

-continued

| Listing of Raw Sequences |
|---|

NTKNTNVTLSKKRKRRFLGFLLGVGSAIASGIAVSKVLHLEGEVNKIKSALLSTNKAVVS
LSNGVSVLTSKVLDLKNYIDKQLLPIVNKQSCSISNIETVIEFQQKNNRLLEITREFSVNA
GVTTPVSTYMLTNSELLSLINDMPITNDQKKLMSSNVQIVRQQSYSIMSIIKEEVLAYVV
QLPLYGVIDTPCWKLHTSPLCTTNTKEGSNICLTRTDRGWYCDNAGSVSFFPQAETCK
VQSNRVFCDTMNSLTLPSEVNLCNIDIFNPKYDCKIMTSKTDVSSSVITSLGAIVSCYGK
TKCTASNKNRGIIKTFSNGCDYVSNKGVDTVSVGNTLYYVNKQEGKSLYVKGEPIINFY
DPLVFPSDEFDASISQVNEKINQSLAFIRKSDELLHNVNAGKSTTNIMITTIIIVIIVILLALIA
VGLLLYCKARSTPVTLSKDQLSGINNIAFSN

SEQ ID NO: 5: RSV RSV A/*Homo sapiens*/USA/LA2_21/2013 F Ectodomain with foldon:
MELPILKTNAITTILAAVTLCFASSQNITEEFYQSTCSAVSKGYLSALRTGWYTSVITIELS
NIKENKCNGTDAKVKLIKQELDKYKNAVTELQLLMQSTPAANSRARRELPRFMNYTLN
NTKNTNVTLSKKRKRRFLGFLLGVGSAIASGIAVSKVLHLEGEVNKIKSALLSTNKAVVS
LSNGVSVLTSKVLDLKNYIDKQLLPIVNKQSCSISNIETVIEFQQKNNRLLEITREFSVNA
GVTTPVSTYMLTNSELLSLINDMPITNDQKKLMSSNVQIVRQQSYSIMSIIKEEVLAYVV
QLPLYGVIDTPCWKLHTSPLCTTNTKEGSNICLTRTDRGWYCDNAGSVSFFPQAETCK
VQSNRVFCDTMNSLTLPSEVNLCNIDIFNPKYDCKIMTSKTDVSSSVITSLGAIVSCYGK
TKCTASNKNRGIIKTFSNGCDYVSNKGVDTVSVGNTLYYVNKQEGKSLYVKGEPIINFY
DPLVFPSDEFDASISQVNEKINQSLAFIRKSDELLSAIGGYIPEAPRDGQAYVRKDGEW
VLLSTFLGGLVPRGSHHHHHHGSWSHPQFEK SEQ ID NO: 6: RSV RSVB/*Homo sapiens*/PER/FPP00592/2011 F (Buenos Aires) Native Amino Acid Sequence (GenBank GI: AHV80758):
MELLIHRSSAIFLTLAINALYLTSSQNITEEFYQSTCSAVSRGYFSALRTGWYTSVITIELS
NIKETKCNGTDTKVKLIKQELDKYKNAVTELQLLMQNTPAANNRARREAPQYMNYTIN
TTKNLNVSISKKRKRRFLGFLLGVGSAIASGIAVSKVLHLEGEVNKIKNALLSTNKAVVS
LSNGVSVLTSKVLDLKNYINNQLLPIVNQQSCRISNIETVIEFQQKNSRLLEITREFSVNA
GVTTPLSTYMLTNSELLSLINDMPITNDQKKLMSSNVQIVRQQSYSIMSIIKEEVLAYVV
QLPIYGVIDTPCWKLHTSPLCTTNIKEGSNICLTRTDRGWYCDNAGSVSFFPQADTCK
VQSNRVFCDTMNSLTLPSEVSLCNTDIFNSKYDCKIMTSKTDISSSVITSLGAIVSCYGK
TKCTASNKNRGIIKTFSNGCDYVSNKGVDTVSVGNTLYYVNKLEGKNLYVKGEPIINYY
DPLVFPSDEFDASISQVNEKINQSLAFIRRSDELLHNVNTGKSTTNIMITAIIIVIIVVLLSLI
AIGLLLYCKAKNTPVTLSKDQLSGINNIAFSK SEQ ID NO: 7: RSV RSVB/*Homo sapiens*/PER/FPP00592/2011 F Ectodomain with foldon:
MELLIHRSSAIFLTLAINALYLTSSQNITEEFYQSTCSAVSRGYFSALRTGWYTSVITIELS
NIKETKCNGTDTKVKLIKQELDKYKNAVTELQLLMQNTPAANNRARREAPQYMNYTIN
TTKNLNVSISKKRKRRFLGFLLGVGSAIASGIAVSKVLHLEGEVNKIKNALLSTNKAVVS
LSNGVSVLTSKVLDLKNYINNQLLPIVNQQSCRISNIETVIEFQQKNSRLLEITREFSVNA
GVTTPLSTYMLTNSELLSLINDMPITNDQKKLMSSNVQIVRQQSYSIMSIIKEEVLAYVV
QLPIYGVIDTPCWKLHTSPLCTTNIKEGSNICLTRTDRGWYCDNAGSVSFFPQADTCK
VQSNRVFCDTMNSLTLPSEVSLCNTDIFNSKYDCKIMTSKTDISSSVITSLGAIVSCYGK
TKCTASNKNRGIIKTFSNGCDYVSNKGVDTVSVGNTLYYVNKLEGKNLYVKGEPIINYY
DPLVFPSDEFDASISQVNEKINQSLAFIRRSDELLSAIGGYIPEAPRDGQAYVRKDGEW
VLLSTFLGGLVPRGSHHHHHHGSWSHPQFEK SEQ ID NO: 8: Nucleotide Sequence Encoding Pre-cursor Polypeptide of pXCS738:
atggaacttctgatcctgaaagccaacgcgattaccactatcctgactgccgtcaccttctgcttcgcatcgggacagaaca
ttaccgaggagttctaccagtccacctgttcggcggtgtccaagggttacctctcggccctgagaactggctggtaccactg
tgtgattactatcgagctgagcaacatcaaggagaacaagtgcaatggaacggacgcgaaggtcaagctgattaagca
ggaactcgataagtacaagaacgccgtgaccgagctccagctgctgatgcaatcgacccctgccactaacaacagag
ctcgccgggaactgccgcgcttcatgaattacaccctcaacaacgcgaagaaaaccaacgtgaccctgtccaagaagc
gcaagcggaggttcctgggattcctgtgtggcgtgggctccgcaatcgcatccggagtggccgtgtccaaagtgctgcatc
tggagggggaagtgaacaagatcaagtccgccctcctgtcaactaataaggcggtggtgtccctgagcaacggagtca
gcgtgtgtacatccaaggtcctggacctcaagaactacatcgacaagcagctgttgcccatcgtcaacaagcagtcatgc
tcgattagcaatatcgaaaccgtgattgagttccagcagaagaacaacagactgctcgaaattacccgggagttttccgtg
aacgccggagtgaccactcctgtgtccacctacatgcttacgaactccgaactgctcagcctcatcaacgatatgccgatc
actaacgaccagaagaagttgatgagcaacaatgtgcagatcgtgcgccaacagtcctactcaatcatgtcaattatcaa
ggaggaaatcctcgcctatgtggtgcaattgcctctgtacggagtcatcgacacaccctgctggaagctgcacactagcc
cactctgtacgaccaacaccaaggaaggttccaacatctgcctgactaggaccgatcggggctggtattgcgataatgct
gggtccgtgagcttcttcccgcaagccgagacttgcaaagtgcagtcaaaccgcgtgttctgtgacaccatgtgtagcctg
accctgccatccgaagtcaacctctgcaacgtggacatctttaacccgaaatacgactgcaagattatgacctccaagac
cgacgtcagcagctctgtcatcactagcctgggagctattgtgtcctgctacggaaagaccaaatgcactgcctcgaaca
agaacagaggcatcatcaagaccttcagcaacggctgtgactacgtgtccaacaagggagtggacaccgtgtccgtcg
ggaacaccctgtactacgtgaacaagcaggaggggaagtcgctctacgtcaaggggaaccgattatcaatttctacga
ccccctggtgttcccttccgacgagttcgatgcctccatatcccaagtcaacgagaagatcaaccagtctcttgccttcatcc
ggaagtcggacgaactgctgtccgccatcggtggctatattccggaagcccccagggatggacaggcctacgtgcgga
aggatggagaatgggtgcttttgtccaccttcctgggcggtctggtgccccgcggctcacaccatcatcaccaccacggttc
gtggtcccaccctcaatttgagaagtga
[Relevant components (bp coordinates): Signal sequence: 1-75; pep27: 328-408; F1: 409-1539; F2: 76-327; foldon: 1552-1632; Thrombin recognition sequence: 1639-1656; His-tag: 1657-1674; Streptag II: 1681-1704; Linker sequences: 1540-1551, 1633-1638, 1675-1680; P102A (naturally-occurring substitution): 304-306; I379V (naturally-occurring substitution): 1135-1137; M447V (naturally-occurring substitution):

-continued

Listing of Raw Sequences 1339-1341; T54H: 160-162; S55C: 163-165; L142C: 424-426; L188C: 562-564; V296I: 886-888; N371C: 1111-1113]

SEQ ID NO: 9: Nucleotide Sequence Encoding Precursor Polypeptide of pXCS780:
atggaacttctgatcctgaaagccaacgcgattaccactatcctgactgccgtcaccttctgcttcgcatcgggacagaaca
ttaccgaggagttctaccagtccacctgttcggcggtgtccaagggttacctctcggccctgagaactggctggtacacctg
tgtgattactatcgagctgagcaacatcaaggagaacaagtgcaatggaacggacgcgaaggtcaagctgattaagca
ggaactcgataagtacaagaacgccgtgaccgagctccagctgctgatgcaatcgacccctgccactaacaacagag
ctcgccgggaactgccgcgcttcatgaattacaccctcaacaacgcgaagaaaaccaacgtgaccctgtccaagaagc
gcaagcggaggttcctgggattcctgttgggcgtgggctccgcaatcgcatccggagtggccgtgtccaaagtgctgcatc
tggagggggaagtgaacaagatcaagtccgccctcctgtcaactaataaggcggtggtgtccctgagcaacggagtca
gcgtgtgtacatccaaggtcctggacctcaagaactacatcgacaagcagctgttgcccatcgtcaacaagcagtcatgc
tcgattagcaatatcgaaaccgtgattgagttccagcagaagaacaacagactgctcgaaattacccgggagttttccgtg
aacgccggagtgaccactcctgtgtccacctacatgcttacgaactccgaactgctcagcctcatcaacgatatgccgatc
actaacgaccagaagaagttgatgagcaacaatgtgcagatcgtgcgccaacagtcctactcaatcatgtcaattatcaa
ggaggaagtgctcgcctatgtggtgcaattgcctctgtacggagtcatcgacacaccctgctggaagctgcacactagcc
cactctgtacgaccaacaccaaggaaggttccaacatctgcctgactaggaccgatcggggctggtattgcgataatgct
gggtccgtgagcttcttcccgcaagccgagacttgcaaagtgcagtcaaaccgcgtgttctgtgacaccatgaacagcct
gaccctgccatccgaagtcaacctctgcaacgtggacatctttaacccgaaatacgactgcaagattatgacctccaaga
ccgacgtcagcagctctgtcatcactagcctgggagctattgtgtcctgctacggaaagaccaaatgcactgcctcgaac
aagaacagaggcatcatcaagaccttcagcaacggctgtgactacgtgtccaacaagggagtggacaccgtgtccgtc
gggaacaccctgtactacgtgaacaagcaggaggggaagtcgctctacgtcaaggggggaaccgattatcaatttctacg
acccccctggtgttcccttcctccgagttcgatgcctccatatcccaagtcaacgagaagatcaaccagtctcttgccttcatcc
ggaagtcggacgaactgctgtccgccatcggtggctatattccggaagcccccagggatggacaggcctacgtgcgga
aggatggagaatgggtgcttttgtccaccttcctgggcggtctggtgccccgcggctcacaccatcatcaccaccacggttc
gtggtcccaccctcaatttgagaagtga
[Relevant components (bp coordinates): Signal sequence: 1-75; pep27: 328-408; F1: 409-1539; F2: 76-327; foldon: 1552-1632; Thrombin recognition sequence: 1639-1656; His-tag: 1657-1674; Streptag II: 1681-1704; Linker sequences: 1540-1551, 1633-1638, 1675-1680; P102A (naturally-occurring substitution): 304-306; I379V (naturally-occurring substitution): 1135-1137; M447V (naturally-occurring substitution): 1339-1341; S55C: 163-165; L188C: 562-564; D486S: 1456-1458]

SEQ ID NO: 10: Nucleotide Sequence Nucleotide Sequence Encoding Pre-coursor Polypeptide of pXCS830:
atggaacttctgatcctgaaagccaacgcgattaccactatcctgactgccgtcaccttctgcttcgcatcgggacagaaca
ttaccgaggagttctaccagtccacctgttcggcggtgtccaagggttacctctcggccctgagaactggctggtaccactg
tgtgattactatcgagctgagcaacatcaaggagaacaagtgcaatggaacggacgcgaaggtcaagctgattaagca
ggaactcgataagtacaagaacgccgtgaccgagctccagctgctgatgcaatcgacccctgccactaacaacagag
ctcgccgggaactgccgcgcttcatgaattacaccctcaacaacgcgaagaaaaccaacgtgaccctgtccaagaagc
gcaagcggaggttcctgggattcctgttgggcgtgggctccgcaatcgcatccggagtggccgtgtccaaagtgctgcatc
tggagggggaagtgaacaagatcaagtccgccctcctgtcaactaataaggcggtggtgtccctgagcaacggagtca
gcgtgtgtacaatcaaggtcctggacctcaagaactacatcgacaagcagctgttgcccatcgtcaacaagcagtcatgc
tcgattagcaatatcgaaaccgtgattgagttccagcagaagaacaacagactgctcgaaattacccgggagttttccgtg
aacgccggagtgaccactcctgtgtccacctacatgcttacgaactccgaactgctcagcctcatcaacgatatgccgatc
actaacgaccagaagaagttgatgagcaacaatgtgcagatcgtgcgccaacagtcctactcaatcatgtcaattatcaa
ggaggaagtgctcgcctatgtggtgcaattgcctctgtacggagtcatcgacacaccctgctggaagctgcacactagcc
cactctgtacgaccaacaccaaggaaggttccaacatctgcctgactaggaccgatcggggctggtattgcgataatgct
gggtccgtgagcttcttcccgcaagccgagacttgcaaagtgcagtcaaaccgcgtgttctgtgacaccatgaacagcct
gaccctgccatccgaagtcaacctctgcaacgtggacatctttaacccgaaatacgactgcaagattatgacctccaaga
ccgacgtcagcagctctgtcatcactagcctgggagctattgtgtcctgctacggaaagaccaaatgcactgcctcgaac
aagaacagaggcatcatcaagaccttcagcaacggctgtgactacgtgtccaacaagggagtggacaccgtgtccgtc
gggaacaccctgtactacgtgaacaagcaggaggggaagtcgctctacgtcaaggggggaaccgattatcaatttctacg
acccccctggtgttcccttccgacgagttcgatgcctccatatcccaagtcaacgagaagatcaaccagtctcttgccttcatc
cggaagtcggacgaactgctgtccgccatcggtggctatattccggaagcccccagggatggacaggcctacgtgcgg
aaggatggagaatgggtgcttttgtccaccttcctgggcggtctggtgccccgcggctcacaccatcatcaccaccacggtt
cgtggtcccaccctcaatttgagaagtga
[Relevant components (bp coordinates): Signal sequence: 1-75; pep27: 328-408; F1: 409-1539; F2: 76-327; foldon: 1552-1632; Thrombin recognition sequence: 1639-1656; His-tag: 1657-1674; Streptag II: 1681-1704; Linker sequences: 1540-1551, 1633-1638, 1675-1680; P102A (naturally-occurring substitution): 304-306; I379V (naturally-occurring substitution): 1135-1137; M447V (naturally-occurring substitution): 1339-1341; T54H: 160-162; S55C: 163-165; L188C: 562-564; S190I: 568-570]

SEQ ID NO: 11: Nucleotide Sequence Nucleotide Sequence Encoding Pre-coursor Polypeptide of pXCS847:
atggaacttctgatcctgaaagccaacgcgattaccactatcctgactgccgtcaccttctgcttcgcatcgggacagaaca
ttaccgaggagttctaccagtccacctgttcggcggtgtccaagggttacctctcggccctgagaactggctggtacacca
gcgtgattactatcgagctgagcaacatcaaggagaacaagtgcaatggaacggacgcgaaggtcaagctgattaag
caggaactcgataagtacaagaacgccgtgaccgagctccagctgctgatgcaatcgacccctgcctgtaacaacaga
gctcgccgggaactgccgcgcttcatgaattacaccctcaacaacgcgaagaaaaccaacgtgaccctgtccaagaag
cgcaagcggaggttcctgggattcctgttgggcgtgggctccgcatgtgcatccggagtggccgtgtccaaagtgctgcat
ctggagggggaagtgaacaagatcaagtccgccctcctgtcaactaataaggcggtggtgtccctgagcaacggagtc
agcgtgctgacaatcaaggtcctggacctcaagaactacatcgacaagcagctgttgcccatcgtcaacaagcagtcat
gctcgattagcaatatcgaaaccgtgattgagttccagcagaagaacaacagactgctcgaaattacccgggagttttcc
gtgaacgccggagtgaccactcctgtgtccacctacatgcttacgaactccgaactgctcagcctcatcaacgatatgccg
atcactaacgaccagaagaagttgatgagcaacaatgtgcagatcgtgcgccaacagtcctactcaatcatgtcaattat -continued Listing of Raw Sequences caaggaggaagtgctcgcctatgtggtgcaattgcctctgtacggagtcatcgacacaccctgctggaagctgcacacta
gcccactctgtacgaccaacaccaaggaaggttccaacatctgcctgactaggaccgatcggggctggtattgcgataat
gctgggtccgtgagcttcttcccgcaagccgagacttgcaaagtgcagtcaaaccgcgtgttctgtgacaccatgaacag
cctgaccctgccatccgaagtcaacctctgcaacgtggacatctttaacccgaaatacgactgcaagattatgacctccaa
gaccgacgtcagcagctctgtcatcactagcctgggagctattgtgtcctgctacggaaagaccaaatgcactgcctcga
acaagaacagaggcatcatcaagaccttcagcaacggctgtgactacgtgtccaacaagggagtggacaccgtgtccg
tcgggaacaccctgtactacgtgaacaagcaggaggggaagtcgctctacgtcaaggggaaccgattatcaatttcta
cgacccccctggtgttcccttcctccgagttcgatgcctccatatcccaagtcaacgagaagatcaaccagtctcttgccttcat
ccggaagtcggacgaactgctgtccgccatcggtggctatattccggaagcccccagggatggacaggcctacgtgcg
gaaggatggagaatgggtgcttttgtccaccttcctgggcggtctggtgccccgcggctcacaccatcatcaccaccacgg
ttcgtggtcccaccctcaatttgagaagtga
[Relevant components (bp coordinates): Signal sequence: 1-75; pep27: 328-408; F1: 409-1539; F2: 76-327; foldon: 1552-1632; Thrombin recognition sequence: 1639-1656; His-tag: 1657-1674; Streptag II: 1681-1704; Linker sequences: 1540-1551, 1633-1638, 1675-1680; P102A (naturally-occurring substitution): 304-306; I379V (naturally-occurring substitution): 1135-1137; M447V (naturally-occurring substitution): 1339-1341; T103C: 307-309; I148C: 442-444; S190I: 568-570; D486S: 1456-1458]

SEQ ID NO: 12: Nucleotide Sequence Nucleotide Sequence Encoding Pre-coursor Polypeptide of pXCS851:
atggaacttctgatcctgaaagccaacgcgattaccactatcctgactgccgtcaccttctgcttcgcatcgggacagaaca
ttaccgaggagttctaccagtccacctgttcggcggtgtccaagggttacctctcggccctgagaactggctggtaccaca
gcgtgattactatcgagctgagcaacatcaaggagaacaagtgcaatggaacggacgcgaaggtcaagctgattaag
caggaactcgataagtacaagaacgccgtgaccgagctccagctgctgatgcaatcgacccctgcctgtaacaacaga
gctcgccgggaactgccgcgcttcatgaattacaccctcaacaacgcgaagaaaaccaacgtgaccctgtccaagaag
cgcaagcggaggttcctgggattcctgttgggcgtgggctccgcatgtgcatccggagtggccgtgtccaaagtgctgcat
ctggagggggaagtgaacaagatcaagtccgccctcctgtcaactaataaggcggtggtgtccctgagcaacggagtc
agcgtgctgacaatcaaggtcctggacctcaagaactacatcgacaagcagctgttgcccatcgtcaacaagcagtcat
gctcgattagcaatatcgaaaccgtgattgagttccagcagaagaacaacagactgctcgaaattacccgggagttttcc
gtgaacgccggagtgaccactcctgtgtccacctacatgcttacgaactccgaactgctcagcctcatcaacgatatgccg
atcactaacgaccagaagaagttgatgagcaacaatgtgcagatcgtgcgccaacagtcctactcaatcatgtcaattat
caaggaggaaatcctcgcctatgtggtgcaattgcctctgtacggagtcatcgacacaccctgctggaagctgcacacta
gcccactctgtacgaccaacaccaaggaaggttccaacatctgcctgactaggaccgatcggggctggtattgcgataat
gctgggtccgtgagcttcttcccgcaagccgagacttgcaaagtgcagtcaaaccgcgtgttctgtgacaccatgaacag
cctgaccctgccatccgaagtcaacctctgcaacgtggacatctttaacccgaaatacgactgcaagattatgacctccaa
gaccgacgtcagcagctctgtcatcactagcctgggagctattgtgtcctgctacggaaagaccaaatgcactgcctcga
acaagaacagaggcatcatcaagaccttcagcaacggctgtgactacgtgtccaacaagggagtggacaccgtgtccg
tcgggaacaccctgtactacgtgaacaagcaggaggggaagtcgctctacgtcaaggggaaccgattatcaatttcta
cgacccccctggtgttcccttcctccgagttcgatgcctccatatcccaagtcaacgagaagatcaaccagtctcttgccttcat
ccggaagtcggacgaactgctgtccgccatcggtggctatattccggaagcccccagggatggacaggcctacgtgcg
gaaggatggagaatgggtgcttttgtccaccttcctgggcggtctggtgccccgcggctcacaccatcatcaccaccacgg
ttcgtggtcccaccctcaatttgagaagtga
[Relevant components (bp coordinates): Signal sequence: 1-75; pep27: 328-408; F1: 409-1539; F2: 76-327; foldon: 1552-1632; Thrombin recognition sequence: 1639-1656; His-tag: 1657-1674; Streptag II: 1681-1704; Linker sequences: 1540-1551, 1633-1638, 1675-1680; P102A (naturally-occurring substitution): 304-306; I379V (naturally-occurring substitution): 1135-1137; M447V (naturally-occurring substitution): 1339-1341; T54H: 160-162; T103C: 307-309; I148C: 442-444; S190I: 568-570; V296I: 886-888; D486S: 1456-1458]

SEQ ID NO: 13: Nucleotide Sequence Nucleotide Sequence Encoding Pre-coursor Polypeptide of pXCS852:
atggaacttctgatcctgaaagccaacgcgattaccactatcctgactgccgtcaccttctgcttcgcatcgggacagaaca
ttaccgaggagttctaccagtccacctgttcggcggtgtccaagggttacctctcggccctgagaactggctggtaccactg
tgtgattactatcgagctgagcaacatcaaggagaacaagtgcaatggaacggacgcgaaggtcaagctgattaagca
ggaactcgataagtacaagaacgccgtgaccgagctccagctgctgatgcaatcgacccctgccactaacaacagag
ctcgccgggaactgccgcgcttcatgaattacaccctcaacaacgcgaagaaaaccaacgtgaccctgtccaagaagc
gcaagcggaggttcctgggattcctgttgggcgtgggctccgcaatcgcatccggagtggccgtgtccaaagtgctgcatc
tggagggggaagtgaacaagatcaagtccgccctcctgtcaactaataaggcggtggtgtccctgagcaacggagtca
gcgtgtgtacatccaaggtcctggacctcaagaactacatcgacaagcagctgttgcccatcgtcaacaagcagtcatgc
tcgattagcaatatcgaaaccgtgattgagttccagcagaagaacaacagactgctcgaaattacccgggagttttccgtg
aacgccggagtgaccactcctgtgtccacctacatgcttacgaactccgaactgctcagcctcatcaacgatatgccgatc
actaacgaccagaagaagttgatgagcaacaatgtgcagatcgtgcgccaacagtcctactcaatcatgtcaattatcaa
ggaggaagtgctcgcctatgtggtgcaattgcctctgtacggagtcatcgacacaccctgctggaagctgcacactagcc
cactctgtacgaccaacaccaaggaaggttccaacatctgcctgactaggaccgatcggggctggtattgcgataatgct
gggtccgtgagcttcttcccgcaagccgagacttgcaaagtgcagtcaaaccgcgtgttctgtgacaccatgaacagcct
gaccctgccatccgaagtcaacctctgcaacgtggacatctttaacccgaaatacgactgcaagattatgacctccaaga
ccgacgtcagcagctctgtcatcactagcctgggagctattgtgtcctgctacggaaagaccaaatgcactgcctcgaac
aagaacagaggcatcatcaagaccttcagcaacggctgtgactacgtgtccaacaagggagtggacaccgtgtccgtc
gggaacaccctgtactacgtgaacaagcaggaggggaagtcgctctacgtcaaggggaaccgattatcaatttctacg
acccccctggtgttcccttcctccgagttcgatgcctccatatcccaagtcaacgagaagatcaaccagtctcttgccttcatcc
ggaagtcggacgaactgctgtccgccatcggtggctatattccggaagcccccagggatggacaggcctacgtgcgga
aggatggagaatgggtgcttttgtccaccttcctgggcggtctggtgccccgcggctcacaccatcatcaccaccacggttc
gtggtcccaccctcaatttgagaagtga
[Relevant components (bp coordinates): Signal sequence: 1-75; pep27: 328-408; F1: 409-1539 (only including native RSV F sequence); F2: 76-327; foldon: 1552-1632; Thrombin recognition sequence: 1639-1656; His-tag: 1657-1674; Streptag II: 1681-

-continued

Listing of Raw Sequences

1704; Linker sequences: 1540-1551, 1633-1638, 1675-1680; P102A (naturally-occurring substitution): 304-306; I379V (naturally-occurring substitution): 1135-1137; M447V (naturally-occurring substitution): 1339-1341; T54H: 160-162; S55C: 163-165; L188C: 562-564; D486S: 1456-1458]

SEQ ID NO: 14: Nucleotide Sequence Encoding Pre-cursor Polypeptide of pXCS853:
atggaacttctgatcctgaaagccaacgcgattaccactatcctgactgccgtcaccttctgcttcgcatcgggacagaaca
ttaccgaggagttctaccagtccacctgttcggcggtgtccaagggttacctctcggccctgagaactggctggtacacctg
tgtgattactatcgagctgagcaacatcaaggagaacaagtgcaatggaacggacgcgaaggtcaagctgattaagca
ggaactcgataagtacaagaacgccgtgaccgagctccagctgctgatgcaatcgacccctgccactaacaacagag
ctcgccgggaactgccgcgcttcatgaattacaccctcaacaacgcgaagaaaaccaacgtgaccctgtccaagaagc
gcaagcggaggttcctgggattcctgttgggcgtgggctccgcaatcgcatccggagtggccgtgtccaaagtgctgcatc
tggagggggaagtgaacaagatcaagtccgccctcctgtcaactaataaggcggtggtgtccctgagcaacggagtca
gcgtgtgtacaatcaaggtcctggacctcaagaactacatcgacaagcagctgttgcccatcgtcaacaagcagtcatgc
tcgattagcaatatcgaaaccgtgattgagttccagcagaagaacaacagactgctcgaaattacccgggagttttccgtg
aacgccggagtgaccactcctgtgtccacctacatgcttacgaactccgaactgctcagcctcatcaacgatatgccgatc
actaacgaccagaagaagttgatgagcaacaatgtgcagatcgtgcgccaacagtcctactcaatcatgtcaattatcaa
ggaggaagtgctcgcctatgtggtgcaattgcctctgtacggagtcatcgacacaccctgctggaagctgcacactagcc
cactctgtacgaccaacaccaaggaaggttccaacatctgcctgactaggaccgatcggggctggtattgcgataatgct
gggtccgtgagcttcttcccgcaagccgagacttgcaaagtgcagtcaaaccgcgtgttctgtgacaccatgaacagcct
gaccctgccatccgaagtcaacctctgcaacgtggacatctttaacccgaaatacgactgcaagattatgacctccaaga
ccgacgtcagcagctctgtcatcactagcctgggagctattgtgtcctgctacggaaagaccaaatgcactgcctcgaac
aagaacagaggcatcatcaagaccttcagcaacggctgtgactacgtgtccaacaagggagtggacaccgtgtccgtc
gggaacaccctgtactacgtgaacaagcaggaggggaagtcgctctacgtcaaggggggaaccgattatcaatttctacg
acccctggtgttcccttcctccgagttcgatgcctccatatcccaagtcaacgagaagatcaaccagtctcttgccttcatcc
ggaagtcggacgaactgctgtccgccatcggtggctatattccggaagcccccagggatggacaggcctacgtgcgga
aggatggagaatgggtgcttttgtccaccttcctgggcggtctggtgccccgcggctcacaccatcatcaccaccacggttc
gtggtcccaccctcaatttgagaagtga
[Relevant components (bp coordinates): Signal sequence: 1-75; pep27: 328-408; F1: 409-1539; F2: 76-327; foldon: 1552-1632; Thrombin recognition sequence: 1639-1656; His-tag: 1657-1674; Streptag II: 1681-1704; Linker sequences: 1540-1551, 1633-1638, 1675-1680; P102A (naturally-occurring substitution): 304-306; I379V (naturally-occurring substitution): 1135-1137; M447V (naturally-occurring substitution): 1339-1341; S55C: 163-165; L188C: 562-564; S190I: 568-570; D486S: 1456-1458]

SEQ ID NO: 15: Nucleotide Sequence Encoding Pre-cursor Polypeptide of pXCS855:
atggaacttctgatcctgaaagccaacgcgattaccactatcctgactgccgtcaccttctgcttcgcatcgggacagaaca
ttaccgaggagttctaccagtccacctgttcggcggtgtccaagggttacctctcggccctgagaactggctggtaccactg
tgtgattactatcgagctgagcaacatcaaggagaacaagtgcaatggaacggacgcgaaggtcaagctgattaagca
ggaactcgataagtacaagaacgccgtgaccgagctccagctgctgatgcaatcgacccctgccactaacaacagag
ctcgccgggaactgccgcgcttcatgaattacaccctcaacaacgcgaagaaaaccaacgtgaccctgtccaagaagc
gcaagcggaggttcctgggattcctgttgggcgtgggctccgcaatcgcatccggagtggccgtgtccaaagtgctgcatc
tggagggggaagtgaacaagatcaagtccgccctcctgtcaactaataaggcggtggtgtccctgagcaacggagtca
gcgtgtgtacaatcaaggtcctggacctcaagaactacatcgacaagcagctgttgcccatcgtcaacaagcagtcatgc
tcgattagcaatatcgaaaccgtgattgagttccagcagaagaacaacagactgctcgaaattacccgggagttttccgtg
aacgccggagtgaccactcctgtgtccacctacatgcttacgaactccgaactgctcagcctcatcaacgatatgccgatc
actaacgaccagaagaagttgatgagcaacaatgtgcagatcgtgcgccaacagtcctactcaatcatgtcaattatcaa
ggaggaagtgctcgcctatgtggtgcaattgcctctgtacggagtcatcgacacaccctgctggaagctgcacactagcc
cactctgtacgaccaacaccaaggaaggttccaacatctgcctgactaggaccgatcggggctggtattgcgataatgct
gggtccgtgagcttcttcccgcaagccgagacttgcaaagtgcagtcaaaccgcgtgttctgtgacaccatgaacagcct
gaccctgccatccgaagtcaacctctgcaacgtggacatctttaacccgaaatacgactgcaagattatgacctccaaga
ccgacgtcagcagctctgtcatcactagcctgggagctattgtgtcctgctacggaaagaccaaatgcactgcctcgaac
aagaacagaggcatcatcaagaccttcagcaacggctgtgactacgtgtccaacaagggagtggacaccgtgtccgtc
gggaacaccctgtactacgtgaacaagcaggaggggaagtcgctctacgtcaaggggggaaccgattatcaatttctacg
acccctggtgttcccttcctccgagttcgatgcctccatatcccaagtcaacgagaagatcaaccagtctcttgccttcatcc
ggaagtcggacgaactgctgtccgccatcggtggctatattccggaagcccccagggatggacaggcctacgtgcgga
aggatggagaatgggtgcttttgtccaccttcctgggcggtctggtgccccgcggctcacaccatcatcaccaccacggttc
gtggtcccaccctcaatttgagaagtga
[Relevant features (bp coordinates): Signal sequence: 1-75; pep27: 328-408; F1: 409-1539; F2: 76-327; foldon: 1552-1632; Thrombin recognition sequence: 1639-1656; His-tag: 1657-1674; Streptag II: 1681-1704; Linker sequences: 1540-1551, 1633-1638, 1675-1680; P102A (naturally-occurring substitution): 304-306; I379V (naturally-occurring substitution): 1135-1137; M447V (naturally-occurring substitution): 1339-1341; T54H: 160-162; S55C: 163-165; L188C: 562-564; S190I: 568-570; D486S: 1456-1458]

SEQ ID NO: 16: Nucleotide Sequence Encoding Precursor Polypeptide of pXCS874:
atggaacttctgatcctgaaagccaacgcgattaccactatcctgactgccgtcaccttctgcttcgcatcgggacagaaca
ttaccgaggagttctaccagtccacctgttcggcggtgtccaagggttacctctcggccctgagaactggctggtacacca
gcgtgattactatcgagctgagcaacatcaaggagaacaagtgcaatggaacggacgcgaaggtcaagctgattaag
caggaactcgataagtacaagaacgccgtgaccgagctccagctgctgatgcaatcgacccctgccactaacaacag
agctcgccgggaactgccgcgcttcatgaattacaccctcaacaacgcgaagaaaaccaacgtgaccctgtccaagaa
gcgcaagcggaggttcctgggattcctgttgggcgtgggctccgcaatcgcatccggagtggccgtgtgtaaagtgctgc
atctggagggggaagtgaacaagatcaagtccgccctcctgtcaactaataaggcggtggtgtccctgagcaacggagt -continued

| Listing of Raw Sequences |
|---|
| cagcgtgctgacaatcaaggtcctggacctcaagaactacatcgacaagcagctgttgcccatcgtcaacaagcagtca<br>tgctcgattagcaatatcgaaaccgtgattgagttccagcagaagaacaacagactgctcgaaattacccgggagttttcc<br>gtgaacgccggagtgaccactcctgtgtccacctacatgcttacgaactccgaactgctcagcctcatcaacgatatgccg<br>atcactaacgaccagaagaagttgatgagcaacaatgtgcagatcgtgcgccaacagtcctactcaatcatgtgcattat<br>caaggaggaagtgctcgcctatgtggtgcaattgcctctgtacggagtcatcgacacaccctgctggaagctgcacacta<br>gcccactctgtacgaccaacaccaaggaaggttccaacatctgcctgactaggaccgatcggggctggtattgcgataat<br>gctgggtccgtgagcttcttcccgcaagccgagacttgcaaagtgcagtcaaaccgcgtgttctgtgacaccatgaacag<br>cctgaccctgccatccgaagtcaacctctgcaacgtggacatctttaacccgaaatacgactgcaagattatgacctccaa<br>gaccgacgtcagcagctctgtcatcactagcctgggagctattgtgtcctgctacggaaagaccaaatgcactgcctcga<br>acaagaacagaggcatcatcaagaccttcagcaacggctgtgactacgtgtccaacaagggagtggacaccgtgtccg<br>tcgggaacaccctgtactacgtgaacaagcaggaggggaagtcgctctacgtcaaggggggaaccgattatcaatttcta<br>cgacccccctggtgttcccttcctccgagttcgatgcctccatatcccaagtcaacgagaagatcaaccagtctcttgccttcat<br>ccggaagtcggacgaactgctgtccgccatcggtggctatattccggaagccccccagggatggacaggcctacgtgcg<br>gaaggatggagaatgggtgcttttgtccaccttcctgggcggtctggtgccccgcggctcacaccatcatcaccaccacgg<br>ttcgtggtcccaccctcaatttgagaagtga<br>[Relevant features (bp coordinates): Signal sequence: 1-75; pep27: 328-408; F1: 409-1539; F2: 76-327; foldon: 1552-1632; Thrombin recognition sequence: 1639-1656; His-tag: 1657-1674; Streptag II: 1681-1704; Linker sequences: 1540-1551, 1633-1638, 1675-1680; P102A (naturally-occurring substitution): 304-306; I379V (naturally-occurring substitution): 1135-1137; M447V (naturally-occurring substitution): 1339-1341; S155C: 463-465; S190I: 568-570; S290C: 868-870; D486S: 1456-1458]<br><br>SEQ ID NO: 17: Nucleotide Sequence Encoding Precursor Polypeptide of pXCS881:<br>atggaacttctgatcctgaaagccaacgcgattaccactatcctgactgccgtcaccttctgcttcgcatcgggacagaaca<br>ttaccgaggagttctaccagtccacctgttcggcggtgtccaagggttacctctcggccctgagaactggctggtaccactg<br>tgtgattactatcgagctgagcaacatcaaggagaacaagtgcaatggaacggacgcgaaggtcaagctgattaagca<br>ggaactcgataagtacaagaacgccgtgaccgagctccagctgctgatgcaatcgacccctgccactaacaacagag<br>ctcgccgggaactgccgcgcttcatgaattacaccctcaacaacgcgaagaaaaccaacgtgaccctgtccaagaagc<br>gcaagcggaggttcctgggattcctgtgtggcgtgggctccgcaatcgcatccggagtggccgtgtccaaagtgctgcatc<br>tggaggggggaagtgaacaagatcaagtccgccctcctgtcaactaataaggcggtggtgtccctgagcaacggagtca<br>gcgtgtgtacatccaaggtcctggacctcaagaactacatcgacaagcagctgttgcccatcgtcaacaagcagtcatgc<br>tcgattagcaatatcgaaaccgtgattgagttccagcagaagaacaacagactgctcgaaattacccgggagttttccgtg<br>aacgccggagtgaccactcctgtgtccacctacatgcttacgaactccgaactgctcagcctcatcaacgatatgccgatc<br>actaacgaccagaagaagttgatgagcaacaatgtgcagatcgtgcgccaacagtcctactcaatcatgtcaattatcaa<br>ggaggaaatcctcgcctatgtggtgcaattgcctctgtacggagtcatcgacacaccctgctggaagctgcacactagcc<br>cactctgtacgaccaacaccaaggaaggttccaacatctgcctgactaggaccgatcggggctggtattgcgataatgct<br>gggtccgtgagcttcttcccgcaagccgagacttgcaaagtgcagtcaaaccgcgtgttctgtgacaccatgtgtagcctg<br>accctgccatccgaagtcaacctctgcaacgtggacatctttaacccgaaatacgactgcaagattatgacctccaagac<br>cgacgtcagcagctctgtcatcactagcctgggagctattgtgtcctgctacggaaagaccaaatgcactgcctcgaaca<br>agaacagaggcatcatcaagaccttcagcaacggctgtgactacgtgtccaacaagggagtggacaccgtgtccgtcg<br>ggaacaccctgtactacgtgaacaagcaggaggggaagtcgctctacgtcaaggggggaaccgattatcaatttctacga<br>cccccctggtgttcccttccagccagttcagtgcctccatatcccaagtcaacgagaagatcaaccagtctcttgccttcatcc<br>ggaagtcggacgaactgctgtccgccatcggtggctatattccggaagccccccagggatggacaggcctacgtgcgga<br>aggatggagaatgggtgcttttgtccaccttcctgggcggtctggtgccccgcggctcacaccatcatcaccaccacggttc<br>gtggtcccaccctcaatttgagaagtga<br>[Relevant features (bp coordinates): Signal sequence: 1-75; pep27: 328-408; F1: 409-1539; F2: 76-327; foldon: 1552-1632; Thrombin recognition sequence: 1639-1656; His-tag: 1657-1674; Streptag II: 1681-1704; Linker sequences: 1540-1551, 1633-1638, 1675-1680; P102A (naturally-occurring substitution): 304-306; I379V (naturally-occurring substitution): 1135-1137; M447V (naturally-occurring substitution): 1339-1341; T54H: 160-162; S55C: 163-165; L1420: 424-426; L188C: 562-564; V296I: 886-888; N371C: 1111-1113; D486S: 1456-1458; E487Q: 1459-1461; D489S: 1465-1467]<br><br>SEQ ID NO: 18: Nucleotide Sequence Encoding Precursor Polypeptide of pXCS898:<br>atggaacttctgatcctgaaagccaacgcgattaccactatcctgactgccgtcaccttctgcttcgcatcgggacagaaca<br>ttaccgaggagttctaccagtccacctgttcggcggtgtccaagggttacctctcggccctgagaactggctggtaccaca<br>gcgtgattactatcgagctgagcaacatcaaggagaacaagtgcaatggaacggacgcgaaggtcaagctgattaag<br>caggaactcgataagtacaagaacgccgtgaccgagctccagctgctgatgcaatcgacccctgccactaacaacag<br>agctcgccgggaactgccgcgcttcatgaattacaccctcaacaacgcgaagaaaaccaacgtgaccctgtccaagaa<br>gcgcaagcggaggttcctgggattcctgttgggcgtgggctccgcaatcgcatccggagtggccgtgtgtaaagtgctgc<br>atctggaggggggaagtgaacaagatcaagtccgccctcctgtcaactaataaggcggtggtgtccctgagcaacggagt<br>cagcgtgctgacaatcaaggtcctggacctcaagaactacatcgacaagcagctgttgcccatcgtcaacaagcagtca<br>tgctcgattagcaatatcgaaaccgtgattgagttccagcagaagaacaacagactgctcgaaattacccgggagttttcc<br>gtgaacgccggagtgaccactcctgtgtccacctacatgcttacgaactccgaactgctcagcctcatcaacgatatgccg<br>atcactaacgaccagaagaagttgatgagcaacaatgtgcagatcgtgcgccaacagtcctactcaatcatgtgcattat<br>caaggaggaaatcctcgcctatgtggtgcaattgcctctgtacggagtcatcgacacaccctgctggaagctgcacacta<br>gcccactctgtacgaccaacaccaaggaaggttccaacatctgcctgactaggaccgatcggggctggtattgcgataat<br>gctgggtccgtgagcttcttcccgcaagccgagacttgcaaagtgcagtcaaaccgcgtgttctgtgacaccatgaacag<br>cctgaccctgccatccgaagtcaacctctgcaacgtggacatctttaacccgaaatacgactgcaagattatgacctccaa<br>gaccgacgtcagcagctctgtcatcactagcctgggagctattgtgtcctgctacggaaagaccaaatgcactgcctcga<br>acaagaacagaggcatcatcaagaccttcagcaacggctgtgactacgtgtccaacaagggagtggacaccgtgtccg<br>tcgggaacaccctgtactacgtgaacaagcaggaggggaagtcgctctacgtcaaggggggaaccgattatcaatttcta<br>cgacccccctggtgttcccttccgacgagttcgatgcctccatatcccaagtcaacgagaagatcaaccagtctcttgccttc<br>atccggaagtcggacgaactgctgtccgccatcggtggctatattccggaagccccccagggatggacaggcctacgtgc |

-continued

Listing of Raw Sequences ggaaggatggagaatgggtgcttttgtccaccttcctgggcggtctggtgccccgcggctcacaccatcatcaccaccacg
gttcgtggtcccaccctcaatttgagaagtga
[Relevant features (bp coordinates): Signal sequence: 1-75; pep27: 328-408; F1: 409-1539; F2: 76-327; foldon: 1552-1632; Thrombin recognition sequence: 1639-1656; His-tag: 1657-1674; Streptag II: 1681-1704; Linker sequences: 1540-1551, 1633-1638, 1675-1680; P102A (naturally-occurring substitution): 304-306; I379V (naturally-occurring substitution): 1135-1137; M447V (naturally-occurring substitution): 1339-1341; T54H: 160-162; S155C: 463-465; S190I: 568-570; S290C: 868-870; V296I: 886-888]

SEQ ID NO: 19: Amino Acid Sequence of Precursor Polypeptide of pXCS847:
MELLILKANAITTILTAVTFCFASGQNITEEFYQSTCSAVSKGYLSALRTGWYTSVITIELS
NIKENKCNGTDAKVKLIKQELDKYKNAVTELQLLMQSTPACNNRARRELFRFMNYTLN
NAKKTNVTLSKKRKRRFLGFLLGVGSACASGVAVSKVLHLEGEVNKIKSALLSTNKAVV
SLSNGVSVLTIKVLDLKNYIDKQLLPIVNKQSCSISNIETVIEFQQKNNRLLEITREFSVNA
GVTTPVSTYMLTNSELLSLINDMPITNDQKKLMSNNVQIVRQQSYSIMSIIKEEVLAYVV
QLPLYGVIDTPCWKLHTSPLCTTNTKEGSNICLTRTDRGWYCDNAGSVSFFPQAETCK
VQSNRVFCDTMNSLTLPSEVNLCNVDIFNPKYDCKIMTSKTDVSSSVITSLGAIVSCYG
KTKCTASNKNRGIIKTFSNGCDYVSNKGVDTVSVGNTLYYVNKQEGKSLYVKGEPIINF
YDPLVFPSSEFDASISQVNEKINQSLAFIRKSDELLSAIGGYIPEAPRDGQAYVRKDGE
WVLLSTFLGGLVPRGSHHHHHHGSWSHPQFEK
[Relevant features (amino acid residue coordinates): Signal sequence (not present in final product): 1-25; pep27 (not present in final product): 110-136; F1: 137-513; F2: 26-109; foldon: 518-544; Thrombin recognition sequence: 547-552; His-tag: 553-558; Streptag II: 561-568; P102A (naturally-occurring substitution); I379V (naturally-occurring substitution); M447V (naturally-occurring substitution); T103C, I148C, S190I, D486S]

SEQ ID NO: 20: Amino Acid Sequence of Precursor Polypeptide of pXCS851:
MELLILKANAITTILTAVTFCFASGQNITEEFYQSTCSAVSKGYLSALRTGWYHSVITIEL
SNIKENKCNGTDAKVKLIKQELDKYKNAVTELQLLMQSTPACNNRARRELPRFMNYTL
NNAKKTNVTLSKKRKRRFLGFLLGVGSACASGVAVSKVLHLEGEVNKIKSALLSTNKA
VVSLSNGVSVLTIKVLDLKNYIDKQLLPIVNKQSCSISNIETVIEFQQKNNRLLEITREFSV
NAGVTTPVSTYMLTNSELLSLINDMPITNDQKKLMSNNVQIVRQQSYSIMSIIKEEILAYV
VQLPLYGVIDTPCWKLHTSPLCTTNTKEGSNICLTRTDRGWYCDNAGSVSFFPQAETC
KVQSNRVFCDTMNSLTLPSEVNLCNVDIFNPKYDCKIMTSKTDVSSSVITSLGAIVSCY
GKTKCTASNKNRGIIKTFSNGCDYVSNKGVDTVSVGNTLYYVNKQEGKSLYVKGEPIIN
FYDPLVFPSSEFDASISQVNEKINQSLAFIRKSDELLSAIGGYIPEAPRDGQAYVRKDGE
WVLLSTFLGGLVPRGSHHHHHHGSWSHPQFEK
[Relevant features (amino acid residue coordinates): Signal sequence (not present in final product): 1-25; pep27 (not present in final product): 110-136; F1: 137-513; F2: 26-109; foldon: 518-544; Thrombin recognition sequence: 547-552; His-tag: 553-558; Streptag II: 561-568; P102A (naturally-occurring substitution); I379V (naturally-occurring substitution); M447V (naturally-occurring substitution); T54H, T103C, I148C, S190I, V296I, D486S]

SEQ ID NO: 21: Amino Acid Sequence of Precursor Polypeptide of pXCS852:
MELLILKANAITTILTAVTFCFASGQNITEEFYQSTCSAVSKGYLSALRTGWYHCVITIEL
SNIKENKCNGTDAKVKLIKQELDKYKNAVTELQLLMQSTPATNNRARRELPRFMNYTL
NNAKKTNVTLSKKRKRRFLGFLLGVGSAIASGVAVSKVLHLEGEVNKIKSALLSTNKAV
VSLSNGVSVCTSKVLDLKNYIDKQLLPIVNKQSCSISNIETVIEFQQKNNRLLEITREFSV
NAGVTTPVSTYMLTNSELLSLINDMPITNDQKKLMSNNVQIVRQQSYSIMSIIKEEVLAY
VVQLPLYGVIDTPCWKLHTSPLCTTNTKEGSNICLTRTDRGWYCDNAGSVSFFPQAET
CKVQSNRVFCDTMNSLTLPSEVNLCNVDIFNPKYDCKIMTSKTDVSSSVITSLGAIVSC
YGKTKCTASNKNRGIIKTFSNGCDYVSNKGVDTVSVGNTLYYVNKQEGKSLYVKGEPII
NFYDPLVFPSSEFDASISQVNEKINQSLAFIRKSDELLSAIGGYIPEAPRDGQAYVRKDG
EWVLLSTFLGGLVPRGSHHHHHHGSWSHPQFEK
[Relevant features (amino acid residue coordinates): Signal sequence (not present in final product): 1-25; pep27 (not present in final product): 110-136; F1: 137-513 (only including native RSV F sequence); F2: 26-109; foldon: 518-544; Thrombin recognition sequence: 547-552; His-tag: 553-558; Streptag II: 561-568; P102A (naturally-occurring substitution); I379V (naturally-occurring substitution); M447V (naturally-occurring substitution); T54H (introduced mutation); S55C (introduced mutation); L188C (introduced mutation); D486S (introduced mutation)]

-continued

| Listing of Raw Sequences |
|---|

SEQ ID NO: 22: Amino Acid Sequence of Heavy Chain Variable Domain of Antibody D25:
QVQLVQSGAEVKKPGSSVMVSCQASGGPLRNYIINWLRQAPGQGPEWMGGIIPVLGT
VHYAPKFQGRVTITADESTDTAYIHLISLRSEDTAMYYCATETALVVSTTYLPHYFDNW
GQGTLVTVSS SEQ ID NO: 23: Amino Acid Sequence of Light Chain Variable Domain of Antibody D25:
DIQMTQSPSSLSAAVGDRVTITCQASQDIVNYLNWQQKPGKAPKLLIYVASNLETGV
PSRFSGSGSGTDFSLTISSLQPEDVATYYCQQYDNLPLTFGGGTKVEIKR SEQ ID NO: 24: Amino Acid Sequence of Heavy Chain Variable Domain of Antibody AM14:
EVQLVESGGGWQPGRSLRLSCAASGFSFSHYAMHWVRQAPGKGLEWVAVISYDGE
NTYYADSVKGRFSISRDNSKNTVSLQMNSLRPEDTALYYCARDRIVDDYYYYGMDVW
GQGATVTVSS SEQ ID NO: 25: Amino Acid Sequence of Light Chain Variable Domain of Antibody AM14:
DIQMTQSPSSLSASVGDRVTITCQASQDIKKYLNWYHQKPGKVPELLMHDASNLETGV
PSRFSGRGSGTDFTLTISSLQPEDIGTYYCQQYDNLPPLTFGGGTKVEIKRTV SEQ ID NO: 26: Amino Acid Sequence of Heavy Chain Variable Domain of Antibody AM22
QVQLVQSGAEVKKPGATVKVSCKISGHTLIKLSIHWVRQAPGKGLEWMGGYEGEVDE
IFYAQKFQHRLTVIADTATDTVYMELGRLTSDDTAVYFCGTLGVTVTEAGLGIDDYWG
QGTLVTVSS SEQ ID NO: 27: Amino Acid Sequence of Light Chain Variable Domain of Antibody AM22
EIVLTQSPGTLSLSPGERATLSCRASQIVSRNHLAWYQQKPGQAPRLLIFGASSRATGI
PVRFSGSGSGTDFTLTINGLAPEDFAVYYCLSSDSSIFTFGPGTKVDFK SEQ ID NO: 28: Amino Acid Sequence of Heavy Chain Variable Domain of Antibody MPE8:
EVQLVESGGGLVKPGGSLRLSCAASGFTFSSYSMNWVRQAPGKGLEWVSSISASSS
YSDYADSAKGRFTISRDNAKTSLFLQMNSLRAEDTAIYFCARARATGYSSITPYFDIWG
QGTLVTVSS SEQ ID NO: 29: Amino Acid Sequence of Light Chain Variable Domain of Antibody MPE8:
QSVVTQTPSVSGAPGQRVTISCTGSSSNIGAGYDVHWYQQLPGTAPKWYDNNNRP
SGVPDRFSASKSGTSASLAITGLQAEDEADYYCQSYDRNLSGVFGTGTKVTVL SEQ ID NO: 30: Amino Acid Sequence of Heavy Chain Variable Domain of Antibody 101F:
QVTLKESGPGILQPSQTLSLTCSFSGFSLSTSGMGVSWIRQPSGKGLEWLAHIYWDD
DKRYNPSLKSRLTISKDTSRNQVFLKITSVDTADTATYYCARLYGFTYGFAYWGQGTL
VTVSA SEQ ID NO: 31: Amino Acid Sequence of Light Chain Variable Domain of Antibody 101F:
DIVLTQSPASLAVSLGQRATIFCRASQSVDYNGISYMHWFQQKPGQPPKLLIYAASNP
ESGIPARFTGSGSGTDFTLNIHPVEEEDAATYYCQQIIEDPWTFGGGTKLEIK SEQ ID NO: 32: Amino Acid Sequence of Precursor Polypeptide of pXCS738:
MELLILKANAITTILTAVTFCFASGQNITEEFYQSTCSAVSKGYLSALRTGWYHCVITIEL
SNIKENKCNGTDAKVKLIKQELDKYKNAVTELQLLMQSTPATNNRARRELPRFMNYTL
NNAKKTNVTLSKKRKRRFLGFLCGVGSAIASGVAVSKVLHLEGEVNKIKSALLSTNKAV
VSLSNGVSVCTSKVLDLKNYIDKQLLPIVNKQSCSISNIETVIEFQQKNNRLLEITREFSV
NAGVTTPVSTYMLTNSELLSLINDMPITNDQKKLMSNNVQIVRQQSYSIMSIIKEEILAYV
VQLPLYGVIDTPCWKLHTSPLCTTNTKEGSNICLTRTDRGWYCDNAGSVSFFPQAETC
KVQSNRVFCDTMCSLTLPSEVNLCNVDIFNPKYDCKIMTSKTDVSSSVITSLGAIVSCY
GKTKCTASNKNRGIIKTFSNGCDYVSNKGVDTVSVGNTLYYVNKQEGKSLYVKGEPIIN
FYDPLVFPSDEFDASISQVNEKINQSLAFIRKSDELLSAIGGYIPEAPRDGQAYVRKDGE
WVLLSTFLGGLVPRGSHHHHHHGSWSHPQFEK
[Relevant features (amino acid residue coordinates): Signal sequence (not present in final product): 1-25; pep27 (not present in final product): 110-136; F1: 137; F2: 26-109; foldon: 518-544; Thrombin recognition sequence: 547-552; His-tag: 553-558; Streptag II: 561-568; Linker sequences: 514-517, 545-546, 559-560; P102A (naturally-occurring substitution); I379V (naturally-occurring substitution); M447V (naturally-occurring substitution); T54H (introduced mutation); S55C (introduced mutation); L142C (introduced mutation); L188C (introduced mutation); V296I (introduced mutation); N371C (introduced mutation)]

SEQ ID NO: 33 : Amino Acid Sequence of Precursor Polypeptide of pXCS780:
MELLILKANAITTILTAVTFCFASGQNITEEFYQSTCSAVSKGYLSALRTGWYTCVITIEL -continued Listing of Raw Sequences SNIKENKCNGTDAKVKLIKQELDKYKNAVTELQLLMQSTPATNNRARRELPRFMNYTL
NNAKKTNVTLSKKRKRRFLGFLLGVGSAIASGVAVSKVLHLEGEVNKIKSALLSTNKAV
VSLSNGVSVCTSKVLDLKNYIDKQLLPIVNKQSCSISNIETVIEFQQKNNRLLEITREFSV
NAGVTTPVSTYMLTNSELLSLINDMPITNDQKKLMSNNVQIVRQQSYSIMSIIKEEVLAY
VVQLPLYGVIDTPCWKLHTSPLCTTNTKEGSNICLTRTDRGWYCDNAGSVSFFPQAET
CKVQSNRVFCDTMNSLTLPSEVNLCNVDIFNPKYDCKIMTSKTDVSSSVITSLGAIVSC
YGKTKCTASNKNRGIIKTFSNGCDYVSNKGVDTVSVGNTLYYVNKQEGKSLYVKGEPII
NFYDPLVFPSSEFDASISQVNEKINQSLAFIRKSDELLSAIGGYIPEAPRDGQAYVRKDG
EWVLLSTFLGGLVPRGSHHHHHHGSWSHPQFEK
[Relevant features (amino acid residue coordinates): Signal sequence (not present in final product): 1-25; pep27 (not present in final product): 110-136; F1: 137-513; F2: 26-109; foldon: 518-544; Thrombin recognition sequence: 547-552; His-tag: 553-558; Streptag II: 561-568; Linker sequences: 514-517, 545-546, 559-560; P102A (naturally-occurring substitution); I379V (naturally-occurring substitution); M447V (naturally-occurring substitution); S55C (introduced mutation); L188C (introduced mutation); D486S (introduced mutation)]

SEQ ID NO: 34: Amino Acid Sequence of Precursor Polypeptide of pXCS830:
MELLILKANAITTILTAVTFCFASGQNITEEFYQSTCSAVSKGYLSALRTGWYHCVITIEL
SNIKENKCNGTDAKVKLIKQELDKYKNAVTELQLLMQSTPATNNRARRELPRFMNYTL
NNAKKTNVTLSKKRKRRFLGFLLGVGSAIASGVAVSKVLHLEGEVNKIKSALLSTNKAV
VSLSNGVSVCTIKVLDLKNYIDKQLLPIVNKQSCSISNIETVIEFQQKNNRLLEITREFSVN
AGVTTPVSTYMLTNSELLSLINDMPITNDQKKLMSNNVQIVRQQSYSIMSIIKEEVLAYV
VQLPLYGVIDTPCWKLHTSPLCTTNTKEGSNICLTRTDRGWYCDNAGSVSFFPQAETC
KVQSNRVFCDTMNSLTLPSEVNLCNVDIFNPKYDCKIMTSKTDVSSSVITSLGAIVSCY
GKTKCTASNKNRGIIKTFSNGCDYVSNKGVDTVSVGNTLYYVNKQEGKSLYVKGEPIIN
FYDPLVFPSDEFDASISQVNEKINQSLAFIRKSDELLSAIGGYIPEAPRDGQAYVRKDGE
WVLLSTFLGGLVPRGSHHHHHHGSWSHPQFEK
[Relevant features (amino acid residue coordinates): Signal sequence (not present in final product): 1-25; pep27 (not present in final product): 110-136; F1: 137-513; F2: 26-109; foldon: 518-544; Thrombin recognition sequence: 547-552; His-tag: 553-558; Streptag II: 561-568; Linker sequences: 514-517, 545-546, 559-560; P102A (naturally-occurring substitution); I379V (naturally-occurring substitution); M447V (naturally-occurring substitution); T54H (introduced mutation); S55C (introduced mutation); L188C (introduced mutation); S190I (introduced mutation)]

SEQ ID NO: 35: Amino Acid Sequence of Precursor Polypeptide of pXCS853:
MELLILKANAITTILTAVTFCFASGQNITEEFYQSTCSAVSKGYLSALRTGWYTCVITIEL
SNIKENKCNGTDAKVKLIKQELDKYKNAVTELQLLMQSTPATNNRARRELPRFMNYTL
NNAKKTNVTLSKKRKRRFLGFLLGVGSAIASGVAVSKVLHLEGEVNKIKSALLSTNKAV
VSLSNGVSVCTIKVLDLKNYIDKQLLPIVNKQSCSISNIETVIEFQQKNNRLLEITREFSVN
AGVTTPVSTYMLTNSELLSLINDMPITNDQKKLMSNNVQIVRQQSYSIMSIIKEEVLAYV
VQLPLYGVIDTPCWKLHTSPLCTTNTKEGSNICLTRTDRGWYCDNAGSVSFFPQAETC
KVQSNRVFCDTMNSLTLPSEVNLCNVDIFNPKYDCKIMTSKTDVSSSVITSLGAIVSCY
GKTKCTASNKNRGIIKTFSNGCDYVSNKGVDTVSVGNTLYYVNKQEGKSLYVKGEPIIN
FYDPLVFPSSEFDASISQVNEKINQSLAFIRKSDELLSAIGGYIPEAPRDGQAYVRKDGE
WVLLSTFLGGLVPRGSHHHHHHGSWSHPQFEK
[Relevant features (amino acid residue coordinates): Signal sequence (not present in final product): 1-25; pep27 (not present in final product): 110-136; F1: 137-513; F2: 26-109; foldon: 518-544; Thrombin recognition sequence: 547-552; His-tag: 553-558; Streptag II: 561-568; Linker sequences: 514-517, 545-546, 559-560; P102A (naturally-occurring substitution); I379V (naturally-occurring substitution); M447V (naturally-occurring substitution); S55C (introduced mutation); L188C (introduced mutation); S190I (introduced mutation); D486S (introduced mutation)]

SEQ ID NO: 36: Amino Acid Sequence of Precursor Polypeptide of pXCS855:
MELLILKANAITTILTAVTFCFASGQNITEEFYQSTCSAVSKGYLSALRTGWYHCVITIEL
SNIKENKCNGTDAKVKLIKQELDKYKNAVTELQLLMQSTPATNNRARRELPRFMNYTL
NNAKKTNVTLSKKRKRRFLGFLLGVGSAIASGVAVSKVLHLEGEVNKIKSALLSTNKAV
VSLSNGVSVCTIKVLDLKNYIDKQLLPIVNKQSCSISNIETVIEFQQKNNRLLEITREFSVN
AGVTTPVSTYMLTNSELLSLINDMPITNDQKKLMSNNVQIVRQQSYSIMSIIKEEVLAYV
VQLPLYGVIDTPCWKLHTSPLCTTNTKEGSNICLTRTDRGWYCDNAGSVSFFPQAETC
KVQSNRVFCDTMNSLTLPSEVNLCNVDIFNPKYDCKIMTSKTDVSSSVITSLGAIVSCY
GKTKCTASNKNRGIIKTFSNGCDYVSNKGVDTVSVGNTLYYVNKQEGKSLYVKGEPIIN
FYDPLVFPSSEFDASISQVNEKINQSLAFIRKSDELLSAIGGYIPEAPRDGQAYVRKDGE
WVLLSTFLGGLVPRGSHHHHHHGSWSHPQFEK
[Relevant features (amino acid residue coordinates): Signal sequence (not present in final product): 1-25; pep27 (not present in final product): 110-136; F1: 137-513; F2: 26-109; foldon: 518-544; Thrombin recognition sequence: 547-552; His-tag: 553-558; Streptag II: 561-568; Linker sequences: 514-517, 545-546, 559-560; P102A (naturally-occurring substitution); I379V (naturally-occurring substitution); M447V (naturally-occurring substitution); T54H (introduced mutation); S55C (introduced mutation); L188C (introduced mutation); S190I (introduced mutation); D486S (introduced mutation)]

SEQ ID NO: 37: Amino Acid Sequence of Precursor Polypeptide of pXCS874:
MELLILKANAITTILTAVTFCFASGQNITEEFYQSTCSAVSKGYLSALRTGWYTSVITIELS
NIKENKCNGTDAKVKLIKQELDKYKNAVTELQLLMQSTPATNNRARRELPRFMNYTLN -continued

| Listing of Raw Sequences |
| --- |

NAKKTNVTLSKKRKRRFLGFLLGVGSAIASGVAVCKVLHLEGEVNKIKSALLSTNKAVV
SLSNGVSVLTIKVLDLKNYIDKQLLPIVNKQSCSISNIETVIEFQQKNNRLLEITREFSVNA
GVTTPVSTYMLTNSELLSLINDMPITNDQKKLMSNNVQIVRQQSYSIMCIIKEEVLAYVV
QLPLYGVIDTPCWKLHTSPLCTTNTKEGSNICLTRTDRGWYCDNAGSVSFFPQAETCK
VQSNRVFCDTMNSLTLPSEVNLCNVDIFNPKYDCKIMTSKTDVSSSVITSLGAIVSCYG
KTKCTASNKNRGIIKTFSNGCDYVSNKGVDTVSVGNTLYYVNKQEGKSLYVKGEPIINF
YDPLVFPSSEFDASISQVNEKINQSLAFIRKSDELLSAIGGYIPEAPRDGQAYVRKDGE
WVLLSTFLGGLVPRGSHHHHHHGSWSHPQFEK
[Relevant features (amino acid residue coordinates): Signal sequence (not present in final product): 1-25; pep27 (not present in final product): 110-136; F1: 137-513; F2: 26-109; foldon: 518-544; Thrombin recognition sequence: 547-552; His-tag: 553-558; Streptag II: 561-568; Linker sequences: 514-517, 545-546, 559-560; P102A (naturally-occurring substitution); I379V (naturally-occurring substitution); M447V (naturally-occurring substitution); S155C (introduced mutation); S190I (introduced mutation); S290C (introduced mutation); D486S (introduced mutation)]

SEQ ID NO: 38: Amino Acid Sequence of Precursor Polypeptide of pXCS881:
MELLILKANAITTILTAVTFCFASGQNITEEFYQSTCSAVSKGYLSALRTGWYHCVITIEL
SNIKENKCNGTDAKVKLIKQELDKYKNAVTELQLLMQSTPATNNRARRELPRFMNYTL
NNAKKTNVTLSKKRKRRFLGFLCGVGSAIASGVAVSKVLHLEGEVNKIKSALLSTNKAV
VSLSNGVSVCTSKVLDLKNYIDKQLLPIVNKQSCSISNIETVIEFQQKNNRLLEITREFSV
NAGVTTPVSTYMLTNSELLSLINDMPITNDQKKLMSNNVQIVRQQSYSIMSIIKEEILAYV
VQLPLYGVIDTPCWKLHTSPLCTTNTKEGSNICLTRTDRGWYCDNAGSVSFFPQAETC
KVQSNRVFCDTMCSLTLPSEVNLCNVDIFNPKYDCKIMTSKTDVSSSVITSLGAIVSCY
GKTKCTASNKNRGIIKTFSNGCDYVSNKGVDTVSVGNTLYYVNKQEGKSLYVKGEPIIN
FYDPLVFPSSQFSASISQVNEKINQSLAFIRKSDELLSAIGGYIPEAPRDGQAYVRKDGE
WVLLSTFLGGLVPRGSHHHHHHGSWSHPQFEK
[Relevant features (amino acid residue coordinates): Signal sequence (not present in final product): 1-25; pep27 (not present in final product): 110-136; F1: 137-513; F2: 26-109; foldon: 518-544; Thrombin recognition sequence: 547-552; His-tag: 553-558; Streptag II: 561-568; Linker sequences: 514-517, 545-546, 559-560; P102A (naturally-occurring substitution); I379V (naturally-occurring substitution); M447V (naturally-occurring substitution); T54H (introduced mutation); S55C (introduced mutation); L142C (introduced mutation); L188C (introduced mutation); V296I (introduced mutation); N371C (introduced mutation); D486S (introduced mutation); E487Q (introduced mutation); D489S (introduced mutation)]

SEQ ID NO: 39: Amino Acid Sequence of Precursor Polypeptide of pXCS898:
MELLILKANAITTILTAVTFCFASGQNITEEFYQSTCSAVSKGYLSALRTGWYHSVITIEL
SNIKENKCNGTDAKVKLIKQELDKYKNAVTELQLLMQSTPATNNRARRELPRFMNYTL
NNAKKTNVTLSKKRKRRFLGFLLGVGSAIASGVAVCKVLHLEGEVNKIKSALLSTNKAV
VSLSNGVSVLTIKVLDLKNYIDKQLLPIVNKQSCSISNIETVIEFQQKNNRLLEITREFSVN
AGVTTPVSTYMLTNSELLSLINDMPITNDQKKLMSNNVQIVRQQSYSIMCIIKEEILAYVV
QLPLYGVIDTPCWKLHTSPLCTTNTKEGSNICLTRTDRGWYCDNAGSVSFFPQAETCK
VQSNRVFCDTMNSLTLPSEVNLCNVDIFNPKYDCKIMTSKTDVSSSVITSLGAIVSCYG
KTKCTASNKNRGIIKTFSNGCDYVSNKGVDTVSVGNTLYYVNKQEGKSLYVKGEPIINF
YDPLVFPSDEFDASISQVNEKINQSLAFIRKSDELLSAIGGYIPEAPRDGQAYVRKDGE
WVLLSTFLGGLVPRGSHHHHHHGSWSHPQFEK
[Relevant features (amino acid residue coordinates): Signal sequence (not present in final product): 1-25; pep27 (not present in final product): 110-136; F1: 137-513; F2: 26-109; foldon: 518-544; Thrombin recognition sequence: 547-552; His-tag: 553-558; Streptag II: 561-568; Linker sequences: 514-517, 545-546, 559-560; P102A (naturally-occurring substitution); I379V (naturally-occurring substitution); M447V (naturally-occurring substitution); T54H (introduced mutation); S155C (introduced mutation); S190I (introduced mutation); S290C (introduced mutation); V296I (introduced mutation)]

SEQ ID NO: 40: Amino acid Sequence of the T4 Fibritin Foldon:
GYIPEAPRDGQAYVRKDGEWVLLSTFL SEQ ID NO: 271. Amino Acid Sequence of Precursor Polypeptide of pXCS899
MELLILKANAITTILTAVTFCFASGQNITEEFYQSTCSAVSKGYLSALRTGWYHCVITIEL
SNIKENKCNGTDAKVKLIKQELDKYKNAVTELQLLMQSTPATNNRARRELPRFMNYTL
NNAKKTNVTLSKKRKRRFLGFLLGVGSAIASGVAVSKVLHLEGEVNKIKSALLSTNKAV
VSLSNGVSVCTSKVLDLKNYIDKQLLPIVNKQSCSISNIETVIEFQQKNNRLLEITREFSV
NAGVTTPVSTYMLTNSELLSLINDMPITNDQKKLMSNNVQIVRQQSYSIMSIIKEEVLAY
VVQLPLYGVIDTPCWKLHTSPLCTTNTKEGSNICLTRTDRGWYCDNAGSVSFFPQAET
CKVQSNRVFCDTMNSLTLPSEVNLCNVDIFNPKYDCKIMTSKTDVSSSVITSLGAIVSC
YGKTKCTASNKNRGIIKTFSNGCDYVSNKGVDTVSVGNTLYYVNKQEGKSLYVKGEPII
NFYDPLVFPSSEFDASISQVNEKINQSLAFIRKSDELLGGLVPRGSHHHHHHGSWSHP
QFEK SEQ ID NO: 272. Amino Acid Sequence of Precursor Polypeptide of pXCS1106
MELLILKANAITTILTAVTFCFASGQNITEEFYQSTCSAVSKGYLSALRTGWYHCVITIEL
SNIKENKCNGTDAKVKLIKQELDKYKNAVTELQLLMQSTPATGSAIASGVAVSKVLHLE
GEVNKIKSALLSTNKAVVSLSNGVSVCTSKVLDLKNYIDKQLLPIVNKQSCSISNIETVIE
FQQKNNRLLEITREFSVNAGVTTPVSTYMLTNSELLSLINDMPITNDQKKLMSNNVQIV
RQQSYSIMSIIKEEVLAYVVQLPLYGVIDTPCWKLHTSPLCTTNTKEGSNICLTRTDRG -continued Listing of Raw Sequences WYCDNAGSVSFFPQAETCKVQSNRVFCDTMNSLTLPSEVNLCNVDIFNPKYDCKIMT
SKTDVSSSVITSLGAIVSCYGKTKCTASNKNRGIIKTFSNGCDYVSNKGVDTVSVGNTL
YYVNKQEGKSLYVKGEPIINFYDPLVFPSSEFDASISQVNEKINQSLAFIR αcDELLHNV
NAGKSTTNIMITTLVPRGSGGSAIGGYIPEAPRDGQAYVRKDGEWVLLSTFLGGHHHH
HHGSWSHPQFEK SEQ ID NO: 273. Amino Acid Sequence of Precursor Polypeptide of pXCS1107
MELLILKANAITTILTAVTFCFASGQNITEEFYQSTCSAVSKGYLSALRTGWYHCVITIEL
SNIKENKCNGTDAKVKLIKQELDKYKNAVTELQLLMQSTPATGSAIASGVAVSKVLHLE
GEVNKIKSALLSTNKAVVSLSNGVSVCTSKVLDLKNYIDKQLLPIVNKQSCSISNIETVIE
FQQKNNRLLEITREFSVNAGVTTPVSTYMLTNSELLSLINDMPITNDQKKLMSNNVQIV
RQQSYSIMSIIKEEVLAYVVQLPLYGVIDTPCWKLHTSPLCTTNTKEGSNICLTRTDRG
WYCDNAGSVSFFPQAETCKVQSNRVFCDTMNSLTLPSEVNLCNVDIFNPKYDCKIMT
SKTDVSSSVITSLGAIVSCYGKTKCTASNKNRGIIKTFSNGCDYVSNKGVDTVSVGNTL
YYVNKQEGKSLYVKGEPIINFYDPLVFPSSEFDASISQVNEKINQSLAFIRKSDELLH αc
NAGKSTTNIMITTLVPRGSGGSAIGGYIPEAPRDGQAYVRKDGEWVLLSTFLGGHHHH
HHGSWSHPQFEK SEQ ID NO: 274. Amino Acid Sequence of Precursor Polypeptide of pXCS1108
MELLILKANAITTILTAVTFCFASGQNITEEFYQSTCSAVSKGYLSALRTGWYHCVITIEL
SNIKENKCNGTDAKVKLIKQELDKYKNAVTELQLLMQSTPATGSAIASGVAVSKVLHLE
GEVNKIKSALLSTNKAVVSLSNGVSVCTSKVLDLKNYIDKQLLPIVNKQSCSISNIETVIE
FQQKNNRLLEITREFSVNAGVTTPVSTYMLTNSELLSLINDMPITNDQKKLMSNNVQIV
RQQSYSIMSIIKEEVLAYVVQLPLYGVIDTPCWKLHTSPLCTTNTKEGSNICLTRTDRG
WYCDNAGSVSFFPQAETCKVQSNRVFCDTMNSLTLPSEVNLCNVDIFNPKYDCKIMT
SKTDVSSSVITSLGAIVSCYGKTKCTASNKNRGIIKTFSNGCDYVSNKGVDTVSVGNTL
YYVNKQEGKSLYVKGEPIINFYDPLVFPSSEFDASISQVNEKINQSLAFIRKSDELLHNV
NAGKS αcNIMITTLVPRGSGGSAIGGYIPEAPRDGQAYVRKDGEWVLLSTFLGGHHHH
HHGSWSHPQFEK SEQ ID NO: 275. Amino Acid Sequence of Precursor Polypeptide of pXCS1109
MELLILKANAITTILTAVTFCFASGQNITEEFYQSTCSAVSKGYLSALRTGWYHCVITIEL
SNIKENKCNGTDAKVKLIKQELDKYKNAVTELQLLMQSTPATGSAIASGVAVSKVLHLE
GEVNKIKSALLSTNKAVVSLSNGVSVCTSKVLDLKNYIDKQLLPIVNKQSCSISNIETVIE
FQQKNNRLLEITREFSVNAGVTTPVSTYMLTNSELLSLINDMPITNDQKKLMSNNVQIV
RQQSYSIMSIIKEEVLAYVVQLPLYGVIDTPCWKLHTSPLCTTNTKEGSNICLTRTDRG
WYCDNAGSVSFFPQAETCKVQSNRVFCDTMNSLTLPSEVNLCNVDIFNPKYDCKIMT
SKTDVSSSVITSLGAIVSCYGKTKCTASNKNRGIIKTFSNGCDYVSNKGVDTVSVGNTL
YYVNKQEGKSLYVKGEPIINFYDPLVFPSSEFDASISQVNEKINQSLAFIR αcDELLH αc
NAGKSTTNIMITTLVPRGSGGSAIGGYIPEAPRDGQAYVRKDGEWVLLSTFLGGHHHH
HHGSWSHPQFEK SEQ ID NO: 276. Amino Acid Sequence of Precursor Polypeptide of pXCS1110
MELLILKANAITTILTAVTFCFASGQNITEEFYQSTCSAVSKGYLSALRTGWYHCVITIEL
SNIKENKCNGTDAKVKLIKQELDKYKNAVTELQLLMQSTPATGSAIASGVAVSKVLHLE
GEVNKIKSALLSTNKAVVSLSNGVSVCTSKVLDLKNYIDKQLLPIVNKQSCSISNIETVIE
FQQKNNRLLEITREFSVNAGVTTPVSTYMLTNSELLSLINDMPITNDQKKLMSNNVQIV
RQQSYSIMSIIKEEVLAYVVQLPLYGVIDTPCWKLHTSPLCTTNTKEGSNICLTRTDRG
WYCDNAGSVSFFPQAETCKVQSNRVFCDTMNSLTLPSEVNLCNVDIFNPKYDCKIMT
SKTDVSSSVITSLGAIVSCYGKTKCTASNKNRGIIKTFSNGCDYVSNKGVDTVSVGNTL
YYVNKQEGKSLYVKGEPIINFYDPLVFPSSEFDASISQVNEKINQSLAFIR αcDELLHNV
NAGKS αcNIMITTLVPRGSGGSAIGGYIPEAPRDGQAYVRKDGEWVLLSTFLGGHHHH
HHGSWSHPQFEK SEQ ID NO: 277. Amino Acid Sequence of Precursor Polypeptide of pXCS1111
MELLILKANAITTILTAVTFCFASGQNITEEFYQSTCSAVSKGYLSALRTGWYHCVITIEL
SNIKENKCNGTDAKVKLIKQELDKYKNAVTELQLLMQSTPATGSAIASGVAVSKVLHLE
GEVNKIKSALLSTNKAVVSLSNGVSVCTSKVLDLKNYIDKQLLPIVNKQSCSISNIETVIE
FQQKNNRLLEITREFSVNAGVTTPVSTYMLTNSELLSLINDMPITNDQKKLMSNNVQIV
RQQSYSIMSIIKEEVLAYVVQLPLYGVIDTPCWKLHTSPLCTTNTKEGSNICLTRTDRG
WYCDNAGSVSFFPQAETCKVQSNRVFCDTMNSLTLPSEVNLCNVDIFNPKYDCKIMT
SKTDVSSSVITSLGAIVSCYGKTKCTASNKNRGIIKTFSNGCDYVSNKGVDTVSVGNTL
YYVNKQEGKSLYVKGEPIINFYDPLVFPSSEFDASISQVNEKINQSLAFIRKSDELLH αc
NAGKS αcNIMITTLVPRGSGGSAIGGYIPEAPRDGQAYVRKDGEWVLLSTFLGGHHHH
HHGSWSHPQFEK SEQ ID NO: 278. Amino Acid Sequence of Precursor Polypeptide of pXCS1112
MELLILKANAITTILTAVTFCFASGQNITEEFYQSTCSAVSKGYLSALRTGWYHCVITIEL
SNIKENKCNGTDAKVKLIKQELDKYKNAVTELQLLMQSTPATGSAIASGVAVSKVLHLE
GEVNKIKSALLSTNKAVVSLSNGVSVCTSKVLDLKNYIDKQLLPIVNKQSCSISNIETVIE
FQQKNNRLLEITREFSVNAGVTTPVSTYMLTNSELLSLINDMPITNDQKKLMSNNVQIV
RQQSYSIMSIIKEEVLAYVVQLPLYGVIDTPCWKLHTSPLCTTNTKEGSNICLTRTDRG
WYCDNAGSVSFFPQAETCKVQSNRVFCDTMNSLTLPSEVNLCNVDIFNPKYDCKIMT

| Listing of Raw Sequences |
|---|
| SKTDVSSSVITSLGAIVSCYGKTKCTASNKNRGIIKTFSNGCDYVSNKGVDTVSVGNTL<br>YVVNKQEGKSLYVKGEPIINFYDPLVFPSSEFDASISQVNEKINQSLAFIR CC DELLH CC<br>NAGKS CC NIMITTLVPRGSGGSAIGGYIPEAPRDGQAYVRKDGEWVLLSTFLGGHHHH<br>HHGSWSHPQFEK |

The invention claimed is:

1. A method of preventing Respiratory Syncytial Virus (RSV) infection in a human infant comprising administering to a pregnant woman an effective amount of a pharmaceutical composition comprising (1) a mutant of a wild-type RSV F protein and (2) a pharmaceutically acceptable carrier, wherein the mutant comprises (a) a F1 polypeptide and a F2 polypeptide and (b) at least one introduced amino acid mutation relative to the amino acid sequence of the wild-type RSV F protein, wherein the introduced amino acid mutation is a pair of cysteine mutations selected from the group consisting of: (i) 55C and 188C; (ii) 103C and 148C; and (iii) 142C and 371C, and wherein amino acid positions are numbered according to SEQ ID NO:1.

2. The method of claim 1, wherein the pharmaceutical composition comprises: (1) a mutant of the F protein of a subtype-A wild-type RSV; (2) a mutant of the F protein of a subtype-B wild-type RSV; and (3) a pharmaceutically acceptable carrier, wherein each of the mutants comprises a F2 polypeptide and F1 polypeptide, wherein the F2 polypeptide and F1 polypeptide of the mutant of the F protein of the subtype-A wild-type RSV comprise the amino acid sequence of SEQ ID NO:45 and the amino acid sequence of SEQ ID NO:46, respectively, and wherein the F2 polypeptide and F1 polypeptide of the mutant of the F protein of the subtype-B wild-type RSV comprise the amino acid sequence of SEQ ID NO: 49 and the amino acid sequence of SEQ ID NO:50, respectively.

3. A method of eliciting an immune response against Respiratory Syncytial Virus (RSV) in a human infant comprising administering to a pregnant woman an effective amount of a pharmaceutical composition comprising a mutant of a wild-type RSV F protein and a pharmaceutically acceptable carrier, wherein the mutant comprises (a) a F1 polypeptide and a F2 polypeptide and (b) at least one introduced amino acid mutation relative to the amino acid sequence of the wild-type RSV F protein, wherein the introduced amino acid mutation is a pair of cysteine mutations selected from the group consisting of: (i) 55C and 188C; (ii) 103C and 148C; and (iii) 142C and 371C, and wherein amino acid positions are numbered according to SEQ ID NO:1.

4. The method of claim 3, wherein the pharmaceutical composition comprises: (1) a mutant of the F protein of a subtype-A wild-type RSV; (2) a mutant of the F protein of a subtype-B wild-type RSV; and (3) a pharmaceutically acceptable carrier, wherein each of the mutants comprises a F2 polypeptide and F1 polypeptide, wherein the F2 polypeptide and F1 polypeptide of the mutant of the F protein of the subtype-A wild-type RSV comprise the amino acid sequence of SEQ ID NO:45 and the amino acid sequence of SEQ ID NO:46, respectively, and wherein the F2 polypeptide and F1 polypeptide of the mutant of the F protein of the subtype-B wild-type RSV comprise the amino acid sequence of SEQ ID NO:49 and the amino acid sequence of SEQ ID NO:50, respectively.

5. The method according to claim 4, wherein the C-terminus of the F1 polypeptide of the mutant is linked to a phage T4 fibritin foldon domain.

6. The method according to claim 5, wherein the pharmaceutical composition further comprises an adjuvant.

7. The method according to claim 6, wherein the adjuvant is aluminum hydroxide.

8. The method according to claim 4, wherein the human infant is a newborn.

9. The method according to claim 4, wherein the human infant is an infant in utero.

10. The method according to claim 5, wherein the human infant is a newborn.

11. The method according to claim 5, wherein the human infant is an infant in utero.

12. The method according to claim 2, wherein the C-terminus of the F1 polypeptide of the mutant is linked to a phage T4 fibritin foldon domain.

13. The method according to claim 12, wherein the pharmaceutical composition further comprises an adjuvant.

14. The method according to claim 13, wherein the adjuvant is aluminum hydroxide.

15. The method according to claim 2, wherein the human infant is a newborn.

16. The method according to claim 2, wherein the human infant is an infant in utero.

17. The method according to claim 12, wherein the human infant is a newborn.

18. The method according to claim 12, wherein the human infant is an infant in utero.

* * * * *